United States Patent
Zhu et al.

(10) Patent No.: US 8,809,318 B2
(45) Date of Patent: Aug. 19, 2014

(54) GAMMA SECRETASE MODULATORS

(75) Inventors: Zhaoning Zhu, Plainsboro, NJ (US); William J. Greenlee, Teaneck, NJ (US); Hongmei Li, Warren, NJ (US); Monica L. Vicarel, North Brunswick, NJ (US); Jun Qin, Edison, NJ (US); Pawan Kumar Dhondi, Elizabeth, NJ (US); Xianhai Huang, Warren, NJ (US); Anandan Palani, Bridgewater, NJ (US); Xiaoxiang Liu, River Vale, NJ (US); Zhong-Yue Sun, Parlin, NJ (US); Hubert B. Josien, Jersey City, NJ (US); Ruo Xu, Watchung, NJ (US); David James Cole, Springfield, NJ (US); Duane A. Burnett, Bernardsville, NJ (US); Chad E. Bennett, Metuchen, NJ (US); Troy McCracken, Garwood, NJ (US); Malcolm MacCoss, Seabrook Island, SC (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 350 days.

(21) Appl. No.: 13/128,316

(22) PCT Filed: Nov. 11, 2009

(86) PCT No.: PCT/US2009/063993
§ 371 (c)(1),
(2), (4) Date: Aug. 24, 2011

(87) PCT Pub. No.: WO2010/056722
PCT Pub. Date: May 20, 2010

(65) Prior Publication Data
US 2011/0306593 A1 Dec. 15, 2011

Related U.S. Application Data

(60) Provisional application No. 61/114,147, filed on Nov. 13, 2008.

(51) Int. Cl.
*A61K 31/553* (2006.01)
*C07D 498/04* (2006.01)
*C07D 498/14* (2006.01)
*C07D 498/20* (2006.01)

(52) U.S. Cl.
USPC .................. 514/211.05; 514/211.08; 540/489; 540/545

(58) Field of Classification Search
USPC .................. 514/211.05, 211.08; 540/489, 545
See application file for complete search history.

(56) References Cited

U.S. PATENT DOCUMENTS

| | | |
|---|---|---|
| 3,574,201 A | 4/1971 | Breuer |
| 2005/0042284 A1 | 2/2005 | Hobden et al. |
| 2006/0004013 A1 | 1/2006 | Kimura et al. |
| 2007/0117798 A1 | 5/2007 | Kimura et al. |
| 2007/0117839 A1 | 5/2007 | Kimura et al. |

FOREIGN PATENT DOCUMENTS

| | | |
|---|---|---|
| EP | 1992618 A1 | 11/2008 |
| WO | 01/70674 A1 | 9/2001 |
| WO | 2004/071431 A2 | 8/2004 |
| WO | 2004/110350 A2 | 12/2004 |
| WO | 2005/110422 A2 | 11/2005 |
| WO | 2006/001877 A2 | 1/2006 |
| WO | 2006/045554 A1 | 5/2006 |
| WO | 2007/102580 A1 | 9/2007 |
| WO | 2008/153793 A2 | 12/2008 |
| WO | 2009/061669 A1 | 5/2009 |
| WO | 2010/054067 A1 | 5/2010 |

OTHER PUBLICATIONS

WO2010/056722 Search Report, Feb. 22, 2010.

*Primary Examiner* — Brenda Coleman
(74) *Attorney, Agent, or Firm* — J. Eric Thies; John C. Todaro

(57) ABSTRACT

In its many embodiments, the present invention provides a novel class of heterocyclic compounds of the formula: as modulators of gamma secretase, methods of preparing such compounds, pharmaceutical compositions containing one or more such compounds, methods of preparing pharmaceutical formulations comprising one or more such compounds, and methods of treatment, prevention, inhibition, or amelioration of one or more disease associated with the central nervous system using such compounds or pharmaceutical compositions.

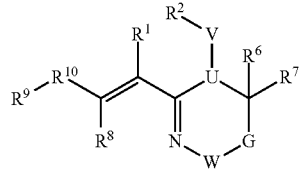

Formula I

7 Claims, No Drawings

GAMMA SECRETASE MODULATORS

CROSS REFERENCE TO RELATED APPLICATION

This application is entered into national stage examination under 37 U.S.C. 371 and stems from international patent application No. PCT/US2009/063993 filed on Nov. 11, 2009, which claims priority to application No. 61/114147 filed Nov. 13, 2008.

REFERENCE TO RELATED APPLICATION

This application claims the benefit of U.S. Provisional Application Ser. No. 61/114,147 filed Nov. 13, 2008.

FIELD OF THE INVENTION

The present invention relates to certain heterocyclic compounds useful as gamma secretase modulators (including inhibitors, antagonists and the like), pharmaceutical compositions containing the compounds, and methods of treatment using the compounds and compositions to treat various diseases including central nervous system disorders such as, for example, neurodegenerative diseases such as Alzheimer's disease and other diseases relating to the deposition of amyloid protein. They are especially useful for reducing Amyloid beta (hereinafter referred to as A$\beta$ production which is effective in the treatment of diseases caused by A$\beta$ such as, for example, Alzheimers and Down Syndrome.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

A$\beta$ protein, which is a metabolite of amyloid precursor protein (hereinafter referred to as APP), is considered to be greatly involved in degeneration and loss of neurons as well as onset of demential conditions (for example, see Klein W L, et al *Proceeding National Academy of Science USA*, Sep. 2, 2003, 100(18), p. 10417-22, suggest a molecular basis for reversible memory loss.

Nitsch R M, and 16 others, *Antibodies against $\beta$-amyloid slow cognitive decline in Alzheimer's disease*, Neuron, May 22, 2003, 38(4), p. 547-554) suggest that the main components of A$\beta$ protein are A$\beta$40 consisting of 40 amino acids and A$\beta$42 having two additional amino acids at the C-terminal. The A$\beta$40 and A$\beta$42 tend to aggregate (for example, see Jarrell J T et al, *The carboxy terminus of the $\beta$ amyloid protein is critical for the seeding of amyloid formation: implications for the pathogenesis of Alzheimer's disease*, Biochemistry, May 11, 1993, 32(18), p. 4693-4697) and constitute main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer disease and Down syndrome*, Proceeding National Academy of Science USA, June 1985, 82(12), p. 4245-4249.).

Furthermore, it is known that mutations of APP and presenelin genes, which is observed in familial Alzheimer's disease, increase production of A$\beta$40 and A$\beta$42 (for example, see Gouras G K, et al, *Intraneuronal A$\beta$42 accumulation in human brain*, American Journal of Pathology, January 2000, 156(1), p. 15-20. Also, see Scheuner D, et al, Nature Medicine, August 1996, 2(8), p. 864-870; and Forman M S, et al, *Differential effects of the Swedish mutant amyloid precursor protein on $\beta$-amyloid accumulation and secretion in neurons and normeuronal cells*, Journal of Biological Chemistry, Dec. 19, 1997, 272(51), p. 32247-32253.). Therefore, compounds which reduce production of A$\beta$40 and A$\beta$42 are expected as an agent for controlling progress of Alzheimer's disease or for preventing the disease.

These A$\beta$s are produced when APP is cleaved by beta secretase and subsequently clipped by gamma secretase. In consideration of this, creation of inhibitors of $\gamma$ secretase and $\beta$ secretase has been attempted for the purpose of reducing production of A$\beta$s. Many of these secretase inhibitors already known are peptides or peptidomimetics such as L-685,458. L-685,458, an aspartyl protease transition stale mimic, is a potent inhibitor of amyloid $\beta$-protein precursor $\gamma$-secretase activity, Biochemistry, Aug. 1, 2000, 39(30), p. 8698-8704).

Also of interest in connection with the present invention are: US 2007/0117798 (Eisai, published May 24, 2007); US 2007/0117839 (Eisai, published May 24, 2007); US 2006/0004013 (Eisai, published Jan. 5, 2006); WO 2005/110422 (Boehringer Ingelheim, published Nov. 24, 2005); WO 2006/045554 (Cellzone AG, published May 4, 2006); WO 2004/110350 (Neurogenetics™, published Dec. 23, 2004); WO 2004/071431 (Myriad Genetics, published Aug. 26, 2004); US 2005/0042284 (Myriad Genetics, published Feb. 23, 2005) and WO 2006/001877 (Myriad Genetics, published Jan. 5, 2006).

There is a need for new compounds, formulations, treatments and therapies to treat diseases and disorders associated with A$\beta$. It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds as gamma secretase modulators (including inhibitors, antagonists and the like), methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the A$\beta$ using such compounds or pharmaceutical compositions.

The compounds of this invention (Formula I) can be useful as gamma secretase modulators and can be useful in the treatment and prevention of diseases such as, for example, Alzheimers disease, mild cognitive impairment (MC1), Downs Syndrome, Glaucoma (Guo et. al., Proc. Natl. Acad. Sci. USA 104, 13444-13449 (2007)), Cerebral amyloid angiopathy, stroke or dementia (Frangione et al., Amyloid: J. Protein folding Disord. 8, suppl. 1, 36-42 (2001), Microgliosis and brain inflammation (M P Lamber, Proc. Natl. Acad.

Sci. USA 95, 6448-53 (1998)), Olfactory function loss (Getchell, et al. Neurobiology of Aging, 663-673, 24, 2003).

This invention provides compounds of formula I:

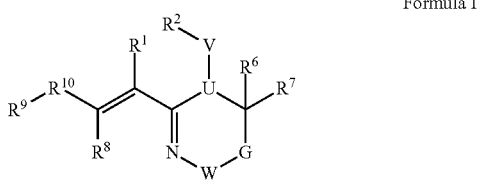

Formula I or a pharmaceutically acceptable salt, ester, solvate or prodrug thereof, wherein $R^1$, $R^2$, $R^6$, $R^7$, $R^8$, $R^9$, $R^{10}$, G, U and W are independently selected and are as defined below.

This invention also provides compounds of formula I.

The present invention further includes the compound of formula I in all its isolated forms.

This invention also provides compounds of formula I in pure and isolated form.

This invention also provides compounds of formula I selected from the group consisting of: compounds of formulas Z1 to Z24.

This invention also provides compounds of formula I selected from the group consisting of: compounds 1 to 117, the final compound of Method T and the final compound of Method U.

This invention also provides compounds of formula I selected from the group consisting of: compounds 1 to 68.

This invention also provides pharmaceutical compositions comprising an effective amount of one or more (e.g., one) compounds of formula I, or a pharmaceutically acceptable salt, ester or solvate thereof, and a pharmaceutically acceptable carrier.

This invention also provides pharmaceutical compositions comprising an effective amount of one or more (e.g., one) compounds of formula I, or a pharmaceutically acceptable salt, ester or solvate thereof, and an effective amount of one or more (e.g., one) other pharmaceutically active ingredients (e.g., drugs), and a pharmaceutically acceptable carrier.

The compounds of Formula I can be useful as gamma secretase modulators and can be useful in the treatment and prevention of diseases such as, for example, central nervous system disorders such as Alzheimers disease and Downs Syndrome.

Thus, this invention also provides methods for: (1) method for modulating (including inhibiting, antagonizing and the like) gamma-secretase; (2) treating one or more neurodegenerative diseases; (3) inhibiting the deposition of amyloid protein (e.g., amyloid beta protein) in, on or around neurological tissue (e.g., the brain); (4) Alzheimer's disease; and (5) treating Downs syndrome; wherein each method comprises administering an effective amount of one or more (e.g., one) compounds of formula I to a patient in need of such treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula I and the administration of an effective amount of one or more (e.g., one) other pharmaceutical active ingredients (e.g., drugs).

This invention also provides methods for: (1) treating mild cognitive impairment; (2) treating glaucoma; (3) treating cerebral amyloid angiopathy; (4) treating stroke; (5) treating dementia; (6) treating microgliosis; (7) treating brain inflammation; and (8) treating olfactory function loss; wherein each method comprises administering an effective amount of one or more (e.g., one) compounds of formula I to a patient in need of such treatment.

This invention also provides a kit comprising, in separate containers, in a single package, pharmaceutical compositions for use in combination, wherein one container comprises an effective amount of a compound of formula I in a pharmaceutically acceptable carrier, and another container (i.e., a second container) comprises an effective amount of another pharmaceutically active ingredient (as described below), the combined quantities of the compound of formula I and the other pharmaceutically active ingredient being effective to treat the diseases or conditions mentioned in any of the above methods.

This invention also provides any of the above mentioned methods, pharmaceutical compositions or kit wherein the compound of formula I is selected from the group consisting of: compounds of formulas Z1 to Z24.

This invention also provides any of the above mentioned methods, pharmaceutical compositions or kit wherein the compound of formula I is selected from the group consisting of: compounds compounds 1 to 117, the final compound of Method T and the final compound of Method U.

This invention also provides any of the above mentioned methods, pharmaceutical compositions or kit wherein the compound of formula I is selected from the group consisting of: compounds compounds 1 to 68.

DETAILED DESCRIPTION

In one embodiment, the present invention discloses compounds which are represented by structural Formula I, or a pharmaceutically acceptable salt, solvate, ester or prodrug thereof, wherein the various moieties are described below.

Thus, one embodiment is directed to a compound of formula I:

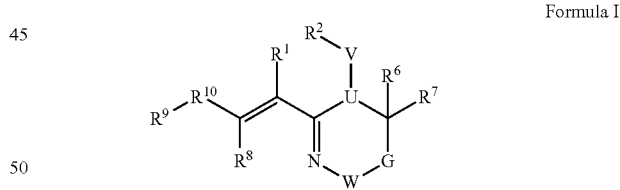

Formula I or a pharmaceutically acceptable salt, solvate, ester or prodrug thereof, wherein:
either
(i) $R^1$ and $R^2$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, (c) said cycloalkenyl moiety is optionally substituted with 1-5 independently selected $R^{21}$ substituents, (d) said heterocyclenyl moiety is optionally substituted with 1-5 independently selected $R^{21}$ substituents, and (e) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (ii) $R^2$ and $R^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, (c) said cycloalkenyl moiety is optionally substituted with 1-5 independently selected $R^{21}$ substituents, (d) said heterocyclenyl moiety is optionally substituted with 1-5 independently selected $R^{21}$ substituents, and (e) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (iii)
  (a) $R^1$ and $R^2$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, (2) said heterocyclyl moiety is optionally substituted with 1-5 independently selected $R^{21}$ substituents, (3) said cycloalkenyl moiety is optionally substituted with 1-5 independently selected $R^{21}$ substituents, (4) said heterocyclenyl moiety is optionally substituted with 1-5 independently selected $R^{21}$ substituents; and
  (b) $R^2$ and $R^6$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents, (3) said cycloalkenyl moiety is optionally substituted with 1-5 independently selected $R^{21}$ substituents, (4) said heterocyclenyl moiety is optionally substituted with 1-5 independently selected $R^{21}$ substituents; and
  (c) said $R^2$ and $R^6$ cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (iv) $R^6$ and either $R^3$ or $R^4$ of the —$C(R^3)(R^4)$— G moiety, are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, (c) said cycloalkenyl moiety is optionally substituted with 1-5 independently selected $R^{21}$ substituents, (d) said heterocyclenyl moiety is optionally substituted with 1-5 independently selected $R^{21}$ substituents, and (e) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (v) $R^6$ and $R^{13}$ of the —$N(R^{13})$— G moiety, are joined together to form a 5-8 membered heterocyclyl or 5-8 membered heterocyclenyl moiety, wherein; (a) said heterocyclyl moiety is optionally substituted with 1-5 independently selected $R^{21}$ substituents, (b) said heterocyclenyl moiety is optionally substituted with 1-5 independently selected $R^{21}$ substituents, and (c) said heterocyclyl or heterocyclenyl moiety is optionally fused with an aryl or heteroaryl ring, and the ring moiety resulting from the fusion is optionally substituted with 1-5 independently selected $R^{21}$ substituents; or (vi) $R^3$ and $R^4$ of the —$C(R^3)(R^4)$— G moiety are joined together to form a cycloalkyl, cycloalkenyl, heterocycloalkyl, or heterocycloalkenyl spiro ring, wherein
  (a) said spiro cycloalkyl ring is a 3 to 8 carbon membered ring (including the carbon atom common to both rings), and
  (b) said spiro cycloalkenyl ring is a 5 to 8 carbon membered ring (including the carbon atom common to both rings) comprising one or two double bonds (and in one example one double bond, and in another example two double bonds), provided that there is no double bond to the carbon common to both rings and
  (c) said spiro heterocycloalkyl ring is a 4 to 8 membered ring (including the carbon atom common to both rings) comprising 1 to 3 ring members independently selected from the group consisting of: O, S, $NR^2$, P(O)alkyl (e.g., $P(O)CH_3$), P(O)Oalkyl (e.g., $P(O)OCH_3$), S(O), and $S(O)_2$, and wherein the remaining ring members are independently selected from the group consisting of carbon and C(O), and
  (d) said spiro heterocycloalkenyl ring is a 5 to 8 membered ring (including the carbon atom common to both rings) comprising one or two double bonds (and in one example one double bond, and in another example two double bonds), and comprising 1 to 3 ring members independently selected from the group consisting of: O, S, $NR^2$, P(O)alkyl (e.g., $P(O)CH_3$), P(O)Oalkyl (e.g., $P(O)OCH_3$), S(O), and $S(O)_2$, and wherein the remaining ring members are independently selected from the group consisting of carbon and C(O), provided that there is no double bond to the carbon common to both rings, and
  (e) wherein said spiro ring is optionally fused with an aryl ring (e.g. phenyl), or is optionally fused with a heteroaryl ring (e.g., pyridyl), to form a fused spiro ring moiety, and
  (f) wherein said spiro ring, or said fused spiro ring, is optionally substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, —$C(O)R^{15}$, —$C(O)OR^{15}$, —$C(O)N(R^{15})(R^{16})$, $S(O)N(R^{15})(R^{16})$, —$S(O)_2N(R^{15})(R^{16})$, —$C(=NOR^{15})R^{16}$, —$P(O)(OR^{15})(OR^{16})$, —$OR^{15}$ (e.g., —$OCH_3$), and —$S(O)_2R^{15A}$ (e.g., —$S(O)_2CH_3$); or (vii) one $R^3$ and one $R^4$ on one carbon of the —$(C(R^3)(R^4))_2$— G moiety are joined together to form a cycloalkyl, cycloalkenyl, heterocycloalkyl, or heterocycloalkenyl spiro ring, wherein
  (a) said spiro cycloalkyl ring is a 3 to 8 carbon membered ring (including the carbon atom common to both rings), and
  (b) said spiro cycloalkenyl ring is a 5 to 8 carbon membered ring (including the carbon atom common to both rings) comprising one or two double bonds (and in one example one double bond, and in another example two double bonds), provided that there is no double bond to the carbon common to both rings and (c) said spiro heterocycloalkyl ring is a 4 to 8 membered ring (including the carbon atom common to both rings) comprising 1 to 3 ring members independently selected from the group consisting of: O, S, NR$^2$, P(O)alkyl (e.g., P(O)CH$_3$), P(O)Oalkyl (e.g., P(O)OCH$_3$), S(O), and S(O)$_2$, and wherein the remaining ring members are independently selected from the group consisting of carbon and C(O), and (d) said spiro heterocycloalkenyl ring is a 5 to 8 membered ring (including the carbon atom common to both rings) comprising one or two double bonds (and in one example one double bond, and in another example two double bonds), and comprising 1 to 3 ring members independently selected from the group consisting of: O, S, NR$^2$, P(O)alkyl (e.g., P(O)CH$_3$), P(O)Oalkyl (e.g., P(O)OCH$_3$), S(O), and S(O)$_2$, and wherein the remaining ring members are independently selected from the group consisting of carbon and C(O), provided that there is no double bond to the carbon common to both rings, and (e) wherein said spiro ring is optionally fused with an aryl ring (e.g. phenyl), or is optionally fused with a heteroaryl ring (e.g., pyridyl), to form a fused spiro ring moiety, and (f) wherein said spiro ring is optionally substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —OR$^{15}$ (e.g., —OCH$_3$), and —S(O)$_2$R$^{15A}$ (e.g., —S(O)$_2$CH$_3$); or (viii) an R$^3$ and an R$^4$ on adjacent carbons of the —(C(R$^3$)(R$^4$))$_2$-G moiety are joined together to form a cycloalkyl, cycloalkenyl, heterocycloalkyl, or heterocycloalkenyl ring (that is one R$^3$ on one carbon, and one R$^4$ on the adjacent carbon of the —(C(R$^3$)(R$^4$))$_2$— G moiety are taken together to form a cycloalkyl, cycloalkenyl, heterocycloalkyl, or heterocycloalkenyl ring), wherein (a) said cycloalkyl ring is a 3 to 8 carbon membered ring (including the carbon atoms common to both rings), and (b) said cycloalkenyl ring is a 5 to 8 carbon membered ring (including the carbon atoms common to both rings) comprising one or two double bonds (and in one example one double bond, and in another example two double bonds), provided that there is no double bond to the carbon common to both rings and (c) said heterocycloalkyl ring is a 4 to 8 membered ring (including the carbon atoms common to both rings) comprising 1 to 3 ring members independently selected from the group consisting of: O, S, NR$^2$, P(O)alkyl (e.g., P(O)CH$_3$), P(O)Oalkyl (e.g., P(O)OCH$_3$), S(O), and S(O)$_2$, and wherein the remaining ring members are independently selected from the group consisting of carbon and C(O), and (d) said heterocycloalkenyl ring is a 5 to 8 membered ring (including the carbon atoms common to both rings) comprising one or two double bonds (and in one example one double bond, and in another example two double bonds), and comprising 1 to 3 ring members independently selected from the group consisting of: O, S, NR$^2$, P(O)alkyl (e.g., P(O)CH$_3$), P(O)Oalkyl (e.g., P(O)OCH$_3$), S(O), and S(O)$_2$, and wherein the remaining ring members are independently selected from the group consisting of carbon and C(O), provided that there is no double bond to the carbon common to both rings, and (e) wherein said ring (as described in (a) to (d)) is optionally fused with an aryl ring (e.g. phenyl), or is optionally fused with a heteroaryl ring (e.g., pyridyl), to form a fused ring moiety, and (f) wherein said ring (as described in (a) to (e) is optionally substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, P(O)(OR$^{15}$)(OR$^{16}$), —OR$^{15}$ (e.g., —OCH$_3$), and —S(O)$_2$R$^{15A}$ (e.g., —S(O)$_2$CH$_3$); or (ix) (a) R$^1$ and R$^2$ are joined together to form a C4-C8 cycloalkyl, C4-C8 cycloalkenyl, 5-8 membered heterocyclyl or 5-8 membered heterocyclenyl moiety as described in (i) above, and (b) R$^6$ and either R$^3$ or R$^4$ of the —C(R$^3$)(R$^4$)-G moiety, are joined together to form a C4-C8 cycloalkyl, C4-C8 cycloalkenyl, 5-8 membered heterocyclyl or 5-8 membered heterocyclenyl moiety as described in (iv) above (those skilled in the art will appreciate that reference to the definitions in (i) and (iv) above is reference to the entire definitions in (i) and (iv)); or (x) R$^1$ and R$^2$ are joined together to form a C4-C8 cycloalkyl, C4-C8 cycloalkenyl, 5-8 membered heterocyclyl or 5-8 membered heterocyclenyl moiety as described in (i) above, and (b) R$^3$ and R$^4$ of the —C(R$^3$)(R$^4$)— G moiety are joined together to form a cycloalkyl, cycloalkenyl, heterocycloalkyl, or heterocycloalkenyl spiro ring as described in (vi) above (those skilled in the art will appreciate that reference to the definitions in (i) and (vi) above is reference to the entire definitions in (i) and (vi)); or (xi) R$^1$ and R$^2$ are joined together to form a C4-C8 cycloalkyl, C4-C8 cycloalkenyl, 5-8 membered heterocyclyl or 5-8 membered heterocyclenyl moiety as described in (i) above, and (b) one R$^3$ and one R$^4$ on one carbon of the —(C(R$^3$)(R$^4$))$_2$— G moiety are joined together to form a cycloalkyl, cycloalkenyl, heterocycloalkyl, or heterocycloalkenyl spiro ring as described in (vii) above (those skilled in the art will appreciate that reference to the definitions in (i) and (vii) above is reference to the entire definitions in (i) and (vii)); or (xii) R$^1$ and R$^2$ are joined together to form a C4-C8 cycloalkyl, C4-C8 cycloalkenyl, 5-8 membered heterocyclyl or 5-8 membered heterocyclenyl moiety as described in (i) above, and (b) an R$^3$ and an R$^4$ on adjacent carbons of the —(C(R$^3$)(R$^4$))$_2$— G moiety are joined together to form a cycloalkyl, cycloalkenyl, heterocycloalkyl, or heterocycloalkenyl ring as described in (viii) above (those skilled in the art will appreciate that reference to the definitions in (i) and (iv) above is reference to the entire definitions in (i) and (viii)); or (xiii) (a) R$^1$ and R$^2$ are not joined together, and (b) R$^2$ and R$^6$ are not joined together, and (c) R$^1$ and R$^2$ are not joined together, and R$^2$ and R$^6$ are not joined together (i.e., R$^2$ is not joined together with R$^1$ and R$^6$), and (d) R$^6$ is not joined together with either R$^3$ or R$^4$ (i.e., R$^6$ and R$^3$ are not joined together, or R$^6$ and R$^4$ are not joined together), and (e) $R^6$ and $R^{13}$ of the —$N(R^{13})$— G moiety, are not joined together, and (f) $R^3$ and $R^4$ of the —$C(R^3)(R^4)$— G moiety are not joined together, and (g) one $R^3$ and one $R^4$ on one carbon of the —$(C(R^3)(R^4))_2$— G moiety are not joined together, and (h) an $R^3$ and an $R^4$ on adjacent carbons of the —$(C(R^3)(R^4))_2$— G moiety are not joined together, and (i) $R^1$ and $R^2$, and $R^6$ and either $R^3$ or $R^4$, are not joined together to form the rings described in (ix) above, and (j) $R^1$ and $R^2$, and $R^3$ and $R^4$, are not joined together to form the rings described in (x) above, and (k) $R^1$ and $R^2$, and $R^3$ and $R^4$, are not joined together to form the rings described in (xi) above, and (l) $R^1$ and $R^2$, and $R^3$ and $R^4$, are not joined together to form the rings described in (xii) above (that is none of the rings described above in (i) to (xii) are formed); and U is $\overset{\xi}{\text{---}}C(R^5)$ or N;

W is selected from the group consisting of a bond, —NH—, —O—, —C(O)—, —S—, —S(O)—, —S(O$_2$)—, and —$C(R^{11})(R^{12})$—;

G is selected from the group consisting of —$C(R^3)(R^4)$— (wherein $R^3$ and $R^4$ are independently selected), —$(C(R^3)(R^4))_2$— (wherein each $R^3$ and each $R^4$ are independently selected), —C(O)— and —$N(R^{13})$—, with the proviso that when W is —O— or —S—, G is not —$N(R^{13})$— or —C(O)—, and with the proviso that when G is —$(C(R^3)(R^4))_2$— then W is not a bond, and with the proviso that when G is —$N(R^{13})$—, then W is not —NH—;

V is selected from the group consisting of a bond, —O—, —C(O)— and —$N(R^{14})$—;

Each $R^1$ (when $R^1$ is not joined to $R^2$), $R^2$ (when $R^2$ is not joined to $R^1$ or $R^6$), $R^5$, $R^6$ (when $R^6$ is not joined to $R^2$), and $R^7$ is independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents; or $R^6$ and $R^7$ are taken together to form =O, and $R^1$, $R^2$, and $R^5$ are as defined above;

or, alternatively, $R^1$ (when $R^1$ is not joined to $R^2$) and $R^8$ are taken together to form a bond (i.e., there is a triple bond between the carbon atom to which $R^1$ was bonded to and the carbon to which $R^8$ was bonded to, i.e., the compound of formula I is a compound of formula II:

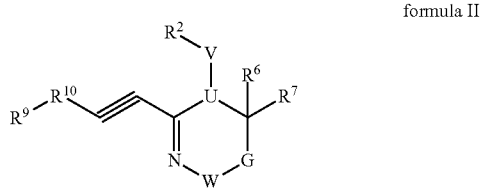

formula II and G, U, V, W $R^2$, $R^6$, $R^7$, $R^9$ and $R^{10}$ are as defined for formula I;

Each $R^3$ is independently selected from the group consisting of H, halo (and in one example, F), —$OR^{16}$ (and in one example $R^{15}$ is H), —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —C(O)$R^{15}$, —C(O)$OR^{15}$, —C(=$NOR^{15}$)$R^{16}$, —C(O)N($R^{15}$)($R^{16}$), —S(O)N($R^{15}$)($R^{16}$), S(O)$_2$N($R^{15}$)($R^{16}$), —S(O)$R^{15}$, —S(O)$_2R^{24}$, —P(O)($OR^{16}$)($OR^{16}$), =$NOR^{18}$, —N$_3$, alkyl-, alkenyl-, alkynyl-, aryl-, arylalkyl-, alkylaryl-, cycloalkyl-, cycloalkyl alkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents; or $R^3$ and $R^6$ taken together form a bond (i.e., $R^3$ and $R^6$ form a bond between G and the carbon to which $R^6$ is bound), provided that when $R^3$ and $R^6$ form a bond: (1) W is not a bond, (2) $R^2$ and $R^6$ are not joined together to form a cycloalkyl, cycloalkenyl, heterocyclyl or heterocyclenyl moiety (as described in (ii) and (iii) above), (3) $R^6$ and either $R^3$ or $R^4$ of the —$C(R^3)(R^4)$— G moiety are not joined together to form a cycloalkyl, cycloalkenyl, heterocyclyl or heterocyclenyl moiety (as described in (iv) above), (4) $R^6$ and $R^{13}$ of the —$N(R^{13})$— G moiety are not joined together to form a heterocyclyl or heterocyclenyl moiety (as described in (v) above), (5) $R^3$ and $R^4$, when G is —$C(R^3)(R^4)$—, are not joined to form a bond (as described in (vi) above); and (6) $R^3$ and $R^4$, on the carbon adjacent to the carbon to which $R^6$ is bound, when G is —$(C(R^3)(R^4))_2$—, are not joined to form a cycloalkyl, cycloalkenyl, heterocycloalkyl, or heterocycloalkenyl spiro ring (as described in (vii) above);

Each $R^4$, $R^{11}$ and $R^{12}$ is independently selected from the group consisting of H, halo (and in one example, F), —$OR^{15}$ (and in one example $R^{15}$ is H), —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —C(O)$R^{15}$, —C(O)$OR^{15}$, —C(=$NOR^{15}$)$R^{16}$, —C(O)N($R^{15}$)($R^{16}$), —S(O)N($R^{15}$)($R^{16}$), —S(O)$_2$N($R^{15}$)($R^{16}$), —S(O)$R^{15}$, —S(O)$_2R^{24}$, —P(O)($OR^{15}$)($OR^{16}$), =$NOR^{15}$, —N$_3$, alkyl-, alkenyl-, alkynyl-, aryl-, arylalkyl-, alkylaryl-, cycloalkyl-, cycloalkyl alkyl-, heteroaryl-, heteroarylalkyl-, heterocyclyl- and heterocyclylalkyl-, wherein each of said alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents, and provided that when one of $R^3$ or $R^4$ is selected from the group consisting of: —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —S(O)N($R^{15}$)($R^{16}$), —S(O)$_2$N($R^{15}$)($R^{16}$), —S(O)$R^{15}$, —S(O)$_2R^{24}$, —P(O)($OR^{15}$)($OR^{16}$), =$NOR^{15}$, and —N$_3$, then the other is not selected from the group consisting of: —$OR^{15}$, —CN, —$SR^{15}$, and —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —S(O)N($R^{15}$)($R^{16}$), —S(O)$_2$N($R^{15}$)($R^{16}$), —S(O)$R^{15}$, —S(O)$_2R^{24}$, —P(O)($OR^{15}$)($OR^{16}$), =$NOR^{15}$, and —N$_3$ (i.e., if one of $R^3$ or $R^4$ is —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —S(O)N($R^{15}$)($R^{16}$), —S(O)$_2$N($R^{15}$)($R^{16}$), —S(O)$R^{15}$, —S(O)$_2R^{24}$, —P(O)($OR^{15}$)($OR^{16}$), =$NOR^{15}$, or —N$_3$, then the other one is not —$OR^{15}$, —CN, —$SR^{15}$, and —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)$ —OR$^{16}$, —S(O)N(R$^{15}$)(R$^{16}$), —S(O)$_2$N(R$^{15}$)(R$^{16}$), —S(O)R$^{15}$, —S(O)$_2$R$^{24}$, —P(O)(OR$^{15}$)(OR$^{16}$), =NOR$^{15}$, or —N$_3$); and provided that when one of R$^{11}$ or R$^{12}$ is selected from the group consisting of: —OR$^{15}$, —CN, —SR$^{15}$, —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —S(O)N(R$^{15}$)(R$^{16}$), —S(O)$_2$N(R$^{15}$)(R$^{16}$), —S(O)R$^{15}$, —S(O)$_2$R$^{24}$, —P(O)(OR$^{15}$)(OR$^{16}$), =NOR$^{15}$, and —N$_3$, then the other is not selected from the group consisting of: —OR$^{15}$, —CN, —SR$^{15}$, —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —S(O)N(R$^{15}$)(R$^{16}$), —S(O)$_2$N(R$^{15}$)(R$^{16}$), —S(O)R$^{15}$, —S(O)$_2$R$^{24}$, —P(O)(OR$^{15}$)(OR$^{16}$), =NOR$^{15}$, and —N$_3$ (i.e., if one of R$^{11}$ or R$^{12}$ is —OR$^{15}$, —CN, —SR$^{15}$, —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —S(O)N(R$^{15}$)(R$^{16}$), —S(O)$_2$N(R$^{15}$)(R$^{16}$), —S(O)R$^{15}$, —S(O)$_2$R$^{24}$, —P(O)(OR$^{15}$)(OR$^{16}$), =NOR$^{15}$, or —N$_3$, then the other is not —OR$^{15}$, —CN, —SR$^{15}$, —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —S(O)N(R$^{15}$)(R$^{16}$), —S(O)$_2$N(R$^{15}$)(R$^{16}$), —S(O)R$^{15}$, —S(O)$_2$R$^{24}$, —P(O)(OR$^{15}$)(OR$^{16}$), =NOR$^{15}$, or —N$_3$);

R$^{13}$ is independently selected from the group consisting of H, alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl-, aryl heterocycloalkyl-, heteroarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkylheteroaryl-, heterocycloalkylheteroaryl-, cycloalkenylaryl-, heterocycloalkenylaryl-, —OR$^{15}$, —CN, —C(O)R$^8$, —C(O)OR$^9$, —S(O)R$^{10}$, —S(O)$_2$R$^{10}$—S(O)N(R$^{11}$)(R$^{12}$), —S(O)$_2$N(R$^{11}$)(R$^{12}$), —NO$_2$, —N=C(R$^8$)$_2$ and —N(R$^8$)$_2$; and wherein said R$^{13}$ alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroaryl heterocycloalkylalkyl-, cycloalkyl, arylcycloalkyl-, heteroarylcycloalkyl-, heterocycloalkyl, arylheterocycloalkyl-, heteroarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkylheteroaryl-, heterocycloalkylheteroaryl-, cycloalkenylaryl-, and heterocycloalkenylaryl- groups are optionally substituted with 1 to 5 groups independently selected from the group consisting of: alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N (R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S (O)$_2$R$^{16}$, —N(R$^{15}$)S(O)$_2$N(R$^{16}$)(R$^{17}$), —N(R$^{15}$)S(O)N(R$^{16}$) (R$^{17}$), —N(R$^{15}$)C(O)N(R$^{16}$)(R$^{17}$), —CH$_2$—N(R$^{15}$)C(O)N (R$^{16}$)(R$^{17}$), —N(R$^{15}$)C(O)OR$^{16}$, —CH$_2$—N(R$^{15}$)C(O) OR$^{16}$, —S(O)R$^{15}$, =NOR$^{15}$, —N$_3$, —NO$_2$ and —S(O)$_2$R$^{24}$;

R$^8$ is selected from the group consisting of H, halo (e.g., F), alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being optionally substituted with 1-3 independently selected R$^{21}$ substituents;

R$^9$ is selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each R$^9$ group is optionally substituted with 1-3 independently selected R$^{21}$ substituents;

R$^{10}$ is selected from the group consisting of a bond, alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

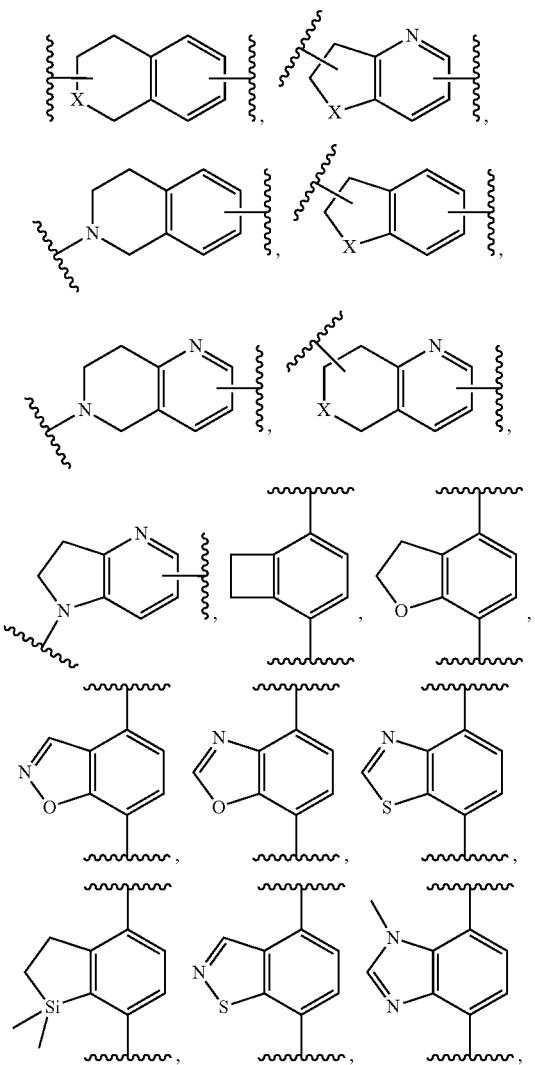

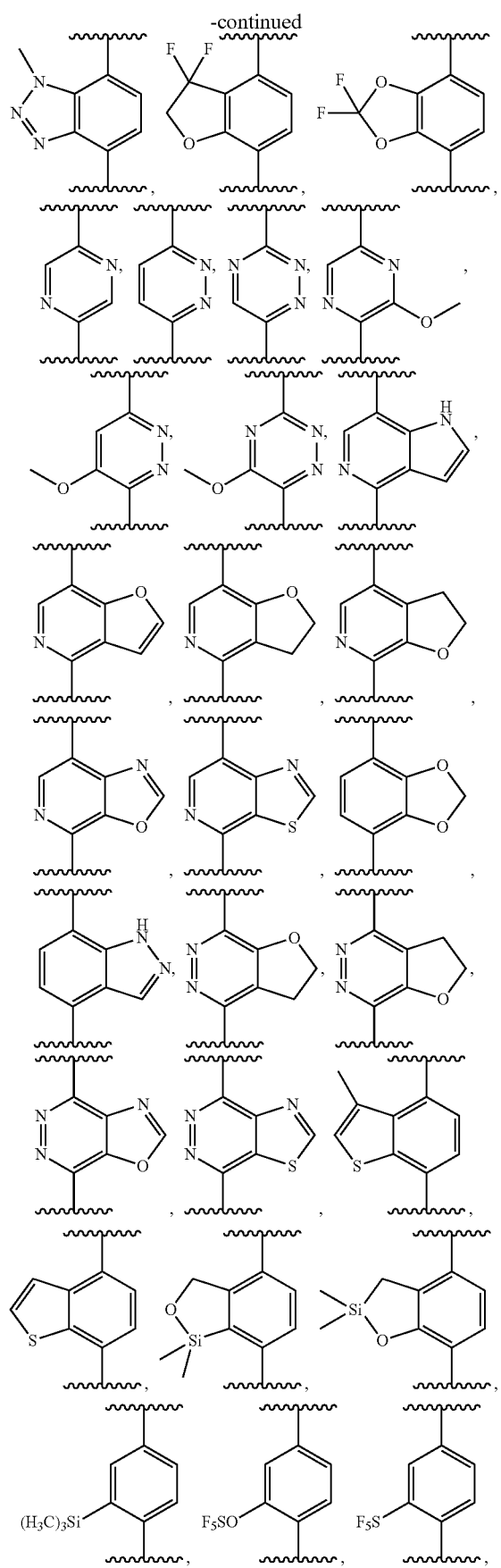
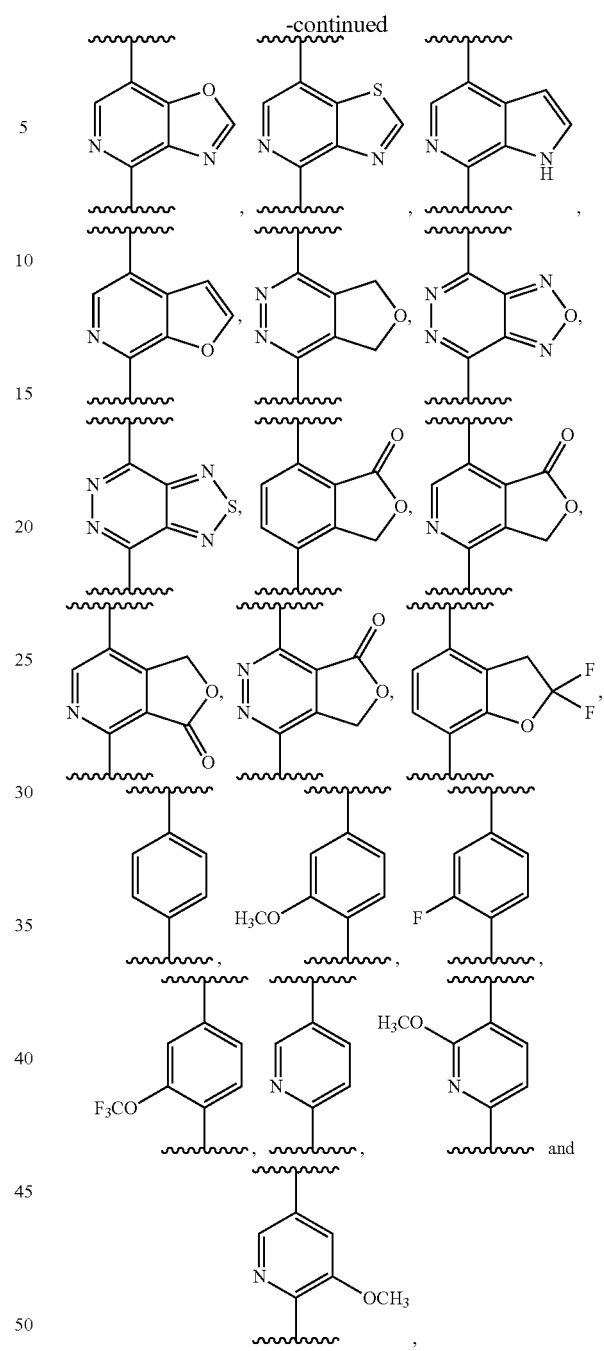

wherein X is selected from the group consisting of; O, N(R$^{14}$) and S;
wherein each of said R$^{10}$ groups (except for the bond) is optionally substituted with 1-3 independently selected R$^{21}$ substituents;
R$^{14}$ is selected from the group consisting of H, alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, —CN, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$), wherein each of said alkyl, alkenyl, alkynyl, cycloalkyl, cycloalkylalkyl-, cycloalkenyl, heterocyclyl, heterocyclylalkyl-, aryl, arylalkyl-, heteroaryl, and heteroarylalkyl- is optionally substituted with 1-5 independently selected R$^{21}$ substitutents;

Each $R^{15A}$ is independently selected from the group consisting of alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl-, arylheterocyclyl-, $(R^{18})_r$-alkyl, $(R^{18})_r$-cycloalkyl-, $(R^{18})_r$-cycloalkylalkyl-, $(R^{18})_r$-heterocyclyl-, $(R^{18})_r$-heterocyclylalkyl-, $(R^{18})_r$-aryl-, $(R^{18})_r$-arylalkyl-, $(R^{18})_r$-heteroaryl- and $(R^{18})_r$-heteroarylalkyl-, wherein r is 1 to 5 and each $R^{18}$ is independently selected (and those skilled in the art will appreciate that the $R^{18}$ moieties can be bound to any available substitutable atom);

$R^{15}$, $R^{16}$ and $R^{17}$ are independently selected from the group consisting of H, alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl-, arylheterocyclyl-, $(R^{18})_r$-alkyl-, $(R^{18})_r$-cycloalkyl-, $(R^{18})_r$-cycloalkylalkyl-, $(R^{18})_r$-heterocyclyl-, $(R^{18})_r$-heterocyclylalkyl-, $(R^{18})_r$-aryl, $(R^{18})_r$-arylalkyl-, $(R^{18})_r$-heteroaryl- and $(R^{18})_r$-heteroarylalkyl-, wherein r is 1-5;

Each $R^{18}$ is independently selected from the group consisting of alkyl, alkenyl, alkynyl, aryl, arylalkyl-, arylalkenyl-, arylalkynyl-, —$NO_2$, halo, heteroaryl, HO-alkyoxyalkyl-, —$CF_3$, —CN, alkyl-CN, —C(O)$R^{19}$, —C(O)OH, —C(O)O$R^{19}$, —C(O)NH$R^{20}$, —C(O)NH$_2$, —C(O)NH$_2$—C(O)N(alkyl)$_2$, —C(O)N(alkyl)(aryl), —C(O)N(alkyl)(heteroaryl), —S$R^{19}$, —S(O)$_2R^{20}$, —S(O)NH$_2$, —S(O)NH(alkyl), —S(O)N(alkyl)(alkyl), —S(O)NH(aryl), —S(O)$_2$NH$_2$, —S(O)$_2$NH$R^{19}$, —S(O)$_2$NH(heterocyclyl), —S(O)$_2$N(alkyl)$_2$, —S(O)$_2$N(alkyl)(aryl), —OCF$_3$, —OH, —O$R^{20}$, —O-heterocyclyl, —O-cycloalkylalkyl, —O-heterocyclylalkyl, —NH$_2$, —NH$R^{20}$, —N(alkyl)$_2$, —N(arylalkyl)$_2$, —N(arylalkyl)-(heteroarylalkyl), —NHC(O)$R^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternately, two $R^{18}$ moieties on adjacent carbons can be linked together to form:

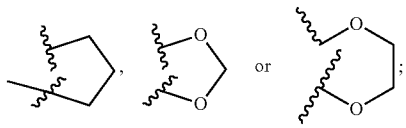

$R^{19}$ is selected from the group consisting of: alkyl, cycloalkyl, aryl, arylalkyl- and heteroarylalkyl-;

$R^{20}$ is selected from the group consisting of: alkyl, cycloalkyl, aryl, halo substituted aryl, arylalkyl-, heteroaryl and heteroarylalkyl-;

Each $R^{21}$ group is independently selected from the group consisting of alkyl, alkenyl, alkynyl, cycloalkyl, cycloalkenyl, heterocyclyl, heterocyclylalkyl-, aryl, arylalkyl-, heteroaryl, heteroarylalkyl-, halo, —CN, —O$R^{15}$—C(O)$R^{15}$, —C(O)O$R^{15}$, —C(O)N($R^{15}$)($R^{16}$), —SF$_5$, —OSF$_5$, —Si($R^{24}$)$_3$ wherein each $R^{24}$ is independently selected, —S$R^{15}$, —S(O)N($R^{15}$)($R^{16}$), —CH($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —CH$_2$—N($R^{15}$)C(O)$R^{16}$, —CH$_2$—N($R^{15}$)C(O)N($R^{16}$)($R^{17}$), —CH$_2$—$R^{15}$, —CH$_2$—N($R^{15}$)($R^{16}$), —N($R^{15}$)S(O)$R^{16}$, —N($R^{15}$)S(O)$_2R^{16}$, —CH$_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$), —N($R^{15}$)C(O)O$R^{16}$, —CH$_2$—N($R^{15}$)C(O)O$R^{16}$, —S(O)$R^{15}$, =NO$R^{15}$, —N$_3$, —NO$_2$ and —S(O)$_2R^{24}$; and wherein each of the $R^{21}$ alkyl, cycloalkenyl, cycloalkyl, cycloalkylalkyl-, heterocyclyl, heterocyclylalkyl-, aryl, arylalkyl-, heteroaryl, heteroarylalkyl-, alkenyl and alkynyl groups is optionally substituted with 1 to 5 independently selected $R^{22}$ groups;

Each $R^{22}$ is independently selected from the group consisting of: alkyl, cycloalkyl, cycloalkenyl, heterocyclyl, aryl, heteroaryl, halo, —CF$_3$, —CN, —O$R^{15}$, —C(O)$R^{15}$, —C(O)O$R^{15}$, -alkyl-C(O)O$R^{15}$, C(O)N($R^{15}$)($R^{16}$), —SF$_5$, —OSF$_5$, —Si($R^{24}$)$_3$, wherein each $R^{24}$ is independently selected —S$R^{15}$, —S(O)N($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —CH$_2$—N($R^{15}$)C(O)$R^{16}$, —N($R^{15}$)S(O)$R^{16}$, —N($R^{15}$)S(O)$_2R^{16}$, —CH$_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$), —N($R^{15}$)C(O)O$R^{16}$, —CH$_2$—N($R^{15}$)C(O)O$R^{16}$, —N$_3$, =NO$R^{15}$, —NO$_2$, —S(O)$R^{15}$ and —S(O)$_2R^{24}$; and Each $R^{24}$ is independently selected from the group consisting of alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl-, aryl heterocyclyl-, $(R^{18})_r$-alkyl-, $(R^{18})_r$-cycloalkyl-, $(R^{18})_r$-cycloalkylalkyl-, $(R^{18})_r$-heterocyclyl-, $(R^{18})_r$-heterocyclylalkyl-, $(R^{18})_r$-aryl-, $(R^{18})_r$-arylalkyl-, $(R^{18})_r$-heteroaryl- and $(R^{18})_r$, -heteroarylalkyl- (wherein $R^{18}$ and r are as defined above); and With the proviso that:

(a) G is —C($R^3$)($R^4$)$_2$— (wherein each $R^3$ and each $R^4$ are independently selected); or (b) there is present at least one (e.g., 1 to 3, or 1-2, or 1) group selected from the group consisting of: —SF$_5$, —OSF$_5$, and —Si($R^{24}$)$_3$ (wherein each $R^{24}$ is independently selected), and when there is more than one group, each group is independently selected, or (c) there is present an $R^{10}$ group selected from the group consisting of:

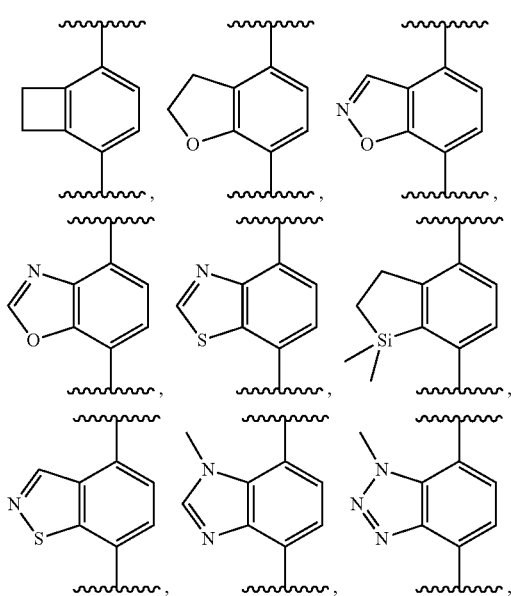

-continued
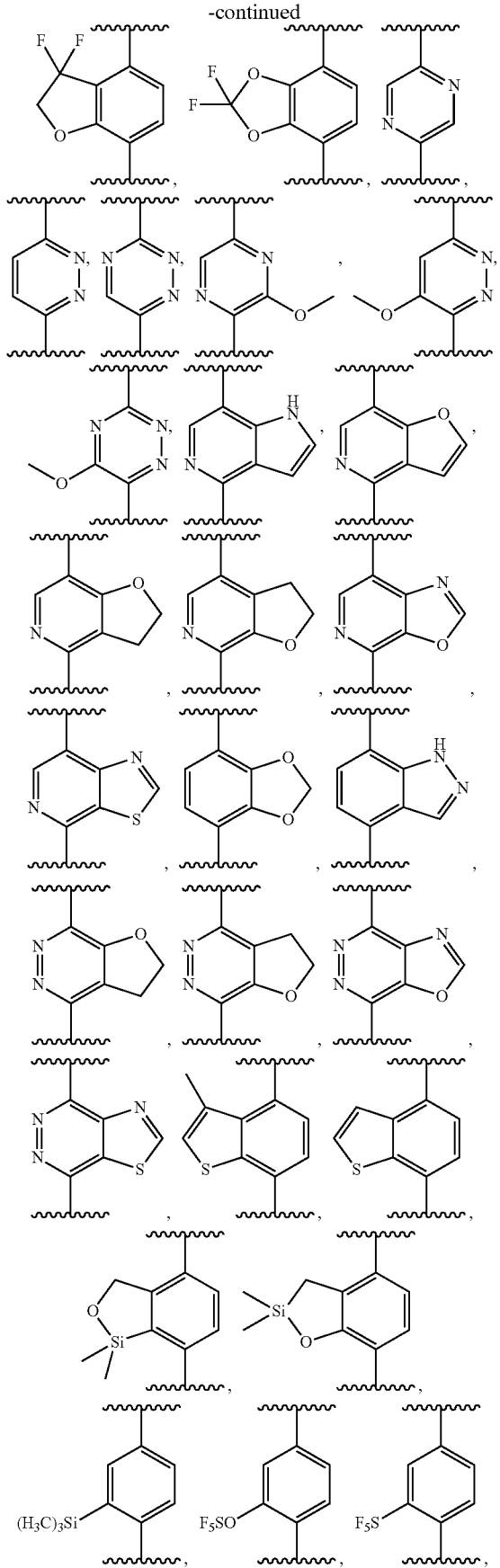
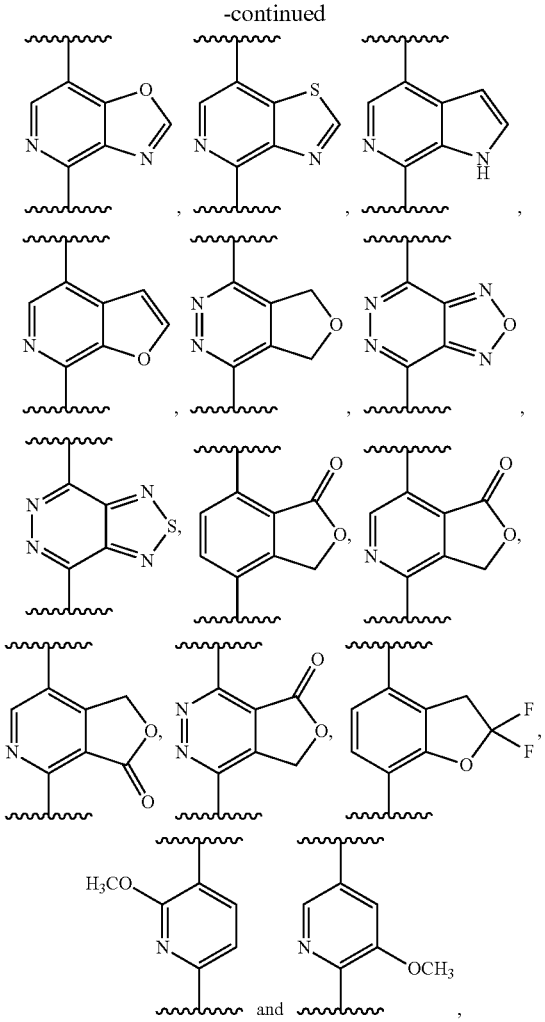
(and in one embodiment there is present an R[10] group selected from the group consisting of:
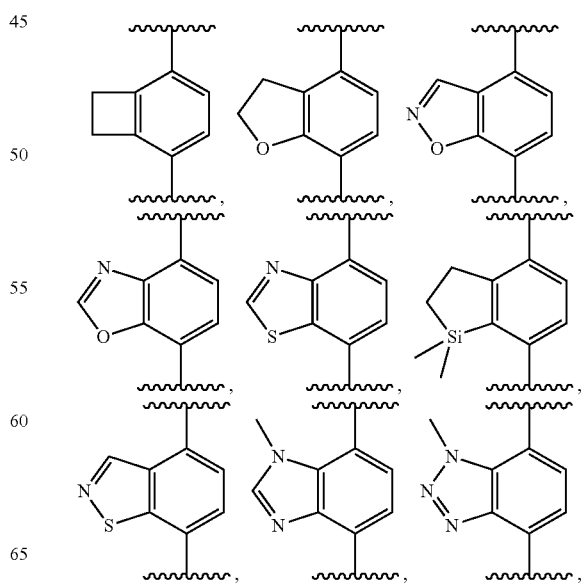

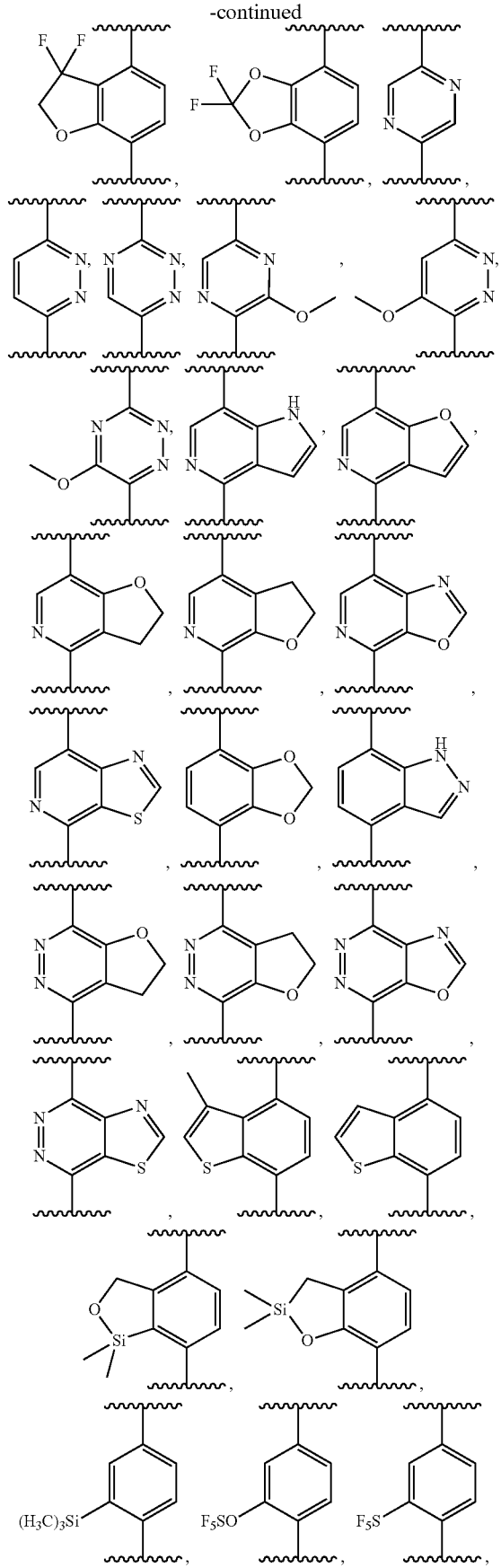
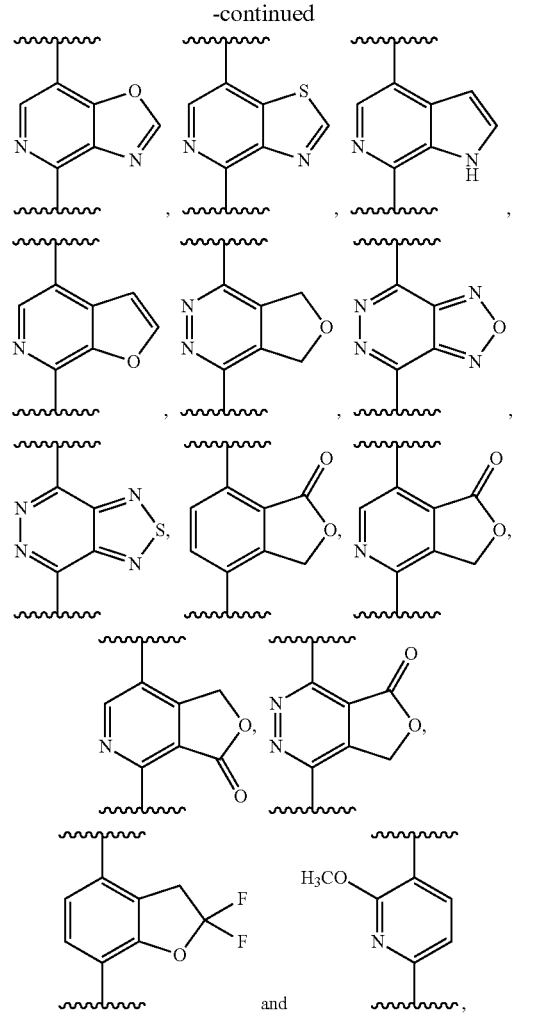
and in another embodiment there is present an $R^{10}$ group selected from the group consisting of:
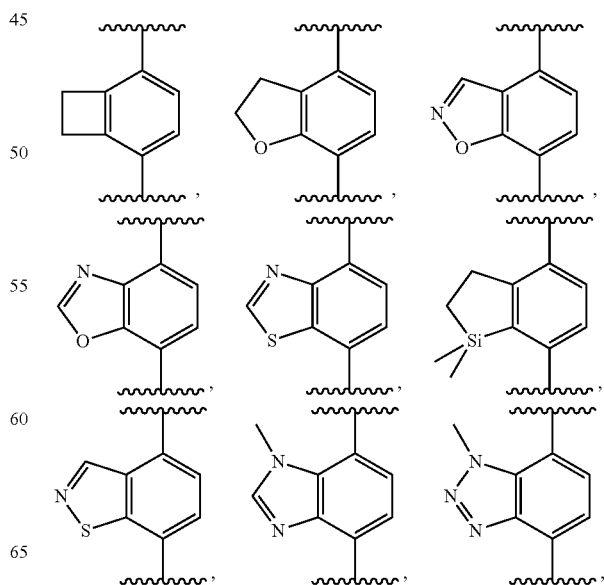

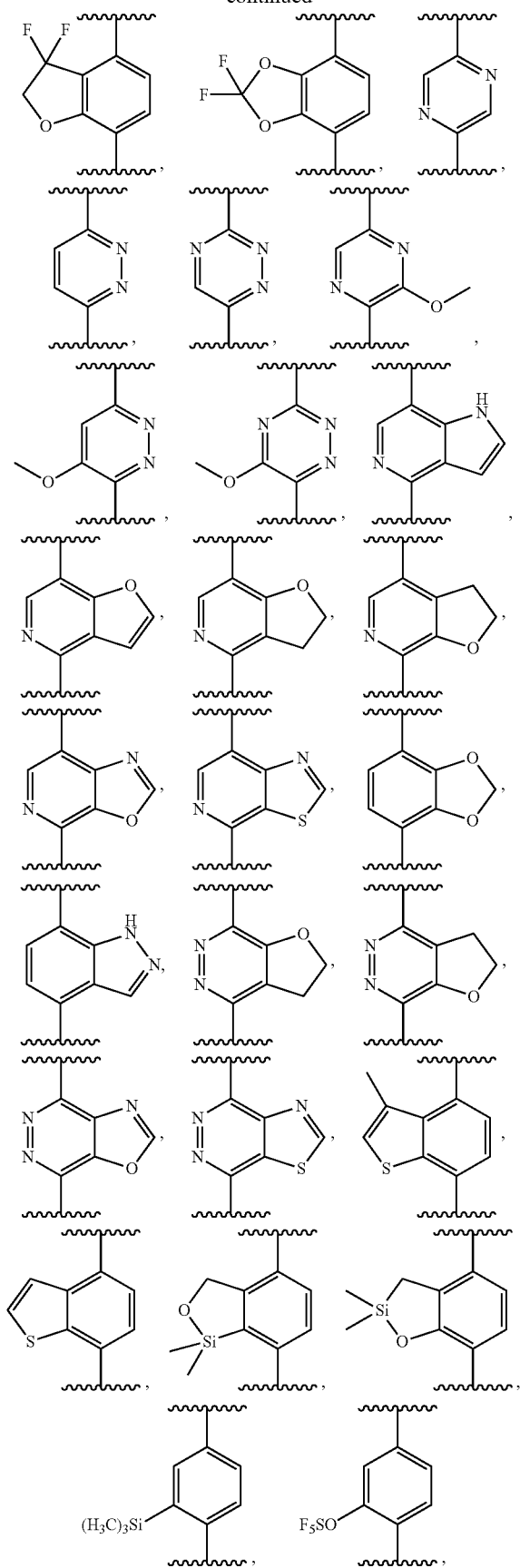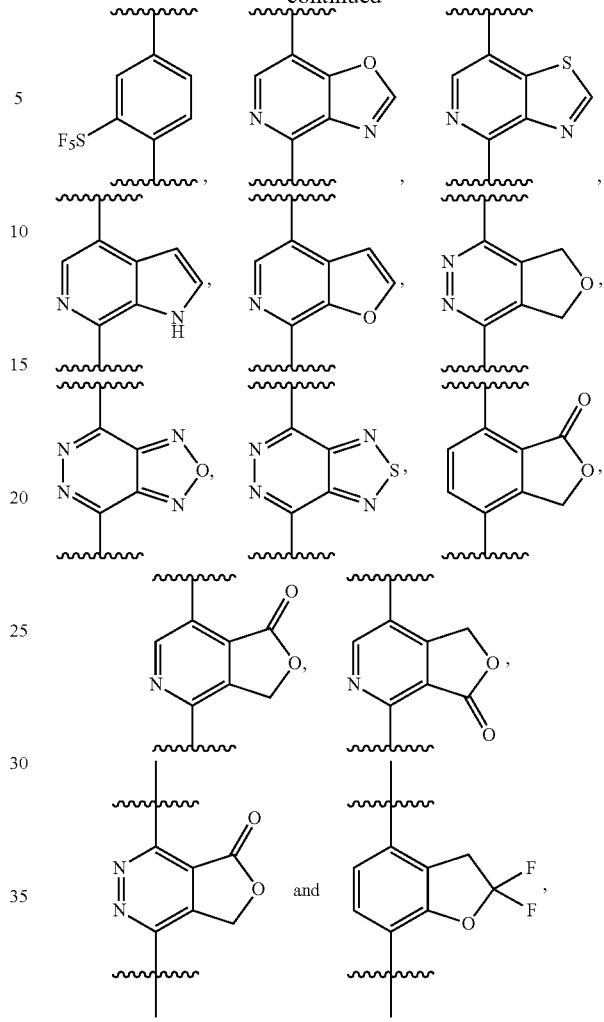
and in another embodiment there is present an $R^{10}$ group selected from the group consisting of:
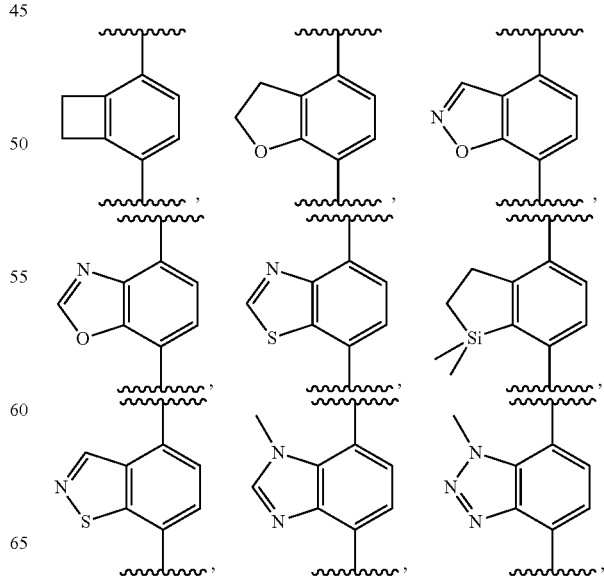

-continued

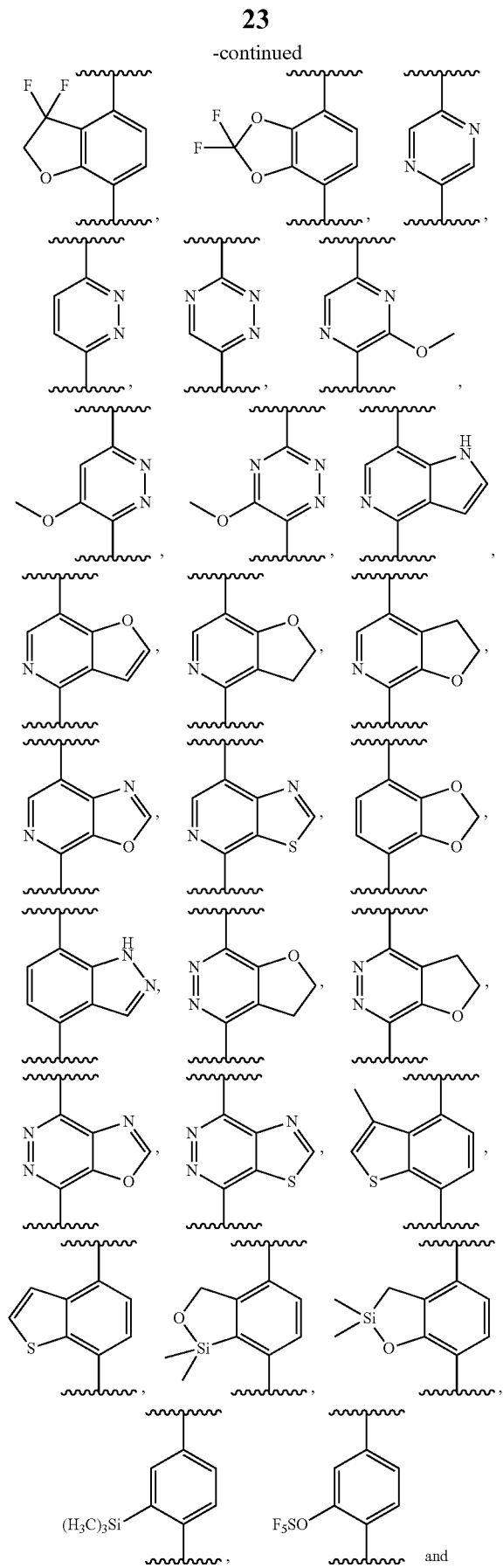

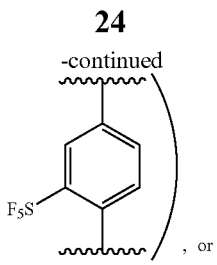

, or (d) there is present a spiro ring formed by joining $R^3$ and $R^4$ of the —C($R^3$)($R^4$)— G moiety together to form a cycloalkyl, cycloalkenyl, heterocycloalkyl, or heterocycloalkenyl spiro ring (i.e., there is present a spiro ring described in (vi) above); or (e) there is present a spiro ring formed by joining one $R^3$ and one $R^4$ on one carbon of the —(C($R^3$)($R^4$))$_2$— G moiety to form a cycloalkyl, cycloalkenyl, heterocycloalkyl, or heterocycloalkenyl spiro ring (as described in (vii) above), or (f) there is present a ring formed by joining an $R^3$ and an $R^4$ on adjacent carbons of the —(C($R^3$)($R^4$))$_2$— G moiety to form a cycloalkyl, cycloalkenyl, heterocycloalkyl, or heterocycloalkenyl ring (as described in (viii) above), or (g) none of the rings described above in (i) to (xii) are present (that is (1) $R^1$ and $R^2$ are not joined together, and (2) $R^2$ and $R^6$ are not joined together, and (3) $R^1$ and $R^2$ are not joined together, and $R^2$ and $R^6$ are not joined together (i.e., $R^2$ is not joined together with $R^1$ and $R^6$), and (4) $R^6$ is not joined together with either $R^3$ or $R^4$ (i.e., $R^6$ and $R^3$ are not joined together, or $R^6$ and $R^4$ are not joined together), and (5) $R^6$ and $R^{13}$ of the —N($R^{13}$)— G moiety, are not joined together, and (6) $R^3$ and $R^4$ of the —C($R^3$)($R^4$)— G moiety are not joined together), (7) one $R^3$ and one $R^4$ on one carbon of the —(C($R^3$)($R^4$))$_2$— G moiety are not joined together), (8) an $R^3$ and an $R^4$ on adjacent carbons of the —(C($R^3$)($R^4$))$_2$— G moiety are not joined together, (9) $R^1$ and $R^2$, and $R^6$ and either $R^3$ or $R^4$, are not joined together to form the rings described in (ix) above, (10) $R^1$ and $R^2$, and $R^3$ and $R^4$, are not joined together to form the rings described in (x) above, (11) $R^1$ and $R^2$, and $R^3$ and $R^4$, are not joined together to form the rings described in (xi) above, and (12) $R^1$ and $R^2$, and $R^3$ and $R^4$, are not joined together to form the rings described in (xii) above), or (h) there is present a ring formed by joining $R^1$ and $R^2$ together as described in (i) above, and there is present a ring formed by joining $R^6$ and either $R^3$ or $R^4$ of the —C($R^3$)($R^4$)— G moiety together as described in (iv) above; or (i) there is present a ring formed by joining $R^1$ and $R^2$ together as described in (i) above, and (b) there is present a ring formed by joining $R^3$ and $R^4$ of the —C($R^3$)($R^4$)— G moiety together as described in (vi) above; or (j) there is present a ring formed by joining $R^1$ and $R^2$ together as described in (i) above, and there is present a ring formed by joining one $R^3$ and one $R^4$ on one carbon of the —(C($R^3$)($R^4$))$_2$— G moiety together as described in (vii) above; or (k) there is present a ring formed by joining $R^1$ and $R^2$ together as described in (i) above, and there is present a ring formed by joining an $R^3$ and an $R^4$ on adjacent carbons of the —(C($R^3$)($R^4$))$_2$— G moiety together as described in (viii) above; or (l) $R^6$ and $R^7$ are taken together to form =O.

In one embodiment of this invention:

(a) Each $R^1$ (when $R^1$ is not joined to $R^2$), $R^2$ (when $R^2$ is not joined to $R^1$ or $R^6$), $R^5$, $R^6$ (when $R^6$ is not joined to $R^2$), and $R^7$ in formula I is independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;

(b) the remaining substituents for formula I are as defined for formula I above; and (c) at least one of provisos (a) to (k) is present for the compounds of formula I.

While provisos (a) to (l) are given in the alternative, more than one proviso can be present in the compounds of formula I. Thus, in one embodiment of the compounds of formula I there is present at least two (e.g., 2, 3, 4, or 5) provisos selected from the group consisting of provisos (a) to (l) provided that one proviso does not exclude another proviso. Thus:

(i) proviso (a) is not present when provisos (d), (e), (f), or (h) to (k) is present, and (ii) proviso (d) is not present when proviso (a), (e) (f), or (h) to (k) is present, and (iii) proviso (g) is not present when provisos (d), (e), (f) or (h) to (k) is present, and (iv) when there is more than one proviso present, and one proviso is selected from the group consisting of provisos (d), (e), (f), and (h) to (k) is present, then the remaining provisos are selected from the group consisting of: (b) and (c).

Also, proviso (h) is not present when proviso (l) is present. Thus, when there is more than one proviso present, and one proviso is selected from the group consisting of provisos (d), (e), (f), and (i) to (l) is present, then the remaining provisos are selected from the group consisting of: (b) and (c).

Examples of the compounds of formula I include compounds wherein: (1) provisos (a) and (b) are present, (2) provisos (a) and (c) are present, (3) provisos (a) and (e) are present, (4) provisos (a) and (f) are present, (5) provisos (a) and (g) are present, (6) provisos (b) and (c) are present, (7) provisos (b) and (d) are present, (8) provisos (b) and (e) are present, (9) provisos (b) and (f) are present, (10) provisos (b) and (g) are present, (11) provisos (c) and (d) are present, (12) provisos (c) and (e) are present, (13) provisos (c) and (f) are present, (14) provisos (c) and (g) are present, (15) provisos (d) and (g) are present, (16) provisos (e) and (g) are present, (17) provisos (a), (b) and (c) are present, (18) provisos (a), (b) and (g) are present, (18) provisos (a) (c) and (e) are present, (19) provisos (a) (c) and (f) are present, (20) provisos (a) (c) and (g) are present, (21) provisos (b), (c) and (d) are present, (22) provisos (b), (c) and (e) are present, (23) provisos (b), (c) and (f) are present, (24) provisos (b), (c) and (g) are present, (25) provisos (a), (b), (c) and (g) are present, and (26) provisos (b), (c), (d) and (g) are present.

In another example of the compounds of formula I, proviso I is present.

One embodiment of this invention is directed to compounds of formula I wherein (a) $R^1$ and $R^2$ are joined together to form a C4-C8 cycloalkyl, C4-C8 cycloalkenyl, 5-8 membered heterocyclyl or 5-8 membered heterocyclenyl moiety as described in (i) above, and (b) $R^6$ and either $R^3$ or $R^4$ of the $-C(R^3)(R^4)$-G moiety, are joined together to form a C4-C8 cycloalkyl, C4-C8 cycloalkenyl, 5-8 membered heterocyclyl or 5-8 membered heterocyclenyl moiety as described in (iv) above.

Another embodiment of this invention is directed to compounds of formula I wherein $R^1$ and $R^2$ are joined together to form a C4-C8 cycloalkyl, C4-C8 cycloalkenyl, 5-8 membered heterocyclyl or 5-8 membered heterocyclenyl moiety as described in (i) above, and (b) $R^3$ and $R^4$ of the $—C(R^3)(R^4)—$ G moiety are joined together to form a cycloalkyl, cycloalkenyl, heterocycloalkyl, or heterocycloalkenyl spiro ring as described in (vi) above.

Another embodiment of this invention is directed to compounds of formula I wherein $R^1$ and $R^2$ are joined together to form a C4-C8 cycloalkyl, C4-C8 cycloalkenyl, 5-8 membered heterocyclyl or 5-8 membered heterocyclenyl moiety as described in (i) above, and (b) one $R^3$ and one $R^4$ on one carbon of the $—(C(R^3)(R^4))_2—$ G moiety are joined together to form a cycloalkyl, cycloalkenyl, heterocycloalkyl, or heterocycloalkenyl spiro ring as described in (vii) above.

Another embodiment of this invention is directed to compounds of formula I wherein $R^1$ and $R^2$ are joined together to form a C4-C8 cycloalkyl, C4-C8 cycloalkenyl, 5-8 membered heterocyclyl or 5-8 membered heterocyclenyl moiety as described in (i) above, and (b) an $R^3$ and an $R^4$ on adjacent carbons of the $—(C(R^3)(R^4))_2—$ G moiety are joined together to form a cycloalkyl, cycloalkenyl, heterocycloalkyl, or heterocycloalkenyl ring as described in (viii) above.

Those skilled in the art will appreciate that the $—SF_5$, $—OSF_5$, and $—Si(R^{24})_3$ groups are present in the compounds of formula I: (a) due to the presence of at least one $R^{21}$ group that is selected from the group consisting of: $—SF_5$, $—OSF_5$, and $—Si(R^{24})_3$, or (b) due to the presence of at least one $R^{22}$ substituent on at least one $R^{21}$ group, wherein said $R^{22}$ substituent is selected from the group consisting of: $—SF_5$, $—OSF_5$, and $—Si(R^{24})_3$, and wherein said $R^{21}$ group is other than a $—SF_5$, $—OSF_5$, or $—Si(R^{24})_3$ group.

The compounds of this invention are useful for treating central nervous system disorders such as, for example, neurodegenerative diseases such as Alzheimer's disease and other diseases relating to the deposition of amyloid protein. They are especially useful for reducing Amyloid beta (hereinafter referred to as Aβ) production which is effective in the treatment of diseases caused by Aβ such as, for example, Alzheimers and Down Syndrome.

Thus, for example, the compounds of this invention can be used to treat the following diseases or conditions: Alzheimers disease, mild cognitive impairment (MCI), Downs Syndrome, Glaucoma (Guo et. al., Proc. Natl. Acad. Sci. USA 104, 13444-13449 (2007)), Cerebral amyloid angiopathy, stroke or dementia (Frangione et al., Amyloid: J. Protein folding Disord. 8, suppl. 1, 36-42 (2001), Microgliosis and brain inflammation (M P Lamber, Proc. Natl. Acad. Sci. USA 95, 6448-53 (1998)), and Olfactory function loss (Getchell, et. al. Neurobiology of Aging, 663-673, 24, 2003).

One embodiment of this invention is directed to compounds of formula I wherein G is $—C(R^3)(R^4)—$ (wherein each $R^3$ and each $R^4$ are independently selected), and all other substituents are as defined for formula I. One embodiment of this invention is directed to compounds of formula I wherein G is $—(C(R^3)(R^4))_2—$ (wherein each $R^3$ and each $R^4$ are independently selected), and all other substituents are as defined for formula I.

Another embodiment of this is directed to compounds of formula I wherein at least one (e.g., 1 to 3, or 1-2, or 1) group selected from the group consisting of: $—SF_5$, $—OSF_5$, and $—Si(R^{24})_3$ is present, and wherein each $R^{24}$ is independently selected, and wherein when there is more than one group, each group is independently selected.

Another embodiment of this is directed to compounds of formula I wherein at least one (e.g., 1 to 3, or 1-2, or 1) group selected from the group consisting of: —SF$_5$ and —OSF$_5$ is present, and wherein when there is more than one group, each group is independently selected.

In one embodiment of this invention one group selected from the group consisting of: —SF$_5$, —OSF$_5$, and —Si(R$^{24}$)$_3$ (wherein each R$^{24}$ is independently selected) is present in the compounds of formula I.

In another embodiment of this invention two groups selected from the group consisting of: —SF$_5$, —OSF$_5$, and —Si(R$^{24}$)$_3$ (wherein each R$^{24}$ is independently selected) are present in the compounds of formula I.

In another embodiment of this invention three groups selected from the group consisting of: —SF$_5$, —OSF$_5$, and —Si(R$^{24}$)$_3$ (wherein each R$^{24}$ is independently selected) are present in the compounds of formula I.

In another embodiment of this invention two groups selected from the group consisting of: —SF$_5$, —OSF$_5$, and —Si(R$^{24}$)$_3$ (wherein each R$^{24}$ is independently selected) are present in the compounds of formula I, wherein at least one group is other than —Si(R$^{24}$)$_3$.

In another embodiment of this invention three groups selected from the group consisting of: —SF$_5$, —OSF$_5$, and —Si(R$^{24}$)$_3$ (wherein each R$^{24}$ is independently selected) are present in the compounds of formula I, wherein at least one group is other than —Si(R$^{24}$)$_3$.

In another embodiment of this invention one group selected from the group consisting of: —SF$_5$, —OSF$_5$, and —Si(R$^{24}$)$_3$ (wherein each R$^{24}$ is independently selected from the group consisting of alkyl (e.g., methyl and ethyl) and aryl (e.g., phenyl)) is present in the compounds of formula I.

In another embodiment of this invention two groups selected from the group consisting of: —SF$_5$, —OSF$_5$, and —Si(R$^{24}$)$_3$ (wherein each R$^{24}$ is independently selected from the group consisting of alkyl (e.g., methyl and ethyl) and aryl (e.g., phenyl)) are present in the compounds of formula I.

In another embodiment of this invention three groups selected from the group consisting of: —SF$_5$, —OSF$_5$, and —Si(R$^{24}$)$_3$ (wherein each R$^{24}$ is independently selected from the group consisting of alkyl (e.g., methyl and ethyl) and aryl (e.g., phenyl)) are present in the compounds of formula I.

In another embodiment of this invention two groups selected from the group consisting of: —SF$_5$, —OSF$_5$, and —Si(R$^{24}$)$_3$ (wherein each R$^{24}$ is independently selected from the group consisting of alkyl (e.g., methyl and ethyl) and aryl (e.g., phenyl)) are present in the compounds of formula I, wherein at least one group is other than —Si(R$^{24}$)$_3$.

In another embodiment of this invention three groups selected from the group consisting of: —SF$_5$, —OSF$_5$, and —Si(R$^{24}$)$_3$ (wherein each R$^{24}$ is independently selected from the group consisting of alkyl (e.g., methyl and ethyl) and aryl (e.g., phenyl)) are present in the compounds of formula I, wherein at least one group is other than —Si(R$^{24}$)$_3$.

In another embodiment of this invention one group selected from the group consisting of: —SF$_5$, —OSF$_5$, and —Si(R$^{24}$)$_3$ (wherein each R$^{24}$ is independently selected from the group consisting of methyl, ethyl and phenyl) is present in the compounds of formula I.

In another embodiment of this invention two groups selected from the group consisting of: —SF$_5$, —OSF$_5$, and —Si(R$^{24}$)$_3$ (wherein each R$^{24}$ is independently selected from the group consisting of methyl, ethyl and phenyl) are present in the compounds of formula I.

In another embodiment of this invention three groups selected from the group consisting of: —SF$_5$, —OSF$_5$, and —Si(R$^{24}$)$_3$ (wherein each R$^{24}$ is independently selected from the group consisting of methyl, ethyl and phenyl) are present in the compounds of formula I.

In another embodiment of this invention two groups selected from the group consisting of: —SF$_5$, —OSF$_5$, and —Si(R$^{24}$)$_3$ (wherein each R$^{24}$ is independently selected from the group consisting of methyl, ethyl and phenyl) are present in the compounds of formula I, wherein at least one group is other than —Si(R$^{24}$)$_3$.

In another embodiment of this invention three groups selected from the group consisting of: —SF$_5$, —OSF$_5$, and —Si(R$^{24}$)$_3$ (wherein each R$^{24}$ is independently selected from the group consisting of methyl, ethyl and phenyl) are present in the compounds of formula I, wherein at least one group is other than —Si(R$^{24}$)$_3$.

In another embodiment of this invention one group selected from the group consisting of: —SF$_5$, —OSF$_5$, and —Si(R$^{24}$)$_3$ (wherein each R$^{24}$ is independently selected from the group consisting of methyl and ethyl) is present in the compounds of formula I.

In another embodiment of this invention two groups selected from the group consisting of: —SF$_5$, —OSF$_5$, and —Si(R$^{24}$)$_3$ (wherein each R$^{24}$ is independently selected from the group consisting of methyl and ethyl) are present in the compounds of formula I.

In another embodiment of this invention three groups selected from the group consisting of: —SF$_5$, —OSF$_5$, and —Si(R$^{24}$)$_3$ (wherein each R$^{24}$ is independently selected from the group consisting of methyl and ethyl) are present in the compounds of formula I.

In another embodiment of this invention two groups selected from the group consisting of: —SF$_5$, —OSF$_5$, and —Si(R$^{24}$)$_3$ (wherein each R$^{24}$ is independently selected from the group consisting of methyl and ethyl) are present in the compounds of formula I, wherein at least one group is other than —Si(R$^{24}$)$_3$.

In another embodiment of this invention three groups selected from the group consisting of: —SF$_5$, —OSF$_5$, and —Si(R$^{24}$)$_3$ (wherein each R$^{24}$ is independently selected from the group consisting of methyl and ethyl) are present in the compounds of formula I, wherein at least one group is other than —Si(R$^{24}$)$_3$.

In another embodiment of this invention one group selected from the group consisting of: —SF$_5$, —OSF$_5$, and —Si(R$^{24}$)$_3$ is present in the compounds of formula I, and said —Si(R$^{24}$)$_3$ group is selected from the group consisting of: —Si(CH$_3$)$_3$, —Si(CH$_3$)$_2$-phenyl, and —Si(CH$_2$CH$_3$)$_2$CH$_3$.

In another embodiment of this invention two groups selected from the group consisting of: —SF$_5$, —OSF$_5$, and —Si(R$^{24}$)$_3$ are present in the compounds of formula I, and said —Si(R$^{24}$)$_3$ group is selected from the group consisting of: —Si(CH$_3$)$_3$, —Si(CH$_3$)$_2$-phenyl, and —Si(CH$_2$CH$_3$)$_2$CH$_3$.

In another embodiment of this invention three groups selected from the group consisting of: —SF$_5$, —OSF$_5$, and —Si(R$^{24}$)$_3$ are present in the compounds of formula I, and said —Si(R$^{24}$)$_3$ group is selected from the group consisting of: —Si(CH$_3$)$_3$, —Si(CH$_3$)$_2$-phenyl, and —Si(CH$_2$CH$_3$)$_2$CH$_3$.

In another embodiment of this invention two groups selected from the group consisting of: —SF$_5$, —OSF$_5$, and —Si(R$^{24}$)$_3$ are present in the compounds of formula I, wherein at least one group is other than —Si(R$^{24}$)$_3$, and said —Si(R$^{24}$)$_3$ group is selected from the group consisting of: —Si(CH$_3$)$_3$, —Si(CH$_3$)$_2$-phenyl, and —Si(CH$_2$CH$_3$)$_2$CH$_3$.

In another embodiment of this invention three groups selected from the group consisting of: —SF$_5$, —OSF$_5$, and —Si(R$^{24}$)$_3$ are present in the compounds of formula I, wherein at least one group is other than —Si(R$^{24}$)$_3$, and said —Si(R$^{24}$)$_3$ group is selected from the group consisting of: —Si(CH$_3$)$_3$, —Si(CH$_3$)$_2$ phenyl, and —Si(CH$_2$CH$_3$)$_2$CH$_3$.

In another embodiment of this invention one group selected from the group consisting of: —SF$_5$, —OSF$_5$, and —Si(R$^{24}$)$_3$ is present in the compounds of formula I, and said —Si(R$^{24}$)$_3$ group is selected from the group consisting of: —Si(CH$_3$)$_3$ and —Si(CH$_2$CH$_3$)$_2$CH$_3$.

In another embodiment of this invention two groups selected from the group consisting of: —SF$_5$, —OSF$_5$, and —Si(R$^{24}$)$_3$ are present in the compounds of formula I, and said —Si(R$^{24}$)$_3$ group is selected from the group consisting of: —Si(CH$_3$)$_3$ and —Si(CH$_2$CH$_3$)$_2$CH$_3$.

In another embodiment of this invention three groups selected from the group consisting of: —SF$_5$, —OSF$_5$, and —Si(R$^{24}$)$_3$ are present in the compounds of formula I, and said —Si(R$^{24}$)$_3$ group is selected from the group consisting of: —Si(CH$_3$)$_3$ and —Si(CH$_2$CH$_3$)$_2$CH$_3$.

In another embodiment of this invention two groups selected from the group consisting of: —SF$_5$, —OSF$_5$, and —Si(R$^{24}$)$_3$ are present in the compounds of formula f, wherein at least one group is other than —Si(R$^{24}$)$_3$, and said —Si(R$^{24}$)$_3$ group is selected from the group consisting of: —Si(CH$_3$)$_3$ and —Si(CH$_2$CH$_3$)$_2$CH$_3$.

In another embodiment of this invention three groups selected from the group consisting of: —SF$_5$, —OSF$_5$, and —Si(R$^{24}$)$_3$ are present in the compounds of formula I, wherein at least one group is other than —Si(R$^{24}$)$_3$, and said —Si(R$^{24}$)$_3$ group is selected from the group consisting of: —Si(CH$_3$)$_3$, —Si(CH$_3$)$_2$-phenyl, and —Si(CH$_2$CH$_3$)$_2$CH$_3$.

In another embodiment of this invention one group selected from the group consisting of: —SF$_5$, —OSF$_5$, and —Si(CH$_3$)$_3$.

In another embodiment of this invention two groups selected from the group consisting of: —SF$_5$, —OSF$_5$, and —Si(CH$_3$)$_3$ are present in the compounds of formula I.

In another embodiment of this invention three groups selected from the group consisting of: —SF$_5$, —OSF$_5$, and —Si(CH$_3$)$_3$ are present in the compounds of formula I.

In another embodiment of this invention two groups selected from the group consisting of: —SF$_5$, —OSF$_5$, and —Si(CH$_3$)$_3$ are present in the compounds of formula I, wherein at least one group is other than —Si(CH$_3$)$_3$.

In another embodiment of this invention three groups selected from the group consisting of: —SF$_5$, —OSF$_5$, and —Si(R$^{24}$)$_3$ are present in the compounds of formula I, wherein at least one group is other than —Si(CH$_3$)$_3$.

In another embodiment of this invention one group selected from the group consisting of: —SF$_5$ and —OSF$_5$ is present in the compounds of formula I.

In another embodiment of this invention two groups selected from the group consisting of: —SF$_5$ and —OSF$_5$ are present in the compounds of formula I.

In another embodiment of this invention three groups selected from the group consisting of: —SF$_5$ and —OSF$_5$ are present in the compounds of formula I.

In another embodiment of this invention one —SF$_5$ group is present in the compounds of formula I.

In another embodiment of this invention two —SF$_5$ groups are present in the compounds of formula I.

In another embodiment of this invention three —SF$_5$ groups are present in the compounds of formula I.

In another embodiment of this invention one —OSF$_5$ group is present in the compounds of formula I.

In another embodiment of this invention two —OSF$_5$ groups are present in the compounds of formula I.

In another embodiment of this invention three —OSF$_5$ groups are present in the compounds of formula I.

In another embodiment of this invention one group selected from the group consisting of: —SF$_5$ and —OSF$_5$ is present in the compounds of formula I, no —Si(R$^{24}$)$_3$ groups are present, and R$^{10}$ is any of the groups defined in formula I.

In another embodiment of this invention two groups selected from the group consisting of: —SF$_5$ and —OSF$_5$ are present in the compounds of formula I, no Si(R$^{24}$)$_3$ groups are present, and R$^{10}$ is any of the groups defined in formula I.

In another embodiment of this invention three groups selected from the group consisting of: —SF$_5$ and —OSF$_5$ are present in the compounds of formula I, no —Si(R$^{24}$)$_3$ groups are present, and R$^{10}$ is any of the groups defined in formula I.

In another embodiment of this invention one —SF$_5$ group is present in the compounds of formula I, no —Si(R$^{24}$)$_3$ groups are present, and R$^{10}$ is any of the groups defined in formula I.

In another embodiment of this invention two —SF$_5$ groups are present in the compounds of formula I, no —Si(R$^{24}$)$_3$ groups are present, and R$^{10}$ is any of the groups defined in formula I.

In another embodiment of this invention three —SF$_5$ groups are present in the compounds of formula I, no —Si(R$^{24}$)$_3$ groups are present, and R$^{10}$ is any of the groups defined in formula I.

In another embodiment of this invention one —OSF$_5$ group is present in the compounds of formula I, no —Si(R$^{24}$)$_3$ groups are present, and R$^{10}$ is any of the groups defined in formula I.

In another embodiment of this invention two —OSF$_5$ groups are present in the compounds of formula I, no —Si(R$^{24}$)$_3$ groups are present, and R$^{10}$ is any of the groups defined in formula I.

In another embodiment of this invention three —OSF$_5$ groups are present in the compounds of formula I, no —Si(R$^{24}$)$_3$ groups are present, and R$^{10}$ is any of the groups defined in formula I.

In another embodiment of this invention one —Si(R$^{24}$)$_3$ (wherein each R$^{24}$ is independently selected) group is present in the compounds of formula I.

In another embodiment of this invention two —Si(R$^{24}$)$_3$ (wherein each R$^{24}$ is independently selected) groups are present in the compounds of formula I.

In another embodiment of this invention three —Si(R$^{24}$)$_3$ (wherein each R$^{24}$ is independently selected) groups are present in the compounds of formula I.

In another embodiment of this invention one —Si(R$^{24}$)$_3$ (wherein each R$^{24}$ is independently selected from the group consisting of alkyl (e.g., methyl and ethyl) and aryl (e.g., phenyl)) is present in the compounds of formula I.

In another embodiment of this invention two —Si(R$^{24}$)$_3$ (wherein each R$^{24}$ is independently selected from the group consisting of alkyl (e.g., methyl and ethyl) and aryl (e.g., phenyl)) is present in the compounds of formula I.

In another embodiment of this invention three —Si(R$^{24}$)$_3$ (wherein each R$^{24}$ is independently selected from the group consisting of alkyl (e.g., methyl and ethyl) and aryl (e.g., phenyl)) is present in the compounds of formula I.

In another embodiment of this invention one —Si(R$^{24}$)$_3$ (wherein each R$^{24}$ is independently selected from the group consisting of methyl, ethyl and phenyl) is present in the compounds of formula I.

In another embodiment of this invention two —Si(R$^{24}$)$_3$ (wherein each R$^{24}$ is independently selected from the group consisting of methyl, ethyl and phenyl) is present in the compounds of formula I.

In another embodiment of this invention three —Si(R$^{24}$)$_3$ (wherein each R$^{24}$ is independently selected from the group consisting of methyl, ethyl and phenyl) is present in the compounds of formula I.

In another embodiment of this invention one —Si(R$^{24}$)$_3$ (wherein each R$^{24}$ is independently selected from the group consisting of methyl and ethyl) is present in the compounds of formula I.

In another embodiment of this invention two —Si(R$^{24}$)$_3$ (wherein each R$^{24}$ is independently selected from the group consisting of methyl and ethyl) is present in the compounds of formula I.

In another embodiment of this invention three —Si(R$^{24}$)$_3$ (wherein each R$^{24}$ is independently selected from the group consisting of methyl and ethyl) is present in the compounds of formula I.

In another embodiment of this invention one —Si(R$^{24}$)$_3$ group is present in the compounds of formula I, and said —Si(R$^{24}$)$_3$ group is selected from the group consisting of: —Si(CH$_3$)$_3$, —Si(CH$_3$)$_2$-phenyl, and —Si(CH$_2$CH$_3$)$_2$CH$_3$.

In another embodiment of this invention two —Si(R$^{24}$)$_3$ groups are present in the compounds of formula I, and said —Si(R$^{24}$)$_3$ groups are independently selected from the group consisting of: —Si(CH$_3$)$_3$, —Si(CH$_3$)$_2$-phenyl, and —Si(CH$_2$CH$_3$)$_2$CH$_3$ In another embodiment of this invention three —Si(R$^{24}$)$_3$ groups are present in the compounds of formula I, and said —Si(R$^{24}$)$_3$ groups are independently selected from the group consisting of: —Si(CH$_3$)$_3$, —Si(CH$_3$)$_2$-phenyl, and —Si(CH$_2$CH$_3$)$_2$CH$_3$.

In another embodiment of this invention one —Si(R$^{24}$)$_3$ group is present in the compounds of formula I, and said —Si(R$^{24}$)$_3$ group is selected from the group consisting of: —Si(CH$_3$)$_3$ and —Si(CH$_2$CH$_3$)$_2$CH$_3$.

In another embodiment of this invention two —Si(R$^{24}$)$_3$ groups are present in the compounds of formula I, and said —Si(R$^{24}$)$_3$ groups are independently selected from the group consisting of: —Si(CH$_3$)$_3$ and —Si(CH$_2$CH$_3$)$_2$CH$_3$.

In another embodiment of this invention three —Si(R$^{24}$)$_3$ groups are present in the compounds of formula I, and said —Si(R$^{24}$)$_3$ groups are independently selected from the group consisting of: —Si(CH$_3$)$_3$ and —Si(CH$_2$CH$_3$)$_2$CH$_3$.

In another embodiment of this invention one —Si(R$^{24}$)$_3$ group is present in the compounds of formula I, and said —Si(R$^{24}$)$_3$ group is —Si(CH$_3$)$_3$.

In another embodiment of this invention two —Si(R$^{24}$)$_3$ groups are present in the compounds of formula I, and said —Si(R$^{24}$)$_3$ groups are —Si(CH$_3$)$_3$.

In another embodiment of this invention three —Si(R$^{24}$)$_3$ groups are present in the compounds of formula I, and said —Si(R$^{24}$)$_3$ groups are —Si(CH$_3$)$_3$.

In another embodiment of this invention one group selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula I.

In another embodiment of this invention one group selected from the group consisting of: —SF$_5$, —OSF$_5$, —Si(CH$_3$)$_3$, and —Si(CH$_2$CH$_3$)$_2$CH$_3$) is present in the compounds of formula I.

In another embodiment of this invention one group selected from the group consisting of: —SF$_5$, —OSF$_5$, and —Si(CH$_3$)$_3$, is present in the compounds of formula I.

In another embodiment of this invention one —SF$_5$ group is present in the compounds of formula I, and one or two additional groups selected from the group consisting of: —SF$_5$, —OSF$_5$, and —Si(R$^{24}$)$_3$ (wherein each R$^{24}$ is independently selected) are also present in the compounds of formula I.

In another embodiment of this invention one —SF$_5$ group is present in the compounds of formula I, and one or two additional groups selected from the group consisting of: —OSF$_5$, and —Si(R$^{24}$)$_3$ (wherein each R$^{24}$ is independently selected) are also present in the compounds of formula I.

In another embodiment of this invention one —OSF$_5$ group is present in the compounds of formula I, and one or two additional groups selected from the group consisting of: —SF$_5$, —OSF$_5$, and —Si(R$^{24}$)$_3$ (wherein each R$^{24}$ is independently selected) are also present in the compounds of formula I.

In another embodiment of this invention one —OSF$_5$ group is present in the compounds of formula I, and one or two additional groups selected from the group consisting of: —SF$_5$ and —Si(R$^{24}$)$_3$ (wherein each R$^{24}$ is independently selected) are also present in the compounds of formula I.

In another embodiment of this invention one —SF$_5$ group is present in the compounds of formula I, and one or two additional groups selected from the group consisting of: —SF$_5$ and —OSF$_5$ are also present in the compounds of formula I.

In another embodiment of this invention one —OSF$_5$ group is present in the compounds of formula I, and one or two additional groups selected from the group consisting of: —SF$_5$ and —OSF$_5$ are also present in the compounds of formula I.

In another embodiment of this invention one —Si(R$^{24}$)$_3$ (wherein each R$^{24}$ is independently selected) group is present in the compounds of formula I, and one or two groups selected from the group consisting of: —SF$_5$, —OSF$_5$, and —Si(R$^{24}$)$_3$ (wherein each R$^{24}$ is independently selected) are also present in the compounds of formula I.

In another embodiment of this invention one —Si(R$^{24}$)$_3$ (wherein each R$^{24}$ is independently selected) group is present in the compounds of formula I, and one or two groups selected from the group consisting of: —SF$_5$ and —OSF$_5$ are also present in the compounds of formula I.

In another embodiment of this invention at least one group selected from the group consisting of: —SF$_5$, —OSF$_5$, and —Si(R$^{24}$)$_3$ (wherein each R$^{24}$ is independently selected from the group consisting of alkyl (e.g., methyl and ethyl) and aryl (e.g., phenyl)) is present in the compounds of formula I.

In another embodiment of this invention at least one group selected from the group consisting of: —SF$_5$, —OSF$_5$, and —Si(R$^{24}$)$_3$ (wherein each R$^{15}$ is independently selected from the group consisting of alkyl (e.g., methyl and ethyl) and phenyl) is present in the compounds of formula I.

In another embodiment of this invention at least one group selected from the group consisting of: —SF$_5$, —OSF$_5$, and —Si(R$^{15}$)$_3$ (wherein each R$^{15}$ is independently selected from the group consisting of methyl, ethyl and phenyl) is present in the compounds of formula I.

In another embodiment of this invention at least one group selected from the group consisting of: —SF$_5$, —Si(CH$_3$)$_3$, —Si(CH$_3$)$_2$-phenyl, and —Si(CH$_2$CH$_3$)$_2$CH$_3$) is present in the compounds of formula I.

In another embodiment of this invention at least one group selected from the group consisting of: —SF$_5$, —OSF$_5$, and —Si(CH$_3$)$_3$ is present in the compounds of formula I.

In another embodiment of this invention one group selected from the group consisting of: —SF$_5$, —OSF$_5$, and —Si(R$^{15}$)$_3$ (wherein each R$^{15}$ is independently selected) is present in the compounds of formula I.

In another embodiment of this invention one group selected from the group consisting of: —SF$_5$, —OSF$_5$, and —Si(R$^{15}$)$_3$ (wherein each R$^{15}$ is independently selected from the group consisting of alkyl (e.g., methyl and ethyl) and aryl (e.g., phenyl)) is present in the compounds of formula I.

In another embodiment of this invention one group selected from the group consisting of: —SF$_5$, —OSF$_5$, and —Si(R$^{15}$)$_3$ (wherein each R$^{15}$ is independently selected from the group consisting of alkyl (e.g., methyl and ethyl) and phenyl) is present in the compounds of formula I.

In another embodiment of this invention one group selected from the group consisting of: —SF$_5$, —OSF$_5$, and —Si(R$^{15}$)$_3$ (wherein each R$^{15}$ is independently selected from the group consisting of methyl, ethyl and phenyl) is present in the compounds of formula I.

In another embodiment of this invention one group selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula I.

In another embodiment of this invention one group selected from the group consisting of: —SF$_5$, —Si(CH$_3$)$_3$, and —Si(CH$_2$CH$_3$)$_2$CH$_3$) is present in the compounds of formula I.

In another embodiment of this invention one group selected from the group consisting of: —SF$_5$, —OSF$_5$, and —Si(CH$_3$)$_3$, is present in the compounds of formula I.

In another embodiment of this invention two groups selected from the group consisting of: —SF$_5$, —OSF$_5$, and —Si(R$^{15}$)$_3$ (wherein each R$^{15}$ is independently selected) are present in the compounds of formula I.

In another embodiment of this invention two groups independently selected from the group consisting of: —SF$_5$, —OSF$_5$, and —Si(R$^{15}$)$_3$ (wherein each R$^{15}$ is independently selected from the group consisting of alkyl (e.g., methyl and ethyl) and aryl (e.g., phenyl)) are present in the compounds of formula I.

In another embodiment of this invention two groups independently selected from the group consisting of: —SF$_5$, —OSF$_5$, and —Si(R$^{15}$)$_3$ (wherein each R$^{15}$ is independently selected from the group consisting of alkyl (e.g., methyl and ethyl) and phenyl) are present in the compounds of formula I.

In another embodiment of this invention two groups selected from the group consisting of: —SF$_5$, —OSF$_5$, and —Si(R$^{15}$)$_3$ (wherein each R$^{15}$ is independently selected from the group consisting of methyl, ethyl and phenyl) are present in the compounds of formula I.

In another embodiment of this invention two groups independently selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula I.

In another embodiment of this invention two groups independently selected from the group consisting of: —SF$_5$, —OSF$_5$, —Si(CH$_3$)$_3$, and —Si(CH$_2$CH$_3$)$_2$CH$_3$) are present in the compounds of formula I.

In another embodiment of this invention two groups independently selected from the group consisting of: —SF$_5$, —OSF$_5$, and —Si(CH$_3$)$_3$ are present in the compounds of formula I.

In another embodiment of this invention three groups selected from the group consisting of: —SF$_5$, —OSF$_5$, and —Si(R$^{15}$)$_3$ (wherein each R$^{15}$ is independently selected) are present in the compounds of formula I.

In another embodiment of this invention three groups independently selected from the group consisting of: —SF$_5$, —OSF$_5$, and —Si(R$^{15}$)$_3$ (wherein each R$^{15}$ is independently selected from the group consisting of alkyl (e.g., methyl and ethyl) and aryl (e.g., phenyl)) are present in the compounds of formula I.

In another embodiment of this invention three groups independently selected from the group consisting of: —SF$_5$, —OSF$_5$, and —Si(R$^{15}$)$_3$ (wherein each R$^{15}$ is independently selected from the group consisting of alkyl (e.g., methyl and ethyl) and phenyl) are present in the compounds of formula I.

In another embodiment of this invention three groups selected from the group consisting of: —SF$_5$, —OSF$_5$, and —Si(R$^{15}$)$_3$ (wherein each R$^{15}$ is independently selected from the group consisting of methyl, ethyl and phenyl) are present in the compounds of formula I.

In another embodiment of this invention three groups independently selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula I.

In another embodiment of this invention three groups independently selected from the group consisting of: —SF$_5$, —OSF$_5$, —Si(CH$_3$)$_3$, and —Si(CH$_2$CH$_3$)$_2$CH$_3$) are present in the compounds of formula I.

In another embodiment of this invention three groups independently selected from the group consisting of: —SF$_5$, —OSF$_5$, and —Si(CH$_3$)$_3$ are present in the compounds of formula I.

In another embodiment of this invention at least one group selected from the group consisting of: —SF$_5$, —OSF$_5$, and —Si(R$^{15}$)$_3$ (wherein each R$^{15}$ is the same or different alkyl group) is present in the compounds of formula I.

In another embodiment of this invention at least one group selected from the group consisting of: —SF$_5$, —OSF$_5$, and —Si(R$^{15}$)$_3$ (wherein each R$^{15}$ is independently selected from the group consisting of methyl and ethyl) is present in the compounds of formula I.

In another embodiment of this invention one —SF$_5$ group is present in the compounds of formula I, and one or two groups selected from the group consisting of: —SF$_5$ and —OSF$_5$ are also present in the compounds of formula I.

In another embodiment of this invention one —OSF$_5$ group is present in the compounds of formula I, and one or two groups selected from the group consisting of: —SF$_5$ and —OSF$_5$ are also present in the compounds of formula I.

Another embodiment of this invention is directed to compounds of formula I wherein R$^{10}$ is selected from the group consisting of a bond, alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

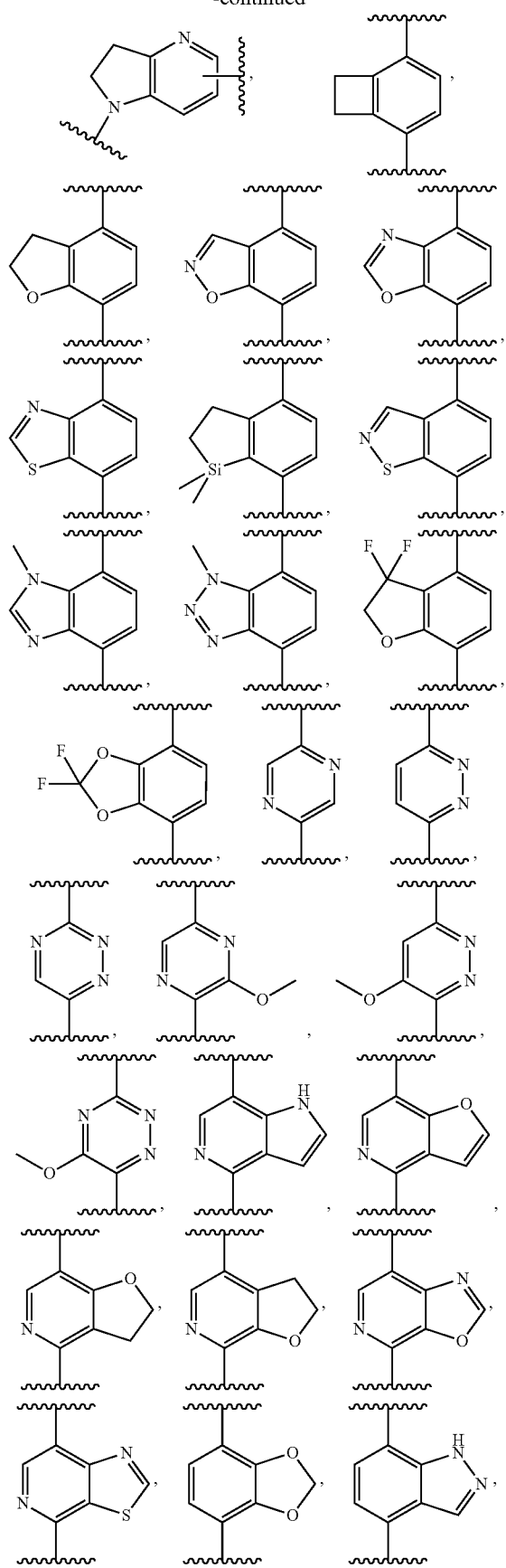
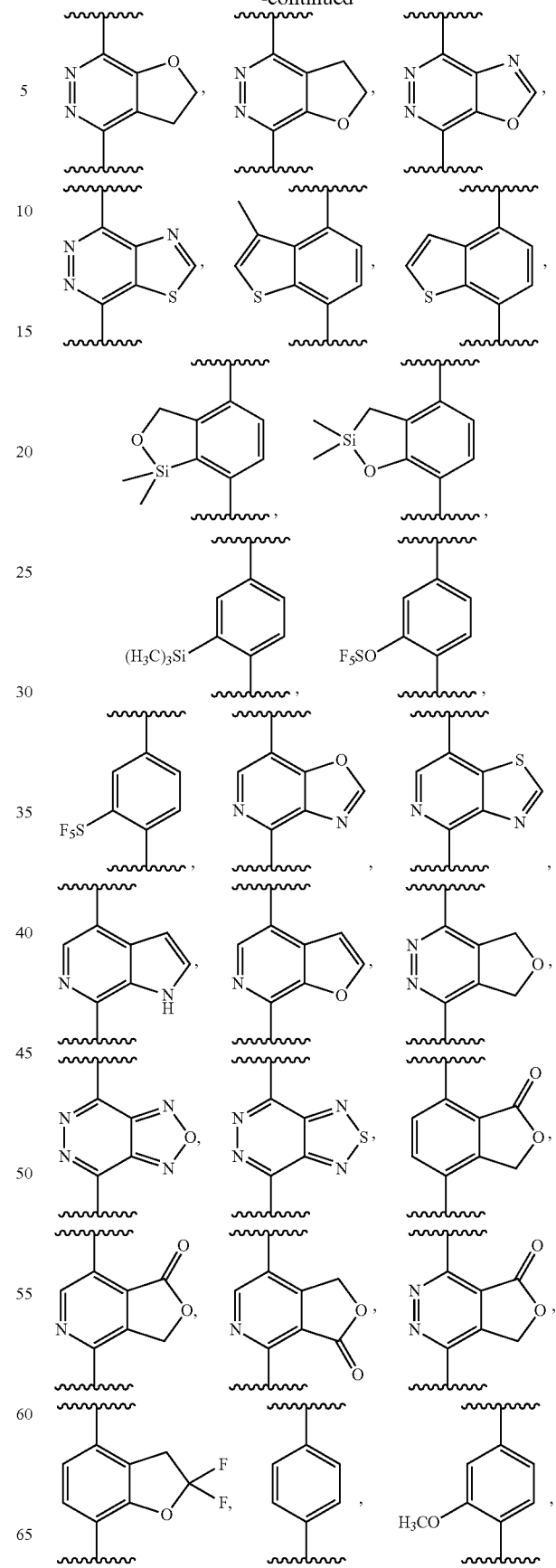

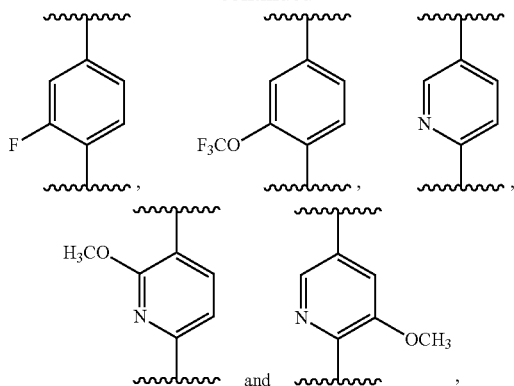
wherein X is selected from the group consisting of; O, N(R$^{14}$) and S;
wherein each of said R$^{10}$ groups (except for the bond) is optionally substituted with 1-3 independently selected R$^{21}$ substituents.
Another embodiment of this invention is directed to compounds of formula I wherein R$^{10}$ is selected from the group consisting of:
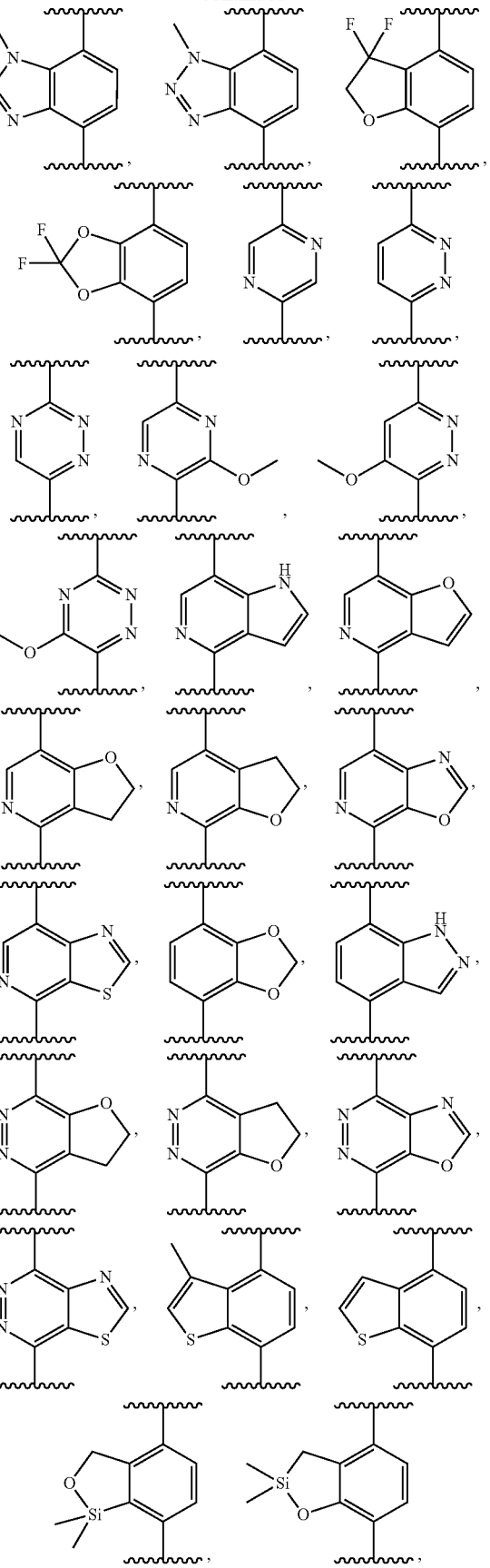

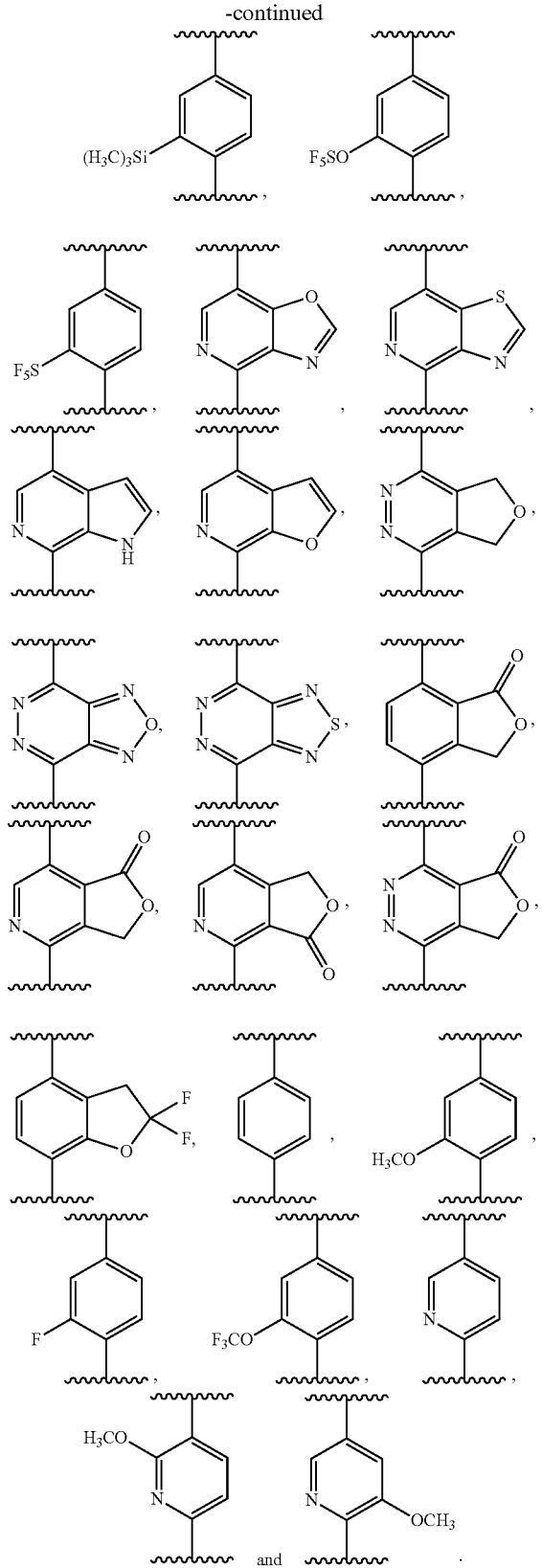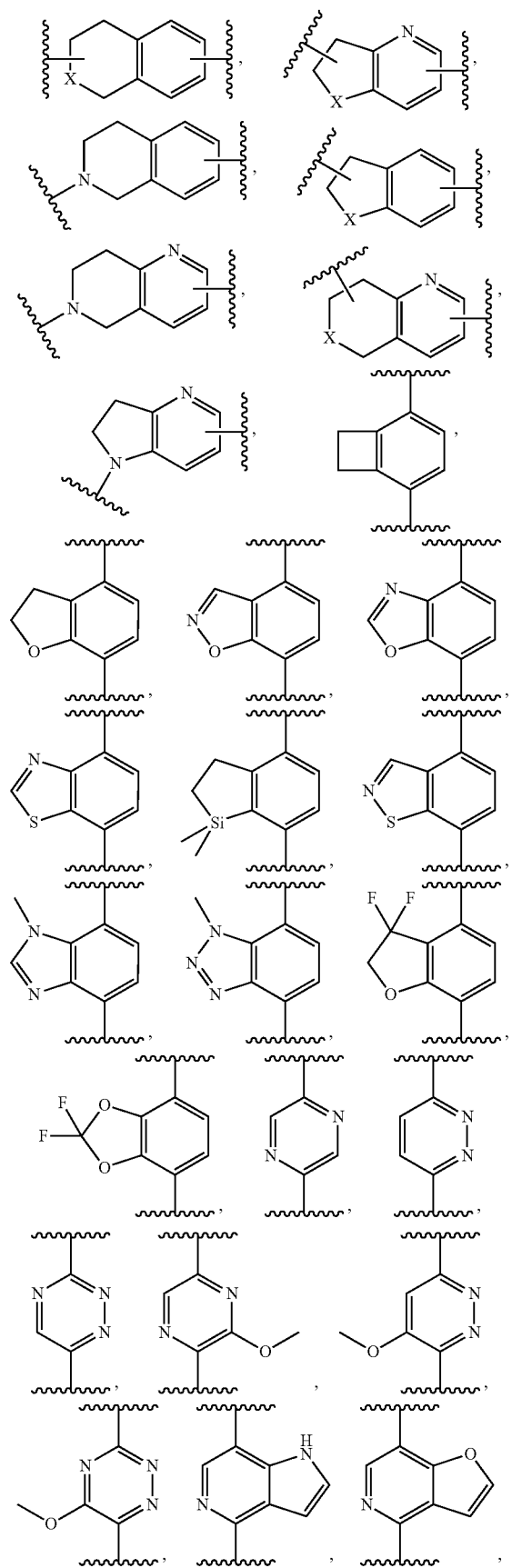
Another embodiment of this invention is directed to compounds of formula I wherein $R^{10}$ is selected from the group consisting of:

-continued
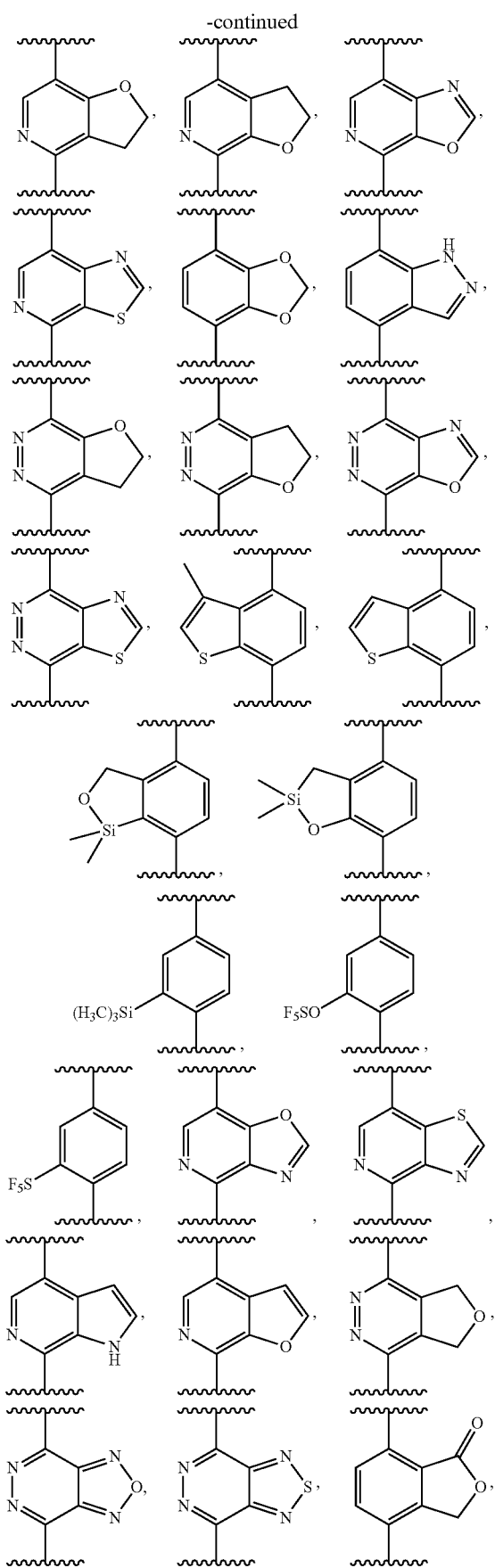
-continued
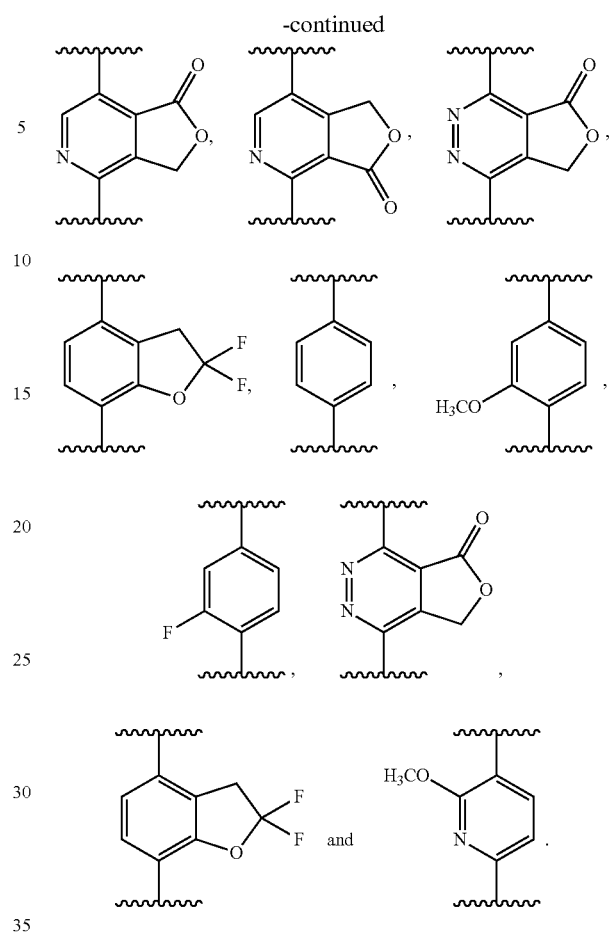
Another embodiment of this invention is directed to compounds of formula I wherein $R^{10}$ is selected from the group consisting of: a bond, alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:
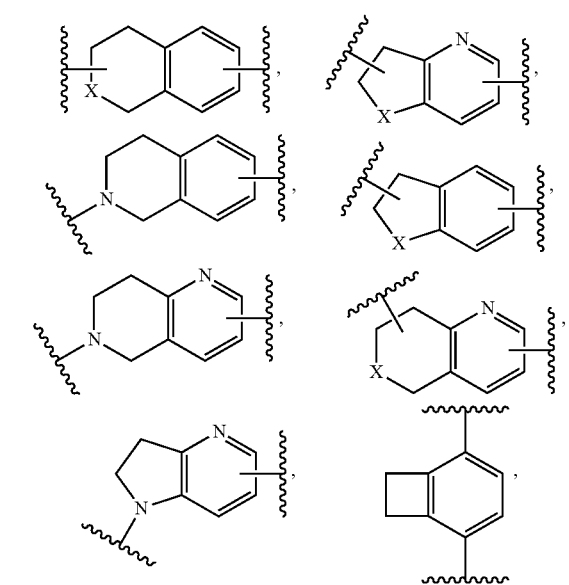

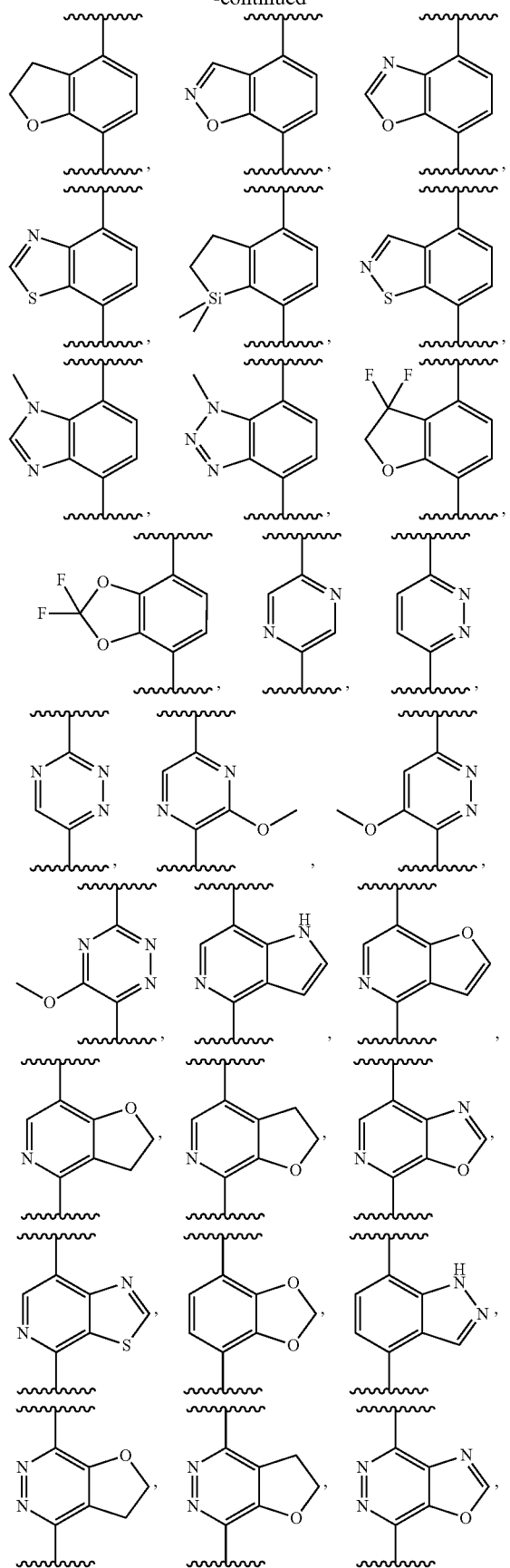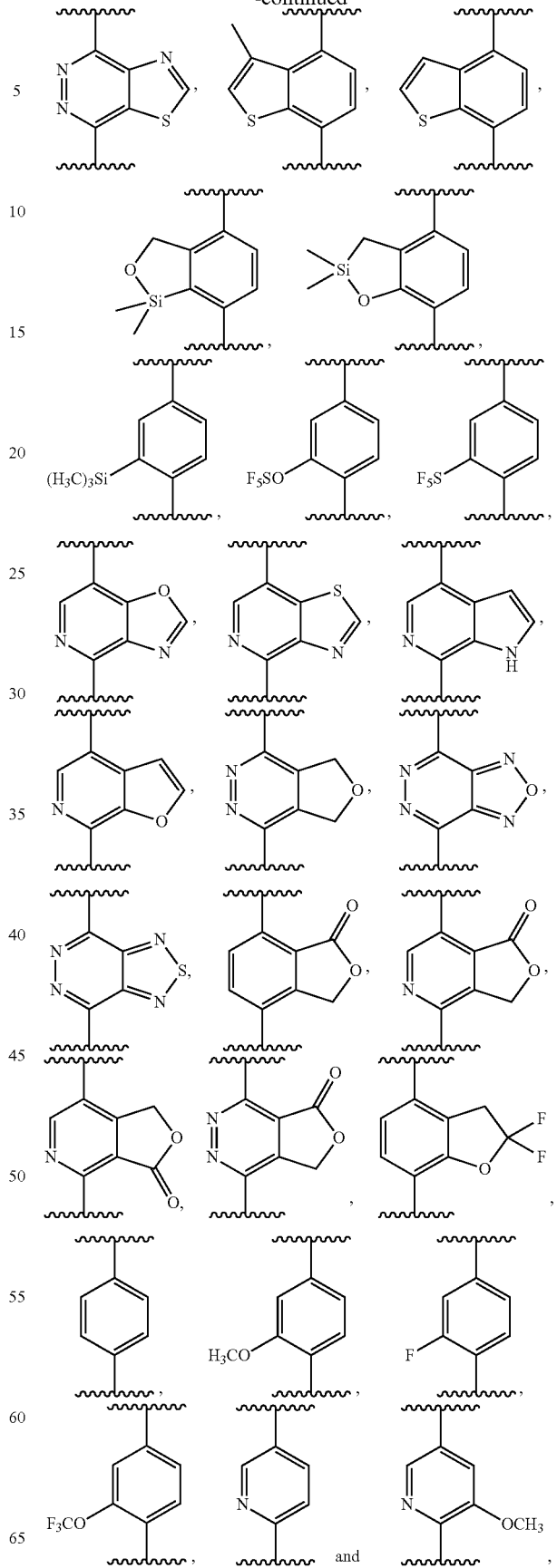

wherein X is selected from the group consisting of; O, N(R$^{14}$) and S;
wherein each of said R$^{10}$ groups (except for the bond) is optionally substituted with 1-3 independently selected R$^{21}$ substituents.
Another embodiment of this is directed to compounds of formula I wherein R$^{10}$ is selected from the group consisting of:
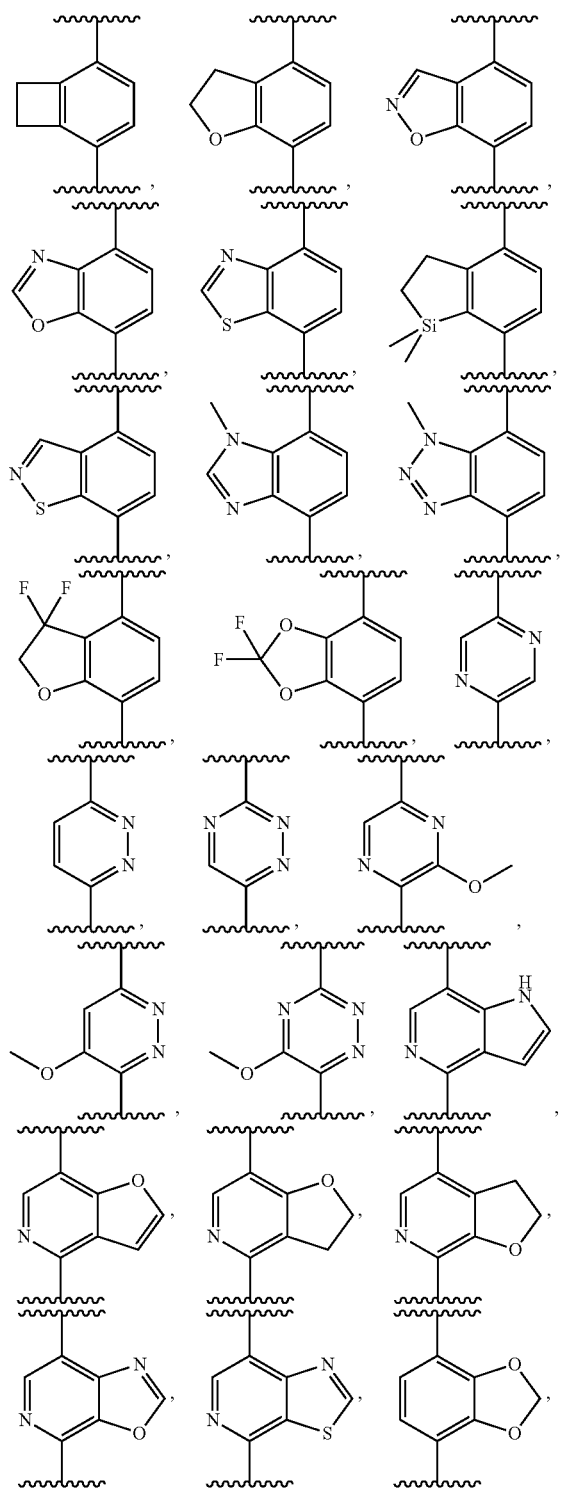
-continued
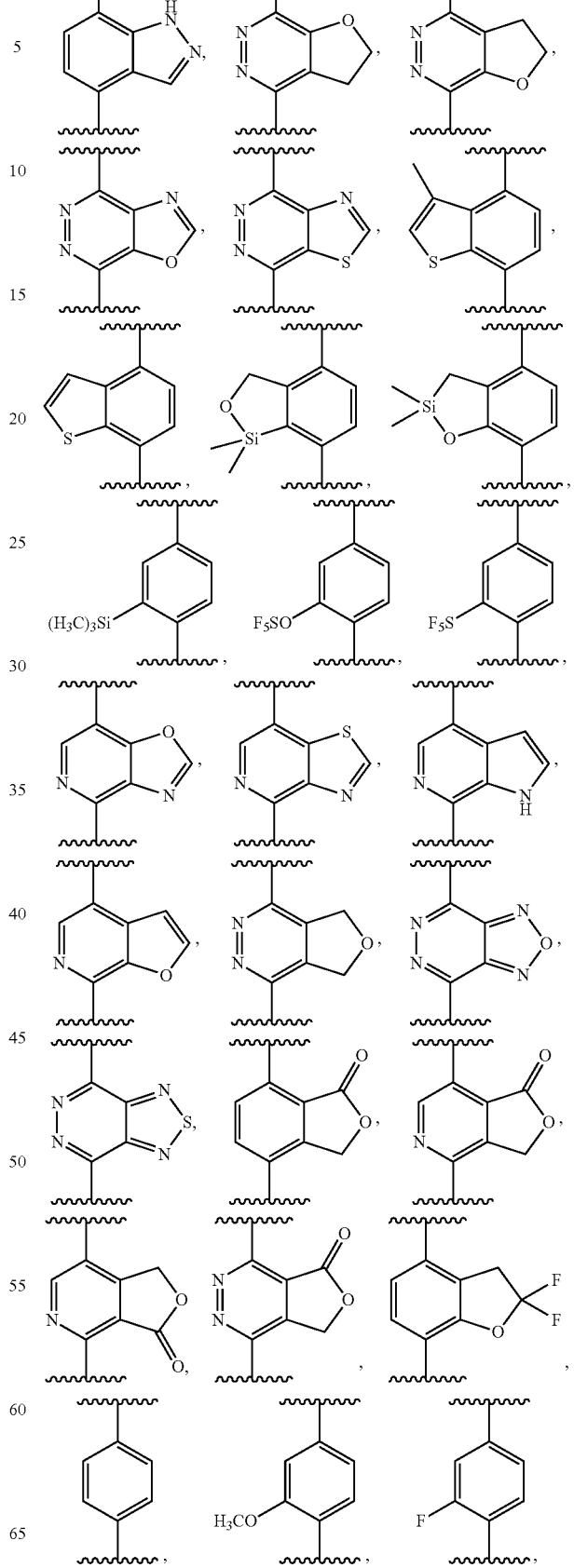

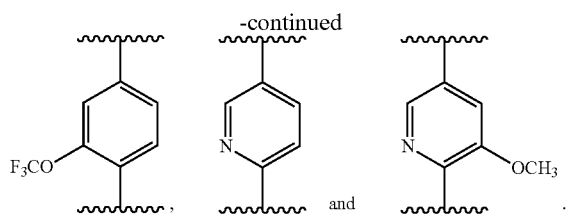
In another embodiment R$^{10}$ is selected from the group consisting of a bond, alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:
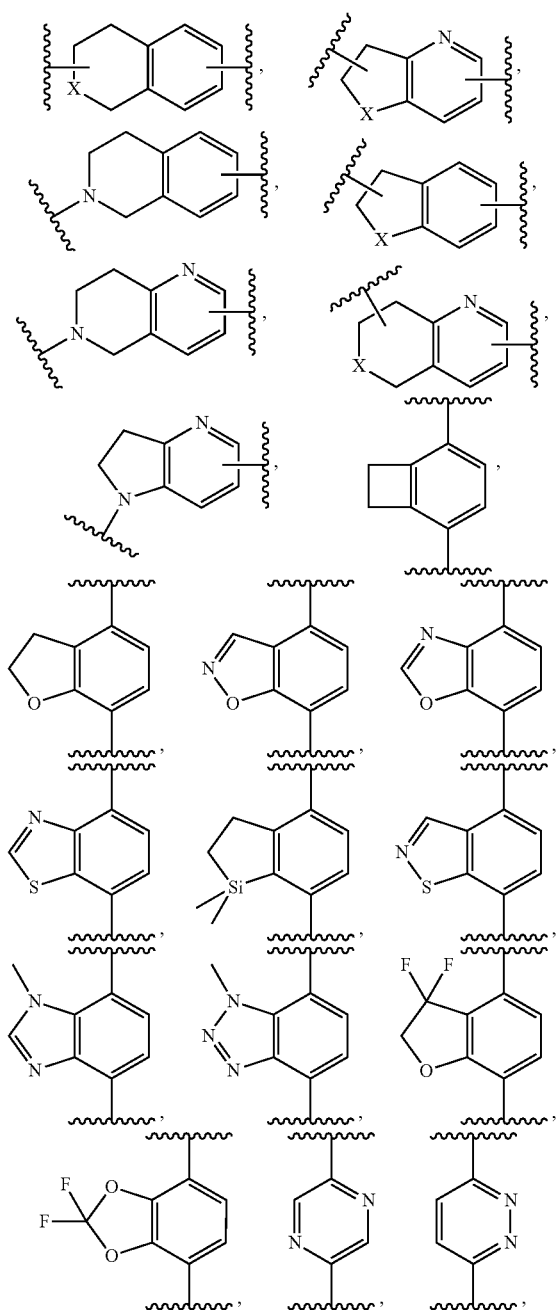
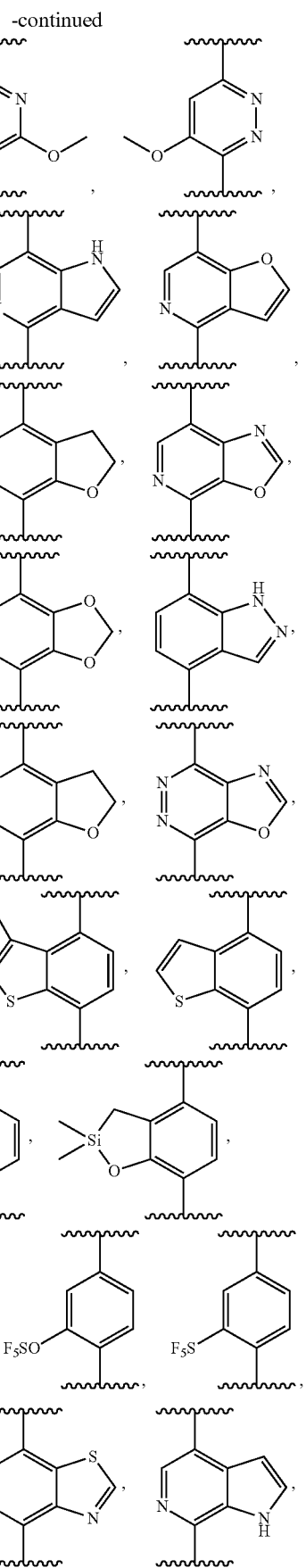

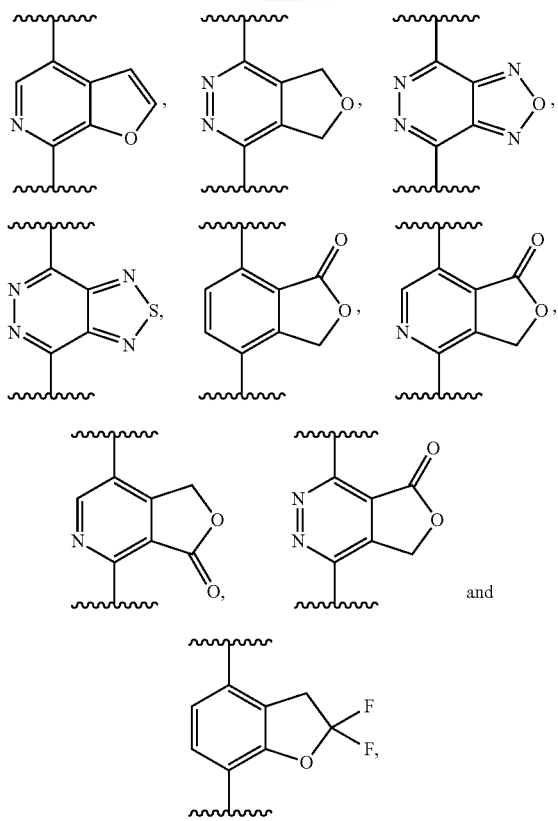
wherein X is selected from the group consisting of; O, N(R$^{14}$) and S;
wherein each of said R$^{10}$ groups (except for the bond) is optionally substituted with 1-3 independently selected R$^{21}$ substituents.
In another embodiment R$^{10}$ is selected from the group consisting of:
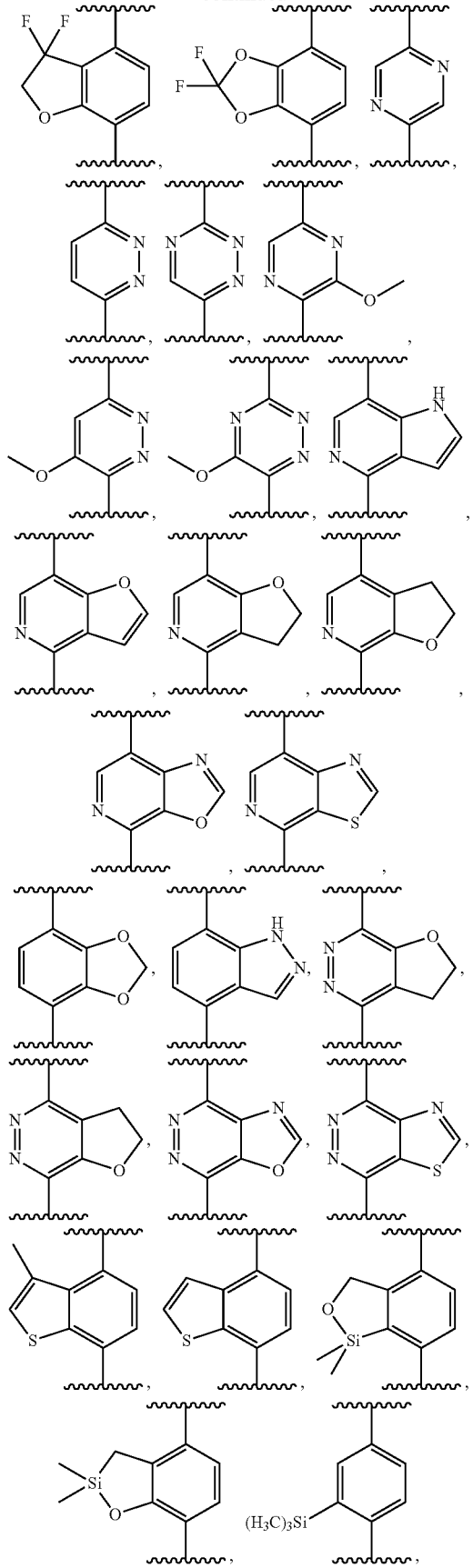

-continued
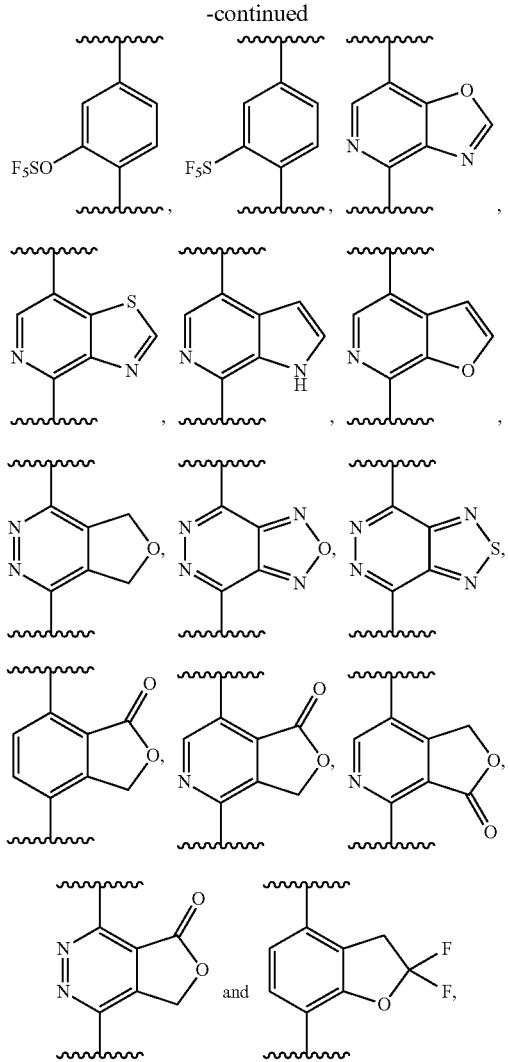
Another embodiment of this is directed to compounds of formula I wherein $R^{10}$ is selected from the group consisting of: a bond, alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:
-continued
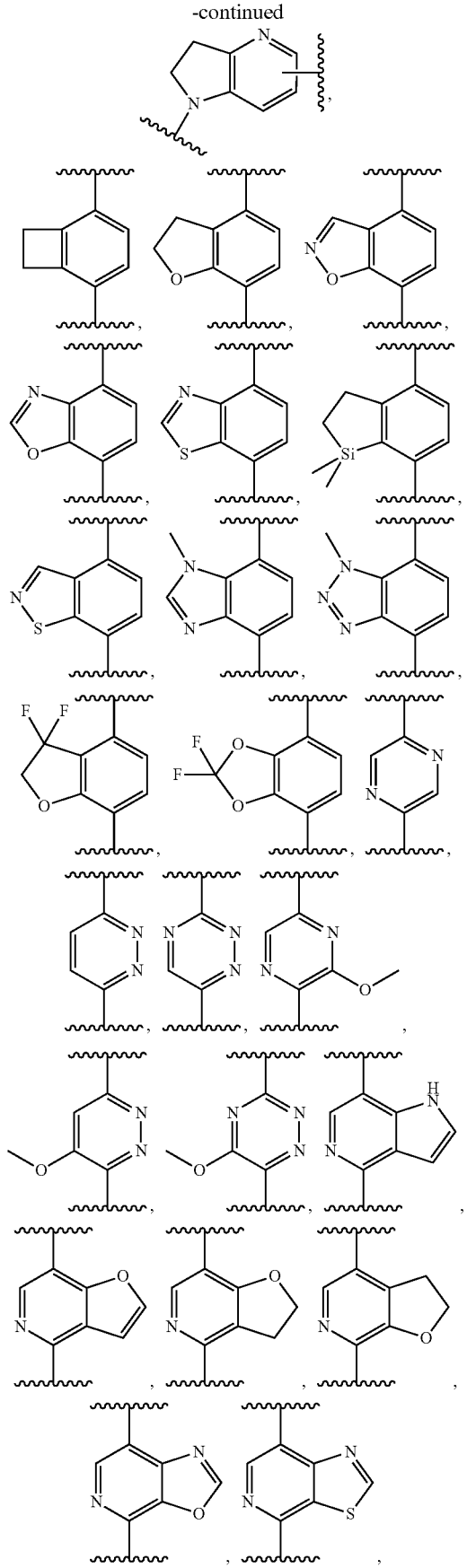

-continued
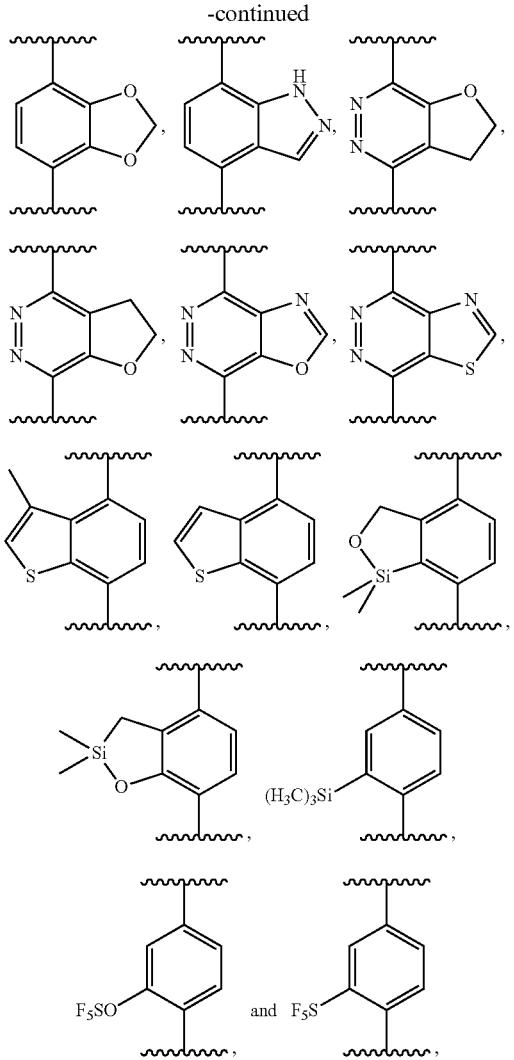
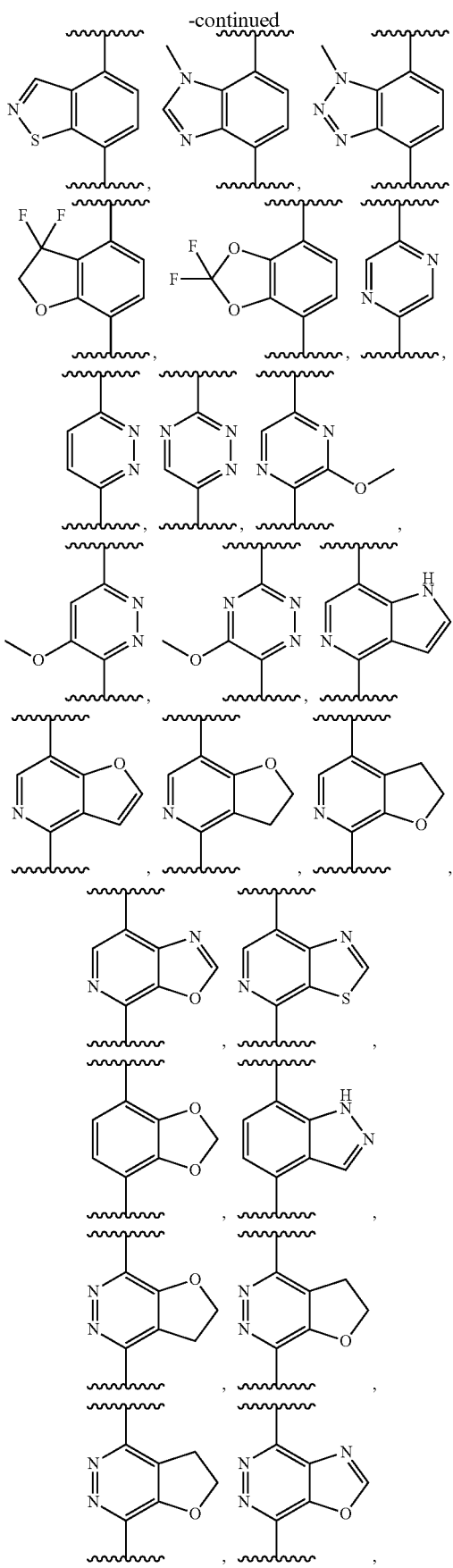
wherein X is selected from the group consisting of; O, N(R$^{14}$) and S;
wherein each of said R$^{10}$ groups (except for the bond) is optionally substituted with 1-3 independently selected R$^{21}$ substituents. Another embodiment of this is directed to compounds of formula I wherein
R$^{10}$ is selected from the group consisting of:
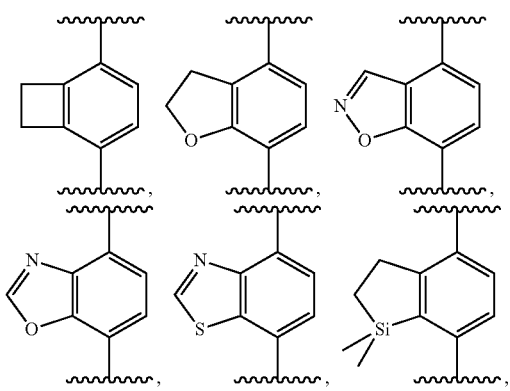

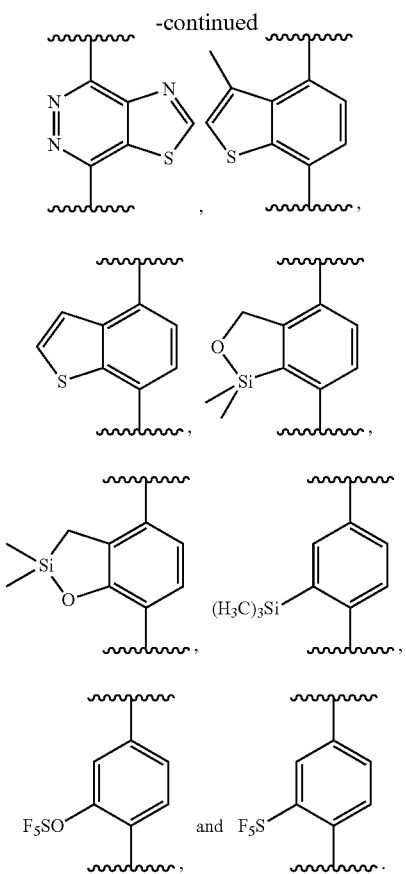

Another embodiment of this invention is directed to compounds of formula I wherein W is selected from the group consisting of a bond, —O—, —O(O)—, —S—, —S(O)—, —S(O₂)—, and —C(R¹¹)(R¹²)—.

Another embodiment of this invention is directed to compounds of formula I wherein W is selected from the group consisting of a bond, —O—, —C(O)—, —S—, —S(O)—, —S(O₂)—, and —C(R¹¹)(R¹²)—; and G is selected from the group consisting of —C(R³)(R⁴)— (wherein R³ and R⁴ are independently selected), —(C(R³)(R⁴))₂—(wherein each R³ and each R⁴ are independently selected), —C(O)— and —N(R¹³)—, with the proviso that when W is —O— or —S—, G is not —N(R¹³)— or —C(O)—, and with the proviso that when G is —(C(R³)(R⁴))₂— then W is not a bond.

Another embodiment of this invention is directed to compounds of formula I wherein G is —C(R³)(R⁴)— and R³ and R⁴ are joined together to form a cycloalkyl, cycloalkenyl, heterocycloalkyl, or heterocycloalkenyl spiro ring.

Another embodiment of this invention is directed to compounds of formula I wherein G is —C(R³)(R⁴)— and R³ and R⁴ are joined together to form a cycloalkyl spiro ring. One example of said cycloalkyl spiro ring is:

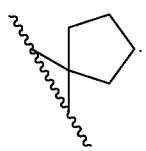

Another example of said cycloalkyl spiro ring is:

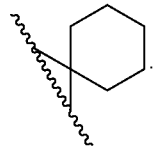

Another embodiment of this invention is directed to compounds of formula I wherein G is —C(R³)(R⁴)— and R³ and R⁴ are joined together to form a cycloalkyl spiro ring, and said cycloalkyl ring is fused with an aryl ring (e.g., phenyl) to form a fused spiro ring moiety, and said fused spiro ring moiety is optionally substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, —C(O)R¹⁵, —C(O)OR¹⁵, —C(O)N(R¹⁵)(R¹⁶), —S(O)N(R¹⁵)(R¹⁶), —S(O)₂N(R¹⁵)(R¹⁶), —C(=NOR¹⁵)R¹⁶, —P(O)(OR¹⁵)(OR¹⁶), —OR¹⁵ (e.g., —OCH₃), and —S(O)₂R¹⁵ᴬ (e.g., —S(O)₂CH₃). In one example said fused spiro ring moiety is substituted with 1-3 halos (e.g., 1-3 F). In another example said fused spiro ring moiety is substituted with 1 halo (e.g., F). In another example said aryl moiety of said fused spiro ring moiety is phenyl, and said phenyl is substituted with 1-3 halos (e.g., 1-3 F). In another example said aryl moiety of said fused spiro ring moiety is phenyl, and said phenyl is substituted with 1 halo (e.g., 1 F). In another example said cycloalkyl moiety of said fused spiro ring moiety is cyclopentyl, and said aryl moiety of said fused spiro ring moiety is phenyl. In another example said cycloalkyl moiety of said fused spiro ring moiety is cyclopentyl, and said aryl moiety of said fused spiro ring moiety is phenyl, and said fused spiro ring moiety is substituted with 1-3 substituents as described above. In another example said cycloalkyl moiety of said fused spiro ring moiety is cyclopentyl, and said aryl moiety of said fused spiro ring moiety is phenyl, and said fused spiro ring moiety is substituted with 1-3 halos (e.g., 1-3 F). In another example said cycloalkyl moiety of said fused spiro ring moiety is cyclopentyl, and said aryl moiety of said fused spiro ring moiety is phenyl, and said fused spiro ring moiety is substituted with 1 halo (e.g., 1 F). In another example said fused spiro ring moiety is:

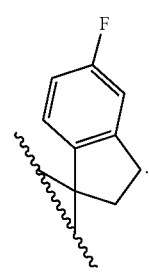

Another embodiment of this invention is directed to compounds of formula I wherein G is —C(R³)(R⁴)— and R³ and R⁴ are joined together to form a cycloalkyl spiro ring, and said cycloalkyl ring is fused with an heteroaryl ring (e.g., pyridyl) to form a fused spiro ring moiety, and said fused spiro ring moiety is optionally substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —OR$^{15}$ (e.g., —OCH$_3$), and —S(O)$_2$R$^{15A}$ (e.g., —S(O)$_2$CH$_3$).

Another embodiment of this invention is directed to compounds of formula I wherein G is —C(R$^3$)(R$^4$)— and R$^3$ and R$^4$ are joined together to form a cycloalkenyl spiro ring.

Another embodiment of this invention is directed to compounds of formula I wherein G is —C(R$^3$)(R$^4$)— and R$^3$ and R$^4$ are joined together to form a heterocycloalkyl spiro ring. One example of said heterocycloalkyl spiro ring is:

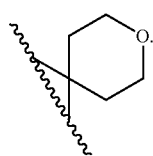

Another example of said spiro heterocycloalkyl ring is:

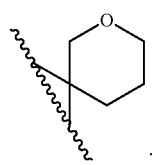

Another example of said spiro heterocycloalkyl ring is:

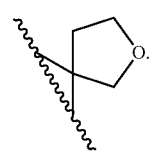

Another embodiment of this invention is directed to compounds of formula I wherein G is —C(R$^3$)(R$^4$)— and R$^3$ and R$^4$ are joined together to form a heterocycloalkyl spiro ring, and said heterocycloalkyl ring is fused with an aryl ring (e.g., phenyl) to form a fused spiro ring moiety, and said fused spiro ring moiety is optionally substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$ —C(=NOR$^{15}$)R$^{16}$, P(O)(OR$^{15}$)(OR$^{16}$), —OR$^{15}$ (e.g., —OCH$_3$), and —S(O)$_2$R$^{15A}$ (e.g., —S(O)$_2$CH$_3$). In one example said fused spiro ring moiety is substituted with 1-3 halos (e.g., 1-3 F). In another example said fused spiro ring moiety is substituted with 1 halo (e.g., F). In another example said aryl moiety of said fused spiro ring moiety is phenyl, and said phenyl is substituted with 1-3 halos (e.g., 1-3 F). In another example said aryl moiety of said fused spiro ring moiety is phenyl, and said phenyl is substituted with 1 halo (e.g., 1 F). In another example said heterocycloalkyl moiety of said fused spiro ring moiety is tetrahydrofuran, and said aryl moiety of said fused spiro ring moiety is phenyl. In another example said cycloalkyl moiety of said fused spiro ring moiety is tetrahydrofuran, and said aryl moiety of said fused spiro ring moiety is phenyl, and said fused spiro ring moiety is substituted with 1-3 substituents as described above. In another example said cycloalkyl moiety of said fused spiro ring moiety is tetrahydrofuran, and said aryl moiety of said fused spiro ring moiety is phenyl, and said fused spiro ring moiety is substituted with 1-3 halos (e.g., 1-3 F). In another example said cycloalkyl moiety of said fused spiro ring moiety is tetrahydrofuran, and said aryl moiety of said fused spiro ring moiety is phenyl, and said fused spiro ring moiety is substituted with 1 halo (e.g., 1 F). In another example said fused spiro ring moiety is:

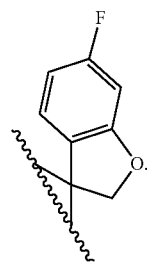

Another embodiment of this invention is directed to compounds of formula I wherein G is —C(R$^3$)(R$^4$)— and R$^3$ and R$^4$ are joined together to form a heterocycloalkyl spiro ring, and said heterocycloalkyl ring is fused with an heteroaryl ring (e.g., pyridyl) to form a fused spiro ring moiety, and said fused spiro ring moiety is optionally substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, P(O)(OR$^{15}$)(OR$^{16}$), —OR$^{15}$ (e.g., —OCH$_3$), and —S(O)$_2$R$^{15A}$ (e.g., —S(O)$_2$CH$_3$).

Another embodiment of this invention is directed to compounds of formula I wherein G is —C(R$^3$)(R$^4$)— and R$^3$ and R$^4$ are joined together to form a heterocycloalkenyl spiro ring.

Another embodiment of this invention is directed to compounds of formula I wherein G is —(C(R$^3$)(R$^4$))$_2$— and one R$^3$ and one R$^4$ on one carbon are joined together to form a cycloalkyl, cycloalkenyl, heterocycloalkyl, or heterocycloalkenyl spiro ring.

Another embodiment of this invention is directed to compounds of formula I wherein G is —(C(R$^3$)(R$^4$))$_2$— (wherein each R$^3$ and each R$^4$ are independently selected), and an R$^3$ and an R$^4$ on adjacent carbons form a cycloalkyl, cycloalkenyl, heterocycloalkyl, or heterocycloalkenyl ring (as described in (viii) above).

Another embodiment of this invention is directed to compounds of formula I selected), and an R$^3$ and an R$^4$ on adjacent carbons form a cycloalkyl ring (as described in (viii) above).

Another embodiment of this invention is directed to compounds of formula I wherein G is —(C(R$^3$)(R$^4$))$_2$— (wherein each R$^3$ and each R$^4$ are independently selected), and an R$^3$ and an R$^4$ on adjacent carbons form a cycloalkenyl ring (as described in (viii) above).

Another embodiment of this invention is directed to compounds of formula I wherein G is —(C(R$^3$)(R$^4$))$_2$— (wherein each R$^3$ and each R$^4$ are independently selected), and an R$^3$ and an R$^4$ on adjacent carbons form a heterocycloalkyl ring (as described in (viii) above).

Another embodiment of this invention is directed to compounds of formula I wherein G is —(C(R$^3$)(R$^4$))$_2$— (wherein each $R^3$ and each $R^4$ are independently selected), and an $R^3$ and an $R^4$ on adjacent carbons form a heterocycloalkenyl ring (as described in (viii) above).

Another embodiment of this invention is directed to compounds of formula I wherein none of the rings described in paragraphs (i) to (xii) of formula I are present in formula I (that is (1) $R^1$ and $R^2$ are not joined together, and (2) $R^2$ and $R^6$ are not joined together, and (3) $R^1$ and $R^2$ are not joined together, and $R^2$ and $R^6$ are not joined together (i.e., $R^2$ is not joined together with $R^1$ and $R^6$), and (4) $R^6$ is not joined together with either $R^3$ or $R^4$ (i.e., $R^6$ and $R^3$ are not joined together, or $R^6$ and $R^4$ are not joined together), and (5) $R^6$ and $R^{13}$ of the —N($R^{13}$)— G moiety, are not joined together, and (6) $R^3$ and $R^4$ of the —C($R^3$)($R^4$)— G moiety are not joined together) and (7) one $R^3$ and one $R^4$ on one carbon of the —C($R^3$)($R^4$))$_2$— G moiety are not joined together), and (8) an $R^3$ and an $R^4$ on adjacent carbons of the —(C($R^3$)($R^4$))$_2$— G moiety are not joined together, and (9) $R^1$ and $R^2$, and $R^6$ and either $R^3$ or $R^4$, are not joined together to form the rings described in (ix) above, and (10) $R^1$ and $R^2$, and $R^3$ and $R^4$, are not joined together to form the rings described in (x) above, and (11) $R^1$ and $R^2$, and $R^3$ and $R^4$, are not joined together to form the rings described in (xi) above, and (12) $R^1$ and $R^2$, and $R^3$ and $R^4$, are not joined together to form the rings described in (xii) above).

Another embodiment of this invention is directed to compounds of formula I wherein the conditions described in provisos (a) and (b) are present.

Another embodiment of this invention is directed to compounds of formula I wherein: (1) proviso (a) is present, and (2) wherein at least one (e.g., 1 to 3, or 1-2, or 1) group selected from the group consisting of: —SF$_5$ and —OSF$_5$ is present, and when there is more than one group, each group is independently selected.

Another embodiment of this invention is directed to compounds of formula I wherein provisos (a) and (c) are present.

Another embodiment of this invention is directed to compounds of formula I wherein provisos (a) and (e) are present.

Another embodiment of this invention is directed to compounds of formula I wherein provisos (a) and (f) are present.

Another embodiment of this invention is directed to compounds of formula I wherein provisos (a) and (g) are present.

Another embodiment of this invention is directed to compounds of formula I wherein provisos (b) and (c) are present.

Another embodiment of this invention is directed to compounds of formula I wherein (1) proviso (c) is present, and (2) wherein at least one (e.g., 1 to 3, or 1-2, or 1) group selected from the group consisting of: —SF$_5$ and —OSF$_5$ is present, and when there is more than one group, each group is independently selected.

Another embodiment of this invention is directed to compounds of formula I wherein provisos (b) and (d) are present.

Another embodiment of this invention is directed to compounds of formula I wherein (1) proviso (d) is present, and (2) wherein at least one (e.g., 1 to 3, or 1-2, or 1) group selected from the group consisting of: —SF$_5$ and —OSF$_5$ is present, and when there is more than one group, each group is independently selected.

Another embodiment of this invention is directed to compounds of formula I wherein provisos (b) and (e) are present.

Another embodiment of this invention is directed to compounds of formula I wherein (1) proviso (e) is present, and (2) wherein at least one (e.g., 1 to 3, or 1-2, or 1) group selected from the group consisting of: —SF$_5$ and —OSF$_5$ is present, and when there is more than one group, each group is independently selected.

Another embodiment of this invention is directed to compounds of formula I wherein provisos (b) and (f) are present.

Another embodiment of this invention is directed to compounds of formula I wherein (1) proviso (f) is present, and (2) wherein at least one (e.g., 1 to 3, or 1-2, or 1) group selected from the group consisting of: —SF$_5$ and —OSF$_5$ is present, and when there is more than one group, each group is independently selected.

Another embodiment of this invention is directed to compounds of formula I wherein provisos (b) and (g) are present.

Another embodiment of this invention is directed to compounds of formula I wherein (1) proviso (g) is present, and (2) wherein at least one (e.g., 1 to 3, or 1-2, or 1) group selected from the group consisting of: —SF$_5$ and —OSF$_5$ is present, and when there is more than one group, each group is independently selected.

Another embodiment of this invention is directed to compounds of formula I wherein provisos (c) and (d) are present.

Another embodiment of this invention is directed to compounds of formula wherein provisos (c) and (e) are present.

Another embodiment of this invention is directed to compounds of formula wherein provisos (c) and (f) are present.

Another embodiment of this invention is directed to compounds of formula wherein provisos (c) and (g) are present.

Another embodiment of this invention is directed to compounds of formula wherein provisos (d) and (g) are present.

Another embodiment of this invention is directed to compounds of formula wherein provisos (e) and (g) are present.

Another embodiment of this invention is directed to compounds of formula I wherein provisos (a), (b) and (c) are present.

Another embodiment of this invention is directed to compounds of formula I wherein (1) proviso (a) is present, and (2) proviso (c) is present, and (3) wherein at least one (e.g., 1 to 3, or 1-2, or 1) group selected from the group consisting of: —SF$_5$ and —OSF$_5$ is present, and when there is more than one group, each group is independently selected.

Another embodiment of this invention is directed to compounds of formula I wherein provisos (a), (b) and (g) are present.

Another embodiment of this invention is directed to compounds of formula I wherein (1) proviso (a) is present, and (2) proviso (g) is present, and (3) wherein at least one (e.g., 1 to 3, or 1-2, or 1) group selected from the group consisting of: —SF$_5$ and —OSF$_5$ is present, and when there is more than one group, each group is independently selected.

Another embodiment of this invention is directed to compounds of formula I wherein provisos (a), (c) and (g) are present.

Another embodiment of this invention is directed to compounds of formula I wherein provisos (b), (c) and (d) are present.

Another embodiment of this invention is directed to compounds of formula I wherein (1) proviso (c) is present, and (2) proviso (d) is present, and (3) wherein at least one (e.g., 1 to 3, or 1-2, or 1) group selected from the group consisting of: —SF$_5$ and —OSF$_5$ is present, and when there is more than one group, each group is independently selected.

Another embodiment of this invention is directed to compounds of formula I wherein the conditions described in provisos (b), (c) and (e) are present.

Another embodiment of this invention is directed to compounds of formula I wherein (1) proviso (c) is present, and (2) proviso (e) is present, and (3) wherein at least one (e.g., 1 to 3, or 1-2, or 1) group selected from the group consisting of: —SF$_5$ and —OSF$_5$ is present, Another embodiment of this invention is directed to compounds of formula I wherein the conditions described in provisos (b), (c) and (f) are present.

Another embodiment of this invention is directed to compounds of formula I wherein (1) proviso (c) is present, and (2) proviso (f) is present, and (3) wherein at least one (e.g., 1 to 3, or 1-2, or 1) group selected from the group consisting of: —SF$_5$ and —OSF$_5$ is present, Another embodiment of this invention is directed to compounds of formula I wherein the conditions described in provisos (b), (c) and (g) are present.

Another embodiment of this invention is directed to compounds of formula I wherein (1) proviso (c) is present, and (2) proviso (g) is present, and (3) wherein at least one (e.g., 1 to 3, or 1-2, or 1) group selected from the group consisting of: —SF$_5$ and —OSF$_5$ is present.

Another embodiment of this invention is directed to compounds of formula I wherein provisos (b), (c), (d) and (g) are present.

Another embodiment of this invention is directed to compounds of formula I wherein (1) proviso (c) is present, and (2) proviso (d) is present, and (3) proviso (g) is present, and (4) wherein at least one (e.g., 1 to 3, or 1-2, or 1) group selected from the group consisting of: —SF$_5$ and —OSF$_5$ is present, Other embodiments of this invention are directed to any one of the above embodiments directed to the provisos (either individually, or in the combinations) wherein: R$^1$ and R$^2$ are joined together to form a C4-C8 cycloalkyl, C4-C8 cycloalkenyl, 5-8 membered heterocyclyl or 5-8 membered heterocyclenyl moiety, wherein each of said cycloalkyl or heterocyclyl moiety is optionally substituted with 1-5 independently selected R$^{21}$ substituents.

Other embodiments of this invention are directed to any one of the above embodiments directed to the provisos (either individually, or in the combinations) wherein: R$^2$ and R$^6$ are joined together to form a C4-C8 cycloalkyl, C4-C8 cycloalkenyl, 5-8 membered heterocyclyl or 5-8 membered heterocyclenyl moiety, wherein each of said cycloalkyl or heterocyclyl moiety is optionally substituted with 1-5 independently selected R$^{21}$ substituents; or Other embodiments of this invention are directed to any one of the above embodiments directed to the provisos (either individually, or in the combinations) wherein: R$^1$ and R$^2$ are joined together to form a C4-C8 cycloalkyl, C4-C8 cycloalkenyl, 5-8 membered heterocyclyl or 5-8 membered heterocyclenyl moiety, wherein each of said cycloalkyl or heterocyclyl moiety is optionally substituted with 1-5 independently selected R$^{21}$ substituents; and R$^2$ and R$^6$ are joined together to form a C4-C8 cycloalkyl, C4-C8 cycloalkenyl, 5-8 membered heterocyclyl or 5-8 membered heterocyclenyl moiety, wherein each of said cycloalkyl or heterocyclyl moiety is optionally substituted with 1-5 independently selected R$^{21}$ substituents.

In another embodiment of this invention R$^{10}$ in formula I is selected from the group consisting of:

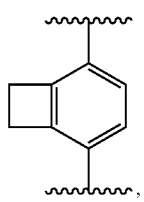
1A

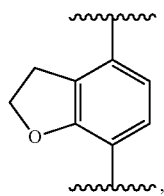
2A

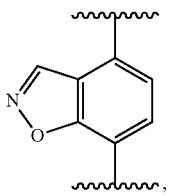
3A

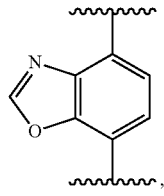
4A

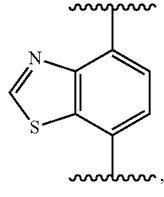
5A

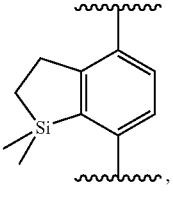
6A

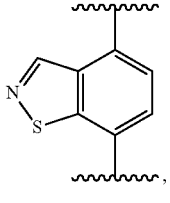
7A

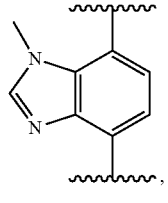
8A

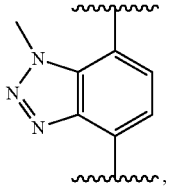
9A

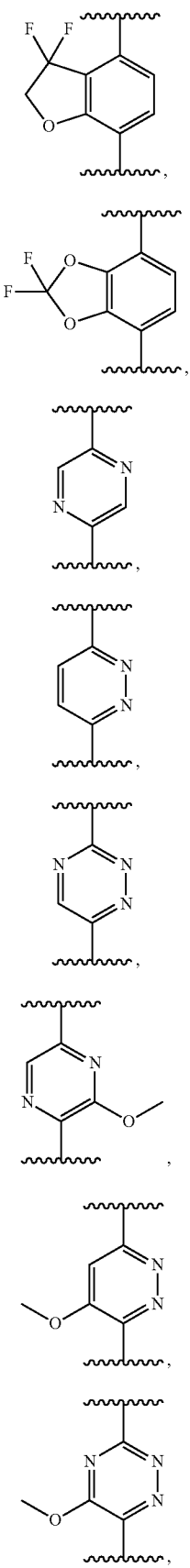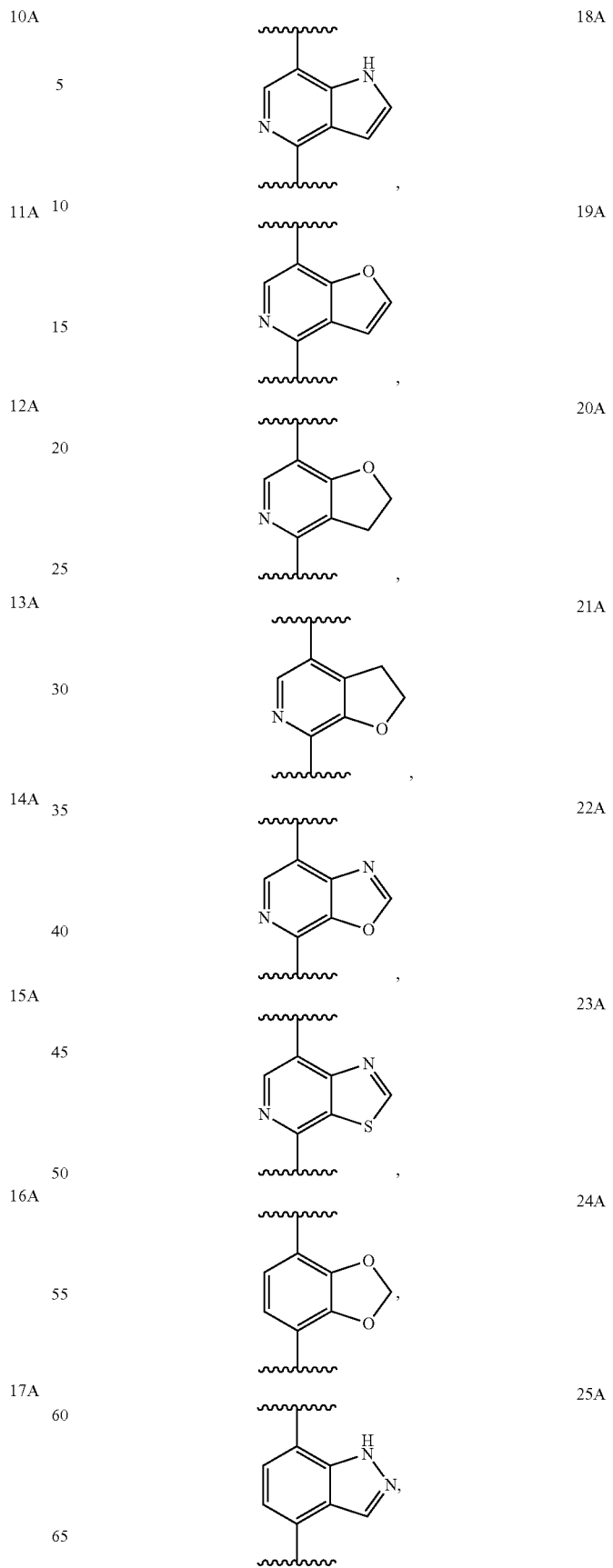

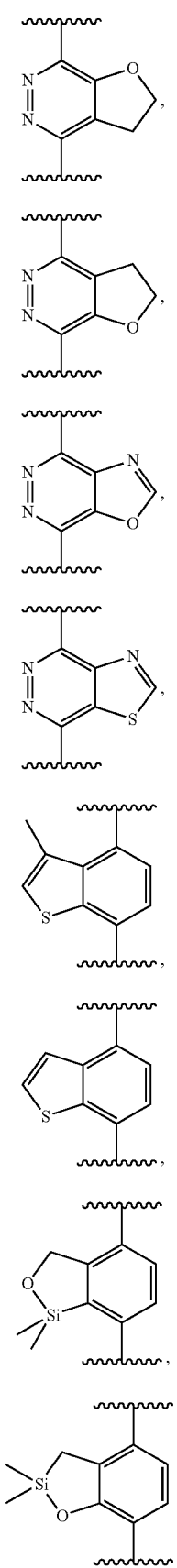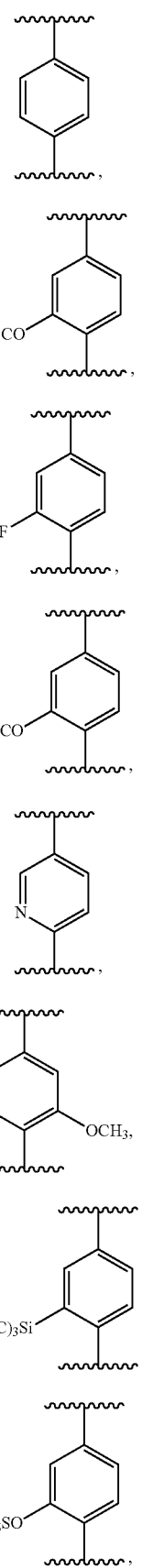

-continued
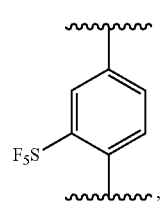 42A
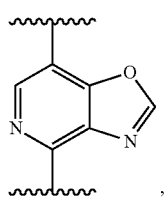 43A
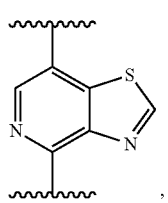 44A
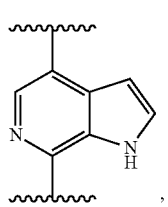 45A
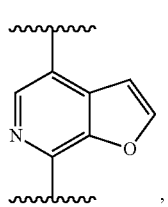 46A
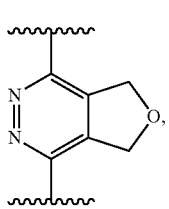 47A
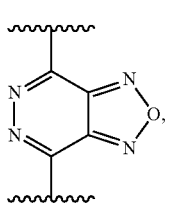 48A
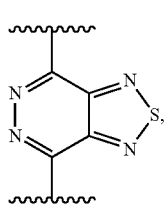 49A
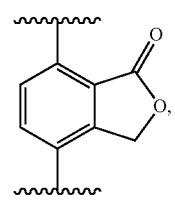 50A
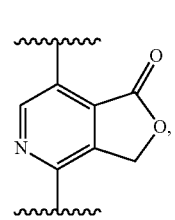 51A
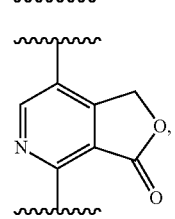 52A
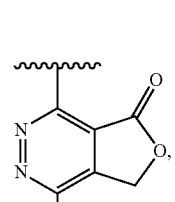 53A
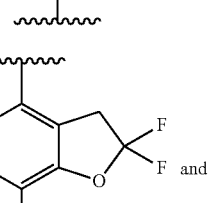 54A
and
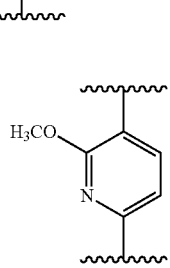 55A
In another embodiment of this invention $R^{10}$ in formula I is selected from the group consisting of:
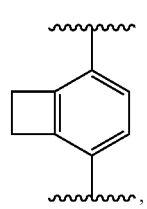 1A

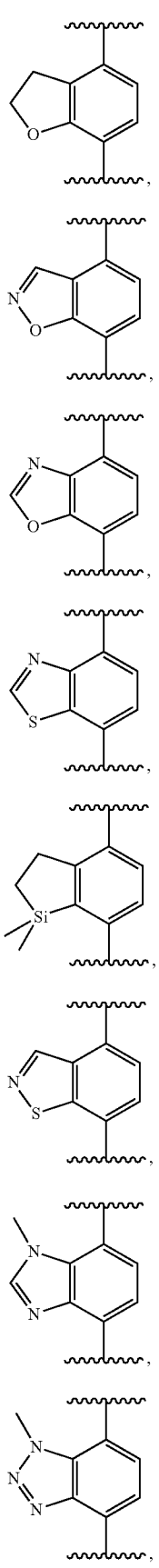
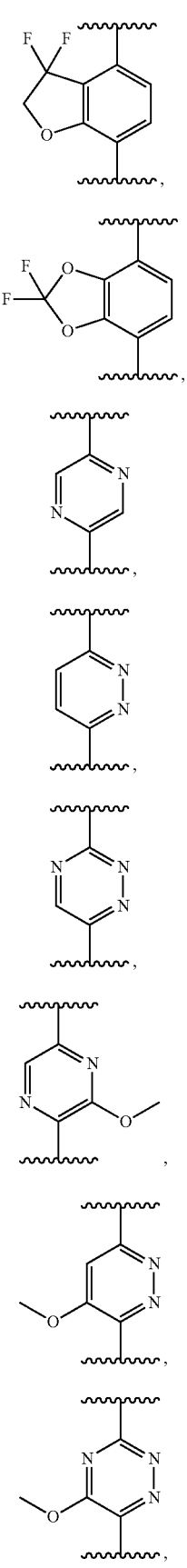

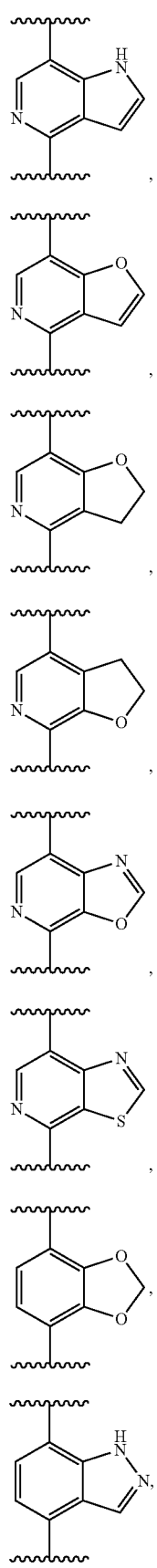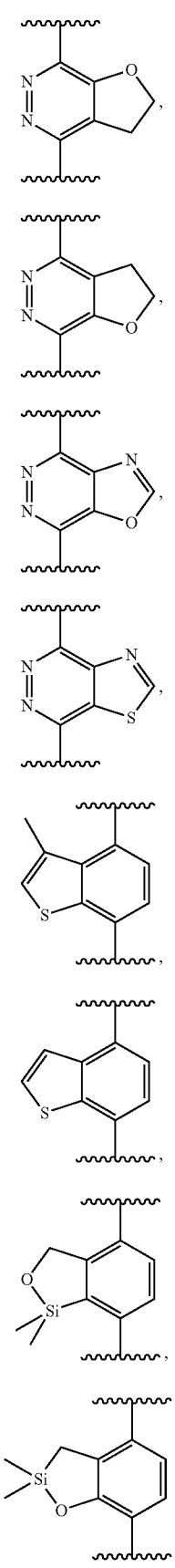

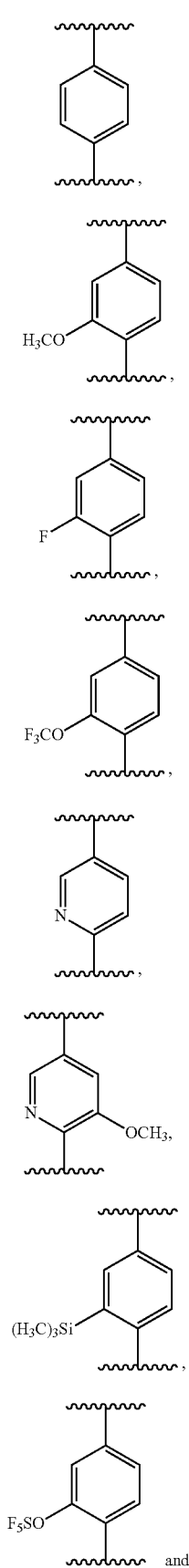

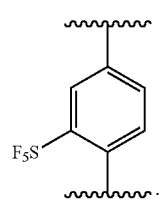

In another embodiment of this invention $R^{10}$ is group 1A. In another embodiment of this invention $R^{10}$ is group 2A. In another embodiment of this invention $R^{10}$ is group 3A. In another embodiment of this invention $R^{10}$ is group 4A. In another embodiment of this invention $R^{10}$ is group 5A. In another embodiment of this invention $R^{10}$ is group 6A. In another embodiment of this invention $R^{10}$ is group 7A. In another embodiment of this invention $R^{10}$ is group 8A. In another embodiment of this invention $R^{10}$ is group 9A. In another embodiment of this invention $R^{10}$ is group 10A. In another embodiment of this invention $R^{10}$ is group 11A. In another embodiment of this invention $R^{10}$ is group 12A. In another embodiment of this invention $R^{10}$ is group 13A. In another embodiment of this invention $R^{10}$ is group 14A. In another embodiment of this invention $R^{10}$ is group 15A. In another embodiment of this invention $R^{10}$ is group 16A. In another embodiment of this invention $R^{10}$ is group 17A. In another embodiment of this invention $R^{10}$ is group 18A. In another embodiment of this invention $R^{10}$ is group 19A. In another embodiment of this invention $R^{10}$ is group 20A. In another embodiment of this invention $R^{10}$ is group 21A. In another embodiment of this invention $R^{10}$ is group 22A. In another embodiment of this invention $R^{10}$ is group 23A. In another embodiment of this invention $R^{10}$ is group 24A. In another embodiment of this invention $R^{10}$ is group 25A. In another embodiment of this invention $R^{10}$ is group 26A. In another embodiment of this invention $R^{10}$ is group 27A. In another embodiment of this invention $R^{10}$ is group 28A. In another embodiment of this invention $R^{10}$ is group 29A. In another embodiment of this invention $R^{10}$ is group 30A. In another embodiment of this invention $R^{10}$ is group 31A. In another embodiment of this invention $R^{10}$ is group 32A. In another embodiment of this invention $R^{10}$ is group 33A. In another embodiment of this invention $R^{10}$ is group 34A. In another embodiment of this invention $R^{10}$ is group 35A. In another embodiment of this invention $R^{10}$ is group 36A. In another embodiment of this invention $R^{10}$ is group 37A. In another embodiment of this invention $R^{10}$ is group 38A. In another embodiment of this invention $R^{10}$ is group 39A. In another embodiment of this invention $R^{10}$ is group 40A. In another embodiment of this invention $R^{10}$ is group 41A. In another embodiment of this invention $R^{10}$ is group 42A. In another embodiment of this invention $R^{10}$ is group 43A. In another embodiment of this invention $R^{10}$ is group 44A. In another embodiment of this invention $R^{10}$ is group 45A. In another embodiment of this invention $R^{10}$ is group 46A. In another embodiment of this invention $R^{10}$ is group 47A. In another embodiment of this invention $R^{10}$ is group 48A. In another embodiment of this invention $R^{10}$ is group 49A. In another embodiment of this invention $R^{10}$ is group 50A. In another embodiment of this invention $R^{10}$ is group 51A. In another embodiment of this invention $R^{10}$ is group 52A. In another embodiment of this invention $R^{10}$ is group 53A. In another embodiment of this invention $R^{10}$ is group 54A. In another embodiment of this invention $R^{10}$ is group 55A.

In another embodiment of this invention at least one group selected from the group consisting of: —SF$_5$, —OSF$_5$, and —Si(R$^{24}$)$_3$ (wherein each R$^{24}$ is independently selected) is present in the compounds of formula I, and R$^{10}$ is selected from the group consisting of 1A to 55A.

In another embodiment of this invention one group selected from the group consisting of: —SF$_5$, —OSF$_5$, and —Si(R$^{24}$)$_3$ (wherein each R$^{24}$ is independently selected) is present in the compounds of formula I, and R$^{10}$ is selected from the group consisting of 1A to 55A.

In another embodiment of this invention two groups selected from the group consisting of: —SF$_5$, —OSF$_5$, and —Si(R$^{24}$)$_3$ (wherein each R$^{24}$ is independently selected) are present in the compounds of formula I, and R$^{10}$ is selected from the group consisting of 1A to 55A.

In another embodiment of this invention three groups selected from the group consisting of: —SF$_5$, —OSF$_5$, and —Si(R$^{24}$)$_3$ (wherein each R$^{15}$ is independently selected) are present in the compounds of formula I, and R$^{10}$ is selected from the group consisting of 1A to 55A.

In another embodiment of this invention at least one group selected from the group consisting of: —SF$_5$ and —OSF$_5$ is present in the compounds of formula I, and R$^{15}$ is selected from the group consisting of 1A to 55A.

In another embodiment of this invention one group selected from the group consisting of: —SF$_5$ and —OSF$_5$ is present in the compounds of formula I, and R$^{10}$ is selected from the group consisting of 1A to 55A.

In another embodiment of this invention two groups selected from the group consisting of: —SF$_5$ and —OSF$_5$ are present in the compounds of formula I, and R$^{15}$ is selected from the group consisting of 1A to 55A.

In another embodiment of this invention three groups selected from the group consisting of: —SF$_5$ and —OSF$_5$ are present in the compounds of formula I, and R$^{15}$ is selected from the group consisting of 1A to 55A.

In another embodiment of this invention one —SF$_5$ group is present in the compounds of formula I, and R$^{10}$ is selected from the group consisting of 1A to 55A.

In another embodiment of this invention two —SF$_5$ groups are present in the compounds of formula I, and R$^{10}$ is selected from the group consisting of 1A to 55A.

In another embodiment of this invention three —SF$_5$ groups are present in the compounds of formula I, and R$^{10}$ is selected from the group consisting of 1A to 55A.

In another embodiment of this invention one —OSF$_5$ group is present in the compounds of formula I, and R$^{10}$ is selected from the group consisting of 1A to 55A.

In another embodiment of this invention two —OSF$_5$ groups are present in the compounds of formula I, and R$^{10}$ is selected from the group consisting of 1A to 55A.

In another embodiment of this invention three —OSF$_5$ groups are present in the compounds of formula I, and R$^{10}$ is selected from the group consisting of 1A to 55A.

In another embodiment of this invention one —Si(R$^{24}$)$_3$ (wherein each R$^{24}$ is independently selected) group is present in the compounds of formula I, and R$^{10}$ is selected from the group consisting of 1A to 55A.

In another embodiment of this invention two —Si(R$^{24}$)$_3$ (wherein each R$^{24}$ is independently selected) groups are present in the compounds of formula I, and R$^{10}$ is selected from the group consisting of 1A to 55A.

In another embodiment of this invention three —Si(R$^{24}$)$_3$ (wherein each R$^{24}$ is independently selected) groups are present in the compounds of formula I, and R$^{10}$ is selected from the group consisting of 1A to 55A.

In another embodiment of this invention one —Si(R$^{24}$)$_3$ (wherein each R$^{24}$ is independently selected from the group consisting of alkyl (e.g., methyl and ethyl) and aryl (e.g., phenyl)) is present in the compounds of formula I, and R$^{10}$ is selected from the group consisting of 1A to 55A.

In another embodiment of this invention two —Si(R$^{24}$)$_3$ (wherein each R$^{24}$ is independently selected from the group consisting of alkyl (e.g., methyl and ethyl) and aryl (e.g., phenyl)) is present in the compounds of formula I, and R$^{10}$ is selected from the group consisting of 1A to 55A.

In another embodiment of this invention three —Si(R$^{24}$)$_3$ (wherein each R$^{24}$ is independently selected from the group consisting of alkyl (e.g., methyl and ethyl) and aryl (e.g., phenyl)) is present in the compounds of formula I, and R$^{10}$ is selected from the group consisting of 1A to 55A.

In another embodiment of this invention one —Si(R$^{24}$)$_3$ (wherein each R$^{24}$ is independently selected from the group consisting of methyl, ethyl and phenyl) is present in the compounds of formula I, and R$^{10}$ is selected from the group consisting of 1A to 55A.

In another embodiment of this invention two —Si(R$^{24}$)$_3$ (wherein each R$^{24}$ is independently selected from the group consisting of methyl, ethyl and phenyl) is present in the compounds of formula I, and R$^{10}$ is selected from the group consisting of 1A to 55A.

In another embodiment of this invention three —Si(R$^{24}$)$_3$ (wherein each R$^{24}$ is independently selected from the group consisting of methyl, ethyl and phenyl) is present in the compounds of formula I, and R$^{10}$ is selected from the group consisting of 1A to 55A.

In another embodiment of this invention one —Si(R$^{24}$)$_3$ (wherein each R$^{24}$ is independently selected from the group consisting of methyl and ethyl) is present in the compounds of formula I, and R$^{10}$ is selected from the group consisting of 1A to 55A.

In another embodiment of this invention two —Si(R$^{24}$)$_3$ (wherein each R$^{24}$ is independently selected from the group consisting of methyl and ethyl) is present in the compounds of formula I, and R$^{10}$ is selected from the group consisting of 1A to 55A.

In another embodiment of this invention three —Si(R$^{24}$)$_3$ (wherein each R$^{24}$ is independently selected from the group consisting of methyl and ethyl) is present in the compounds of formula I, and R$^{10}$ is selected from the group consisting of 1A to 55A.

In another embodiment of this invention one —Si(R$^{24}$)$_3$ group is present in the compounds of formula I, and said —Si(R$^{24}$)$_3$ group is selected from the group consisting of: —Si(CH$_3$)$_3$, —Si(CH$_3$)$_2$-phenyl, and —Si(CH$_2$CH$_3$)$_2$CH$_3$ and R$^{10}$ is selected from the group consisting of 1A to 55A.

In another embodiment of this invention two —Si(R$^{24}$)$_3$ groups are present in the compounds of formula I, and said —Si(R$^{24}$)$_3$ groups are independently selected from the group consisting of: —Si(CH$_3$)$_3$, —Si(CH$_3$)$_2$-phenyl, and —Si(CH$_2$CH$_3$)$_2$CH$_3$ and R$^{10}$ is selected from the group consisting of 1A to 55A.

In another embodiment of this invention three —Si(R$^{24}$)$_3$ groups are present in the compounds of formula I, and said —Si(R$^{24}$)$_3$ groups are independently selected from the group consisting of: —Si(CH$_3$)$_3$, —Si(CH$_3$)$_2$-phenyl, and —Si(CH$_2$CH$_3$)$_2$CH$_3$ and R$^{10}$ is selected from the group consisting of 1A to 55A.

In another embodiment of this invention one —Si(R$^{24}$)$_3$ group is present in the compounds of formula I, and said —Si(R$^{24}$)$_3$ group is selected from the group consisting of: —Si(CH$_3$)$_3$ and —Si(CH$_2$CH$_3$)$_2$CH$_3$ and R$^{10}$ is selected from the group consisting of 1A to 55A.

In another embodiment of this invention two —Si(R$^{24}$)$_3$ groups are present in the compounds of formula I, and said —Si(R$^{24}$)$_3$ groups are independently selected from the group consisting of: —Si(CH$_3$)$_3$ and —Si(CH$_2$CH$_3$)$_2$CH$_3$ and R$^{10}$ is selected from the group consisting of 1A to 55A.

In another embodiment of this invention three —Si(R$^{24}$)$_3$ groups are present in the compounds of formula I, and said —Si(R$^{24}$)$_3$ groups are independently selected from the group consisting of: —Si(CH$_3$)$_3$ and —Si(CH$_2$CH$_3$)$_2$CH$_3$ and R$^{10}$ is selected from the group consisting of 1A to 55A.

In another embodiment of this invention one —Si(R$^{24}$)$_3$ group is present in the compounds of formula I, and said —Si(R$^{24}$)$_3$ group is —Si(CH$_3$)$_3$ and R$^{10}$ is selected from the group consisting of 1A to 55A.

In another embodiment of this invention two —Si(R$^{24}$)$_3$ groups are present in the compounds of formula I, and said —Si(R$^{24}$)$_3$ groups are —Si(CH$_3$)$_3$ and R$^{10}$ is selected from the group consisting of 1A to 55A.

In another embodiment of this invention three —Si(R$^{24}$)$_3$ groups are present in the compounds of formula I, and said —Si(R$^{24}$)$_3$ groups are —Si(CH$_3$)$_3$ and R$^{10}$ is selected from the group consisting of 1A to 55A.

In another embodiment of this invention one group selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula I, and R$^{10}$ is selected from the group consisting of 1A to 55A.

In another embodiment of this invention one group selected from the group consisting of: —SF$_5$, —OSF$_5$, —Si(CH$_3$)$_3$, and —Si(CH$_2$CH$_3$)$_2$CH$_3$) is present in the compounds of formula I, and R$^{10}$ is selected from the group consisting of 1A to 55A.

In another embodiment of this invention one group selected from the group consisting of: —SF$_5$, —OSF$_5$, and —Si(CH$_3$)$_3$, is present in the compounds of formula I, and R$^{10}$ is selected from the group consisting of 1A to 55A.

In another embodiment of this invention one —SF$_5$ group is present in the compounds of formula I, and one or two additional groups selected from the group consisting of: —SF$_5$, —OSF$_5$, and —Si(R$^{24}$)$_3$ (wherein each R$^{24}$ is independently selected) are also present in the compounds of formula I, and R$^{10}$ is selected from the group consisting of 1A to 55A.

In another embodiment of this invention one —SF$_5$ group is present in the compounds of formula I, and one or two additional groups selected from the group consisting of: —OSF$_5$, and —Si(R$^{24}$)$_3$ (wherein each R$^{24}$ is independently selected) are also present in the compounds formula I, and R$^{10}$ is selected from the group consisting of 1A to 55A.

In another embodiment of this invention one —SF$_5$ group is present in the compounds of formula I, and one or two additional groups selected from the group consisting of: —SF$_5$ and —OSF$_5$ are also present in the compounds of formula I, and R$^{10}$ is selected from the group consisting of 1A to 55A.

In another embodiment of this invention one —OSF$_5$ group is present in the compounds of formula I, and one or two additional groups selected from the group consisting of: —SF$_5$, —OSF$_5$, and —Si(R$^{24}$)$_3$ (wherein each R$^{24}$ is independently selected) are also present in the compounds of formula I, and R$^{10}$ is selected from the group consisting of 1A to 55A.

In another embodiment of this invention one —OSF$_5$ group is present in the compounds of formula I, and one or two additional groups selected from the group consisting of: —SF$_5$ and —Si(R$^{24}$)$_3$ (wherein each R$^{24}$ is independently selected) are also present in the compounds of formula I, and R$^{10}$ is selected from the group consisting of 1A to 55A.

In another embodiment of this invention one —OSF$_5$ group is present in the compounds of formula I, and one or two additional groups selected from the group consisting of: —SF$_5$ and —OSF$_5$ are also present in the compounds of formula I, and R$^{10}$ is selected from the group consisting of 1A to 55A.

In another embodiment of this invention one —Si(R$^{24}$)$_3$ (wherein each R$^{24}$ is independently selected) group is present in the compounds of formula I, and one or two additional groups selected from the group consisting of: —SF$_5$, —OSF$_5$, and —Si(R$^{24}$)$_3$ (wherein each R$^{24}$ is independently selected) are also present in the compounds of formula I, and R$^{10}$ is selected from the group consisting of 1A to 55A.

In another embodiment of this invention one —Si(R$^{24}$)$_3$ (wherein each R$^{15}$ is independently selected) group is present in the compounds of formula I, and one or two additional groups selected from the group consisting of: —SF$_5$ and —OSF$_5$ are also present in the compounds of formula I, and R$^{10}$ is selected from the group consisting of 1A to 55A In another embodiment of this invention at least one group selected from the group consisting of: —SF$_5$, —OSF$_5$, and —Si(R$^{24}$)$_3$ (wherein each R$^{24}$ is independently selected from the group consisting of alkyl (e.g., methyl and ethyl) and aryl (e.g., phenyl)) is present in the compounds of formula I, and R$^{10}$ is selected from the group consisting of 1A to 55A.

In another embodiment of this invention at least one group selected from the group consisting of: —SF$_5$, —OSF$_5$, and —Si(R$^{24}$)$_3$ (wherein each R$^{24}$ is independently selected from the group consisting of alkyl (e.g., methyl and ethyl) and phenyl) is present in the compounds of formula I, and R$^{10}$ is selected from the group consisting of 1A to 55A.

In another embodiment of this invention at least one group selected from the group consisting of: —SF$_5$, —OSF$_5$, and —Si(R$^{24}$)$_3$ (wherein each R$^{24}$ is independently selected from the group consisting of methyl, ethyl and phenyl) is present in the compounds of formula I, and R$^{10}$ is selected from the group consisting of 1A to 55A.

In another embodiment of this invention at least one group selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula I, and R$^{10}$ is selected from the group consisting of 1A to 55A.

In another embodiment of this invention at least one group selected from the group consisting of: —SF$_5$, —OSF$_5$, and —Si(CH$_3$)$_3$ is present in the compounds of formula I, and R$^{10}$ is selected from the group consisting of 1A to 55A.

In another embodiment of this invention one group selected from the group consisting of: —SF$_5$, —OSF$_5$, and —Si(R$^{24}$)$_3$ (wherein each R$^{24}$ is independently selected) is present in the compounds of formula I, and R$^{10}$ is selected from the group consisting of 1A to 55A.

In another embodiment of this invention one group selected from the group consisting of: —SF$_5$, —OSF$_5$, and —Si(R$^{24}$)$_3$ (wherein each R$^{24}$ is independently selected from the group consisting of alkyl (e.g., methyl and ethyl) and aryl (e.g., phenyl)) is present in the compounds of formula I, and R$^{10}$ is selected from the group consisting of 1A to 55A.

In another embodiment of this invention one group selected from the group consisting of: —SF$_5$, —OSF$_5$, and —Si(R$^{24}$)$_3$ (wherein each R$^{24}$ is independently selected from the group consisting of alkyl (e.g., methyl and ethyl) and phenyl) is present in the compounds of formula I, and R$^{10}$ is selected from the group consisting of 1A to 55A.

In another embodiment of this invention one group selected from the group consisting of: —SF$_5$, —OSF$_5$, and —Si($R^{24}$)$_3$ (wherein each $R^{24}$ is independently selected from the group consisting of methyl, ethyl and phenyl) is present in the compounds of formula I, and $R^{10}$ is selected from the group consisting of 1A to 55A.

In another embodiment of this invention one group selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula I, and $R^{10}$ is selected from the group consisting of 1A to 55A.

In another embodiment of this invention one group selected from the group consisting of: —SF$_5$, —OSF$_5$, —Si(CH$_3$)$_3$, and —Si(CH$_2$CH$_3$)$_2$CH$_3$) is present in the compounds of formula I, and $R^{10}$ is selected from the group consisting of 1A to 55A.

In another embodiment of this invention one group selected from the group consisting of: —SF$_5$, —OSF$_5$, and —Si(CH$_3$)$_3$, is present in the compounds of formula I, and $R^{10}$ is selected from the group consisting of 1A to 55A.

In another embodiment of this invention two groups selected from the group consisting of: —SF$_5$, —OSF$_5$, and —Si($R^{24}$)$_3$ (wherein each $R^{24}$ is independently selected) are present in the compounds of formula I, and $R^{10}$ is selected from the group consisting of 1A to 55A In another embodiment of this invention two groups independently selected from the group consisting of: —SF$_5$, —OSF$_5$, and —Si($R^{24}$)$_3$ (wherein each $R^{24}$ is independently selected from the group consisting of alkyl (e.g., methyl and ethyl) and aryl (e.g., phenyl)) are present in the compounds of formula I, and $R^{10}$ is selected from the group consisting of 1A to 55A In another embodiment of this invention two groups independently selected from the group consisting of: —SF$_5$, —OSF$_5$, and —Si($R^{24}$)$_3$ (wherein each $R^{24}$ is independently selected from the group consisting of alkyl (e.g., methyl and ethyl) and phenyl) are present in the compounds of formula I, and $R^{10}$ is selected from the group consisting of IA to 55A.

In another embodiment of this invention two groups selected from the group consisting of: —SF$_5$, —OSF$_5$, and —Si($R^{24}$)$_3$ (wherein each $R^{24}$ is independently selected from the group consisting of methyl, ethyl and phenyl) are present in the compounds of formula I, and $R^{10}$ is selected from the group consisting of 1A to 55A.

In another embodiment of this invention two groups independently selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula I, and $R^{10}$ is selected from the group consisting of 1A to 55A.

In another embodiment of this invention two groups independently selected from the group consisting of: —SF$_5$, —OSF$_5$, —Si(CH$_3$)$_3$, and —Si(CH$_2$CH$_3$)$_2$CH$_3$) are present in the compounds of formula I, and $R^{10}$ is selected from the group consisting of 1A to 55A.

In another embodiment of this invention two groups independently selected from the group consisting of: —SF$_5$, —OSF$_5$, and —Si(CH$_3$)$_3$ are present in the compounds of formula I, and $R^{10}$ is selected from the group consisting of 1A to 55A.

In another embodiment of this invention three groups selected from the group consisting of: —SF$_5$, —OSF$_5$, and —Si($R^{24}$)$_3$ (wherein each $R^{24}$ is independently selected) are present in the compounds of formula I, and $R^{10}$ is selected from the group consisting of 1A to 55A.

In another embodiment of this invention three groups independently selected from the group consisting of: —SF$_5$, —OSF$_5$, and —Si($R^{24}$)$_3$ (wherein each $R^{24}$ is independently selected from the group consisting of alkyl (e.g., methyl and ethyl) and aryl (e.g., phenyl)) are present in the compounds of formula I, and $R^{10}$ is selected from the group consisting of 1A to 55A.

In another embodiment of this invention three groups independently selected from the group consisting of: —SF$_5$, —OSF$_5$, and —Si($R^{24}$)$_3$ (wherein each $R^{24}$ is independently selected from the group consisting of alkyl (e.g., methyl and ethyl) and phenyl) are present in the compounds of formula I, and $R^{10}$ is selected from the group consisting of 1A to 55A.

In another embodiment of this invention three groups selected from the group consisting of: —SF$_5$, —OSF$_5$, and —Si($R^{24}$)$_3$ (wherein each $R^{24}$ is independently selected from the group consisting of methyl, ethyl and phenyl) are present in the compounds of formula I, and $R^{10}$ is selected from the group consisting of 1A to 55A.

In another embodiment of this invention three groups independently selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula I, and $R^{10}$ is selected from the group consisting of 1A to 55A.

In another embodiment of this invention three groups independently selected from the group consisting of: —SF$_5$, —OSF$_5$, —Si(CH$_3$)$_3$, and —Si(CH$_2$CH$_3$)$_2$CH$_3$) are present in the compounds of formula I, and $R^{10}$ is selected from the group consisting of 1A to 55A.

In another embodiment of this invention three groups independently selected from the group consisting of: —SF$_5$, —OSF$_5$, and —Si(CH$_3$)$_3$ are present in the compounds of formula I, and $R^{10}$ is selected from the group consisting of 1A to 55A.

In another embodiment of this invention at least one group selected from the group consisting of: —SF$_5$, —OSF$_5$, and —Si($R^{24}$)$_3$ (wherein each $R^{24}$ is the same or different alkyl group) is present in the compounds of formula I, and $R^{10}$ is selected from the group consisting of 1A to 55A.

In another embodiment of this invention at least one group selected from the group consisting of: —SF$_5$, —OSF$_5$, and —Si($R^{24}$)$_3$ (wherein each $R^{24}$ is independently selected from the group consisting of methyl and ethyl) is present in the compounds of formula I, and $R^{10}$ is selected from the group consisting of 1A to 55A.

Other embodiments of this invention are directed to any one of the embodiments above directed to the groups —SF$_5$, —OSF$_5$, or —Si($R^{24}$)$_3$ wherein $R^{10}$ is 35A.

Another embodiment of this invention is directed to a compound of the formula I, or a pharmaceutically acceptable salt, solvate, ester or prodrug thereof, wherein:

$R^1$ and $R^2$ are joined together to form a C4-C8 cycloalkyl, C4-C8 cycloalkenyl, 5-8 membered heterocyclyl or 5-8 membered heterocyclenyl moiety, wherein each of said cycloalkyl or heterocyclyl moiety is optionally substituted with 1-5 independently selected $R^{21}$ substituents;

U, W, G, V, $R^4$, $R^5$, $R^6$, $R^7$, $R^8$, $R^9$, $R^{10}$ $R^{11}$, $R^{12}$, $R^{13}$, $R^{14}$, $R^{15A}$, $R^{15}$, $R^{16}$, $R^{17}$, $R^{18}$, $R^{19}$, $R^{20}$, $R^{21}$, $R^{22}$ and $R^{24}$ are as defined for formula I; and $R^3$ is as defined for formula I; or $R^3$ and $R^6$ taken together form a bond (i.e., $R^3$ and $R^6$ form a bond between G and the carbon to which $R^6$ is bound), provided that when $R^3$ and $R^6$ form a bond W is not a bond.

In another embodiment the compounds of formula I are compounds of formula II:

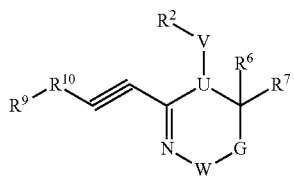

formula II wherein G, U, V, W, $R^2$, $R^6$, $R^7$, $R^9$, and $R^{10}$ are as defined for formula I. In one embodiment of the compounds of formula II, there are 1 to 3 (in one example there is one, in another example there are 2, and in another example there are three) groups selected from the group consisting of —$SF_5$, —$OSF_5$ and —$Si(R^{24})_3$ present on either $R^6$ or $R^7$ (and in one example on $R^6$, and in another example $R^7$, and in another example distributed between $R^6$ and $R^7$ when there is more than one of said groups).

Another embodiment of this invention is directed to a compound of the formula I, or a pharmaceutically acceptable salt, solvate, ester or prodrug thereof, wherein:

$R^1$ and $R^2$ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected $R^{21}$ substituents;

U, W, G, V, $R^4$, $R^5$, $R^6$, $R^7$, $R^8$, $R^9$, $R^{10}$ $R^{11}$, $R^{12}$, $R^{13}$, $R^{14}$, $R^{15A}$, $R^{15}$, $R^{16}$, $R^{17}$, $R^{18}$, $R^{19}$, $R^{20}$, $R^{21}$, $R^{22}$ and $R^{24}$ are as defined for formula I; and $R^3$ is as defined for formula I; or $R^3$ and $R^6$ taken together form a bond (i.e., $R^3$ and $R^6$ form a bond between G and the carbon to which $R^6$ is bound), provided that when $R^3$ and $R^6$ form a bond W is not a bond; and at least one (e.g., 1 to 3, or 1-2, or 1) group selected from the group consisting of: —$SF_5$, —$OSF_5$, and —$Si(R^{24})_3$ is present, and wherein each $R^{24}$ is independently selected, and wherein there is more than one group, each group is independently selected.

Another embodiment of this invention is directed to a compound of the formula I, or a pharmaceutically acceptable salt, solvate, ester or prodrug thereof, wherein:

$R^1$ and $R^2$ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected $R^{21}$ substituents;

U, W, G, V, $R^4$, $R^5$, $R^6$, $R^7$, $R^8$, $R^9$, $R^{10}$ $R^{11}$, $R^{12}$, $R^{13}$, $R^{14}$, $R^{15A}$, $R^{15}$, $R^{16}$, $R^{17}$, $R^{18}$, $R^{19}$, $R^{20}$, $R^{21}$, $R^{22}$ and $R^{24}$ are as defined for formula I; and $R^3$ is as defined for formula I; or $R^3$ and $R^6$ taken together form a bond (i.e., $R^3$ and $R^6$ form a bond between G and the carbon to which $R^6$ is bound), provided that when $R^3$ and $R^6$ form a bond W is not a bond; and at least one (e.g., 1 to 3, or 1-2, or 1) group selected from the group consisting of: —$SF_5$ and —$OSF_5$ is present, and when there is more than one group, each group is independently selected.

In another embodiment of this invention, $R^1$ and $R^2$ are joined together to form a 5 to 8 membered cycloalkyl ring, and said ring is substituted with a group selected from the group consisting of —$SF_5$, —$OSF_5$ and —$Si(R^{24})_3$. In another embodiment said ring is substituted with a group selected from the group consisting of —$SF_5$ and —$OSF_5$. In another embodiment said ring is substituted with a —$SF_5$ group. In another embodiment said ring is substituted with an —$OSF_5$ group. In another embodiment said ring is substituted with a —$Si(R^{24})_3$ group. Examples of the —$Si(R^{24})_3$ group in the embodiments above include groups wherein each $R^{24}$ is the same or different alkyl group (e.g., methyl and ethyl). Thus, —$Si(CH_3)_3$ and —$Si(CH_2CH_3)_2CH_3)$ are examples of the —$Si(R^{24})_3$ group in the above embodiments. And in one example the —$Si(R^{24})_3$ group is —$Si(CH_3)_3$.

In another embodiment of this invention, $R^1$ and $R^2$ are joined together to form a 5 to 8 membered heterocyclyl ring, and said ring is substituted with a group selected from the group consisting of —$SF_5$, —$OSF_5$ and —$Si(R^{24})_3$. In another embodiment said ring is substituted with a group selected from the group consisting of —$SF_5$ and —$OSF_5$. In another embodiment said ring is substituted with a —$SF_5$ group. In another embodiment said ring is substituted with an —$OSF_5$ group. In another embodiment said ring is substituted with a —$Si(R^{24})_3$ group. Examples of the —$Si(R^{24})_3$ group in the embodiments above include groups wherein each $R^{24}$ is the same or different alkyl group (e.g., methyl and ethyl). Thus, —$Si(CH_3)_3$ and —$Si(CH_2CH_3)_2CH_3)$ are examples of the —$Si(R^{24})_3$ group in the above embodiments. And in one example the —$Si(R^{24})_3$ group is —$Si(CH_3)_3$.

Another embodiment of this invention is directed to a compound of the formula I, or a pharmaceutically acceptable salt, solvate, ester or prodrug thereof, wherein:

$R^2$ and $R^6$ are joined together to form a C4-C8 cycloalkyl, C4-C8 cycloalkenyl, 5-8 membered heterocyclyl or 5-8 membered heterocyclenyl moiety, wherein each of said cycloalkyl or heterocyclyl moiety is optionally substituted with 1-5 independently selected $R^{21}$ substituents; and U, W, G, V, $R^1$, $R^3$, $R^4$, $R^5$, $R^6$, $R^7$, $R^8$, $R^9$, $R^{10}$ $R^{11}$, $R^{12}$, $R^{13}$, $R^{14}$, $R^{15A}$, $R^{15}$, $R^{16}$, $R^{17}$, $R^{18}$, $R^{19}$, $R^{20}$, $R^{21}$, $R^{22}$ and $R^{24}$ are as defined for formula I.

Another embodiment of this invention is directed to a compound of the formula I, or a pharmaceutically acceptable salt, solvate, ester or prodrug thereof, wherein:

$R^2$ and $R^6$ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected $R^{21}$ substituents;

U, W, G, V, $R^1$, $R^3$, $R^4$, $R^5$, $R^6$, $R^7$, $R^8$, $R^9$, $R^{10}$$R^{11}$, $R^{12}$, $R^{13}$, $R^{14}$, $R^{15A}$, $R^{15}$, $R^{16}$, $R^{17}$, $R^{18}$, $R^{19}$, $R^{20}$, $R^{21}$, $R^{22}$ and $R^{24}$ are as defined for formula I; and at least one (e.g., 1 to 3, or 1-2, or 1) group selected from the group consisting of: —$SF_5$, —$OSF_5$, and —$Si(R^{24})_3$ is present, and wherein each $R^{24}$ is independently selected, and wherein there is more than one group, each group is independently selected.

Another embodiment of this invention is directed to a compound of the formula I, or a pharmaceutically acceptable salt, solvate, ester or prodrug thereof, wherein:

$R^2$ and $R^6$ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected $R^{21}$ substituents;

U, W, G, V, $R^1$, $R^2$, $R^3$, $R^4$, $R^5$, $R^6$, $R^7$, $R^8$, $R^9$, $R^{10}$$R^{11}$, $R^{12}$, $R^{13}$, $R^{14}$, $R^{15A}$, $R^{15}$, $R^{16}$, $R^{17}$, $R^{18}$, $R^{19}$, $R^{20}$, $R^{21}$, $R^{22}$ and $R^{24}$ are as defined for formula I; and at least one (e.g., 1 to 3, or 1-2, or 1) group selected from the group consisting of: —SF$_5$ and —OSF$_5$ is present, and when there is more than one group, each group is independently selected.

Another embodiment of this invention is directed to a compound of the formula I, or a pharmaceutically acceptable salt, solvate, ester or prodrug thereof, wherein:

R$^1$ and R$^2$ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected R$^{21}$ substituents; and R$^2$ and R$^6$ are joined together to form a C4-C8 cycloalkyl, C4-C8 cycloalkenyl, 5-8 membered heterocyclyl or 5-8 membered heterocyclenyl moiety, wherein each of said cycloalkyl or heterocyclyl moiety is optionally substituted with 1-5 independently selected R$^{21}$ substituents; and U, W, G, V, R$^3$, R$^4$, R$^6$, R$^7$, R$^8$, R$^9$, R$^{10}$R$^{11}$, R$^{12}$, R$^{13}$, R$^{14}$, R$^{15A}$, R$^{15}$, R$^{16}$, R$^{17}$, R$^{18}$, R$^{19}$, R$^{20}$, R$^{21}$, R$^{22}$ and R$^{24}$ are as defined for formula I.

Another embodiment of this invention is directed to a compound of the formula I, or a pharmaceutically acceptable salt, solvate, ester or prodrug thereof, wherein:

R$^1$ and R$^2$ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected R$^{21}$ substituents; and R$^2$ and R$^6$ are joined together to form a C4-C8 cycloalkyl, C4-C8 cycloalkenyl, 5-8 membered heterocyclyl or 5-8 membered heterocyclenyl moiety, wherein each of said cycloalkyl or heterocyclyl moiety is optionally substituted with 1-5 independently selected R$^{21}$ substituents; and U, W, G, V, R$^3$, R$^4$, R$^5$, R$^7$, R$^8$, R$^9$, R$^{10}$ R$^{11}$, R$^{12}$, R$^{13}$, R$^{14}$, R$^{15A}$, R$^{15}$, R$^{16}$, R$^{17}$, R$^{18}$, R$^{19}$, R$^{20}$, R$^{21}$, R$^{22}$ and R$^{24}$ and are as defined for formula I; and at least one (e.g., 1 to 3, or 1-2, or 1) group selected from the group consisting of: —SF$_5$, —OSF$_5$, and —Si(R$^{24}$)$_3$ is present, and wherein each R$^{24}$ is independently selected, and wherein there is more than one group, each group is independently selected.

Another embodiment of this invention is directed to a compound of the formula I, or a pharmaceutically acceptable salt, solvate, ester or prodrug thereof, wherein:

R$^1$ and R$^2$ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected R$^{21}$ substituents; and R$^2$ and R$^6$ are joined together to form a C4-C8 cycloalkyl, C4-C8 cycloalkenyl, 5-8 membered heterocyclyl or 5-8 membered heterocyclenyl moiety, wherein each of said cycloalkyl or heterocyclyl moiety is optionally substituted with 1-5 independently selected R$^{21}$ substituents; and U, W, G, V, R$^3$, R$^4$, R$^5$, R$^7$, R$^8$, R$^9$, R$^{10}$R$^{11}$, R$^{12}$, R$^{13}$, R$^{14}$, R$^{15A}$, R$^{15}$, R$^{16}$, R$^{17}$, R$^{18}$, R$^{19}$, R$^{20}$, R$^{21}$, R$^{22}$ and R$^{24}$ are as defined for formula I; and at least one (e.g., 1 to 3, or 1-2, or 1) group selected from the group consisting of: —SF$_5$ and —OSF$_5$ is present, and when there is more than one group, each group is independently selected.

Other embodiments of this invention are directed to any one of the above formula I embodiments wherein U is N.

Other embodiments of this invention are directed to any one of the above formula I embodiments wherein W is —NH—.

Other embodiments of this invention are directed to any one of the above formula I embodiments wherein W is —O—.

Other embodiments of this invention are directed to any one of the above formula I embodiments wherein W is —C(O)—.

Other embodiments of this invention are directed to any one of the above formula I embodiments wherein W is —S—.

Other embodiments of this invention are directed to any one of the above formula I embodiments wherein W is —S—.

Other embodiments of this invention are directed to any one of the above formula I embodiments wherein W is —S(O)—.

Other embodiments of this invention are directed to any one of the above formula I embodiments wherein W is —S(O)$_2$—.

Other embodiments of this invention are directed to any one of the above formula I embodiments wherein W is —C(R$^{11}$)(R$^{12}$)—.

Other embodiments of this invention are directed to any one of the above formula I embodiments wherein U is N and W is —O—.

Other embodiments of this invention are directed to any one W is selected from the group consisting of a bond; —NH—, —O—, —C(O)—, —S—, —S(O)—, —S(O$_2$)—, and —C(R$^{11}$)(R$^{12}$)—:

G is selected from the group consisting of —C(R$^3$)(R$^4$)— (wherein R$^3$ and R$^4$ are independently selected), —(C(R$^3$) (R$^4$))$_2$— (wherein each R$^3$ and each R$^4$ are independently selected), —C(O)— and —N(R$^{13}$)—, with the proviso that when W is —O— or —S—, G is not —N(R$^{13}$)— or —C(O)—, and with the proviso that when G is —(C(R$^3$) (R$^4$))$_2$— then W is not a bond, and with the proviso that when G is —N(R$^{13}$)—, then W is not —NH—;

Other embodiments of this invention are directed to any one of the above formula I embodiments wherein U is N, G is —C(R$^3$)(R$^4$)— and W is —O—.

Other embodiments of this invention are directed to any one of the above formula I embodiments wherein U is N, G is —C(R$^3$)(R$^4$)— and W is —O—, and wherein R$^3$ and R$^4$ of the —C(R$^3$)(R$^4$)— G moiety are taken together with the carbon to which they are bound to form a cycloalkyl spiro ring, cycloalkenyl spiro ring, heterocycloalkyl spiro ring, or heterocycloalkenyl spiro ring.

Other embodiments of this invention are directed to any one of the above formula I embodiments wherein U is N, G is —(C(R$^3$)(R$^4$))$_2$— and W is —O—.

Other embodiments of this invention are directed to any one of the above formula I embodiments wherein U is N, G is —(C(R$^3$)(R$^4$))$_2$—, and W is —O—, and wherein one R$^3$ and one R$^4$ on one carbon of the —(C(R$^3$)(R$^4$))$_2$— G moiety are taken together with the carbon to which they are bound to form a cycloalkyl spiro ring, cycloalkenyl spiro ring, heterocycloalkyl spiro ring, or heterocycloalkenyl spiro ring.

Other embodiments of this invention are directed to any one of the above formula I embodiments wherein U is CH and W is —O—.

Other embodiments of this invention are directed to any one of the above formula I embodiments wherein U is CH, G is —C(R$^3$)(R$^4$)— and W is —O—, and wherein R$^3$ and R$^4$ of the —C(R$^3$)(R$^4$)— G moiety are taken together with the carbon to which they are bound to form a cycloalkyl spiro ring, cycloalkenyl spiro ring, heterocycloalkyl spiro ring, or heterocycloalkenyl spiro ring.

Other embodiments of this invention are directed to any one of the above formula I embodiments wherein U is CH, G is —C(R$^3$)(R$^4$)— and W is —O—.

Other embodiments of this invention are directed to any one of the above formula I embodiments wherein U is CH, G is —C(R$^3$)(R$^4$))$_2$—, and W is —O—, and wherein one R$^3$ and one R$^4$ on one carbon of the —(C(R$^3$)(R$^4$))$_2$— G moiety are taken together with the carbon to which they are bound to form a cycloalkyl spiro ring, cycloalkenyl spiro ring, heterocycloalkyl spiro ring, or heterocycloalkenyl spiro ring.

Other embodiments of this invention are directed to any one of the above formula I embodiments wherein U is CH, G is —(C(R$^3$)(R$^4$))$_2$—, and W is —O—.

Those skilled in the art will appreciate that for the compounds of the invention:

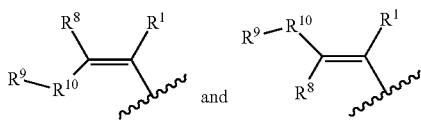

are isomers

Those skilled in the art will appreciate that in the compounds of the invention R$^6$ can be:

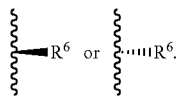

Those skilled in the art will appreciate that in the compounds of the invention R$^7$ can be:

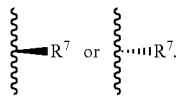

Thus, for example, in embodiments of this invention R$^6$ and R$^7$ can be:

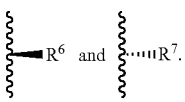

In other embodiments of this invention R$^6$ and R$^7$ can be:

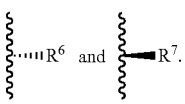

In another embodiment, U is C(R$^5$).
In another embodiment, U is N.
In another embodiment, R$^2$ is H.
In another embodiment, R$^2$ is alkyl.
In another embodiment, R$^2$ is methyl.
In another embodiment, R$^2$ is alkoxyalkyl-.
In another embodiment, R$^2$ is 3-methoxypropyl-.

In another embodiment, U is N and R$^2$ is 3-methoxypropyl-.
In another embodiment, W is a bond.
In another embodiment, W is —NH—.
In another embodiment, W is —O—.
In another embodiment, W is —C(O)—.
In another embodiment, W is —S—.
In another embodiment, W is —S(O)—.
In another embodiment, W is —S(O$_2$)—.
In another embodiment, W is —C(R$^{11}$)(R$^{12}$)—.
In another embodiment, =N—W-G- is =N—C(R$^{11}$R$^{12}$)—C(O)—.
In another embodiment, G is —C(R$^3$)(R$^4$)—.
In another embodiment, G is —C(R$^3$)(R$^4$)—, and one of R$^3$ or R$^4$ is H.
In another embodiment, G is —C(R$^3$)(R$^4$)—, and one of R$^3$ or R$^4$ is aryl (e.g., phenyl).
In another embodiment, G is —C(R$^3$)(R$^4$)—, and one of R$^3$ or R$^4$ is aryl (e.g., phenyl) substituted with 1 to 3 independently selected R$^{21}$ groups.
In another embodiment, G is —C(R$^3$)(R$^4$)—, and one of R$^3$ or R$^4$ is aryl (e.g., phenyl) substituted with 1 to 3 independently selected halos.
In another embodiment, G is —C(R$^3$)(R$^4$)—, and one of R$^3$ or R$^4$ is phenyl substituted with 1 to 3 independently selected R$^{21}$ groups.
In another embodiment, G is —C(R$^3$)(R$^4$)—, and one of R$^3$ or R$^4$ is phenyl substituted with 1 to 3 independently selected halos.
In another embodiment, G is —C(R$^3$)(R$^4$)—, and one of R$^3$ or R$^4$ is phenyl substituted with 1 to 3 independently selected F.
In another embodiment, G is —C(R$^3$)(R$^4$)—, and one of R$^3$ or R$^4$ is aryl (e.g., phenyl), and the other one of said R$^3$ or R$^4$ is H.
In another embodiment, G is —C(R$^3$)(R$^4$)—, and one of R$^3$ or R$^4$ is aryl (e.g., phenyl) substituted with 1 to 3 independently selected R$^{21}$ groups, and the other one of said R$^3$ or R$^4$ is H.
In another embodiment, G is —C(R$^3$)(R$^4$)—, and one of R$^3$ or R$^4$ is aryl (e.g., phenyl) substituted with 1 to 3 independently selected halos, and the other one of said R$^3$ or R$^4$ is H.
In another embodiment, G is —C(R$^3$)(R$^4$)—, and one of R$^3$ or R$^4$ is phenyl substituted with 1 to 3 independently selected R$^{21}$ groups, and the other one of said R$^3$ or R$^4$ is H.
In another embodiment, G is —C(R$^3$)(R$^4$)—, and one of R$^3$ or R$^4$ is phenyl substituted with 1 to 3 independently selected halos, and the other one of said R$^3$ or R$^4$ is H.
In another embodiment, G is —C(R$^3$)(R$^4$)—, and one of R$^3$ or R$^4$ is phenyl substituted with 1 to 3 independently selected F, and the other one of said R$^3$ or R$^4$ is H.
In another embodiment, G is —C(R$^3$)(R$^4$)—, and one of R$^3$ or R$^4$ is heteroaryl (e.g., thienyl).
In another embodiment, G is —C(R$^3$)(R$^4$)—, and one of R$^3$ or R$^4$ is heteroaryl (e.g., thienyl) substituted with 1 to 3 independently selected R$^{21}$ groups.
In another embodiment, G is —C(R$^3$)(R$^4$)—, and one of R$^3$ or R$^4$ is heteroaryl (e.g., thienyl) substituted with 1 to 3 independently selected halos.
In another embodiment, G is —C(R$^3$)(R$^4$)—, and one of R$^3$ or R$^4$ is thienyl substituted with 1 to 3 independently selected R$^{21}$ groups.
In another embodiment, G is —C(R$^3$)(R$^4$)—, and one of R$^3$ or R$^4$ is thienyl substituted with 1 to 3 independently selected halos.

In another embodiment, G is —C($R^3$)($R^4$)—, and one of $R^3$ or $R^4$ is thienyl substituted with 1 to 3 independently selected F.

In another embodiment, G is —C($R^3$)($R^4$)—, and one of $R^3$ or $R^4$ is heteroaryl (e.g., thienyl), and the other one of said $R^3$ or $R^4$ is H.

In another embodiment, G is —C($R^3$)($R^4$)—, and one of $R^3$ or $R^4$ is heteroaryl (e.g., thienyl) substituted with 1 to 3 independently selected $R^{21}$ groups, and the other one of said $R^3$ or $R^4$ is H.

In another embodiment, G is —C($R^3$)($R^4$)—, and one of $R^3$ or $R^4$ is heteroaryl (e.g., thienyl) substituted with 1 to 3 independently selected halos, and the other one of said $R^3$ or $R^4$ is H.

In another embodiment, G is —C($R^3$)($R^4$)—, and one of $R^3$ or $R^4$ is thienyl substituted with 1 to 3 independently selected $R^{21}$ groups, and the other one of said $R^3$ or $R^4$ is H.

In another embodiment, G is —C($R^3$)($R^4$)—, and one of $R^3$ or $R^4$ is thienyl substituted with 1 to 3 independently selected halos, and the other one of said $R^3$ or $R^4$ is H.

In another embodiment, G is —C($R^3$)($R^4$)—, and one of $R^3$ or $R^4$ is thienyl substituted with 1 to 3 independently selected F, and the other one of said $R^3$ or $R^4$ is H.

In another embodiment, G is —C($R^3$)($R^4$)—, and one of $R^3$ or $R^4$ is cycloalkyl (e.g., cyclopropyl).

In another embodiment, G is —C($R^3$)($R^4$)—, and one of $R^3$ or $R^4$ is cycloalkyl (e.g., cyclopropyl) optionally substituted with 1 to 3 independently selected $R^{21}$ groups.

In another embodiment, G is —C($R^3$)($R^4$)—, and one of $R^3$ or $R^4$ is cycloalkyl (e.g., cyclopropyl) optionally substituted with 1 to 3 independently selected halos.

In another embodiment, G is —C($R^3$)($R^4$)—, and one of $R^3$ or $R^4$ is cyclopropyl optionally substituted with 1 to 3 independently selected $R^{21}$ groups.

In another embodiment, G is —C($R^3$)($R^4$)—, and one of $R^3$ or $R^4$ is cyclopropyl optionally substituted with 1 to 3 independently selected halos.

In another embodiment, G is —C($R^3$)($R^4$)—, and one of $R^3$ or $R^4$ is cyclopropyl optionally substituted with 1 to 3 independently selected F.

In another embodiment, G is —C($R^3$)($R^4$)—, and one of $R^3$ or $R^4$ is cycloalkyl (e.g., cyclopropyl), and the other one of said $R^3$ or $R^4$ is H.

In another embodiment, G is —C($R^3$)($R^4$)—, and one of $R^3$ or $R^4$ is cycloalkyl (e.g., cyclopropyl) optionally substituted with 1 to 3 independently selected $R^{21}$ groups, and the other one of said $R^3$ or $R^4$ is H.

In another embodiment, G is —C($R^3$)($R^4$)—, and one of $R^3$ or $R^4$ is cycloalkyl (e.g., cyclopropyl) optionally substituted with 1 to 3 independently selected halos, and the other one of said $R^3$ or $R^4$ is H.

In another embodiment, G is —C($R^3$)($R^4$)—, and one of $R^3$ or $R^4$ is cyclopropyl optionally substituted with 1 to 3 independently selected $R^{21}$ groups, and the other one of said $R^3$ or $R^4$ is H.

In another embodiment, G is —C($R^3$)($R^4$)—, and one of $R^3$ or $R^4$ is cyclopropyl optionally substituted with 1 to 3 independently selected halos, and the other one of said $R^3$ or $R^4$ is H.

In another embodiment, G is —C($R^3$)($R^4$)—, and one of $R^3$ or $R^4$ is cyclopropyl optionally substituted with 1 to 3 independently selected F, and the other one of said $R^3$ or $R^4$ is H.

In another embodiment, G is —C($R^3$)($R^4$)—, and one of $R^3$ or $R^4$ is alkyl (e.g., methyl or ethyl).

In another embodiment, G is —C($R^3$)($R^4$)—, and one of $R^3$ or $R^4$ is alkyl (e.g., methyl or ethyl) optionally substituted with 1 to 3 independently selected $R^{21}$ groups.

In another embodiment, G is —C($R^3$)($R^4$)—, and one of $R^3$ or $R^4$ is alkyl (e.g., methyl or ethyl) substituted with an —$OR^{15}$ group.

In another embodiment, G is —C($R^3$)($R^4$)—, and one of $R^3$ or $R^4$ is alkyl (e.g., methyl or ethyl) substituted with an —$OR^{15}$ group, wherein $R^{15}$ is H.

In another embodiment, G is —C($R^3$)($R^4$)—, and one of $R^3$ or $R^4$ is methyl.

In another embodiment, G is —C($R^3$)($R^4$)—, and one of $R^3$ or $R^4$ is methyl substituted with an —$OR^{15}$ group.

In another embodiment, G is —C($R^3$)($R^4$)—, and one of $R^3$ or $R^4$ is methyl substituted with an —$OR^{15}$ group, wherein $R^{15}$ is H.

In another embodiment, G is —C($R^3$)($R^4$)—, and one of $R^3$ or $R^4$ is ethyl.

In another embodiment, G is —C($R^3$)($R^4$)—, and one of $R^3$ or $R^4$ is ethyl substituted with an —$OR^{15}$ group.

In another embodiment, G is —C($R^3$)($R^4$)—, and one of $R^3$ or $R^4$ is ethyl substituted with an —$OR^{15}$ group, wherein $R^{15}$ is H.

In another embodiment, G is —C($R^3$)($R^4$)—, and one of $R^3$ or $R^4$ is alkyl (e.g., methyl or ethyl), and the other of said $R^3$ or $R^4$ is H.

In another embodiment, G is —C($R^3$)($R^4$)—, and one of $R^3$ or $R^4$ is alkyl (e.g., methyl or ethyl) optionally substituted with 1 to 3 independently selected $R^{21}$ groups, and the other of said $R^3$ or $R^4$ is H.

In another embodiment, G is —C($R^3$)($R^4$)—, and one of $R^3$ or $R^4$ is alkyl (e.g., methyl or ethyl) substituted with an —$OR^{15}$ group, and the other of said $R^3$ or $R^4$ is H.

In another embodiment, G is —C($R^3$)($R^4$)—, and one of $R^3$ or $R^4$ is alkyl (e.g., methyl or ethyl) substituted with an —$OR^{15}$ group, wherein $R^{15}$ is H, and the other of said $R^3$ or $R^4$ is H.

In another embodiment, G is —C($R^3$)($R^4$)—, and one of $R^3$ or $R^4$ is methyl, and the other of said $R^3$ or $R^4$ is H.

In another embodiment, G is —C($R^3$)($R^4$)—, and one of $R^3$ or $R^4$ is methyl substituted with an —$OR^{15}$ group, and the other of said $R^3$ or $R^4$ is H.

In another embodiment, G is —C($R^3$)($R^4$)—, and one of $R^3$ or $R^4$ is methyl substituted with an —$OR^{15}$ group, wherein $R^{15}$ is H, and the other of said $R^3$ or $R^4$ is H.

In another embodiment, G is —C($R^3$)($R^4$)—, and one of $R^3$ or $R^4$ is ethyl, and the other of said $R^3$ or $R^4$ is H.

In another embodiment, G is —C($R^3$)($R^4$)—, and one of $R^3$ or $R^4$ is ethyl substituted with an —$OR^{15}$ group, and the other of said $R^3$ or $R^4$ is H.

In another embodiment, G is —C($R^3$)($R^4$)—, and one of $R^3$ or $R^4$ is ethyl substituted with an —$OR^{15}$ group, wherein $R^{15}$ is H, and the other of said $R^3$ or $R^4$ is H.

In another embodiment, G is —C($R^3$)($R^4$)—, and one of $R^3$ or $R^4$ is alkyl (e.g., methyl or ethyl) substituted with an —$OR^{15}$ group, wherein $R^{15}$ is ($R^{18}$)$_r$-alkyl- (e.g., ($R^{18}$)$_r$—CH$_2$—, or ($R^{18}$)$_r$—(CH$_2$)$_2$—), and $R^{18}$ is —OH, and r is 1.

In another embodiment, G is —C($R^3$)($R^4$)—, and one of $R^3$ or $R^4$ is alkyl (e.g., methyl or ethyl) substituted with an —$OR^{15}$ group, wherein $R^{15}$ is HO-alkyl- (e.g., HO—CH$_2$—, or HO—(CH$_2$)$_2$—).

In another embodiment, G is —C($R^3$)($R^4$)—, and one of $R^3$ or $R^4$ is methyl substituted with an —$OR^{15}$ group, wherein $R^{15}$ is HO-alkyl- (e.g., HO—CH$_2$—, or HO—(CH$_2$)$_2$—).

In another embodiment, G is —C($R^3$)($R^4$)—, and one of $R^3$ or $R^4$ is ethyl substituted with an —$OR^{15}$ group, wherein $R^{15}$ is HO-alkyl- (e.g., HO—CH$_2$—, or HO—(CH$_2$)$_2$—). In another embodiment, G is —C($R^3$)($R^4$)—, and one of $R^3$ or $R^4$ is methyl substituted with an —$OR^{15}$ group, wherein $R^{15}$ is HO—CH$_2$—.

In another embodiment, G is —C($R^3$)($R^4$)—, and one of $R^3$ or $R^4$ is ethyl substituted with an —$OR^{15}$ group, wherein $R^{15}$HO—CH$_2$—.

In another embodiment, G is —C($R^3$)($R^4$)—, and one of $R^3$ or $R^4$ is methyl substituted with an —$OR^{15}$ group, wherein $R^{15}$ is HO—(CH$_2$)$_2$—.

In another embodiment, G is —C($R^3$)($R^4$)—, and one of $R^3$ or $R^4$ is ethyl substituted with an —$OR^{15}$ group, wherein $R^{15}$ is HO—(CH$_2$)$_2$—.

In another embodiment, G is —C($R^3$)($R^4$)—, and one of $R^3$ or $R^4$ is alkyl (e.g., methyl or ethyl) substituted with an —$OR^{15}$ group, wherein $R^{15}$ is ($R^{18}$)$_r$-alkyl- (e.g., ($R^{18}$)$_r$—CH$_2$—, or ($R^{18}$)$_r$—(CH$_2$)$_2$—), and $R^{18}$ is —OH, and r is 1, and the other of said $R^3$ or $R^4$ is H.

In another embodiment, G is —C($R^3$)($R^4$)—, and one of $R^3$ or $R^4$ is alkyl (e.g., methyl or ethyl) substituted with an —$OR^{15}$ group, wherein $R^{15}$ is HO-alkyl- (e.g., HO—CH$_2$—, or HO—(CH$_2$)$_2$—), and the other of said $R^3$ or $R^4$ is H.

In another embodiment, G is —C($R^3$)($R^4$)—, and one of $R^3$ or $R^4$ is methyl substituted with an —$OR^{15}$ group, wherein $R^{15}$ is HO-alkyl- (e.g., HO—CH$_2$—, or HO—(CH$_2$)$_2$—), and the other of said $R^3$ or $R^4$ is H.

In another embodiment, G is —C($R^3$)($R^4$)—, and one of $R^3$ or $R^4$ is ethyl substituted with an —$OR^{15}$ group, wherein $R^{15}$ is HO-alkyl- (e.g., HO—CH$_2$—, or HO—(CH$_2$)$_2$—), and the other of said $R^3$ or $R^4$ is H.

In another embodiment, G is —C($R^3$)($R^4$)—, and one of $R^3$ or $R^4$ is methyl substituted with an —$OR^{15}$ group, wherein $R^{15}$ is HO—CH$_2$—, and the other of said $R^3$ or $R^4$ is H.

In another embodiment, G is —C($R^3$)($R^4$)—, and one of $R^3$ or $R^4$ is ethyl substituted with an —$OR^{15}$ group, wherein $R^{15}$HO—CH$_2$—, and the other of said $R^3$ or $R^4$ is H.

In another embodiment, G is —C($R^3$)($R^4$)—, and one of $R^3$ or $R^4$ is methyl substituted with an —$OR^{15}$ group, wherein $R^{15}$ is HO—(CH$_2$)$_2$—, and the other of said $R^3$ or $R^4$ is H.

In another embodiment, G is —C($R^3$)($R^4$)—, and one of $R^3$ or $R^4$ is ethyl substituted with an —$OR^{15}$ group, wherein $R^{15}$ is HO—(CH$_2$)$_2$—, and the other of said $R^3$ or $R^4$ is H.

In another embodiment, G is —(C($R^3$)($R^4$))$_2$— wherein each $R^3$ and $R^4$ is H, W is O, U is N, $R^1$ and $R^2$ are joined together to form a 5-8 membered (e.g., a 6 membered ring) heterocyclyl ring (such as, for example, piperidine).

In another embodiment, G is —(C($R^3$)($R^4$))$_2$— wherein each $R^3$ and $R^4$ is H, W is O, U is N, $R^1$ and $R^2$ are joined together to form a 5-8 membered (e.g., a 6 membered ring) heterocyclyl ring (such as, for example, piperidine), $R^6$ is H or alkyl (and in one example H), and $R^7$ is aryl (e.g., phenyl) or aryl (e.g., phenyl) substituted with 1-5 independently selected $R^{21}$ groups.

In another embodiment, G is —(C($R^3$)($R^4$))$_2$— wherein each $R^3$ and $R^4$ is H, W is O, U is N, $R^1$ and $R^2$ are joined together to form a 5-8 membered (e.g., a 6 membered ring) heterocyclyl ring (such as, for example, piperidine), $R^6$ is H, and $R^7$ is phenyl or phenyl substituted with 1-3 (e.g., 1 or 2) independently selected $R^{21}$ groups.

In another embodiment, G is —(C($R^3$)($R^4$))$_2$— wherein each $R^3$ and $R^4$ is H, W is O, U is N, $R^1$ and $R^2$ are joined together to form a 5-8 membered (e.g., a 6 membered ring) heterocyclyl ring (such as, for example, piperidine), $R^6$ is H, and $R^7$ is phenyl or phenyl substituted with 1-3 (e.g., 1 or 2) independently selected halo groups (i.e., the $R^{21}$ groups are halo).

In another embodiment, G is —(C($R^3$)($R^4$))$_2$— wherein each $R^3$ and $R^4$ is independently selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), aryl (e.g., phenyl), and aryl (e.g., phenyl) substituted with 1-5 independently selected $R^{21}$ groups.

In another embodiment, G is —(C($R^3$)($R^4$))$_2$— wherein each $R^3$ and $R^4$ is independently selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), phenyl, and phenyl substituted with 1-3 independently selected halo groups (i.e., the $R^{21}$ groups are halo).

In another embodiment, G is —(C($R^3$)($R^4$))$_2$—wherein on one carbon $R^3$ and $R^4$ are H, and on the other carbon $R^3$ and $R^4$ are each independently selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), phenyl, and phenyl substituted with 1-3 independently selected halo groups (i.e., the $R^{21}$ groups are halo).

In another embodiment, G is —(C($R^3$)($R^4$))$_2$—wherein on one carbon $R^3$ and $R^4$ are H, and on the other carbon one of $R^3$ and $R^4$ is H and the other is selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), phenyl, and phenyl substituted with 1-3 independently selected halo groups (i.e., the $R^{21}$ groups are halo).

In another embodiment, G is —(C($R^3$)($R^4$))$_2$—wherein on one carbon $R^3$ and $R^4$ are H, and on the other carbon one of $R^3$ and $R^4$ is H and the other is selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), phenyl, and phenyl substituted with 1-3 independently selected halo groups (i.e., the $R^{21}$ groups are halo), and $R^6$ and $R^7$ are each H.

In another embodiment, G is —(C($R^3$)($R^4$))$_2$—wherein on one carbon $R^3$ and $R^4$ are H, and on the other carbon one of $R^3$ and $R^4$ is H and the other is selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), phenyl, and phenyl substituted with 1-5 independently selected halo groups (i.e., the $R^{21}$ groups are halo), $R^6$ is H or alkyl, and $R^7$ is phenyl or phenyl substituted with 1-3 (e.g., 1 or 2) independently selected $R^{21}$ groups.

In another embodiment, G is —(C($R^3$)($R^4$))$_2$—wherein on one carbon $R^3$ and $R^4$ are H, and on the other carbon one of $R^3$ and $R^4$ is H and the other is selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), phenyl, and phenyl substituted with 1-5 independently selected halo groups (i.e., the $R^{21}$ groups are halo), $R^6$ is H or alkyl, and $R^7$ is phenyl or phenyl substituted with 1-3 (e.g., 1 or 2) independently selected halo groups (i.e., the $R^{21}$ groups are halo).

In another embodiment, G is —(C($R^3$)($R^4$))$_2$— wherein each $R^3$ and $R^4$ is H, and $R^8$ is H.

In another embodiment, G is —(C($R^3$)($R^4$))$_2$— wherein each $R^3$ and $R^4$ is H, W is O, U is N, $R^1$ and $R^2$ are joined together to form a 5-8 membered (e.g., a 6 membered ring) heterocyclyl ring (such as, for example, piperidine), and $R^8$ is H.

In another embodiment, G is —(C($R^3$)($R^4$))$_2$— wherein each $R^3$ and $R^4$ is H, W is O, U is N, $R^1$ and $R^2$ are joined together to form a 5-8 membered (e.g., a 6 membered ring) heterocyclyl ring (such as, for example, piperidine), $R^6$ is H or alkyl (and in one example H), $R^7$ is aryl (e.g., phenyl) or aryl (e.g., phenyl) substituted with 1-5 independently selected $R^{21}$ groups, and $R^8$ is H.

In another embodiment, G is —$(C(R^3)(R^4))_2$— wherein each $R^3$ and $R^4$ is H, W is O, U is N, $R^1$ and $R^2$ are joined together to form a 5-8 membered (e.g., a 6 membered ring) heterocyclyl ring (such as, for example, piperidine), $R^6$ is H, $R^7$ is phenyl or phenyl substituted with 1-3 (e.g., 1 or 2) independently selected $R^{21}$ groups, and $R^8$ is H.

In another embodiment, G is —$(C(R^3)(R^4))_2$— wherein each $R^3$ and $R^4$ is H, W is O, U is N, $R^1$ and $R^2$ are joined together to form a 5-8 membered (e.g., a 6 membered ring) heterocyclyl ring (such as, for example, piperidine), $R^6$ is H, $R^7$ is phenyl or phenyl substituted with 1-3 (e.g., 1 or 2) independently selected halo groups (i.e., the $R^{21}$ groups are halo), and $R^8$ is H.

In another embodiment, G is —$(C(R^3)(R^4))_2$— wherein each $R^3$ and $R^4$ is independently selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), aryl (e.g., phenyl), and aryl (e.g., phenyl) substituted with 1-5 independently selected $R^{21}$ groups, and $R^8$ is H.

In another embodiment, G is —$(C(R^3)(R^4))_2$— wherein each $R^3$ and $R^4$ is independently selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), phenyl, and phenyl substituted with 1-3 independently selected halo groups (i.e., the $R^{21}$ groups are halo), and $R^8$ is H.

In another embodiment, G is —$(C(R^3)(R^4))_2$— wherein on one carbon $R^3$ and $R^4$ are H, and on the other carbon $R^3$ and $R^4$ are each independently selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), phenyl, and phenyl substituted with 1-3 independently selected halo groups (i.e., the $R^{21}$ groups are halo), and $R^8$ is H.

In another embodiment, G is —$(C(R^3)(R^4))_2$— wherein on one carbon $R^3$ and $R^4$ are H, and on the other carbon one of $R^3$ and $R^4$ is H and the other is selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), phenyl, and phenyl substituted with 1-3 independently selected halo groups (i.e., the $R^{21}$ groups are halo), and $R^8$ is H.

In another embodiment, G is —$(C(R^3)(R^4))_2$— wherein on one carbon $R^3$ and $R^4$ are H, and on the other carbon one of $R^3$ and $R^4$ is H and the other is selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), phenyl, and phenyl substituted with 1-3 independently selected halo groups (i.e., the $R^{21}$ groups are halo), $R^6$ and $R^7$ are each H, and $R^8$ is H.

In another embodiment, G is —$(C(R^3)(R^4))_2$— wherein on one carbon $R^3$ and $R^4$ are H, and on the other carbon one of $R^3$ and $R^4$ is H and the other is selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), phenyl, and phenyl substituted with 1-5 independently selected halo groups (i.e., the $R^{21}$ groups are halo), $R^6$ is H or alkyl, $R^7$ is phenyl or phenyl substituted with 1-3 (e.g., 1 or 2) independently selected $R^{21}$ groups, and $R^8$ is H.

In another embodiment, G is —$(C(R^3)(R^4))_2$— wherein on one carbon $R^3$ and $R^4$ are H, and on the other carbon one of $R^3$ and $R^4$ is H and the other is selected from the group consisting of H, alkyl (e.g., methyl), —$OR^{15}$ (e.g., $R^{15}$ is H or alkyl, wherein in one example said —$OR^{15}$ is —OH and in another example said —$OR^{15}$ is —O-propyl), phenyl, and phenyl substituted with 1-5 independently selected halo groups (i.e., the $R^{21}$ groups are halo), $R^6$ is H or alkyl, $R^7$ is phenyl or phenyl substituted with 1-3 (e.g., 1 or 2) independently selected halo groups (i.e., the $R^{21}$ groups are halo), and $R^8$ is H.

In another embodiment of this invention is directed to compounds of formula I wherein:
(1) none of the rings described in (i) to (xii) of formula I are formed (that is (a) $R^1$ and $R^2$ are not joined together, and (b) $R^2$ and $R^6$ are not joined together, and (c) $R^1$ and $R^2$ are not joined together, and $R^2$ and $R^6$ are not joined together (i.e., $R^2$ is not joined together with $R^1$ and $R^6$), and (d) $R^6$ is not joined together with either $R^3$ or $R^4$ (i.e., $R^6$ and $R^3$ are not joined together, or $R^6$ and $R^4$ are not joined together), and (e) $R^6$ and $R^{13}$ of the —$N(R^{13})$—G moiety, are not joined together, and (f) $R^3$ and $R^4$ of the —$C(R^3)(R^4)$—G moiety are not joined together, and (g) one $R^3$ and one $R^4$ on one carbon of the —$(C(R^3)(R^4))_2$—G moiety are not joined together, and (h) an $R^3$ and an $R^4$ on adjacent carbons of the —$(C(R^3)(R^4))_2$-G moiety are not joined together, and (i) $R^1$ and $R^2$, and $R^6$ and either $R^3$ or $R^4$, are not joined together to form the rings described in (ix) above, and (j) $R^1$ and $R^2$, and $R^3$ and $R^4$, are not joined together to form the rings described in (x) above, and (k) $R^1$ and $R^2$, and $R^3$ and $R^4$, are not joined together to form the rings described in (xi) above, and (l) $R^1$ and $R^2$, and $R^3$ and $R^4$, are not joined together to form the rings described in (xii) above (that is none of the rings described above in (i) to (xii) are formed);
(2) U is N;
(3) V is a bond;
(4) W is O;
(5) G is —$C(R^3)(R^4)$—; and
(6) all remaining substituents are as described for formula I.

In another embodiment of this invention is directed to compounds of formula I wherein:
(1) none of the rings described in (i) to (xii) of formula I are formed (that is (a) $R^1$ and $R^2$ are not joined together, and (b) $R^2$ and $R^6$ are not joined together, and (c) $R^1$ and $R^2$ are not joined together, and $R^2$ and $R^6$ are not joined together (i.e., $R^2$ is not joined together with $R^1$ and $R^6$), and (d) $R^6$ is not joined together with either $R^3$ or $R^4$ (i.e., $R^6$ and $R^3$ are not joined together, or $R^6$ and $R^4$ are not joined together), and (e) $R^6$ and $R^{13}$ of the —$N(R^{13})$—G moiety, are not joined together, and (f) $R^3$ and $R^4$ of the —$C(R^3)(R^4)$—G moiety are not joined together, and (g) one $R^3$ and one $R^4$ on one carbon of the —$(C(R^3)(R^4))_2$—G moiety are not joined together, and (h) an $R^3$ and an $R^4$ on adjacent carbons of the —$(C(R^3)(R^4))_2$—G moiety are not joined together, and (i) $R^1$ and $R^2$, and $R^6$ and either $R^3$ or $R^4$, are not joined together to form the rings described in (ix) above, and (j) $R^1$ and $R^2$, and $R^3$ and $R^4$, are not joined together to form the rings described in (x) above, and (k) $R^1$ and $R^2$, and $R^3$ and $R^4$, are not joined together to form the rings described in (xi) above, and (l) $R^1$ and $R^2$, and $R^3$ and $R^4$, are not joined together to form the rings described in (xii) above (that is none of the rings described above in (i) to (xii) are formed);
(2) U is N;
(3) V is a bond;
(4) W is O;

(5) G is —C($R^3$)($R^4$)—;
(6) $R^2$ is selected from the group consisting of (a) H, (b) alkyl, and (c) alkyl substituted with 1 to 5 $R^{21}$ groups; and
(7) all remaining substituents are as described for formula I.

In another embodiment of this invention is directed to compounds of formula I wherein:
(1) none of the rings described in (i) to (xii) of formula I are formed (that is (a) $R^1$ and $R^2$ are not joined together, and (b) $R^2$ and $R^6$ are not joined together, and (c) $R^1$ and $R^2$ are not joined together, and $R^2$ and $R^6$ are not joined together (i.e., $R^2$ is not joined together with $R^1$ and $R^6$), and (d) $R^6$ is not joined together with either $R^3$ or $R^4$ (i.e., $R^6$ and $R^3$ are not joined together, or $R^6$ and $R^4$ are not joined together), and (e) $R^6$ and $R^{13}$ of the —N($R^{13}$)—G moiety, are not joined together, and (f) $R^3$ and $R^4$ of the —C($R^3$)($R^4$)— G moiety are not joined together, and (g) one $R^3$ and one $R^4$ on one carbon of the —(C($R^3$)($R^4$))$_2$— G moiety are not joined together, and (h) an $R^3$ and an $R^4$ on adjacent carbons of the —(C($R^3$)($R^4$))$_2$— G moiety are not joined together, and (i) $R^1$ and $R^2$, and $R^6$ and either $R^3$ or $R^4$, are not joined together to form the rings described in (ix) above, and (j) $R^1$ and $R^2$, and $R^3$ and $R^4$, are not joined together to form the rings described in (x) above, and (k) $R^1$ and $R^2$, and $R^3$ and $R^4$, are not joined together to form the rings described in (xi) above, and (l) $R^1$ and $R^2$, and $R^3$ and $R^4$, are not joined together to form the rings described in (xii) above (that is none of the rings described above in (i) to (xii) are formed);
(2) U is N;
(3) V is a bond;
(4) W is O;
(5) G is —C($R^3$)($R^4$)—;
(6) $R^2$ is selected from the group consisting of H, alkyl, and alkyl substituted with 1 to 5 $R^{21}$ groups;
(7) one of $R^3$ or $R^4$ is H, and the remaining $R^3$ or $R^4$ is selected from the group comprising:
(a) aryl (e.g., phenyl),
(b) aryl (e.g., phenyl) substituted with 1 to 3 independently selected $R^{21}$ groups (and (i) in one example said aryl is substituted with 1 to 3 halos, (ii) in another example said aryl is substituted with 1 to 3 F, (iii) in another example said aryl is substituted with 3 F, (iv) in another example said aryl is substituted with 2 F, and (v) in another example said aryl is substituted with 1 F),
(c) heteroaryl (e.g., thienyl), (d) heteroaryl (e.g., thienyl) substituted with 1 to 3 independently selected $R^{21}$ groups (and (i) in one example said heteroaryl is substituted with 1 to 3 halos, (ii) in another example said heteroaryl is substituted with 1 to 3 F, and (iii) in another example said heteroaryl is substituted with 1 F),
(d) cycloalkyl (e.g., cyclopropyl),
(e) cycloalkyl (e.g., cyclopropyl) substituted with 1 to 3 independently $R^{21}$ substituents (and (i) in one example said cycloalkyl is substituted with 1 to 3 halos, and (ii) in another example said cycloalkyl is substituted with 1 to 3 F),
(f) alkyl (e.g., methyl or ethyl),
(g) alkyl substituted with 1 to 3 independently selected $R^{21}$ groups (and (i) in one example said alkyl is substituted with one —$OR^{15}$ group, (ii) in another example said alkyl is substituted with one —$OR^{15}$ group wherein $R^{15}$ is H, (iii) in another said alkyl is substituted with one —$OR^{15}$ group wherein $R^{15}$ is ($R^{18}$)$_r$-alkyl-, (iv) in another example said alkyl is substituted with one —$OR^{15}$ group wherein $R^{15}$ is ($R^{18}$)$_r$-alkyl- and $R^{18}$ is —OH and r is 1, and (v) in another example said alkyl is substituted with one —$OR^{15}$ wherein $R^{15}$ is HO—$CH_2$—, or HO—($CH_2$)$_2$—); and
(8) all other substituents are as described for formula I.

In another embodiment of this invention is directed to compounds of formula I wherein:
(1) none of the rings described in (i) to (xii) of formula I are formed (that is (a) $R^1$ and $R^2$ are not joined together, and (b) $R^2$ and $R^6$ are not joined together, and (c) $R^1$ and $R^2$ are not joined together, and $R^2$ and $R^6$ are not joined together (i.e., $R^2$ is not joined together with $R^1$ and $R^6$), and (d) $R^6$ is not joined together with either $R^3$ or $R^4$ (i.e., $R^6$ and $R^3$ are not joined together, or $R^6$ and $R^4$ are not joined together), and (e) $R^6$ and $R^{13}$ of the —N($R^{13}$)—G moiety, are not joined together, and (f) $R^3$ and $R^4$ of the —C($R^3$)($R^4$)— G moiety are not joined together, and (g) one $R^3$ and one $R^4$ on one carbon of the —(C($R^3$)($R^4$))$_2$— G moiety are not joined together, and (h) an $R^3$ and an $R^4$ on adjacent carbons of the —(C($R^3$)($R^4$))$_2$— G moiety are not joined together, and (i) $R^1$ and $R^2$, and $R^6$ and either $R^3$ or $R^4$, are not joined together to form the rings described in (ix) above, and (j) $R^1$ and $R^2$, and $R^3$ and $R^4$, are not joined together to form the rings described in (x) above, and (k) $R^1$ and $R^2$, and $R^3$ and $R^4$, are not joined together to form the rings described in (xi) above, and (l) $R^1$ and $R^2$, and $R^3$ and $R^4$, are not joined together to form the rings described in (xii) above (that is none of the rings described above in (i) to (xii) are formed);
(2) U is N;
(3) V is a bond;
(4) W is O;
(5) G is —C($R^3$)($R^4$)—;
(6) $R^2$ is selected from the group consisting of H, alkyl (e.g., methyl, ethyl and propyl, and in one example propyl), and alkyl (e.g., methyl, ethyl and propyl) substituted with 1 —OH group (and in one example the substituted alkyl is —$CH_2CH_2CH_2$—OH),
(7) one of $R^3$ or $R^4$ is H, and the remaining $R^3$ or $R^4$ is selected from the group comprising:
(a) aryl (e.g., phenyl),
(b) aryl (e.g., phenyl) substituted with 1 to 3 independently selected $R^{21}$ groups (and (i) in one example said aryl is substituted with 1 to 3 halos, (ii) in another example said aryl is substituted with 1 to 3 F, (iii) in another example said aryl is substituted with 3 F, (iv) in another example said aryl is substituted with 2 F, and (v) in another example said aryl is substituted with 1 F),
(c) heteroaryl (e.g., thienyl), (d) heteroaryl (e.g., thienyl) substituted with 1 to 3 independently selected $R^{21}$ groups (and (i) in one example said heteroaryl is substituted with 1 to 3 halos, (ii) in another example said heteroaryl is substituted with 1 to 3 F, and (iii) in another example said heteroaryl is substituted with 1 F),
(d) cycloalkyl (e.g., cyclopropyl),
(e) cycloalkyl (e.g., cyclopropyl) substituted with 1 to 3 independently $R^{21}$ substituents (and (i) in one example said cycloalkyl is substituted with 1 to 3 halos, and (ii) in another example said cycloalkyl is substituted with 1 to 3 F),
(f) alkyl (e.g., methyl or ethyl), (g) alkyl substituted with 1 to 3 independently selected $R^{21}$ groups (and (i) in one example said alkyl is substituted with one —$OR^{15}$ group, (ii) in another example said alkyl is substituted with one —$OR^{15}$ group wherein $R^{15}$ is H, (iii) in another example said alkyl is substituted with one —$OR^{15}$ group wherein $R^{15}$ is $(R^{18})_r$-alkyl-, (iv) in another example said alkyl is substituted with one —$OR^{15}$ group wherein $R^{15}$ is $(R^{18})_r$-alkyl- and $R^{18}$ is —OH and r is 1, and (v) in another example said alkyl is substituted with one —$OR^{15}$ wherein $R^{15}$ is HO—$CH_2$—, or HO—$(CH_2)_2$—); and (8) all other substituents are as described for formula I.

In another embodiment of this invention is directed to compounds of formula I wherein:

(1) none of the rings described in (i) to (xii) of formula I are formed (that is (a) $R^1$ and $R^2$ are not joined together, and (b) $R^2$ and $R^6$ are not joined together, and (c) $R^1$ and $R^2$ are not joined together, and $R^2$ and $R^6$ are not joined together (i.e., $R^2$ is not joined together with $R^1$ and $R^6$), and (d) $R^6$ is not joined together with either $R^3$ or $R^4$ (i.e., $R^6$ and $R^3$ are not joined together, or $R^6$ and $R^4$ are not joined together), and (e) $R^6$ and $R^{13}$ of the —$N(R^{13})$— G moiety, are not joined together, and (f) $R^3$ and $R^4$ of the —$C(R^3)(R^4)$— G moiety are not joined together, and (g) one $R^3$ and one $R^4$ on one carbon of the —$(C(R^3)(R^4))_2$— G moiety are not joined together, and (h) an $R^3$ and an $R^4$ on adjacent carbons of the —$(C(R^3)(R^4))_2$— G moiety are not joined together, and (i) $R^1$ and $R^2$, and $R^6$ and either $R^3$ or $R^4$, are not joined together to form the rings described in (ix) above, and (j) $R^1$ and $R^2$, and $R^3$ and $R^4$, are not joined together to form the rings described in (x) above, and (k) $R^1$ and $R^2$, and $R^3$ and $R^4$, are not joined together to form the rings described in (xi) above, and (l) $R^1$ and $R^2$, and $R^3$ and $R^4$, are not joined together to form the rings described in (xii) above (that is none of the rings described above in (i) to (xii) are formed);

(2) U is N;
(3) V is a bond;
(4) W is O;
(5) G is —$C(R^3)(R^4)$—;
(6) $R^2$ is selected from the group consisting of H, alkyl, and alkyl substituted with 1 to 5 $R^{21}$ groups;
(7) one of $R^3$ or $R^4$ is H, and the remaining $R^3$ or $R^4$ is selected from the group comprising:
  (a) phenyl,
  (b) phenyl substituted with 1 to 3 independently selected $R^{21}$ groups (and (i) in one example said phenyl is substituted with 1 to 3 halos, (ii) in another example said phenyl is substituted with 1 to 3 F, (iii) in another example said phenyl is substituted with 3 F, (iv) in another example said phenyl is substituted with 2 F, and (v) in another example said phenyl is substituted with 1 F),
  (c) thienyl,
  (d) thienyl substituted with 1 to 3 independently selected $R^{21}$ groups (and (i) in one example said thienyl is substituted with 1 to 3 halos, (ii) in another example said thienyl is substituted with 1 to 3 F, and (iii) in another example said thienyl is substituted with 1 F),
  (d) cyclopropyl,
  (e) cyclopropyl substituted with 1 to 3 independently $R^{21}$ substituents (and (i) in one example said cyclopropyl is substituted with 1 to 3 halos, and (ii) in another example said cyclopropyl is substituted with 1 to 3 F),
  (f) alkyl (e.g., methyl or ethyl, and (i) in one example methyl, and (ii) in another example ethyl),
  (g) -alkyl-OH (and in one example —$(CH_2)_3OH$),
  (h) -alkyl-O-alkyl-OH (and in one example —$CH_2$—O—$CH_2CH_2$—OH), (8) all other substituents are as described for formula I.

In another embodiment of this invention is directed to compounds of formula I wherein:

(1) none of the rings described in (i) to (xii) of formula I are formed (that is (a) $R^1$ and $R^2$ are not joined together, and (b) $R^2$ and $R^6$ are not joined together, and (c) $R^1$ and $R^2$ are not joined together, and $R^2$ and $R^6$ are not joined together (i.e., $R^2$ is not joined together with $R^1$ and $R^6$), and (d) $R^6$ is not joined together with either $R^3$ or $R^4$ (i.e., $R^6$ and $R^3$ are not joined together, or $R^6$ and $R^4$ are not joined together), and (e) $R^6$ and $R^{13}$ of the —$N(R^{13})$— G moiety, are not joined together, and (f) $R^3$ and $R^4$ of the —$C(R^3)(R^4)$— G moiety are not joined together, and (g) one $R^3$ and one $R^4$ on one carbon of the —$(C(R^3)(R^4))_2$— G moiety are not joined together, and (h) an $R^3$ and an $R^4$ on adjacent carbons of the —$(C(R^3)(R^4))_2$— G moiety are not joined together, and (i) $R^1$ and $R^2$, and $R^6$ and either $R^3$ or $R^4$, are not joined together to form the rings described in (ix) above, and (j) $R^1$ and $R^2$, and $R^3$ and $R^4$, are not joined together to form the rings described in (x) above, and (k) $R^1$ and $R^2$, and $R^3$ and $R^4$, are not joined together to form the rings described in (xi) above, and (l) $R^1$ and $R^2$, and $R^3$ and $R^4$, are not joined together to form the rings described in (xii) above (that is none of the rings described above in (i) to (xii) are formed);

(2) U is N;
(3) V is a bond;
(4) W is O;
(5) G is —$C(R^3)(R^4)$—;
(6) $R^2$ is selected from the group consisting of H, alkyl (e.g., methyl, ethyl and propyl, and in one example propyl), and alkyl (e.g., methyl, ethyl and propyl) substituted with 1 —OH group (and in one example the substituted alkyl is —$CH_2CH_2CH_2$—OH),
(7) one of $R^3$ or $R^4$ is H, and the remaining $R^3$ or $R^4$ is selected from the group comprising:
  (a) phenyl,
  (b) phenyl substituted with 1 to 3 independently selected $R^{21}$ groups (and (i) in one example said phenyl is substituted with 1 to 3 halos, (ii) in another example said phenyl is substituted with 1 to 3 F, (iii) in another example said phenyl is substituted with 3 F, (iv) in another example said phenyl is substituted with 2 F, and (v) in another example said phenyl is substituted with 1 F),
  (c) thienyl,
  (d) thienyl substituted with 1 to 3 independently selected $R^{21}$ groups (and (i) in one example said thienyl is substituted with 1 to 3 halos, (ii) in another example said thienyl is substituted with 1 to 3 F, and (iii) in another example said thienyl is substituted with 1 F),
  (d) cyclopropyl,
  (e) cyclopropyl substituted with 1 to 3 independently $R^{21}$ substituents (and (i) in one example said cyclopropyl is substituted with 1 to 3 halos, and (ii) in another example said cyclopropyl is substituted with 1 to 3 F),
  (f) alkyl (e.g., methyl or ethyl, and (i) in one example methyl, and (ii) in another example ethyl),
  (g) -alkyl-OH (and in one example —$(CH_2)_3OH$), (h) -alkyl-O-alkyl-OH (and in one example —CH$_2$—O—CH$_2$CH$_2$—OH), (8) all other substituents are as described for formula I.

In another embodiment, G is —C(O)—.

In another embodiment, G is —N(R$^{13}$)—.

In another embodiment, V is a bond.

In another embodiment, V is —O—.

In another embodiment, V is —C(O)—.

In another embodiment, V is —N(R$^{14}$)—.

In another embodiment, R$^2$ is arylalkyl-.

In another embodiment, R$^2$ is phenylmethyl-.

In another embodiment, R$^2$ is (4-alkoxy)phenylmethyl-.

In another embodiment, R$^2$ is (4-methoxy)phenylmethyl-.

In another embodiment, R$^1$ is H.

In another embodiment, R$^1$ is alkyl.

In another embodiment, R$^1$ is methyl.

In another embodiment, R$^1$ and R$^2$ are joined together to form a cyclopentyl ring, which is unsubstituted.

In another embodiment, R$^1$ and R$^2$ are joined together to form a cyclopentyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, R$^1$ and R$^2$ are joined together to form a cyclohexyl ring, which is unsubstituted.

In another embodiment, R$^1$ and R$^2$ are joined together to form a cyclohexyl ring, which is substituted with 1-3 substituents which can be the same or different, each being independently selected from the group consisting of halo, alkyl, —ON, —NH$_2$, —NH(alkyl), —N(alkyl)$_2$, hydroxy and alkoxy groups.

In another embodiment, U is N, and R$^1$ and R$^2$ are joined together to form a piperidinyl ring including the N of U as the nitrogen of said piperidinyl ring, which is unsubstituted.

In another embodiment, U is N, and R$^1$ and R$^2$ are joined together to form a piperidinyl ring including the N of U as the nitrogen of said piperidinyl ring, wherein said piperidinyl ring is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, U is N, and R$^1$ and R$^2$ are joined together to form a pyrrolidinyl ring including the N of U as the nitrogen of said pyrrolidinyl ring, which is unsubstituted.

In another embodiment, U is N, and R$^1$ and R$^2$ are joined together to form a pyrrolidinyl ring including the N of U as the nitrogen of said pyrrolidinyl ring, wherein said pyrrolidinyl ring is substituted with 1-3 substituents which can be the same or different, each being independently selected from the group consisting of halo, alkyl, —ON, —NH$_2$, —NH(alkyl), —N(alkyl)$_2$, hydroxy and alkoxy groups.

In another embodiment, U is N, and R$^1$ and R$^2$ are joined together to form a piperazinyl ring including the N of U as a nitrogen of said piperazinyl ring, which is unsubstituted.

In another embodiment, U is N, and R$^1$ and R$^2$ are joined together to form a piperazinyl ring including the N of U as a nitrogen of said piperazinyl ring, wherein said piperazinyl ring is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment R$^1$ and R$^2$ are joined together to form a ring optionally substituted with 1 to 5 independently selected R$^{21}$ substitutents, and said ring is fused with an aryl or heteroaryl ring, and said resulting fused ring is optionally substituted with 1 to 5 independently selected R$^{21}$ substitutents.

In another embodiment R$^1$ and R$^2$ are joined together to form a ring substituted with 1 to 5 independently selected R$^{21}$ substitutents, and said ring is fused with an aryl or heteroaryl ring, and said resulting fused ring is optionally substituted with 1 to 5 independently selected R$^{21}$ substitutents.

In another embodiment R$^1$ and R$^2$ are joined together to form a ring optionally substituted with 1 to 5 independently selected R$^{21}$ substitutents.

In another embodiment R$^1$ and R$^2$ are joined together to form a ring.

In another embodiment R$^1$ and R$^2$ are joined together to form a heterocyclyl ring optionally substituted with 1 to 5 independently selected R$^{21}$ substitutents.

In another embodiment R$^1$ and R$^2$ are joined together to form a heterocyclyl ring substituted with 1 to 5 independently selected R$^{21}$ substitutents.

In another embodiment U is N, and R$^1$ and R$^2$ are joined together to form a heterocyclyl ring optionally substituted with 1 to 5 independently selected R$^{21}$ substitutents.

In another embodiment U is N, and R$^1$ and R$^2$ are joined together to form a heterocyclyl ring substituted with 1 to 5 independently selected R$^{21}$ substitutents.

In another embodiment R$^1$ and R$^2$ are joined together to form a ring, and said ring is fused with an aryl or heteroaryl ring, and said resulting fused ring is optionally substituted with 1 to 5 independently selected R$^{21}$ substitutents.

In another embodiment R$^1$ and R$^2$ are joined together to form a heterocyclyl ring.

In another embodiment U is N, and R$^1$ and R$^2$ are joined together to form a heterocyclyl ring.

In another embodiment R$^1$ and R$^2$ are joined together to form a piperidinyl ring optionally substituted with 1 to 5 independently selected R$^{21}$ substitutents.

In another embodiment R$^1$ and R$^2$ are joined together to form a piperidinyl ring substituted with 1 to 5 independently selected R$^{21}$ substitutents.

In another embodiment U is N, and R$^1$ and R$^2$ are joined together to form a piperidinyl ring optionally substituted with 1 to 5 independently selected R$^{21}$ substitutents.

In another embodiment U is N, and R$^1$ and R$^2$ are joined together to form a piperidinyl ring substituted with 1 to 5 independently selected R$^{21}$ substitutents.

In another embodiment R$^1$ and R$^2$ are joined together to form a piperidinyl ring optionally substituted with a =O moiety.

In another embodiment U is N, and R$^1$ and R$^2$ are joined together to form a piperidinyl ring optionally substituted with a =O moiety.

In another embodiment R$^1$ and R$^2$ are joined together to form a piperidinyl.

In another embodiment U is N, and R$^1$ and R$^2$ are joined together to form a piperidinyl ring.

In another embodiment R$^1$ and R$^2$ are joined together to form a piperidinyl ring substituted with a =O moiety.

In another embodiment U is N, and R$^1$ and R$^2$ are joined together to form a piperidinyl ring substituted with a =O moiety.

In another embodiment R$^2$ and R$^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected R$^{21}$ substitutents, (b) said heterocyclyl moiety is optionally substituted with 1-5 independently selected R$^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment:
(a) $R^1$ and $R^2$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents, and
(b) $R^2$ and $R^6$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents; and
(c) said $R^2$ and $R^6$ cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment $R^6$ and either $R^3$ or $R^4$ of the —C($R^3$)($R^4$)— G moiety, are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety, wherein: (a) said heterocyclyl moiety is optionally substituted with 1-5 independently selected $R^{21}$ substituents, and (b) said heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety, wherein said heterocyclyl moiety is optionally substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety, wherein said heterocyclyl moiety is substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety.

In another embodiment $R^6$ and $R^{13}$ of the —N($R^{13}$)— G moiety, are joined together to form a 5-8 membered heterocyclyl or 5-8 membered heterocyclenyl moiety, wherein: (a) said heterocyclyl moiety is optionally substituted with a =O, and (b) said heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety, wherein said heterocyclyl moiety is optionally substituted with a =O.

In another embodiment $R^6$ and $R^{13}$ of the —N($R^{13}$)— G moiety, are joined together to form a 5-8 membered heterocyclyl or 5-8 membered heterocyclenyl moiety.

In another embodiment $R^6$ and $R^{13}$ of the —N($R^{13}$)— G moiety, are joined together to form a 5-8 membered heterocyclyl or 5-8 membered heterocyclenyl moiety, wherein: (a) said heterocyclyl moiety is substituted with a =O, and (b) said heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety, wherein said heterocyclyl moiety is substituted with a =O.

In another embodiment $R^6$ and $R^{13}$ of the —N($R^{13}$)— G moiety, are joined together to form a 5 membered heterocyclyl moiety, wherein: (a) said heterocyclyl moiety is optionally substituted with 1-5 independently selected $R^{21}$ substituents, and (b) said heterocyclyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 membered heterocyclyl moiety, wherein said heterocyclyl moiety is optionally substituted with 1-5 independently selected $R^{21}$ substituents.

In another embodiment $R^6$ and $R^{13}$ of the —N($R^{13}$)— G moiety, are joined together to form a 5 membered heterocyclyl moiety, wherein: (a) said heterocyclyl moiety is optionally substituted with a =O, and (b) said heterocyclyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 membered heterocyclyl moiety, wherein said heterocyclyl moiety is optionally substituted with a =O.

In another embodiment $R^6$ and $R^{13}$ of the —N($R^{13}$)— G moiety, are joined together to form a 5 membered heterocyclyl moiety, wherein said heterocyclyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 membered heterocyclyl moiety.

In another embodiment $R^6$ and $R^{13}$ of the —N($R^{13}$)— G moiety, are joined together to form a 5 membered heterocyclyl moiety, wherein: (a) said heterocyclyl moiety is substituted with a =O, and (b) said heterocyclyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 membered heterocyclyl moiety, wherein said heterocyclyl moiety is substituted with a =O.

In another embodiment $R^6$ and $R^{13}$ of the —N($R^{13}$)— G moiety, are joined together to form a pyrrolidinyl ring, wherein: (a) said pyrrolidinyl ring is optionally substituted with 1-5 independently selected $R^{21}$ substituents, and (b) said pyrrolidinyl ring is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 pyrrolidinyl ring, wherein said pyrrolidinyl ring is optionally substituted with 1-5 independently selected $R^{21}$ substituents.

In another embodiment $R^6$ and $R^{13}$ of the —N($R^{13}$)— G moiety, are joined together to form a pyrrolidinyl ring, wherein: (a) said pyrrolidinyl ring is optionally substituted with a =O, and (b) said pyrrolidinyl ring is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a pyrrolidinyl ring, wherein said pyrrolidinyl ring is optionally substituted with a =O.

In another embodiment $R^6$ and $R^{13}$ of the —N($R^{13}$)— G moiety, are joined together to form a pyrrolidinyl ring, wherein said pyrrolidinyl ring is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a pyrrolidinyl ring.

In another embodiment $R^6$ and $R^{13}$ of the —N($R^{13}$)— G moiety, are joined together to form a pyrrolidinyl ring, wherein: (a) said pyrrolidinyl ring is substituted with a =O, and (b) said pyrrolidinyl ring is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a pyrrolidinyl ring, wherein said pyrrolidinyl ring is substituted with a=O.

In another embodiment $R^6$ and $R^{13}$ of the —N($R^{13}$)— G moiety, are joined together to form a 5 membered heterocyclyl moiety, wherein: (a) said heterocyclyl moiety is substituted with 1-5 independently selected $R^{21}$ substituents, and (b) said heterocyclyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 membered heterocyclyl moiety, wherein said heterocyclyl moiety is substituted with 1-5 independently selected $R^{21}$ substituents.

In another embodiment $R^6$ and $R^{13}$ of the —N($R^{13}$)— G moiety, are joined together to form a pyrrolidinyl ring, wherein: (a) said pyrrolidinyl ring is substituted with 1-5 independently selected $R^{21}$ substituents, and (b) said pyrrolidinyl ring is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 pyrrolidinyl ring, wherein said pyrrolidinyl ring is substituted with 1-5 independently selected $R^{21}$ substituents.

In another embodiment, $R^6$ is H.
In another embodiment, $R^6$ is alkyl.
In another embodiment, $R^6$ is methyl.
In another embodiment, $R^7$ is aryl.
In another embodiment, $R^7$ is an unsubstituted phenyl.
In another embodiment, $R^7$ is a phenyl which is substituted with 1-4 substituents which can be the same or different, each substituent being independently selected from the group consisting of halo, alkyl, —CN, —$NH_2$, —NH(alkyl), —N(alkyl)$_2$, hydroxy, alkoxy, aryl and heteroaryl groups.

In another embodiment, $R^7$ is unsubstituted naphthyl.
In another embodiment, $R^7$ is naphthyl which is substituted with 1-4 substituents which can be the same or different, each substituent being independently selected from the group consisting of halo, alkyl, —CN, —$NH_2$, —NH(alkyl), —N(alkyl)$_2$, hydroxy, alkoxy, aryl and heteroaryl groups.

In another embodiment, $R^7$ is unsubstituted biphenyl.
In another embodiment, $R^7$ is biphenyl which is substituted with 1-4 substituents which can be the same or different, each substituent being independently selected from the group consisting of halo, alkyl, —CN, —$NH_2$, —NH(alkyl), —N(alkyl)$_2$, hydroxy and alkoxy groups.

In another embodiment, $R^7$ is 3-(1,1'-biphenyl)-yl.
In another embodiment, $R^7$ is 4-(1,1'-biphenyl)-yl.
In another embodiment, $R^6$ is H and $R^7$ is a biphenyl which can be unsubstituted or optionally independently substituted with 1-4 substituents which can be the same or different, each substituent being independently selected from the group consisting of halo, alkyl, —CN, —$NH_2$, —NH(alkyl), —N(alkyl)$_2$, hydroxy and alkoxy groups.

In another embodiment, $R^6$ is methyl, and $R^7$ is a biphenyl which can be unsubstituted or optionally independently substituted with 1-4 substituents which can be the same or different, each substituent being independently selected from the group consisting of halo, alkyl, —CN, —$NH_2$, —NH(alkyl), —N(alkyl)$_2$, hydroxy and alkoxy groups.

In another embodiment, $R^6$ is H, and $R^7$ is a phenyl which can be unsubstituted or optionally independently substituted with 1-4 substituents which can be the same or different, each substituent being independently selected from the group consisting of halo, alkyl, —ON, —$NH_2$, —NH(alkyl), —N(alkyl)$_2$, hydroxy and alkoxy groups.

In another embodiment, $R^6$ is methyl, and $R^7$ is a biphenyl which can be unsubstituted or optionally independently substituted with 1-4 substituents which can be the same or different, each substituent being independently selected from the group consisting of halo, alkyl, —CN, —$NH_2$, —NH(alkyl), —N(alkyl)$_2$, hydroxy and alkoxy groups.

In another embodiment, $R^2$ and $R^6$ are joined together to form a cyclopentyl ring.

In another embodiment, $R^2$ and $R^6$ are joined together to form a cyclopentyl ring, which is substituted with 1-3 substituents which can be the same or different, each being independently selected from the group consisting of halo, alkyl, —CN, —$NH_2$, —NH(alkyl), —N(alkyl)$_2$, hydroxy and alkoxy groups.

In another embodiment, $R^2$ and $R^6$ are joined together to form a cyclohexyl ring.

In another embodiment, $R^2$ and $R^6$ are joined together to form a cyclohexyl ring, which is substituted with 1-3 substituents which can be the same or different, each being independently selected from the group consisting of halo, alkyl, —CN, —$NH_2$, —NH(alkyl), —N(alkyl)$_2$, hydroxy and alkoxy groups.

In another embodiment, U is N, and $R^2$ and $R^6$ are joined together to form a piperidinyl ring including the N of U as the nitrogen of said piperidinyl ring, which is unsubstituted.

In another embodiment, U is N, and $R^2$ and $R^6$ are joined together to form a piperidinyl ring including the N of U as the nitrogen of said piperidinyl ring, wherein said piperidinyl ring is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, U is N, and $R^2$ and $R^6$ are joined together to form a pyrrolidinyl ring including the N of U as the nitrogen of said pyrrolidinyl ring, which is unsubstituted.

In another embodiment, U is N, and $R^2$ and $R^6$ are joined together to form a pyrrolidinyl ring including the N of U as the nitrogen of said pyrrolidinyl ring, wherein said pyrrolidinyl ring is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, U is N, and $R^2$ and $R^6$ are joined together to form a piperazinyl ring including the N of U as a nitrogen of said piperazinyl ring, which is unsubstituted.

In another embodiment, U is N, and $R^2$ and $R^6$ are joined together to form a piperazinyl ring including the N of U as a nitrogen of said piperazinyl ring, wherein said piperazinyl ring is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, $R^2$ and $R^6$ are joined together to form a morpholinyl ring which is unsubstituted.

In another embodiment, $R^2$ and $R^6$ are joined together to form a morpholinyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, $R^2$ and $R^6$ are joined together to form a pyranyl ring which is unsubstituted.

In another embodiment, $R^2$ and $R^6$ are joined together to form a pyranyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, $R^2$ and $R^6$ are joined together to form a pyrrolidinyl ring which is unsubstituted.

In another embodiment, $R^2$ and $R^6$ are joined together to form a pyrrolidinyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, both ($R^1$ and $R^2$) and ($R^2$ and $R^6$) are joined together to form independent cycloalkyl rings.

In another embodiment, both ($R^1$ and $R^2$) and ($R^2$ and $R^6$) are joined together to form independent cycloalkyl rings, each of which is independently optionally substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, both ($R^1$ and $R^2$) and ($R^2$ and $R^6$) are joined together to form independent heterocyclyl rings.

In another embodiment, both ($R^1$ and $R^2$) and ($R^2$ and $R^6$) are joined together to form independent heterocyclyl rings, each of which is independently optionally substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, both ($R^1$ and $R^2$) and ($R^2$ and $R^6$) are joined together to form independent cycloalkyl rings.

In another embodiment, both $R^1$ and $R^2$ are joined together to form a cycloalkyl ring, and $R^2$ and $R^6$ are joined together to form a heterocyclyl ring, each of which is independently optionally substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, both $R^1$ and $R^2$ are joined together to form a heterocyclyl ring, and $R^2$ and $R^6$ are joined together to form a cycloalkyl ring, each of which is independently optionally substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, $R^7$ is 4-fluorophenyl.

In another embodiment $R^7$ is selected from the group consisting of: (a) aryl substituted with 1-3 $R^{21}$ moieties (e.g. phenyl substituted 1-3 halos, such as, 1-3 F), (b) aryl (e.g. phenyl) substituted with —OR$^{15}$ wherein $R^{15}$ is (i) an alkyl substituted with 1-3 halos (e.g, halos independently selected from the group consisting of F and Cl), or (ii) alkyl, (c) aryl (e.g., phenyl), (d) aryl (e.g. phenyl) substituted with alkyl wherein said alkyl is substituted with 1-3 halos (e.g., F), (e) aryl substituted with aryl (e.g. -phenyl-phenyl), (f) alkyl, (g) heteroaryl (e.g. thienyl or pyridyl), (h) arylalkyl-, and (i) cycloalkyl).

In another embodiment $R^7$ is selected from the group consisting of: (a) aryl substituted with 1-3 $R^{21}$ moieties (e.g. phenyl substituted 1-3 halos, such as, 1-3 F), (b) aryl (e.g. phenyl) substituted with —OR$^{15}$ wherein $R^{15}$ is (i) an alkyl substituted with 1-3 halos (e.g. F), or (ii) alkyl, (c) aryl (e.g., phenyl), (d) aryl (e.g. phenyl) substituted with alkyl wherein said alkyl is substituted with 1-3 halos (e.g., F), (e) aryl substituted with aryl (e.g. -phenyl-phenyl), (f) alkyl, (g) heteroaryl (e.g. thienyl or pyridyl), (h) arylalkyl-, and (i) cycloalkyl).

In another embodiment $R^7$ is aryl (e.g., phenyl) substituted with 1 to 3 independently selected $R^{21}$ moieties wherein at least one $R^{21}$ moiety is selected from the group consisting of —SF$_5$, —OSF$_5$ and —Si($R^{24}$)$_3$ (and in one example each $R^{24}$ is the same or different alkyl, and in another example the —Si($R^{24}$)$_3$ group is —Si(CH$_3$)$_3$ or —Si(CH$_2$CH$_3$)$_2$CH$_3$, and in another example the —Si($R^{24}$)$_3$ group is —Si(CH$_3$)$_3$).

In another embodiment $R^7$ is aryl (e.g., phenyl) substituted with 1 to 3 independently selected $R^{21}$ moieties wherein at least one $R^{21}$ moiety is selected from the group consisting of —SF$_5$ and —OSF$_5$.

In another embodiment $R^7$ is aryl (e.g., phenyl) substituted with 1 to 3 $R^{21}$ moieties independently selected from the group consisting of: halo (e.g., F), —SF$_5$, —OSF$_5$ and —Si($R^{24}$)$_3$ (and in one example each $R^{24}$ is the same or different alkyl, and in another example the —Si($R^{24}$)$_3$ group is —Si(CH$_3$)$_3$ or —Si(CH$_2$CH$_3$)$_2$CH$_3$, and in another example the —Si($R^{24}$)$_3$ group is —Si(CH$_3$)$_3$), and wherein at least one $R^{21}$ moiety is selected from the group consisting of —SF$_5$, —OSF$_5$ and —Si($R^{24}$)$_3$ (and in one example each $R^{24}$ is the same or different alkyl, and in another example the —Si($R^{24}$)$_3$) group is —Si(CH$_3$)$_3$ or —Si(CH$_2$CH$_3$)$_2$CH$_3$, and in another example the —Si($R^{24}$)$_3$) group is —Si(CH$_3$)$_3$).

In another embodiment $R^7$ is aryl (e.g., phenyl) substituted with 1 to 3 $R^{21}$ moieties independently selected from the group consisting of: halo (e.g., F), —$SF_5$ and —$OSF_5$, and wherein at least one $R^{21}$ moiety is selected from the group consisting of —$SF_5$ and —$OSF_5$.

In another embodiment $R^7$ is selected from the group consisting of: (a) aryl substituted with 1-3 $R^{21}$ moieties (e.g. phenyl substituted 1-3 halos, such as, 1-3 F), (b) aryl (e.g. phenyl) substituted with —$OR^{15}$ wherein $R^{15}$ is (i) an alkyl substituted with 1-3 halos (e.g. F), or (ii) alkyl, (c) aryl (e.g., phenyl), (d) aryl (e.g. phenyl) substituted with alkyl wherein said alkyl is substituted with 1-3 halos (e.g., F), (e) aryl substituted with aryl (e.g. -phenyl-phenyl), (f) alkyl, (g) heteroaryl (e.g. thienyl or pyridyl), (h) arylalkyl-, and (i) cycloalkyl).

In another embodiment $R^7$ is aryl (e.g., phenyl) substituted with 1 to 3 independently selected $R^{21}$ moieties wherein at least one $R^{21}$ moiety is selected from the group consisting of —$SF_5$, —$OSF_5$ and —$Si(R^{24})_3$ (and in one example each $R^{24}$ is the same or different alkyl, and in another example the —$Si(R^{24})_3$ group is —$Si(CH_3)_3$ or —$Si(CH_2CH_3)_2CH_3$, and in another example the —$Si(R^{24})_3$ group is —$Si(CH_3)_3$).

In another embodiment, $R^7$ is a phenyl which is substituted with 1-4 substituents independently selected from the group consisting of halo, alkyl, —CN, —$NH_2$, —NH(alkyl), —N(alkyl)$_2$, hydroxy, alkoxy, aryl, heteroaryl, —$SF_5$, —$OSF_5$ and —$Si(R^{24})_3$ (and in one example each $R^{24}$ is the same or different alkyl, and in another example the —Si$(R^{24})_3$ group is —$Si(CH_3)_3$ or —$Si(CH_2CH_3)_2CH_3$, and in another example the —$Si(R^{24})_3$ group is —$Si(CH_3)_3$), and wherein at least one $R^{21}$ moiety is selected from the group consisting of —$SF_5$, —$OSF_5$ and —$Si(R^{24})_3$ (and in one example each $R^{24}$ is the same or different alkyl, and in another example the —$Si(R^{24})_3$ group is —$Si(CH_3)_3$ or —Si(CH$_2$CH$_3$)$_2$CH$_3$, and in another example the —$Si(R^{24})_3$ group is —$Si(CH_3)_3$).

In another embodiment, $R^7$ is a phenyl which is substituted with 1-4 substituents independently selected from the group consisting of halo, alkyl, —CN, —$NH_2$, —NH(alkyl), —N(alkyl)$_2$, hydroxy, alkoxy, aryl, heteroaryl —$SF_5$, and —$OSF_5$, and wherein at least one $R^{21}$ moiety is selected from the group consisting of —$SF_5$ and —$OSF_5$.

In another embodiment, $R^7$ is phenyl substituted with 1-3 substituents which can be the same or different, each substituent being independently selected from the group consisting of halo, alkyl, —CN, —$NH_2$, —NH(alkyl), —N(alkyl)$_2$, hydroxy, alkoxy, aryl and heteroaryl groups.

In another embodiment, $R^7$ is phenyl which is substituted with 1-3 substituents independently selected from the group consisting of halo, alkyl, —CN, —$NH_2$, —NH(alkyl), —N(alkyl)$_2$, hydroxy, alkoxy, aryl, heteroaryl, —$SF_5$, —$OSF_5$ and —$Si(R^{24})_3$ (and in one example each $R^{24}$ is the same or different alkyl, and in another example the —Si$(R^{24})_3$ group is —$Si(CH_3)_3$ or —$Si(CH_2CH_3)_2CH_3$, and in another example the —$Si(R^{24})_3$ group is —$Si(CH_3)_3$), and wherein at least one $R^{21}$ moiety is selected from the group consisting of —$SF_5$, —$OSF_5$ and —$Si(R^{24})_3$ (and in one example each $R^{24}$ is the same or different alkyl, and in another example the —$Si(R^{24})_3$) group is —$Si(CH_3)_3$ or —Si(CH$_2$CH$_3$)$_2$CH$_3$, and in another example the In another embodiment, $R^7$ is phenyl which is substituted with 1-3 substituents independently selected from the group consisting of halo, alkyl, —ON, —$NH_2$, —NH(alkyl), —N(alkyl)$_2$, hydroxy, alkoxy, aryl, heteroaryl —$SF_5$, and —$OSF_5$, and wherein at least one $R^{21}$ moiety is selected from the group consisting of —$SF_5$ and —$OSF_5$.

In another embodiment, $R^7$ is phenyl substituted with 1-3 independently selected halos.

In another embodiment, $R^7$ is phenyl substituted with 1-3 halos independently selected from the group consisting of F and Cl. In one example said phenyl is substituted with one F and one Cl.

In another embodiment, $R^7$ is phenyl substituted with 1-3 $R^{21}$ groups independently selected from the group consisting of halos, —$SF_5$ and —$OSF_5$, wherein at least one $R^{21}$ group is —$SF_5$ or —$OSF_5$.

In another embodiment, $R^7$ is phenyl substituted with 1-3 $R^{21}$ groups independently selected from the group consisting of F, Br, —$SF_5$ and —$OSF_5$.

In another embodiment, $R^7$ is phenyl substituted with 1-3 $R^{21}$ groups independently selected from the group consisting of —$SF_5$ and —$OSF_5$.

In another embodiment, $R^7$ is phenyl substituted with 1-3 F.

In another embodiment, $R^7$ is phenyl substituted with 1-3 $R^{21}$ groups independently selected from the group consisting of F, —$SF_5$ and —$OSF_5$, wherein at least one $R^{21}$ group is —$SF_5$ or —$OSF_5$.

In another embodiment, $R^7$ is phenyl substituted with one —$SF_5$ group.

In another embodiment, $R^7$ is phenyl substituted with two —$SF_5$ groups.

In another embodiment, $R^7$ is phenyl substituted with three —$SF_5$ groups.

In another embodiment, $R^7$ is phenyl substituted with one —$OSF_5$ group.

In another embodiment, $R^7$ is phenyl substituted with two —$OSF_5$ groups.

In another embodiment, $R^7$ is phenyl substituted with three —$OSF_5$ groups.

In another embodiment, $R^7$ is phenyl substituted with 1 F.

In another embodiment, $R^7$ is phenyl substituted with 1 F, and also substituted with 1 to 2 groups independently selected from the group consisting of —$SF_5$ and —$OSF_5$.

In another embodiment $R^7$ is phenyl substituted with 2 F.

In another embodiment $R^7$ is phenyl substituted with 3F.

In another embodiment $R^7$ is p-Cl-phenyl.

In another embodiment $R^7$ is p-Cl-phenyl substituted with 1 to 2 groups independently selected from the group consisting of —$SF_5$ and —$OSF_5$.

In another embodiment, $R^7$ is naphthyl substituted with 1-3 $R^{21}$ groups independently selected from the group consisting of —$SF_5$, —$OSF_5$ and —$Si(R^{24})_3$ (and in one example each $R^{24}$ is the same or different alkyl, and in another example the —$Si(R^{24})_3$ group is —$Si(CH_3)_3$ or —$Si(CH_2CH_3)_2CH_3$, and in another example the —$Si(R^{24})_3$ group is —$Si(CH_3)_3$).

In another embodiment, $R^7$ is naphthyl substituted with 1-3 $R^{21}$ groups independently selected from the group consisting of —$SF_5$ and —$OSF_5$.

In another embodiment, $R^7$ is naphthyl substituted with 1-3 $R^{21}$ groups independently selected from the group consisting of halo, —$SF_5$, —$OSF_5$ and —$Si(R^{24})_3$ (and in one example each $R^{24}$ is the same or different alkyl, and in another example the —$Si(R^{24})_3$ group is —$Si(CH_3)_3$ or —$Si(CH_2CH_3)_2CH_3$, and in another example the —$Si(R^{24})_3$ group is —$Si(CH_3)_3$), and wherein at least one $R^{21}$ group is selected from the group consisting of —$SF_5$, —$OSF_5$ and —$Si(R^{24})_3$.

In another embodiment, $R^7$ is naphthyl substituted with 1-3 $R^{21}$ groups independently selected from the group consisting of halo, —$SF_5$ and —$OSF_5$, wherein at least one $R^{21}$ group is selected from the group consisting of —$SF_5$ and —$OSF_5$.

In another embodiment, $R^7$ is naphthyl substituted with 1-3 $R^{21}$ groups independently selected from the group consisting of F, Br, —SF$_5$ and —OSF$_5$, wherein at least one R$^{21}$ group is selected from the group consisting of —SF$_5$ and —OSF$_5$.

In another embodiment, R$^7$ is naphthyl substituted with 1-3 R$^{21}$ groups independently selected from the group consisting of F, —SF$_5$ and —OSF$_5$, wherein at least one R$^{21}$ group is selected from the group consisting of —SF$_5$ and —OSF$_5$.

In another embodiment, R$^7$ is naphthyl which is substituted with 1-4 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment, R$^7$ is naphthyl substituted with 1-4 R$^{21}$ substituents independently selected from the group consisting of halo, alkyl, —CN, —NH$_2$, —NH(alkyl), —N(alkyl)$_2$, hydroxy, alkoxy, aryl, heteroaryl, —SF$_5$, —OSF$_5$ and —Si(R$^{24}$)$_3$ (and in one example each R$^{24}$ is the same or different alkyl, and in another example the —Si(R$^{24}$)$_3$ group is —Si(CH$_3$)$_3$ or —Si(CH$_2$CH$_3$)$_2$CH$_3$, and in another example the —Si(R$^{24}$)$_3$ group is —Si(CH$_3$)$_3$), and wherein at least one R$^{21}$ group is selected from the group consisting of —SF$_5$, —OSF$_5$ and —Si(R$^{24}$)$_3$.

In another embodiment, R$^7$ is naphthyl substituted with 1-4 R$^{21}$ substituents independently selected from the group consisting of halo, alkyl, —CN, —NH$_2$, —NH(alkyl), —N(alkyl)$_2$, hydroxy, alkoxy, aryl, heteroaryl, —SF$_5$ and —OSF$_5$, wherein at least one group is —SF$_5$ or —OSF$_5$.

In another embodiment, R$^7$ is unsubstituted biphenyl.

In another embodiment, R$^7$ is biphenyl substituted with 1-3 R$^{21}$ groups independently selected from the group consisting of —SF$_5$, —OSF$_5$ and —Si(R$^{24}$)$_3$ (and in one example each R$^{24}$ is the same or different alkyl, and in another example the —Si(R$^{24}$)$_3$ group is —Si(CH$_3$)$_3$ or —Si(CH$_2$CH$_3$)$_2$CH$_3$, and in another example the —Si(R$^{24}$)$_3$ group is —Si(CH$_3$)$_3$).

In another embodiment, R$^7$ is biphenyl substituted with 1-3 R$^{21}$ groups independently selected from the group consisting of —SF$_5$ and —OSF$_5$.

In another embodiment, R$^7$ is biphenyl substituted with 1-3 R$^{21}$ groups independently selected from the group consisting of halo, —SF$_5$, —OSF$_5$ and —Si(R$^{24}$)$_3$ (and in one example each R$^{24}$ is the same or different alkyl, and in another example the —Si(R$^{24}$)$_3$ group is —Si(CH$_3$)$_3$ or —Si(CH$_2$CH$_3$)$_2$CH$_3$, and in another example the —Si(R$^{24}$)$_3$ group is —Si(CH$_3$)$_3$), and wherein at least one R$^{21}$ group is selected from the group consisting of —SF$_5$, —OSF$_5$ and —Si(R$^{24}$)$_3$.

In another embodiment, R$^7$ is biphenyl substituted with 1-3 R$^{21}$ groups independently selected from the group consisting of halo, —SF$_5$ and —OSF$_5$, wherein at least one R$^{21}$ group is selected from the group consisting of —SF$_5$ and —OSF$_5$.

In another embodiment, R$^7$ is biphenyl substituted with 1-3 R$^{21}$ groups independently selected from the group consisting of F, Br, —SF$_5$ and —OSF$_5$, wherein at least one R$^{21}$ group is selected from the group consisting of —SF$_5$ and —OSF$_5$.

In another embodiment, R$^7$ is biphenyl substituted with 1-3 R$^{21}$ groups independently selected from the group consisting of F, —SF$_5$ and —OSF$_5$, wherein at least one R$^{21}$ group is selected from the group consisting of —SF$_5$ and —OSF$_5$.

In another embodiment, R$^7$ is biphenyl which is substituted with 1-4 substituents which can be the same or different, each substituent being independently selected from the group consisting of halo, alkyl, —CN, —NH$_2$, —NH(alkyl), —N(alkyl)$_2$, hydroxy and alkoxy groups.

In another embodiment, R$^7$ is biphenyl which is substituted with 1-4 R$^{21}$ substituents independently selected from the group consisting of halo, alkyl, —CN, —NH$_2$, —NH(alkyl), —N(alkyl)$_2$, hydroxyl, alkoxy, —SF$_5$, —OSF$_5$ and —Si(R$^{24}$)$_3$ (and in one example each R$^{24}$ is the same or different alkyl, and in another example the —Si(R$^{24}$)$_3$ group is —Si(CH$_3$)$_3$ or —Si(CH$_2$CH$_3$)$_2$CH$_3$, and in another example the —Si(R$^{24}$)$_3$ group is —Si(CH$_3$)$_3$), and wherein at least one R$^{21}$ group is selected from the group consisting of —SF$_5$, —OSF$_5$ and —Si(R$^{24}$)$_3$.

In another embodiment, R$^7$ is biphenyl which is substituted with 1-4 R$^{21}$ substituents independently selected from the group consisting of halo, alkyl, —CN, —NH$_2$, —NH(alkyl), —N(alkyl)$_2$, hydroxyl, alkoxy, —SF$_5$ and —OSF$_5$, wherein at least one R$^{21}$ group is selected from the group consisting of —SF$_5$ and —OSF$_5$.

In another embodiment, R$^7$ is 3-(1,1'-biphenyl)-yl substituted with 1-3 R$^{21}$ groups independently selected from the group consisting of —SF$_5$ and —OSF$_5$.

In another embodiment, R$^7$ is 3-(1,1'-biphenyl)-yl substituted with 1-3 R$^{21}$ groups independently selected from the group consisting of halo, —SF$_5$ and —OSF$_5$, wherein at least one R$^{21}$ group is selected from the group consisting of —SF$_5$ and —OSF$_5$.

In another embodiment, R$^7$ is 3-(1,1'-biphenyl)-yl substituted with 1-3 R$^{21}$ groups independently selected from the group consisting of F, Br, —SF$_5$ and —OSF$_5$, wherein at least one R$^{21}$ group is selected from the group consisting of —SF$_5$ and —OSF$_5$.

In another embodiment, R$^7$ is 3-(1,1'-biphenyl)-yl substituted with 1-3 R$^{21}$ groups independently selected from the group consisting of F, —SF$_5$ and —OSF$_5$, wherein at least one R$^{21}$ group is selected from the group consisting of —SF$_5$ and —OSF$_5$.

In another embodiment, R$^7$ is 4-(1,1'-biphenyl)-yl substituted with 1-3 R$^{21}$ groups independently selected from the group consisting of —SF$_5$ and —OSF$_5$.

In another embodiment, R$^7$ is 4-(1,1'-biphenyl)-yl substituted with 1-3 R$^{21}$ groups independently selected from the group consisting of halo, —SF$_5$ and —OSF$_5$, wherein at least one R$^{21}$ group is selected from the group consisting of —SF$_5$ and —OSF$_5$.

In another embodiment, R$^7$ is 4-(1,1'-biphenyl)-yl substituted with 1-3 R$^{21}$ groups independently selected from the group consisting of F, Br, —SF$_5$ and —OSF$_5$, wherein at least one R$^{21}$ group is selected from the group consisting of —SF$_5$ and —OSF$_5$.

In another embodiment, R$^7$ is 4-(1,1'-biphenyl)-yl substituted with 1-3 R$^{21}$ groups independently selected from the group consisting of F, —SF$_5$ and —OSF$_5$, wherein at least one R$^{21}$ group is selected from the group consisting of —SF$_5$ and —OSF$_5$.

In another embodiment, R$^6$ is H and R$^7$ is a biphenyl which can be unsubstituted or optionally independently substituted with 1-4 substituents which can be the same or different, each substituent being independently selected from the group consisting of halo, alkyl, —CN, —NH$_2$, —NH(alkyl), —N(alkyl)$_2$, hydroxy and alkoxy groups.

In another embodiment, R$^6$ is H and R$^7$ is a biphenyl optionally substituted with 1-4 R$^{21}$ substituents independently selected from the group consisting of halo, alkyl, —CN, —NH$_2$, —NH(alkyl), —N(alkyl)$_2$, hydroxyl, alkoxy, —SF$_5$ and —OSF$_5$, wherein at least one R$^{21}$ group is selected from the group consisting of —SF$_5$ and —OSF$_5$.

In another embodiment, R$^6$ is methyl, and R$^7$ is a biphenyl which can be unsubstituted or optionally independently substituted with 1-4 substituents which can be the same or different, each substituent being independently selected from the group consisting of halo, alkyl, —CN, —NH$_2$, —NH(alkyl), —N(alkyl)$_2$, hydroxy and alkoxy groups.

In another embodiment, R$^6$ is methyl, and R$^7$ is a biphenyl optionally substituted with 1-4 R$^{21}$ substituents independently selected from the group consisting of halo, alkyl, —CN, —NH$_2$, —NH(alkyl), —N(alkyl)$_2$, hydroxyl, alkoxy, —SF$_5$ and —OSF$_5$, wherein at least one R$^{21}$ group is selected from the group consisting of —SF$_5$ and —OSF$_5$.

In another embodiment, R$^6$ is H, and R$^7$ is a phenyl which can be unsubstituted or optionally independently substituted with 1-4 substituents which can be the same or different, each substituent being independently selected from the group consisting of halo, alkyl, —CN, —NH$_2$, —NH(alkyl), —N(alkyl)$_2$, hydroxy and alkoxy groups.

In another embodiment, R$^6$ is H, and R$^7$ is a phenyl optionally substituted with 1-4 R$^{21}$ substituents independently selected from the group consisting of halo, alkyl, —CN, —NH$_2$, —NH(alkyl), —N(alkyl)$_2$, hydroxyl, alkoxy, —SF$_5$ and —OSF$_5$, wherein at least one R$^{21}$ group is selected from the group consisting of —SF$_5$ and —OSF$_5$.

In another embodiment of this invention, R$^6$ is H, and R$^7$ is phenyl substituted with 1 to 3 halos selected from the group consisting of Cl and F. In one example said phenyl is substituted with one Cl and one F.

In another embodiment of this invention, R$^6$ is H, and R$^7$ is phenyl substituted with 1 to 3 F.

In another embodiment of this invention, R$^6$ is H, and R$^7$ is phenyl substituted with 1 F.

In another embodiment of this invention, R$^6$ is H, and R$^7$ is phenyl substituted with 2 F.

In another embodiment of this invention, R$^6$ is H, and R$^7$ is phenyl substituted with 3 F.

In another embodiment R$^6$ is alkyl, and R$^7$ is phenyl substituted with 1-3 R$^{21}$ substituents independently selected from the group consisting of halo, alkyl, —CN, —NH$_2$, —NH(alkyl), —N(alkyl)$_2$, hydroxy, alkoxy, aryl, heteroaryl, halo, alkyl, —CN, —NH$_2$, —NH(alkyl), —N(alkyl)$_2$, hydroxyl, alkoxy, SF$_5$, —OSF$_5$ and —Si(R$^{24}$)$_3$ (and in one example each R$^{24}$ is the same or different alkyl, and in another example the —Si(R$^{24}$)$_3$ group is —Si(CH$_3$)$_3$ or —Si(CH$_2$CH$_3$)$_2$CH$_3$, and in another example the —Si(R$^{24}$)$_3$ group is —Si(CH$_3$)$_3$), and wherein at least one R$^{21}$ group is selected from the group consisting of —SF$_5$, —OSF$_5$ and —Si(R$^{24}$)$_3$.

In another embodiment R$^6$ is alkyl, and R$^7$ is phenyl substituted with 1-3 R$^{21}$ substituents independently selected from the group consisting of halo, alkyl, —CN, —NH$_2$, —NH(alkyl), —N(alkyl)$_2$, hydroxy, alkoxy, aryl, heteroaryl, halo, alkyl, —CN, —NH$_2$, —NH(alkyl), —N(alkyl)$_2$, hydroxyl, alkoxy, —SF$_5$ and —OSF$_5$, wherein at least one R$^{21}$ group on said phenyl is selected from the group consisting of —SF$_5$ and —OSF$_5$.

In another embodiment R$^6$ is alkyl substituted with 1-5 independently selected R$^{21}$ moieties, and R$^7$ is phenyl substituted with 1-3 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment R$^6$ is alkyl substituted with 1-5 independently selected R$^{21}$ moieties, and R$^7$ is phenyl substituted with 1-3 R$^{21}$ substituents independently selected from the group consisting of halo, alkyl, —CN, —NH$_2$, —NH(alkyl), —N(alkyl)$_2$, hydroxy, alkoxy, aryl, heteroaryl, halo, alkyl, —CN, —NH$_2$, —NH(alkyl), —N(alkyl)$_2$, hydroxyl, alkoxy, SF$_5$, —OSF$_5$ and —Si(R$^{24}$)$_3$ (and in one example each R$^{24}$ is the same or different alkyl, and in another example the —Si(R$^{24}$)$_3$ group is —Si(CH$_3$)$_3$ or —Si(CH$_2$CH$_3$)$_2$CH$_3$, and in another example the —Si(R$^{24}$)$_3$ group is —Si(CH$_3$)$_3$), and wherein at least one R$^{21}$ group is selected from the group consisting of —SF$_5$, —OSF$_5$ and —Si(R$^{24}$)$_3$.

In another embodiment R$^6$ is alkyl substituted with 1-5 independently selected R$^{21}$ moieties, and R$^7$ is phenyl substituted with 1-3 R$^{21}$ substituents independently selected from the group consisting of halo, alkyl, —CN, —NH$_2$, —NH(alkyl), —N(alkyl)$_2$, hydroxy, alkoxy, aryl, heteroaryl, halo, alkyl, —CN, —NH$_2$, —NH(alkyl), —N(alkyl)$_2$, hydroxyl, alkoxy, —SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, and R$^7$ is phenyl substituted with 1-3 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment R$^6$ is alkyl substituted with one R$^{21}$ moiety, and R$^7$ is phenyl substituted with 1-3 R$^{21}$ substituents independently selected from the group consisting of halo, alkyl, —CN, —NH$_2$, —NH(alkyl), —N(alkyl)$_2$, hydroxy, alkoxy, aryl, heteroaryl, SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, and R$^7$ is phenyl substituted with 1-3 independently selected halos.

In another embodiment R$^6$ is alkyl substituted with one R$^{21}$ moiety, and R$^7$ is phenyl substituted with 1-3 R$^{21}$ groups independently selected from the group consisting of halos, SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, and R$^7$ is phenyl substituted with 1-3 F.

In another embodiment R$^6$ is alkyl substituted with one R$^{21}$ moiety, and R$^7$ is phenyl substituted with 1-3 R$^{21}$ groups independently selected from the group consisting of F, SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, and R$^7$ is phenyl substituted with one F.

In another embodiment R$^6$ is alkyl substituted with one R$^{21}$ moiety, and R$^7$ is phenyl substituted with one F, and one or two groups independently selected from the group consisting of SF$_5$ and —OSF$_5$, wherein at least one —SF$_5$ or —OSF$_5$ is present.

In another embodiment R$^6$ is alkyl substituted with one R$^{21}$ moiety, and R$^7$ is phenyl substituted with one F, and one or two groups independently selected from the group consisting of SF$_5$ and —OSF$_5$, wherein at least one —SF$_5$ or —OSF$_5$ is present.

In another embodiment R$^6$ is alkyl substituted with one R$^{21}$ moiety, and R$^7$ is phenyl substituted with 1 to 3 groups independently selected from the group consisting of SF$_5$ and —OSF$_5$.

In another embodiment R$^6$ is alkyl substituted with one R$^{21}$ moiety, and R$^7$ is phenyl substituted with 1 to 2 groups independently selected from the group consisting of SF$_5$ and —OSF$_5$.

In another embodiment R$^6$ is alkyl substituted with one R$^{21}$ moiety, and R$^7$ is phenyl substituted with 1 to 3 —SF$_5$ groups (and in one example one —SF$_5$, and in another example two —SF$_5$ groups, and in another example three —SF$_5$ groups).

In another embodiment R$^6$ is alkyl substituted with one R$^{21}$ moiety, and R$^7$ is phenyl substituted with 1 to 3 —OSF$_5$ groups (and in one example one —OSF$_5$, and in another example two —OSF$_5$ groups, and in another example three —OSF$_5$ groups).

In another embodiment R$^6$ is alkyl substituted with one R$^{21}$ moiety, and said R$^{21}$ moiety is —OR$^{16}$, and R$^7$ is phenyl substituted with 1-3 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment R$^6$ is alkyl substituted with one R$^{21}$ moiety, and said R$^{21}$ moiety is —OR$^{15}$, and R$^7$ is phenyl substituted with 1-3 R$^{21}$ independently selected from the group consisting of halo, alkyl, —CN, —NH$_2$, —NH(alkyl), —N(alkyl)$_2$, hydroxy, alkoxy, aryl, heteroaryl, —SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, and said R$^{21}$ moiety is —OR$^{15}$, and R$^7$ is phenyl substituted with 1-3 independently selected halos.

In another embodiment R$^6$ is alkyl substituted with one R$^{21}$ moiety, and said R$^{21}$ moiety is —OR$^{15}$, and R$^7$ is phenyl substituted with 1-3 R$^{21}$ groups independently selected from the group consisting of halos, —SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, and said R$^{21}$ moiety is —OR$^{16}$, and R$^7$ is phenyl substituted with 1-3 independently selected F.

In another embodiment R$^6$ is alkyl substituted with one R$^{21}$ moiety, and said R$^{21}$ moiety is —OR$^{15}$, and R$^7$ is phenyl substituted with 1-3 R$^{21}$ groups independently selected from the group consisting of F, —SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, and said R$^{21}$ moiety is —OR$^{15}$, and R$^7$ is phenyl substituted with one F.

In another embodiment R$^6$ is alkyl substituted with one R$^{21}$ moiety, and said R$^{21}$ moiety is —OR$^{15}$, and R$^7$ is phenyl substituted with one F, and said phenyl is also subsubstitued with one or two groups independently selected from the group consisting of: —SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, said R$^{21}$ moiety is —OR$^{15}$, and said R$^{15}$ is selected from the group consisting of: H and alkyl, and R$^7$ is phenyl substituted with 1-3 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment R$^6$ is alkyl substituted with one R$^{21}$ moiety, said R$^{21}$ moiety is —OR$^{15}$, and said R$^{15}$ is selected from the group consisting of: H and alkyl, and R$^7$ is phenyl substituted with 1-3 R$^{21}$ substituents independently selected from the group consisting of halo, alkyl, —CN, —NH$_2$, —NH(alkyl), —N(alkyl)$_2$, hydroxy, alkoxy, aryl, heteroaryl, —SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, said R$^{21}$ moiety is —OR$^{15}$, and said R$^{15}$ is selected from the group consisting of: H and alkyl, and R$^7$ is phenyl substituted with 1-3 independently selected halos.

In another embodiment R$^6$ is alkyl substituted with one R$^{21}$ moiety, said R$^{21}$ moiety is —OR$^{15}$, and said R$^{15}$ is selected from the group consisting of: H and alkyl, and R$^7$ is phenyl substituted with 1-3 R$^{21}$ groups independently selected from the group consisting of halos, —SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, said R$^{21}$ moiety is —OR$^{15}$, and said R$^{15}$ is selected from the group consisting of: H and alkyl, and R$^7$ is phenyl substituted with 1-3 independently selected F.

In another embodiment R$^6$ is alkyl substituted with one R$^{21}$ moiety, said R$^{21}$ moiety is —OR$^{15}$, and said R$^{15}$ is selected from the group consisting of: H and alkyl, and R$^7$ is phenyl substituted with 1-3 R$^{21}$ groups independently selected from the group consisting of F, —SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, said R$^{21}$ moiety is —OR$^{15}$, and said R$^{15}$ is selected from the group consisting of: H and alkyl, and R$^7$ is phenyl substituted with one F.

In another embodiment R$^6$ is alkyl substituted with one R$^{21}$ moiety, said R$^{21}$ moiety is —OR$^{15}$, and said R$^{15}$ is selected from the group consisting of: H and alkyl, and R$^7$ is phenyl substituted with one F, and also substituted with one or two groups independently selected from the group consisting of —SF$_5$ and —OSF$_5$.

In another embodiment R$^6$ is alkyl substituted with one R$^{21}$ moiety, said R$^{21}$ moiety is —OR$^{15}$, and said R$^{15}$ is H, and R$^7$ is phenyl substituted with 1-3 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment R$^6$ is alkyl substituted with one R$^{21}$ moiety, said R$^{21}$ moiety is —OR$^{15}$, and said R$^{15}$ is H, and R$^7$ is phenyl substituted with 1-3 R$^{21}$ groups independently selected from the group consisting of halo, alkyl, —ON, —NH$_2$, —NH(alkyl), —N(alkyl)$_2$, hydroxy, alkoxy, aryl, heteroaryl, —SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, said R$^{21}$ moiety is —OR$^{15}$, and said R$^{15}$ is H, and said R$^{15}$ is selected from the group consisting of: H and alkyl, and R$^7$ is phenyl substituted with 1-3 independently selected halos.

In another embodiment R$^6$ is alkyl substituted with one R$^{21}$ moiety, said R$^{21}$ moiety is —OR$^{15}$, and said R$^{15}$ is H, and said R$^{15}$ is selected from the group consisting of: H and alkyl, and R$^7$ is phenyl substituted with 1-3 R$^{21}$ groups independently selected from the group consisting of halos, —SF$_5$ and —OSF$_5$, wherein at least one R$^{21}$ group on said phenyl is selected from the group consisting of —SF$_5$ and —OSF$_5$.

In another embodiment R$^6$ is alkyl substituted with one R$^{21}$ moiety, said R$^{21}$ moiety is —OR$^{15}$, and said R$^{15}$ is H, and said R$^{15}$ is selected from the group consisting of: H and alkyl, and R$^7$ is phenyl substituted with 1-3 independently selected F.

In another embodiment R$^6$ is alkyl substituted with one R$^{21}$ moiety, said R$^{21}$ moiety is —OR$^{15}$, and said R$^{15}$ is H, and said R$^{15}$ is selected from the group consisting of: H and alkyl, and R$^7$ is phenyl substituted with 1-2 F, and said phenyl is also substituted with 1 to 2 R$^{21}$ groups independently selected from the group consisting of —SF$_5$ and —OSF$_5$, wherein at least one R$^{21}$ group on said phenyl is selected from the group consisting of —SF$_5$ and —OSF$_5$, and wherein the total number of substituents on said phenyl is 2 to 3.

In another embodiment R$^6$ is alkyl substituted with one R$^{21}$ moiety, said R$^{21}$ moiety is —OR$^{15}$, and said R$^{15}$ is H, and said R$^{15}$ is selected from the group consisting of: H and alkyl, and R$^7$ is phenyl substituted with one F.

In another embodiment $R^6$ is alkyl substituted with one $R^{21}$ moiety, said $R^{21}$ moiety is —$OR^{15}$, and said $R^{15}$ is H, and said $R^{15}$ is selected from the group consisting of: H and alkyl, and $R^7$ is phenyl substituted with one F, and said phenyl is also substituted with one or two groups selected from the group consisting of —$SF_5$ and —$OSF_5$, wherein at least one $R^{21}$ group on said phenyl is selected from the group consisting of —$SF_5$ and —$OSF_5$.

In another embodiment $R^6$ is alkyl substituted with one $R^{21}$ moiety, said $R^{21}$ moiety is —$OR^{15}$, and said $R^{15}$ is alkyl (e.g. methyl), and $R^7$ is phenyl substituted with 1-3 substituents which can be the same or different, each substituent being independently selected from the group consisting of halo, alkyl, —CN, —$NH_2$, —NH(alkyl), —N(alkyl)$_2$, hydroxy, alkoxy, aryl and heteroaryl groups.

In another embodiment $R^6$ is alkyl substituted with one $R^{21}$ moiety, said $R^{21}$ moiety is —$OR^{15}$, and said $R^{15}$ is alkyl (e.g. methyl), and $R^7$ is phenyl substituted with 1-3 substituents which can be the same or different, each substituent being independently selected from the group consisting of halo, alkyl, —CN, —$NH_2$, —NH(alkyl), —N(alkyl)$_2$, hydroxy, alkoxy, aryl, heteroaryl, —$SF_5$ and —$OSF_5$, wherein at least one $R^{21}$ group on said phenyl is selected from the group consisting of —$SF_5$ and —$OSF_5$.

In another embodiment $R^6$ is alkyl substituted with one $R^{21}$ moiety, said $R^{21}$ moiety is —$OR^{15}$, and said $R^{15}$ is alkyl (e.g. methyl), and $R^7$ is phenyl substituted with 1-3 independently selected halos.

In another embodiment $R^6$ is alkyl substituted with one $R^{21}$ moiety, said $R^{21}$ moiety is —$OR^{15}$, and said $R^{15}$ is alkyl (e.g. methyl), and $R^7$ is phenyl substituted with 1-3 $R^{21}$ groups independently selected from the group consisting of halos, —$SF_5$ and —$OSF_5$, wherein at least one $R^{21}$ group on said phenyl is selected from the group consisting of —$SF_5$ and —$OSF_5$.

In another embodiment $R^6$ is alkyl substituted with one $R^{21}$ moiety, said $R^{21}$ moiety is —$OR^{15}$, and said $R^{15}$ is alkyl (e.g. methyl), and $R^7$ is phenyl substituted with 1-3 independently selected F.

In another embodiment $R^6$ is alkyl substituted with one $R^{21}$ moiety, said $R^{21}$ moiety is —$OR^{15}$, and said $R^{15}$ is alkyl (e.g. methyl), and $R^7$ is phenyl substituted with 1-2 F, and said phenyl is also substituted with one or two groups independently selected from the group consisting of —$SF_5$ and —$OSF_5$, and wherein the total number of substituents on said phenyl is 2 to 3.

In another embodiment $R^6$ is alkyl substituted with one $R^{21}$ moiety, said $R^{21}$ moiety is —$OR^{15}$, and said $R^{15}$ is alkyl (e.g. methyl), and $R^7$ is phenyl substituted with one F.

In another embodiment $R^6$ is alkyl substituted with one $R^{21}$ moiety, said $R^{21}$ moiety is —$OR^{15}$, and said $R^{15}$ is alkyl (e.g. methyl), and $R^7$ is phenyl substituted with one F, and said phenyl is also substituted with one or two substituents selected from the group consisting of —$SF_5$ and —$OSF_5$.

In another embodiment $R^6$ is methyl substituted with 1-3 independently selected $R^{21}$ moieties, and $R^7$ is phenyl substituted with 1-3 substituents which can be the same or different, each substituent being independently selected from the group consisting of halo, alkyl, —CN, —$NH_2$, —NH(alkyl), —N(alkyl)$_2$, hydroxy, alkoxy, aryl and heteroaryl groups.

In another embodiment $R^6$ is methyl substituted with 1-3 independently selected $R^{21}$ moieties, and $R^7$ is phenyl substituted with 1-3 $R^{21}$ substituents independently selected from the group consisting of halo, alkyl, —CN, —$NH_2$, —NH(alkyl), —N(alkyl)$_2$, hydroxy, alkoxy, aryl, heteroaryl, —$SF_5$ and —$OSF_5$, wherein at least one $R^{21}$ group on said phenyl is selected from the group consisting of —$SF_5$ and —$OSF_5$.

In another embodiment $R^6$ is methyl substituted with one $R^{21}$ moiety, and $R^7$ is phenyl substituted with 1-3 substituents which can be the same or different, each substituent being independently selected from the group consisting of halo, alkyl, —CN, —$NH_2$, —NH(alkyl), —N(alkyl)$_2$, hydroxy, alkoxy, aryl and heteroaryl groups.

In another embodiment $R^6$ is methyl substituted with one $R^{21}$ moiety, and $R^7$ is phenyl substituted with 1-3 $R^{21}$ independently selected from the group consisting of halo, alkyl, —CN, —$NH_2$, —NH(alkyl), —N(alkyl)$_2$, hydroxy, alkoxy, aryl, heteroaryl, —$SF_5$ and —$OSF_5$, wherein at least one $R^{21}$ group on said phenyl is selected from the group consisting of —$SF_5$ and —$OSF_5$.

In another embodiment $R^6$ is methyl substituted with one $R^{21}$ moiety, and $R^7$ is phenyl substituted with 1-3 independently selected halos.

In another embodiment $R^6$ is methyl substituted with one $R^{21}$ moiety, and $R^7$ is phenyl substituted with 1-2 independently selected halos, and said phenyl is also substituted with one or two groups independently selected from the group consisting of —$SF_5$ and —$OSF_5$, and wherein the total number of substituents on said phenyl is 2 or three.

In another embodiment $R^6$ is methyl substituted with one $R^{21}$ moiety, and $R^7$ is phenyl substituted with 1-3 F.

In another embodiment $R^6$ is methyl substituted with one $R^{21}$ moiety, and $R^7$ is phenyl substituted with 1-2 F, and said phenyl is also substituted with one or two groups independently selected from the group consisting of —$SF_5$ and —$OSF_5$, and wherein the total number of substituents on said phenyl is 2 or three.

In another embodiment $R^6$ is methyl substituted with one $R^{21}$ moiety, and $R^7$ is phenyl substituted with one F.

In another embodiment $R^6$ is methyl substituted with one $R^{21}$ moiety, and $R^7$ is phenyl substituted with one F, and said phenyl is also substituted with one or two groups independently selected from the group consisting of —$SF_5$ and —$OSF_5$.

In another embodiment $R^6$ is methyl substituted with one $R^{21}$ moiety, and said $R^{21}$ moiety is —$OR^{15}$, and $R^7$ is phenyl substituted with 1-3 substituents which can be the same or different, each substituent being independently selected from the group consisting of halo, alkyl, —CN, —$NH_2$, —NH(alkyl), —N(alkyl)$_2$, hydroxy, alkoxy, aryl and heteroaryl groups.

In another embodiment $R^6$ is methyl substituted with one $R^{21}$ moiety, and said $R^{21}$ moiety is —$OR^{15}$, and $R^7$ is phenyl substituted with 1-3 substituents independently selected from the group consisting of halo, alkyl, —CN, —$NH_2$, —NH(alkyl), —N(alkyl)$_2$, hydroxy, alkoxy, aryl, heteroaryl, —$SF_5$ and —$OSF_5$, wherein at least one $R^{21}$ group on said phenyl is selected from the group consisting of —$SF_5$ and —$OSF_5$.

In another embodiment $R^6$ is methyl substituted with one $R^{21}$ moiety, and said $R^{21}$ moiety is —$OR^{15}$, and $R^7$ is phenyl substituted with 1-3 independently selected halos.

In another embodiment $R^6$ is methyl substituted with one $R^{21}$ moiety, and said $R^{21}$ moiety is —$OR^{16}$, and $R^7$ is phenyl substituted with 1-2 independently selected halos, and said phenyl is also substituted with one or two groups independently selected from the group consisting of —$SF_5$ and —$OSF_5$, and wherein the total number of substituents on said phenyl is 2 or 3.

In another embodiment $R^6$ is methyl substituted with one $R^{21}$ moiety, and said $R^{21}$ moiety is —$OR^{15}$, and $R^7$ is phenyl substituted with 1-3 independently selected F.

In another embodiment $R^6$ is methyl substituted with one $R^{21}$ moiety, and said $R^{21}$ moiety is —$OR^{15}$, and $R^7$ is phenyl substituted with 1-2 independently selected F, and said phenyl is also substituted with one or two groups independently selected from the group consisting of —SF$_5$ and —OSF$_5$, and wherein the total number of substituents on said phenyl is 2 or 3.

In another embodiment R$^6$ is methyl substituted with one R$^{21}$ moiety, and said R$^{21}$ moiety is —OR$^{15}$, and R$^7$ is phenyl substituted with one F.

In another embodiment R$^6$ is methyl substituted with one R$^{21}$ moiety, and said R$^{21}$ moiety is —OR$^{15}$, and R$^7$ is phenyl substituted with one F, and said phenyl is also substituted with one or two groups independently selected from the group consisting of —SF$_5$ and —OSF$_5$.

In another embodiment R$^6$ is methyl substituted with one R$^{21}$ moiety, said R$^{21}$ moiety is —OR$^{15}$, and said R$^{15}$ is selected from the group consisting of: H and alkyl, and R$^7$ is phenyl substituted with 1-3 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment R$^6$ is methyl substituted with one R$^{21}$ moiety, said R$^{21}$ moiety is —OR$^{15}$, and said R$^{15}$ is selected from the group consisting of: H and alkyl, and R$^7$ is phenyl substituted with 1-3 substituents independently selected from the group consisting of halo, alkyl, —CN, —NH$_2$, —NH(alkyl), —N(alkyl)$_2$, hydroxy, alkoxy, aryl, heteroaryl, —SF$_5$ and —OSF$_5$, wherein at least one R$^{21}$ group on said phenyl is selected from the group consisting of —SF$_5$ and —OSF$_5$.

In another embodiment R$^6$ is methyl substituted with one R$^{21}$ moiety, said R$^{21}$ moiety is —OR$^{15}$, and said R$^{15}$ is selected from the group consisting of: H and alkyl, and R$^7$ is phenyl substituted with 1-3 independently selected halos.

In another embodiment R$^6$ is methyl substituted with one R$^{21}$ moiety, said R$^{21}$ moiety is —OR$^{15}$, and said R$^{15}$ is selected from the group consisting of: H and alkyl, and R$^7$ is phenyl substituted with 1-2 independently selected halos, and said phenyl is also substituted with one or two groups independently selected from the group consisting of —SF$_5$ and —OSF$_5$, and wherein the total number of substituents on said phenyl is 2 or 3.

In another embodiment R$^6$ is methyl substituted with one R$^{21}$ moiety, said R$^{21}$ moiety is —OR$^{15}$, and said R$^{15}$ is selected from the group consisting of: H and alkyl, and R$^7$ is phenyl substituted with 1-3 independently selected F.

In another embodiment R$^6$ is methyl substituted with one R$^{21}$ moiety, said R$^{21}$ moiety is —OR$^{15}$, and said R$^{15}$ is selected from the group consisting of: H and alkyl, and R$^7$ is phenyl substituted with 1-2 independently selected F, and said phenyl is also substituted with one or two groups independently selected from the group consisting of —SF$_5$ and —OSF$_5$, and wherein the total number of substituents on said phenyl is 2 or 3.

In another embodiment R$^6$ is methyl substituted with one R$^{21}$ moiety, said R$^{21}$ moiety is —OR$^{15}$, and said R$^{15}$ is selected from the group consisting of: H and alkyl, and R$^7$ is phenyl substituted with one F.

In another embodiment R$^6$ is methyl substituted with one R$^{21}$ moiety, said R$^{21}$ moiety is —OR$^{15}$, and said R$^{15}$ is selected from the group consisting of: H and alkyl, and R$^7$ is phenyl substituted with one F, and said phenyl is also substituted with one or two groups independently selected from the group consisting of —SF$_5$ and —OSF$_5$.

In another embodiment R$^6$ is methyl substituted with one R$^{21}$ moiety, said R$^{21}$ moiety is —OR$^{15}$, and said R$^{15}$ is H, and R$^7$ is phenyl substituted with 1-3 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment R$^6$ is methyl substituted with one R$^{21}$ moiety, said R$^{21}$ moiety is —OR$^{15}$, and said R$^{15}$ is H, and R$^7$ is phenyl substituted with 1-3 substituents independently selected from the group consisting of halo, alkyl, —CN, —NH$_2$, —NH(alkyl), —N(alkyl)$_2$, hydroxy, alkoxy, aryl, heteroaryl, —SF$_5$ and —OSF$_5$, wherein at least one R$^{21}$ group on said phenyl is selected from the group consisting of —SF$_5$ and —OSF$_5$.

In another embodiment R$^6$ is methyl substituted with one R$^{21}$ moiety, said R$^{21}$ moiety is —OR$^{15}$, and said R$^{15}$ is H, and said R$^{15}$ is selected from the group consisting of: H and alkyl, and R$^7$ is phenyl substituted with 1-3 independently selected halos.

In another embodiment R$^6$ is methyl substituted with one R$^{21}$ moiety, said R$^{21}$ moiety is —OR$^{15}$, and said R$^{15}$ is H, and said R$^{15}$ is selected from the group consisting of: H and alkyl, and R$^7$ is phenyl substituted with 1-2 independently selected halos, and said phenyl is also substituted with one or two groups independently selected from the group consisting of —SF$_5$ and —OSF$_5$, and wherein the total number of substituents on said phenyl is 2 or 3.

In another embodiment R$^6$ is methyl substituted with one R$^{21}$ moiety, said R$^{21}$ moiety is —OR$^{15}$, and said R$^{15}$ is H, and said R$^{15}$ is selected from the group consisting of: H and alkyl, and R$^7$ is phenyl substituted with 1-3 F.

In another embodiment R$^6$ is methyl substituted with one R$^{21}$ moiety, said R$^{21}$ moiety is —OR$^{15}$, and said R$^{15}$ is H, and said R$^{15}$ is selected from the group consisting of: H and alkyl, and R$^7$ is phenyl substituted with 1-2 F, and said phenyl is also substituted with one or two groups independently selected from the group consisting of —SF$_5$ and —OSF$_5$, and wherein the total number of substituents on said phenyl is 2 or 3.

In another embodiment R$^6$ is methyl substituted with one R$^{21}$ moiety, said R$^{21}$ moiety is —OR$^{15}$, and said R$^{15}$ is H, and said R$^{15}$ is selected from the group consisting of: H and alkyl, and R$^7$ is phenyl substituted with one F.

In another embodiment R$^6$ is methyl substituted with one R$^{21}$ moiety, said R$^{21}$ moiety is —OR$^{15}$, and said R$^{15}$ is H, and said R$^{15}$ is selected from the group consisting of: H and alkyl, and R$^7$ is phenyl substituted with one F, and said phenyl is also substituted with one or two groups independently selected from the group consisting of —SF$_5$ and —OSF$_5$.

In another embodiment R$^6$ is methyl substituted with one R$^{21}$ moiety, said R$^{21}$ moiety is —OR$^{15}$, and said R$^{15}$ is alkyl (e.g. methyl), and R$^7$ is phenyl substituted with 1-3 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment R$^6$ is methyl substituted with one R$^{21}$ moiety, said R$^{21}$ moiety is —OR$^{15}$, and said R$^{15}$ is alkyl (e.g. methyl), and R$^7$ is phenyl substituted with 1-3 substituents which can be the same or different, each substituent being independently selected from the group consisting of halo, alkyl, —CN, —NH$_2$, —NH(alkyl), —N(alkyl)$_2$, hydroxy, alkoxy, aryl, heteroaryl, —SF$_5$ and —OSF$_5$, wherein at least one R$^{21}$ group on said phenyl is selected from the group consisting of —SF$_5$ and —OSF$_5$.

In another embodiment R$^6$ is methyl substituted with one R$^{21}$ moiety, said R$^{21}$ moiety is —OR$^{15}$, and said R$^{15}$ is alkyl (e.g. methyl), and R$^7$ is phenyl substituted with 1-3 independently selected halos.

In another embodiment R$^6$ is methyl substituted with one R$^{21}$ moiety, said R$^{21}$ moiety is —OR$^{15}$, and said R$^{15}$ is alkyl (e.g. methyl), and $R^7$ is phenyl substituted with 1-2 independently selected halos, and said phenyl is also substituted with one or two groups independently selected from the group consisting of —$SF_5$ and —$OSF_5$, and wherein the total number of substituents on said phenyl is 2 or 3.

In another embodiment $R^6$ is methyl substituted with one $R^{21}$ moiety, said $R^{21}$ moiety is —$OR^{15}$, and said $R^{15}$ is alkyl (e.g. methyl), and $R^7$ is phenyl substituted with 1-3 independently selected F.

In another embodiment $R^6$ is methyl substituted with one $R^{21}$ moiety, said $R^{21}$ moiety is —$OR^{15}$, and said $R^{15}$ is alkyl (e.g. methyl), and $R^7$ is phenyl substituted with 1-2 independently selected F, and said phenyl is also substituted with one or two groups independently selected from the group consisting of —$SF_5$ and —$OSF_5$, and wherein the total number of substituents on said phenyl is 2 or 3.

In another embodiment $R^6$ is methyl substituted with one $R^{21}$ moiety, said $R^{21}$ moiety is —$OR^{15}$, and said $R^{15}$ is alkyl (e.g. methyl), and $R^7$ is phenyl substituted with one F.

In another embodiment $R^6$ is methyl substituted with one $R^{21}$ moiety, said $R^{21}$ moiety is —$OR^{15}$, and said $R^{15}$ is alkyl (e.g. methyl), and $R^7$ is phenyl substituted with one F, and said phenyl is also substituted with one or two groups independently selected from the group consisting of —$SF_5$ and —$OSF_5$.

In another embodiment, $R^8$ is selected from the group consisting of H, halo (e.g., F), alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being optionally substituted with 1-3 independently selected $R^{21}$ substituents.

In another embodiment $R^8$ is halo.
In another embodiment $R^8$ is F.
In another embodiment, $R^8$ is H.
In another embodiment, $R^8$ is alkyl.
In another embodiment, $R^8$ is methyl.
In another embodiment, $R^{10}$ is aryl.
In another embodiment, $R^{10}$ is phenyl.
In another embodiment $R^{10}$ is aryl substituted with 1 halo.
In another embodiment $R^{10}$ is aryl substituted with 1 halo, and said halo is F.
In another embodiment $R^{10}$ is aryl substituted with 1 to 3 independently selected $R^{21}$ moieties.
In another embodiment $R^{10}$ is aryl substituted with 1 to 3 $R^{21}$ moieties, wherein each $R^{21}$ moiety is the same or different —$OR^{18}$ group.
In another embodiment $R^{10}$ is aryl substituted with 1 $R^{21}$ moiety.
In another embodiment $R^{10}$ is phenyl substituted with 1 halo.
In another embodiment $R^{10}$ is phenyl substituted with 1 halo, and said halo is F.
In another embodiment $R^{10}$ is 3-halo-phenyl:

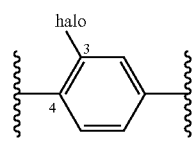

(wherein the bond from the carbon labeled as 4 is to the $R^9$ group).

In another embodiment $R^{10}$ is 3-F-phenyl:

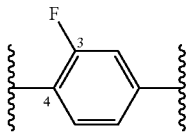 [SMILES: *c1ccc(*)c(F)c1]

(wherein the bond from the carbon labeled as 4 is to the $R^9$ group).

In another embodiment $R^{10}$ is aryl substituted with one —$OR^{15}$ group.
In another embodiment $R^{10}$ is aryl substituted with one —$OR^{15}$ group, and said $R^{15}$ is alkyl (e.g., methyl).
In another embodiment $R^{10}$ is phenyl substituted with 1 to 3 independently selected $R^{21}$ moieties.
In another embodiment $R^{10}$ is phenyl substituted with 1 to 3 $R^{21}$ moieties, wherein each $R^{21}$ moiety is the same or different —$OR^{15}$ group.
In another embodiment $R^{10}$ is phenyl substituted with 1 $R^{21}$ moiety.
In another embodiment $R^{10}$ is phenyl substituted with one —$OR^{15}$ group.
In another embodiment $R^{10}$ is phenyl substituted with one —$OR^{15}$ group, and said $R^{15}$ is alkyl (e.g., methyl).
In another embodiment $R^{10}$ is 3-$OR^{15}$-phenyl:

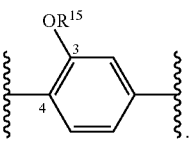

(wherein the bond from the carbon labeled as 4 is to the $R^9$ group).

In another embodiment $R^{10}$ is 3-$OR^{15}$-phenyl:

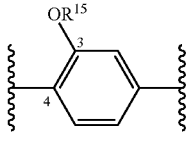

wherein $R^{15}$ is alkyl (wherein the bond from the carbon labeled as 4 is to the $R^9$ group).

In another embodiment $R^{10}$ is 3-$OR^{15}$-phenyl:

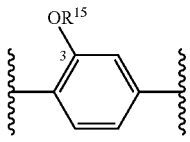

wherein $R^{15}$ is methyl (i.e., $R^{10}$ is 3-methoxy-phenyl).
In another embodiment, $R^{10}$ is heteroaryl.
In another embodiment, $R^{10}$ is unsubstituted heteroaryl.
In another embodiment $R^{10}$ is unsubstituted heteroaryl wherein said heteroaryl is pyridyl.

In another embodiment $R^{10}$ is:

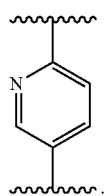

In another embodiment $R^{10}$ is:

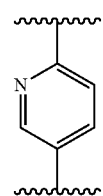

wherein the —$R^{10}$—$R^9$ moiety is:

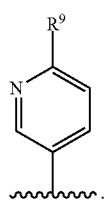

In another embodiment $R^{10}$ is aryl substituted with 1 to 3 $R^{21}$ moieties, wherein each $R^{21}$ moiety is the same or different halo.

In another embodiment $R^{10}$ is aryl substituted with 1 to 3 $R^{21}$ moieties, wherein each $R^{21}$ moiety is F.

In another embodiment $R^{10}$ is aryl substituted with one $R^{21}$ moiety, and said $R^{21}$ moiety is halo.

In another embodiment $R^{10}$ is aryl substituted with one $R^{21}$ moiety, said $R^{21}$ moiety is -halo, and said halo is F.

In another embodiment $R^{10}$ is phenyl substituted with 1 to 3 $R^{21}$ moieties, wherein each $R^{21}$ moiety is the same or different halo.

In another embodiment $R^{10}$ is phenyl substituted with 1 to 3 $R^{21}$ moieties, wherein each $R^{21}$ moiety is F.

In another embodiment $R^{10}$ is selected from the group consisting of:

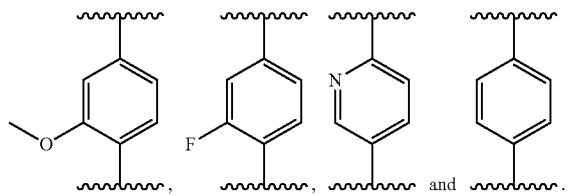

In another embodiment of this invention, $R^9$ is selected from the group consisting of alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each $R^9$ group is optionally substituted with 1-3 independently selected $R^{21}$ substituents.

In another embodiment of this invention $R^9$ is selected from the group consisting of heteroaryl and heteroaryl substituted with 1-3 $R^{21}$ groups, and wherein each $R^{21}$ is independently selected.

In another embodiment, $R^9$ is unsubstituted heteroaryl.

In another embodiment, $R^9$ is heteroaryl which is substituted with 1-3 substituents which can be the same or different, each substituent being independently selected from the group consisting of halo, alkyl, CN, $NH_2$, NH(alkyl), N(alkyl)$_2$, hydroxy and alkoxy groups.

In another embodiment, $R^9$ is heteroaryl substituted with 1 to 3 independently selected alkyl groups.

In another embodiment, $R^9$ is heteroaryl substituted with one is alkyl group (e.g., methyl).

In another embodiment of this invention $R^9$ is selected from the group consisting of imidazolyl and imidazolyl substituted with 1-3 $R^{21}$ groups, and wherein each $R^{21}$ is independently selected.

In another embodiment of this invention $R^9$ is imidazolyl substituted with 1-3 $R^{21}$ groups, and wherein each $R^{21}$ is independently selected.

In another embodiment, $R^9$ is imidazolyl substituted with 1-3 substituents independently selected from the group consisting of halo, alkyl, CN, $NH_2$, NH(alkyl), N(alkyl)$_2$, hydroxy and alkoxy groups.

In another embodiment of this invention $R^9$ is selected from the group consisting of:

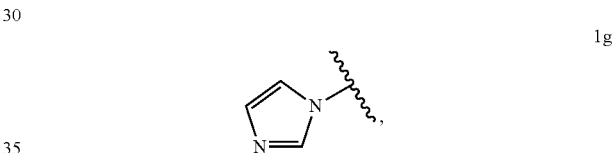

1g

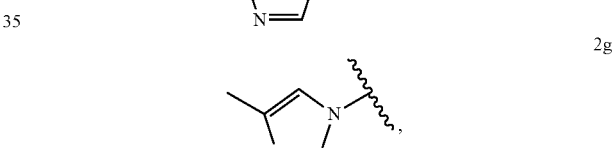

2g

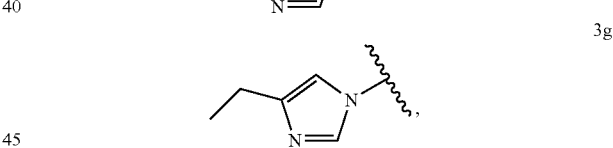

3g

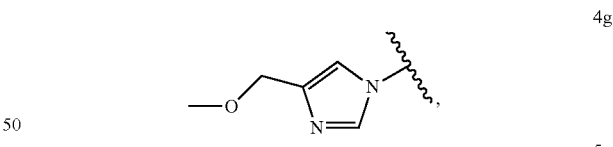

4g

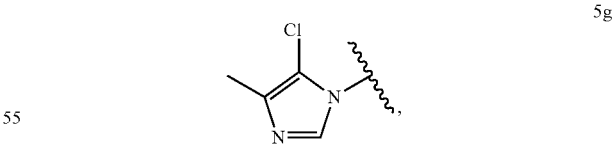

5g

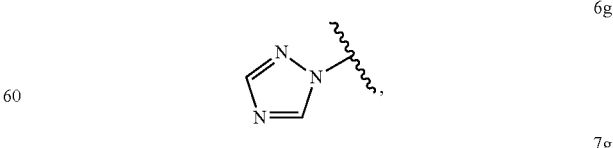

6g

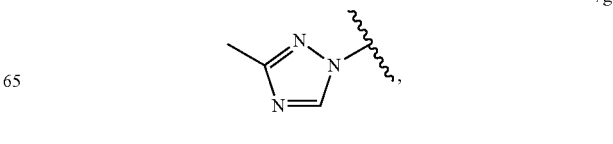

7g

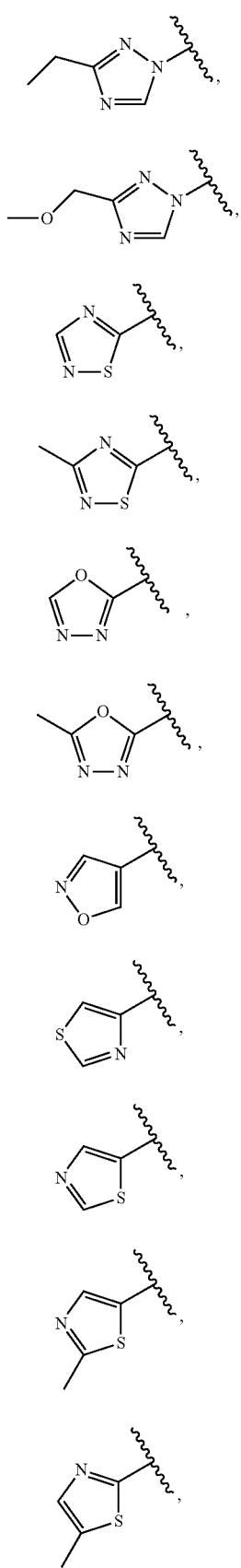
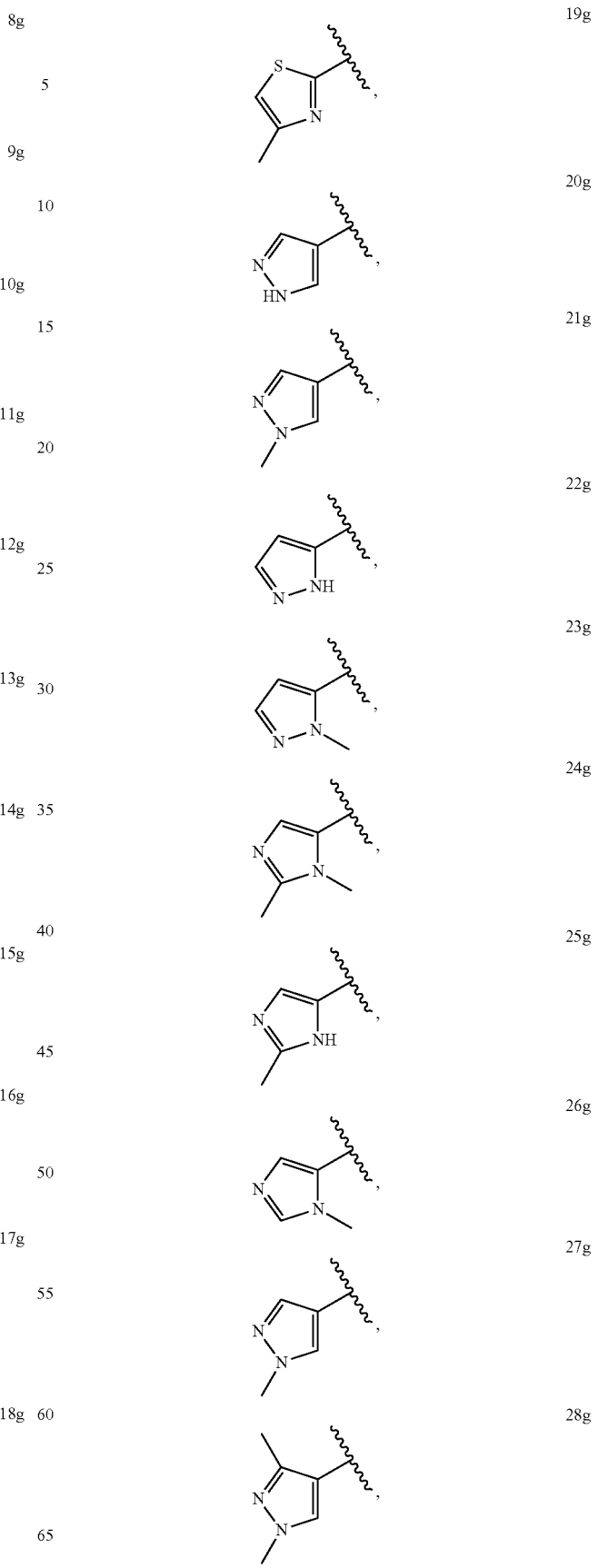

| | |
|---|---|
| 29g 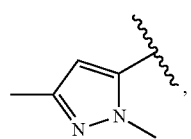 | 39g 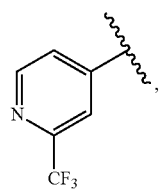 |
| 30g 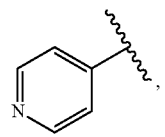 | 40g 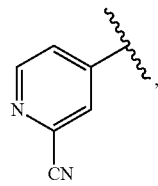 |
| 31g 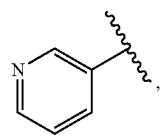 | 41g 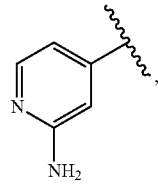 |
| 32g 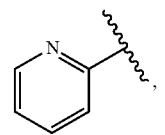 | 42g 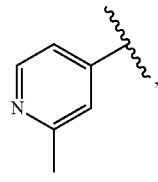 |
| 33g 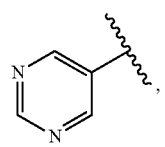 | 43g 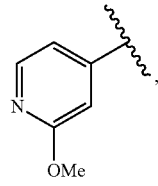 |
| 34g 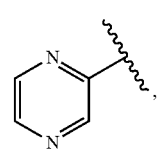 | 44g 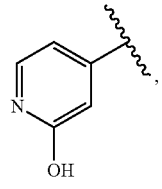 |
| 35g 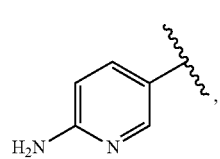 | 45g 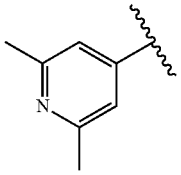 |
| 36g 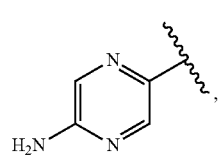 | 46g 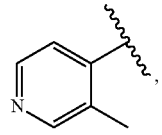 |
| 37g 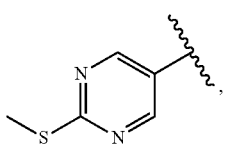 | |
| 38g 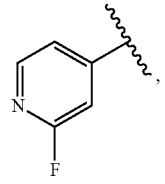 | |

-continued
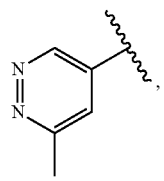 47g
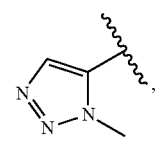 48g
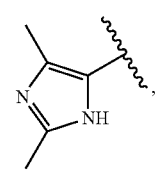 49g
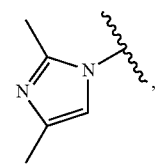 50g
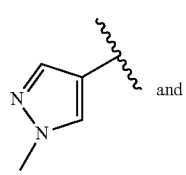 51g and
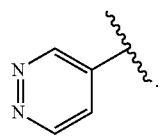 52g
In another embodiment of this invention R⁹ is selected from the group consisting of:
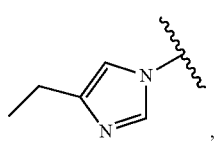 1g
-continued
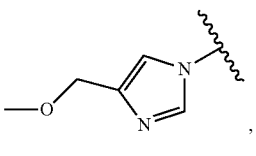 4g
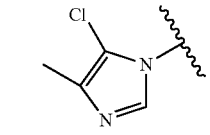 5g
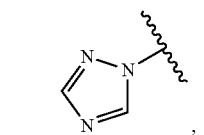 6g
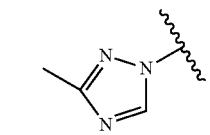 7g
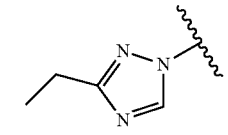 8g
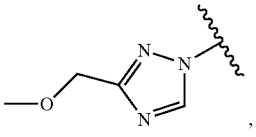 9g
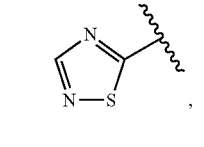 10g
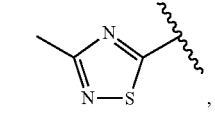 11g
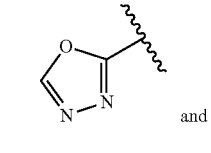 and 12g
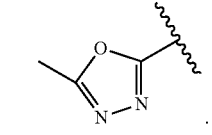 13g
2g
3g
In another embodiment of this invention R⁹ is 1 g. In another embodiment of this invention R⁹ is:

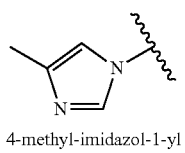

4-methyl-imidazol-1-yl (i.e. 2g). In another embodiment of this invention R⁹ is 3g. In another embodiment of this invention R⁹ is 4g. In another embodiment of this invention R⁹ is 5g. In another embodiment of this invention R⁹ is 6g. In another embodiment of this invention R⁹ is 7g. In another embodiment of this invention R⁹ is 8g. In another embodiment of this invention R⁹ is 9g. In another embodiment of this invention R⁹ is 10g. In another embodiment of this invention R⁹ is 11g. In another embodiment of this invention R⁹ is 12g. In another embodiment of this invention R⁹ is 13g. In another embodiment of this invention R⁹ is 14g. In another embodiment of this invention R⁹ is 15g. In another embodiment of this invention R⁹ is 16g. In another embodiment of this invention R⁹ is 17g. In another embodiment of this invention R⁹ is 18g. In another embodiment of this invention R⁹ is 19g. In another embodiment of this invention R⁹ is 20g. In another embodiment of this invention R⁹ is 21g. In another embodiment of this invention R⁹ is 22g. In another embodiment of this invention R⁹ is 23g. In another embodiment of this invention R⁹ is 24g. In another embodiment of this invention R⁹ is 25g. In another embodiment of this invention R⁹ is 26g. In another embodiment of this invention R⁹ is 27g. In another embodiment of this invention R⁹ is 28g. In another embodiment of this invention R⁹ is 29g. In another embodiment of this invention R⁹ is 30g. In another embodiment of this invention R⁹ is 31g. In another embodiment of this invention R⁹ is 32g. In another embodiment of this invention R⁹ is 33g. In another embodiment of this invention R⁹ is 34g. In another embodiment of this invention R⁹ is 35g. In another embodiment of this invention R⁹ is 36g. In another embodiment of this invention R⁹ is 37g. In another embodiment of this invention R⁹ is 38g. In another embodiment of this invention R⁹ is 39g. In another embodiment of this invention R⁹ is 40g. In another embodiment of this invention R⁹ is 41g. In another embodiment of this invention R⁹ is 42g. In another embodiment of this invention R⁹ is 43g. In another embodiment of this invention R⁹ is 44g. In another embodiment of this invention R⁹ is 45g. In another embodiment of this invention R⁹ is 46g. In another embodiment of this invention R⁹ is 47g. In another embodiment of this invention R⁹ is 48g. In another embodiment of this invention R⁹ is 49g. In another embodiment of this invention R⁹ is 50g. In another embodiment of this invention R⁹ is 51g. In another embodiment of this invention R⁹ is 52g.

In another embodiment, R⁹ is imidazol-1-yl.

In another embodiment, R⁹ is 4-methyl-imidazol-1-yl:

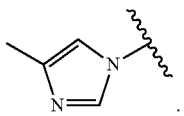 [SMILES: *n1cnc(C)c1]

In another embodiment, R⁹ is 5-chloro-4-methyl-imidazol-1-yl.

In another embodiment R¹⁰ is selected from the group consisting of aryl and aryl substituted with one or more R²¹ groups, and R⁹ is selected from the group consisting of heteroaryl and heteroaryl substituted with one or more R²¹ groups, and wherein each R²¹ is independently selected.

In another embodiment R¹⁰ is selected from the group consisting of phenyl and phenyl substituted with 1-3 independently selected R²¹ groups, and R⁹ is selected from the group consisting of imidazolyl and imidazolyl substituted with 1-3 independently selected R²¹ groups.

In another embodiment R¹⁰ is phenyl substituted with 1-3 independently selected R²¹ groups, and R⁹ is selected from the group consisting of imidazolyl and imidazolyl substituted with 1-3 independently selected R²¹ groups.

In another embodiment R¹⁰ is selected from the group consisting of heteroaryl and heteroaryl substituted with 1-3 R²¹ groups, and the R⁹ group is selected from the group consisting of heteroaryl and heteroaryl substituted with 1-3 R²¹ groups, and wherein each R²¹ is independently selected.

In another embodiment R¹⁰ is selected from the group consisting of pyridyl and pyridyl substituted with 1-3 R²¹ groups, and the R⁹ group is selected from the group consisting of imidazolyl and imidazolyl substituted with 1-3 R²¹ groups, and wherein each R²¹ is independently selected.

In another embodiment R¹⁰ is pyridyl, and the R⁹ group is imidazolyl substituted with 1-3 R²¹ groups, and wherein each R²¹ is independently selected.

In another embodiment of this invention R¹⁰ is selected from the group consisting of 1A to 55A, and R⁹ is selected from the group consisting of 1 g to 52g.

In another embodiment of this invention R¹⁰ is selected from the group consisting of 1A to 42A, and R⁹ is selected from the group consisting of 1 g to 13g.

In another embodiment of this invention R¹⁰ is selected from the group consisting of 1A to 55A, and R⁹ is 2g.

In another embodiment of this invention R¹⁰ is selected from the group consisting of 1A to 55A, and R⁹ is H.

In another embodiment of this invention R¹⁰ is selected from the group consisting of 1A to 42A, and R⁹ is 2g.

In another embodiment of this invention R¹⁰ is selected from the group consisting of 1A to 42A, and R⁹ is H.

In another embodiment of this invention the R¹⁰—R⁹— moiety is selected from the group consisting of:

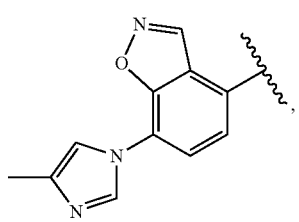

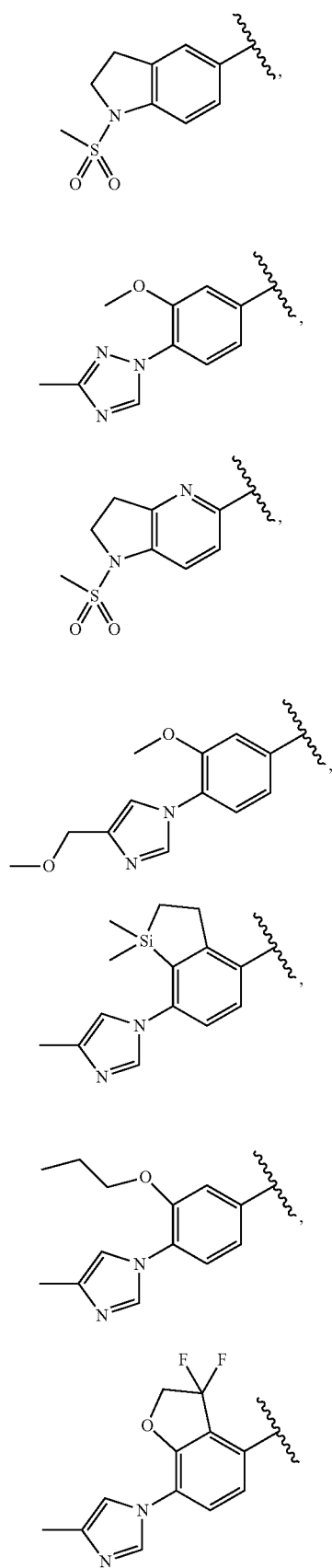
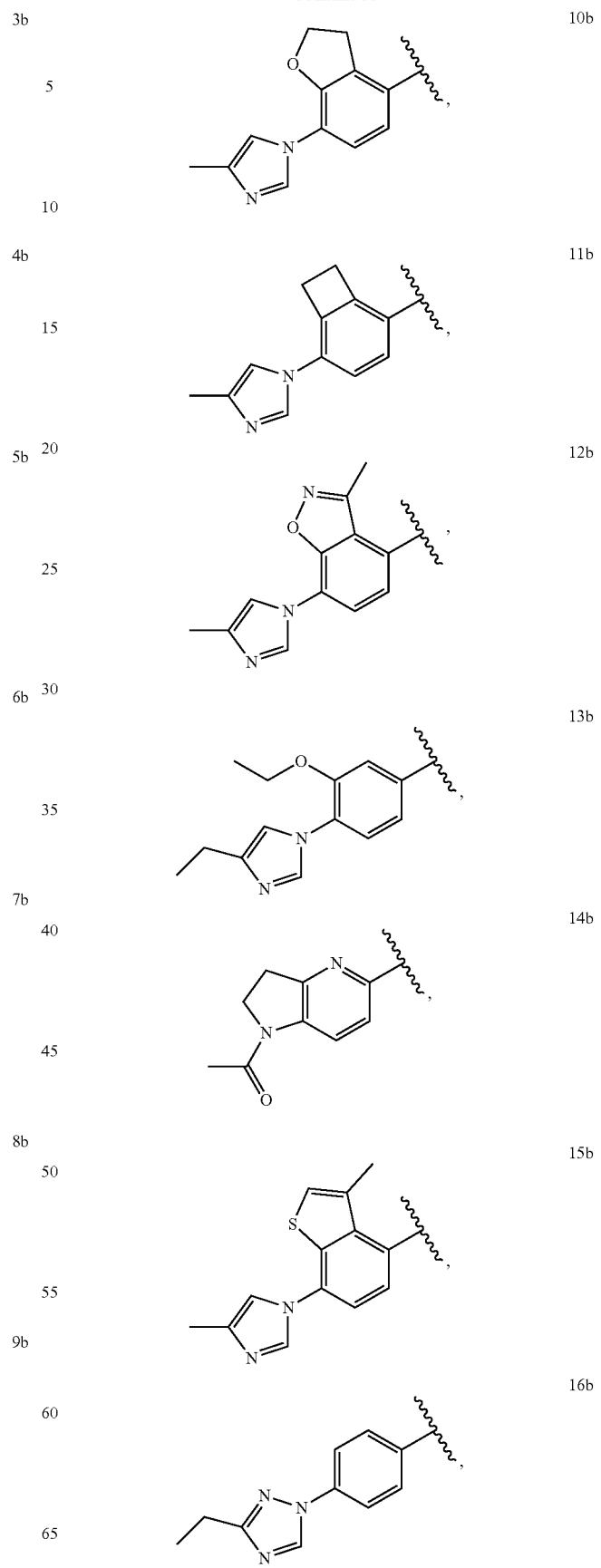

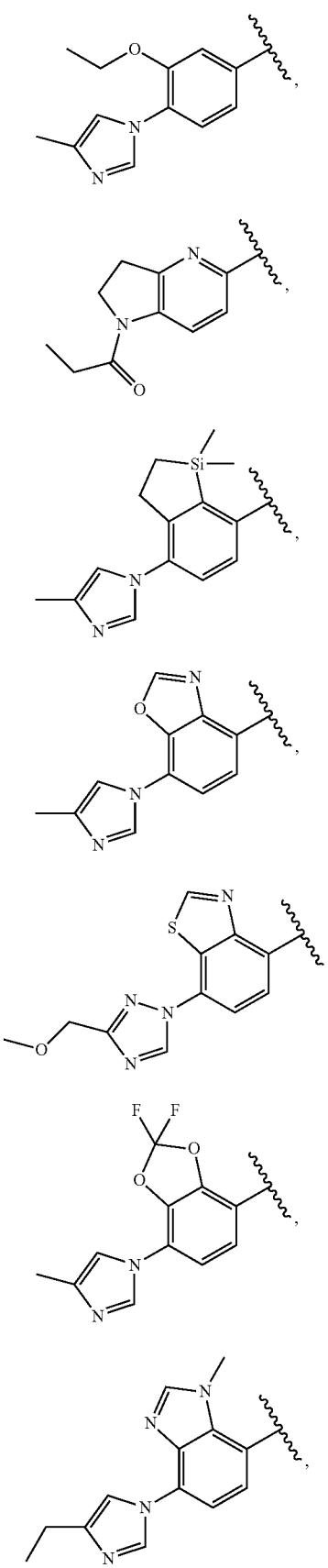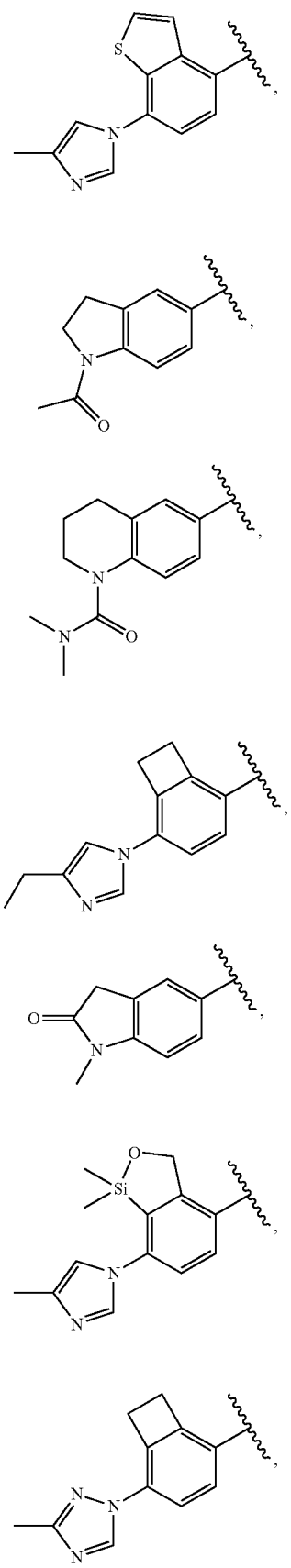

-continued

133

31b

32b

33b

34b

35b

36b

37b

134

-continued

38b

39b

40b

41b

42b

43b

44b

45b 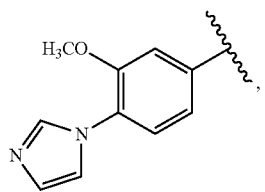

46b 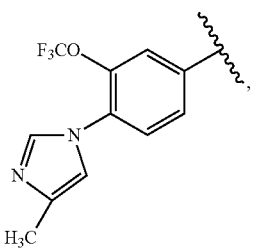

47b 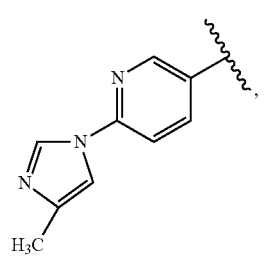

48b 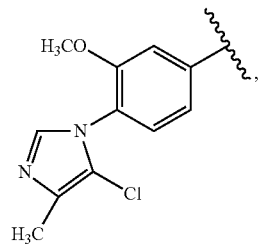

49b 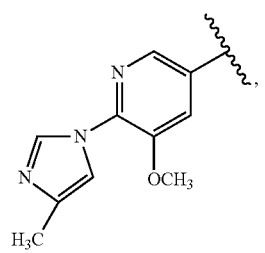

50b 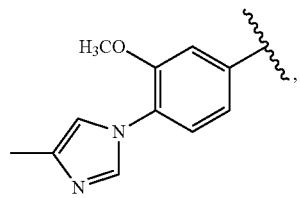

51b 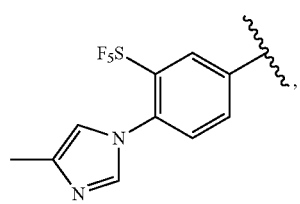

52b 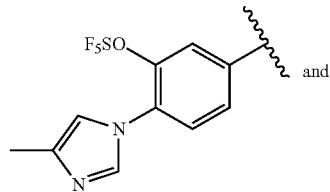 and

53b .

In another embodiment the $R^{10}$—$R^9$— moiety is 1b. In another embodiment the $R^{10}$—$R^9$— moiety is 2b. In another embodiment the $R^{10}$—$R^9$— moiety is 3b. In another embodiment the $R^{10}$—$R^9$— moiety is 4b. In another embodiment the $R^{10}$—$R^9$-moiety is 5b. In another embodiment the $R^{10}$—$R^9$— moiety is 6b. In another embodiment the $R^{10}$—$R^9$— moiety is 7b. In another embodiment the $R^{10}$—$R^9$— moiety is 8b. In another embodiment the $R^{10}$—$R^9$— moiety is 9b. In another embodiment the $R^{10}$—$R^9$— moiety is 10b. In another embodiment the $R^{10}$—$R^9$— moiety is 11b. In another embodiment the $R^{10}$—$R^9$— moiety is 12b. In another embodiment the $R^{10}$—$R^9$— moiety is 13b. In another embodiment the $R^{10}$—$R^9$— moiety is 14b. In another embodiment the $R^{10}$—$R^9$— moiety is 15b. In another embodiment the $R^{10}$—$R^9$— moiety is 16b. In another embodiment the $R^{10}$—$R^9$— moiety is 17b. In another embodiment the $R^{10}$—$R^9$— moiety is 18b. In another embodiment the $R^{10}$—$R^9$— moiety is 19b. In another embodiment the $R^{10}$—$R^9$— moiety is 20b. In another embodiment the $R^{10}$—$R^9$— moiety is 21b. In another embodiment the $R^{10}$—$R^9$— moiety is 22b. In another embodiment the $R^{10}$—$R^9$— moiety is 23b. In another embodiment the $R^{10}$—$R^9$— moiety is 24b. In another embodiment the $R^{10}$—$R^9$— moiety is 25b. In another embodiment the $R^{10}$—$R^9$— moiety is 26b. In another embodiment the $R^{10}$—$R^9$— moiety is 27b. In another embodiment the $R^{10}$—$R^9$— moiety is 28b. In another embodiment the $R^{10}$—$R^9$— moiety is 29b. In another embodiment the $R^{10}$—$R^9$— moiety is 30b. In another embodiment the $R^{10}$—$R^9$— moiety is 31b. In another embodiment the $R^{10}$—$R^9$— moiety is 32b. In another embodiment the $R^{10}$—$R^9$— moiety is 33b. In another embodiment the $R^{10}$—$R^9$— moiety is 34b. In another embodiment the $R^{10}$—$R^9$— moiety is 35b. In another embodiment the $R^{10}$—$R^9$— moiety is 36b. In another embodiment the $R^{10}$—$R^9$— moiety is 37b. In another embodiment the $R^{10}$—$R^9$— moiety is 38b. In another embodiment the $R^{10}$—$R^9$— moiety is 39b. In another embodiment the $R^{10}$—$R^9$— moiety is 40b. In another embodiment the $R^{10}$—$R^9$— moiety is 41b. In another embodiment the $R^{10}$—$R^9$— moiety is 42b. In another embodiment the $R^{10}$—$R^9$— moiety is 43b. In another embodiment the $R^{10}$—$R^9$— moiety is 44b. In another embodiment the $R^{10}$—$R^9$— moiety is 45b. In another embodiment the $R^{10}$—$R^9$— moiety is 46b. In another embodiment the $R^{10}$—$R^9$— moiety is 47b. In another embodiment the $R^{10}$—$R^9$— moiety is 48b. In another embodiment the $R^{10}$—$R^9$— moiety is 49b. In another embodiment the $R^{10}$—$R^9$— moiety is 50b. In another embodiment the R¹⁰—R⁹— moiety is 51b. In another embodiment the R¹⁰—R⁹— moiety is 52b. In another embodiment the R¹⁰—R⁹— moiety is 53b.

In another embodiment the R⁹—R¹⁰— moiety is:

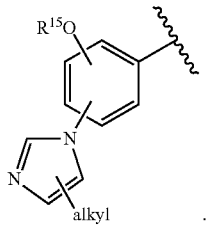

In another embodiment the R⁹—R¹⁰— moiety is:

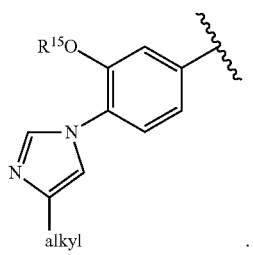

In another embodiment the R⁹—R¹⁰— moiety is:

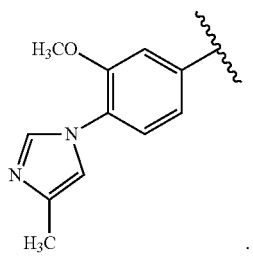

In another embodiment the R⁹—R¹⁰— moiety is:

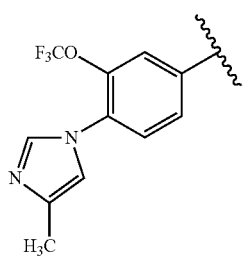

In another embodiment the R⁹—R¹⁰— moiety is:

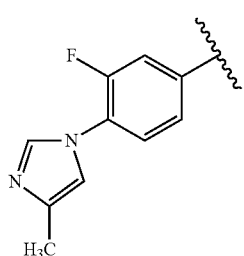

In another embodiment R⁹—R¹⁰— moiety is:

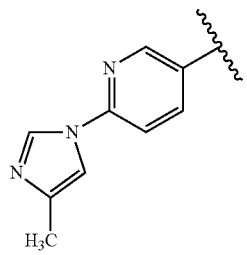

In another embodiment R⁹—R¹⁰— moiety is:

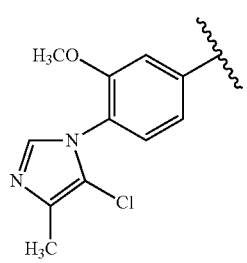

Another embodiment of this invention is directed to compounds of formula I (or pharmaceutically acceptable salts, solvates, esters or prodrugs thereof): wherein:
either
(i) R¹ and R² are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected R²¹ substituents; or
(ii) R² and R⁶ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected R²¹ substituents; or
(iii) R¹ and R² are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected R²¹ substituents; and R² and R⁶ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected R²¹ substituents; and
U is CH;
V is selected from the group consisting of a bond, —O—, and —N(R¹⁴)—;
R¹ (when R¹ is not joined to R²), R² (when R² is not joined to R¹ or R⁶), R³, R⁴, R⁵, R⁶ (when R⁶ is not joined to R²), R⁷, R¹¹ and R¹² are each independently selected from the group consisting of H, alkyl-, alkenyl-, alkynyl-, aryl-, arylalkyl-, alkylaryl-, cycloalkyl-, heteroaryl-, heteroarylalkyl-, heterocyclyl- and heterocyclylalkyl-, and wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents; and all other substituents are as defined for formula I (including the provisos).

Another embodiment of this invention is directed to compounds of formula I (or pharmaceutically acceptable salts, solvates, esters or prodrugs thereof): wherein:
either
  (i) $R^1$ and $R^2$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, (c) said cycloalkenyl moiety is optionally substituted with 1-5 independently selected $R^{21}$ substituents, (d) said heterocyclenyl moiety is optionally substituted with 1-5 independently selected $R^{21}$ substituents, and (e) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or
  (ii) $R^2$ and $R^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, (c) said cycloalkenyl moiety is optionally substituted with 1-5 independently selected $R^{21}$ substituents, (d) said heterocyclenyl moiety is optionally substituted with 1-5 independently selected $R^{21}$ substituents, and (e) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or
  (iii)
    (a) $R^1$ and $R^2$ are joined together to form a C4-C8 cycloalkyl, $C_4$-$C_8$ cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, (2) said heterocyclyl moiety is optionally substituted with 1-5 independently selected $R^{21}$ substituents, (3) said cycloalkenyl moiety is optionally substituted with 1-5 independently selected $R^{21}$ substituents, (4) said heterocyclenyl moiety is optionally substituted with 1-5 independently selected $R^{21}$ substituents; and
    (b) $R^2$ and $R^6$ are joined together to form a C4-C8 cycloalkyl, $C_4$-$C_8$ cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents, (3) said cycloalkenyl moiety is optionally substituted with 1-5 independently selected $R^{21}$ substituents, (4) said heterocyclenyl moiety is optionally substituted with 1-5 independently selected $R^{21}$ substituents; and
    (c) said $R^2$ and $R^6$ cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or
  (iv) $R^6$ and either $R^3$ or $R^4$ of the —C($R^3$)($R^4$)— G moiety, are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, (c) said cycloalkenyl moiety is optionally substituted with 1-5 independently selected $R^{21}$ substituents, (d) said heterocyclenyl moiety is optionally substituted with 1-5 independently selected $R^{21}$ substituents, and (e) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or
  (v) $R^6$ and $R^{13}$ of the —N($R^{13}$)— G moiety, are joined together to form a 5-8 membered heterocyclyl or 5-8 membered heterocyclenyl moiety, wherein: (a) said heterocyclyl moiety is optionally substituted with 1-5 independently selected $R^{21}$ substituents, (b) said heterocyclenyl moiety is optionally substituted with 1-5 independently selected $R^{21}$ substituents, and (c) said heterocyclyl or heterocyclenyl moiety is optionally fused with an aryl or heteroaryl ring, and the ring moiety resulting from the fusion is optionally substituted with 1-5 independently selected $R^{21}$ substituents; and
  U is CH; and
all other substituents are as defined in formula I (including the provisos).

Another embodiment of this invention is directed to compounds of formula I (or pharmaceutically acceptable salts, solvates, esters or prodrugs thereof):
wherein:
either
  (i) $R^1$ and $R^2$ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected $R^{21}$ substituents; or
  (ii) $R^2$ and $R^6$ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected $R^{21}$ substituents; or
  (iii) $R^1$ and $R^2$ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected $R^{21}$ substituents; and $R^2$ and $R^6$ are joined together to form a C4-C8 cycloalkyl, C4-C8 cycloalkenyl, 5-8 membered heterocyclyl or 5-8 membered heterocyclenyl moiety, wherein each of said cycloalkyl, cycloalkenyl, heterocyclyl, or heterocyclenyl moiety is optionally substituted with 1-5 independently selected $R^{21}$ substituents; and
  U is N;
  V is selected from the group consisting of a bond, —O—, and —N($R^{14}$)—;
  $R^1$ (when $R^1$ is not joined to $R^2$), $R^2$ (when $R^2$ is not joined to $R^1$ or $R^6$), $R^3$, $R^4$, $R^5$, $R^6$ (when $R^6$ is not joined to $R^2$), $R^7$, $R^{11}$ and $R^{12}$ can be the same or different, each being independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents; and all other substituents are as defined in formula I (including the provisos).

Another embodiment of this invention is directed to compounds of formula I (or pharmaceutically acceptable salts, solvates, esters or prodrugs thereof):
wherein:
either
(i) $R^1$ and $R^2$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, (c) said cycloalkenyl moiety is optionally substituted with 1-5 independently selected $R^{21}$ substituents, (d) said heterocyclenyl moiety is optionally substituted with 1-5 independently selected $R^{21}$ substituents, and (e) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or
(ii) $R^2$ and $R^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, (c) said cycloalkenyl moiety is optionally substituted with 1-5 independently selected $R^{21}$ substituents, (d) said heterocyclenyl moiety is optionally substituted with 1-5 independently selected $R^{21}$ substituents, and (e) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or
(iii)
(a) $R^1$ and $R^2$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, (2) said heterocyclyl moiety is optionally substituted with 1-5 independently selected $R^{21}$ substituents, (3) said cycloalkenyl moiety is optionally substituted with 1-5 independently selected $R^{21}$ substituents, (4) said heterocyclenyl moiety is optionally substituted with 1-5 independently selected $R^{21}$ substituents; and
(b) $R^2$ and $R^6$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents, (3) said cycloalkenyl moiety is optionally substituted with 1-5 independently selected $R^{21}$ substituents, (4) said heterocyclenyl moiety is optionally substituted with 1-5 independently selected $R^{21}$ substituents; and (c) said $R^2$ and $R^6$ cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or
(iv) $R^6$ and either $R^3$ or $R^4$ of the —C($R^3$)($R^4$)— G moiety, are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, (c) said cycloalkenyl moiety is optionally substituted with 1-5 independently selected $R^{21}$ substituents, (d) said heterocyclenyl moiety is optionally substituted with 1-5 independently selected $R^{21}$ substituents, and (e) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or
(v) $R^6$ and $R^{13}$ of the —N($R^{13}$)— G moiety, are joined together to form a 5-8 membered heterocyclyl or 5-8 membered heterocyclenyl moiety, wherein: (a) said heterocyclyl moiety is optionally substituted with 1-5 independently selected $R^{21}$ substituents, (b) said heterocyclenyl moiety is optionally substituted with 1-5 independently selected $R^{21}$ substituents, and (c) said heterocyclyl or heterocyclenyl moiety is optionally fused with an aryl or heteroaryl ring, and the ring moiety resulting from the fusion is optionally substituted with 1-5 independently selected $R^{21}$ substituents; and
U is N; and
all other substituents are as defined in formula I (including the provisos).

Another embodiment of this invention is directed to compounds of formula I (or pharmaceutically acceptable salts, solvates, esters or prodrugs thereof):
wherein:
U is C($R^5$);
$R^1$ is H;
$R^2$ and $R^6$ are connected to form a 4-7 membered cycloalkyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is phenyl;
$R^9$ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is C($R^5$);
$R^6$ is H;

$R^1$ and $R^2$ are connected to form a 4-7 membered cycloalkyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is phenyl;
$R^9$ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$ or N;
$R^1$ is H;
$R^2$ and $R^6$ are connected to form a 5-8 membered heterocyclyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is phenyl; and
$R^5$ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$;
$R^6$ is H;
$R^1$ and $R^2$ are connected to form a 5-8 membered heterocyclyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is phenyl;
$R^9$ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$ or N;
$R^1$ and $R^2$ are connected to form a 5-8 membered heterocyclyl ring;

$R^2$ and $R^6$ are connected to form a 5-8 membered heterocyclyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is phenyl;
$R^9$ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$;
$R^2$ and $R^6$ are connected to form a 4-7 membered cycloalkyl ring;
$R^1$ and $R^2$ are connected to form a 4-7 membered cycloalkyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is phenyl;
$R^9$ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$ or N;
$R^1$ and $R^2$ are connected to form a piperidinyl ring;
$R^2$ and $R^6$ are connected to form a piperidinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is phenyl;
$R^9$ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is N;
$R^1$ and $R^2$ are connected to form a piperazinyl ring;
$R^2$ and $R^6$ are connected to form a piperazinyl ring;

R⁷ is 3-(1,1'-biphenyl)-yl;
R⁸ is H;
R⁵ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected R²¹ substituents;
R¹⁰ is phenyl;
R⁹ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is C(R⁵) or N;
R¹ and R² are connected to form a piperidinyl ring;
R² and R⁶ are connected to form a piperazinyl ring;
R⁷ is 3-(1,1'-biphenyl)-yl;
R⁸ is H;
R⁵ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected R²¹ substituents;
R¹⁰ is phenyl;
R⁹ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is C(R⁵) or N;
R¹ and R² are connected to form a piperazinyl ring;
R² and R⁶ are connected to form a piperidnyl ring;
R⁷ is 3-(1,1'-biphenyl)-yl;
R⁸ is H;
R⁵ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroaryl alkyl-, heterocyclyl- and heterocyclylalkyl- is optionally substituted with 1-5 independently selected R²¹ substituents;
R¹⁰ is phenyl;
R⁹ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is C(R⁵);
R¹ and R² are connected to form a cyclohexyl ring;
R² and R⁶ are connected to form a piperidinyl ring;
R⁷ is 3-(1,1'-biphenyl)-yl;
R⁸ is H;
R⁵ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected R²¹ substituents;
R¹⁰ is phenyl;
R⁹ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is C(R⁵);
R¹ and R² are connected to form a cyclohexyl ring;
R² and R⁶ are connected to form a piperazinyl ring;
R⁷ is 3-(1,1'-biphenyl)-yl;
R⁸ is H;
R⁵ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected R²¹ substituents;
R¹⁰ is phenyl;
R⁹ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is C(R⁵);
R¹ and R² are connected to form a piperidinyl ring;
R² and R⁶ are connected to form a cyclohexyl ring;
R⁷ is 3-(1,1'-biphenyl)-yl;
R⁸ is H;
R⁵ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected R²¹ substituents;
R¹⁰ is phenyl;
R⁹ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is C(R⁵);
R¹ and R² are connected to form a piperazinyl ring;
R² and R⁶ are connected to form a cyclohexyl ring;
R⁷ is 3-(1,1'-biphenyl)-yl;
R⁸ is H;
R⁵ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyland heterocyclylalkyl- is optionally substituted with 1-5 independently selected $R^{21}$ substituents;
$R^{10}$ is phenyl;
$R^9$ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$ or N;
$R^6$ is H;
$R^1$ and $R^2$ are connected to form a piperidinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is phenyl;
$R^9$ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$ or N;
$R^1$ is H;
$R^1$ and $R^2$ are connected to form a piperazinyl ring;
$R^7$ is 3-(1,1'-biphenyl)-yl;
$R^5$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is phenyl;
$R^9$ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$ or N;
$R^1$ is H;
$R^6$ and $R^2$ are connected to form a piperidinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclyl alkyl- is optionally substituted with 1-5 independently selected $R^{21}$ substituents;
$R^{10}$ is phenyl;
$R^9$ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$ or N;
$R^1$ is H;
$R^6$ and $R^2$ are connected to form a piperazinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is phenyl;
$R^9$ is imidazol-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$;
$R^1$ is H;
$R^2$ and $R^6$ are connected to form a 4-7 membered cycloalkyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);
$R^9$ is 4-methyl-imidazolyl-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$;
$R^6$ is H;
$R^1$ and $R^2$ are connected to form a 4-7 membered cycloalkyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);
$R^9$ is 4-methyl-imidazolyl-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$ or N;
$R^1$ is H;
$R^2$ and $R^6$ are connected to form a 5-8 membered heterocyclyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally isubstituted with 1-5 independently selected $R^{21}$ substituents;
$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);
$R^9$ is 4-methyl-imidazolyl-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$;
$R^6$ is H;
$R^1$ and $R^2$ are connected to form a 5-8 membered heterocyclyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);
$R^9$ is 4-methyl-imidazolyl-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$ or N;
$R^1$ and $R^2$ are connected to form a 5-8 membered heterocyclyl ring;
$R^2$ and $R^6$ are connected to form a 5-8 membered heterocyclyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);
$R^9$ is 4-methyl-imidazolyl-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$;
$R^2$ and $R^6$ are connected to form a 4-7 membered cycloalkyl ring;
$R^1$ and $R^2$ are connected to form a 4-7 membered cycloalkyl ring;
$R^7$ is 3-(1,1'-biphenyl)-yl;
$R^5$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is selected from the group consisting of: 3-methoxyphenyl and 3-F-phenyl (and in one example $R^{10}$ is 3-methoxy-phenyl, and in another example $R^{16}$ is 3-F-phenyl);
$R^9$ is 4-methyl-imidazolyl-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$ or N;
$R^1$ and $R^2$ are connected to form a piperidinyl ring;
$R^2$ and $R^6$ are connected to form a piperidinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);
$R^9$ is 4-methyl-imidazolyl-1-yl; and
all other substituents are as defined in formula I (including the provisos).

Another embodiment of this invention is directed to compounds of formula I (or pharmaceutically acceptable salts, solvates, esters or prodrugs thereof):
wherein:
U is N;
$R^1$ and $R^2$ are connected to form a piperazinyl ring;
$R^2$ and $R^6$ are connected to form a piperazinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyland alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl; and all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$ or N;
$R^1$ and $R^2$ are connected to form a piperidinyl ring;
$R^2$ and $R^6$ are connected to form a piperazinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl; and all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$ or N;
$R^1$ and $R^2$ are connected to form a piperazinyl ring;
$R^2$ and $R^6$ are connected to form a piperidnyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl; and all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$;
$R^1$ and $R^2$ are connected to form a cyclohexyl ring;
$R^2$ and $R^6$ are connected to form a piperidinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl; and all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$;
$R^1$ and $R^2$ are connected to form a cyclohexyl ring;
$R^2$ and $R^6$ are connected to form a piperazinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl; and all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$;
$R^1$ and $R^2$ are connected to form a piperidinyl ring;
$R^2$ and $R^6$ are connected to form a cyclohexyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl; and all other substituents are as defined in formula I (including the provisos).

Another embodiment of this invention is directed to compounds of formula I (or pharmaceutically acceptable salts, solvates, esters or prodrugs thereof):
wherein:
U is $C(R^5)$;
$R^1$ and $R^2$ are connected to form a piperazinyl ring;
$R^2$ and $R^6$ are connected to form a cyclohexyl ring;
$R^7$ is 3-(1,1'-biphenyl)-yl;
$R^8$ is H;

R$^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected R$^{21}$ substituents;

R$^{10}$ is selected from the group consisting of: 3-methoxyphenyl and 3-F-phenyl (and in one example R$^{10}$ is 3-methoxy-phenyl, and in another example R$^{10}$ is 3-F-phenyl);

R$^9$ is 4-methyl-imidazolyl-1-yl; and all other substituents are as defined in formula I (including the provisos). Another embodiment of this invention is directed to compounds of formula I (or pharmaceutically acceptable salts, solvates, esters or prodrugs thereof):

wherein:
U is C(R$^5$) or N;
R$^6$ is H;
R$^1$ and R$^2$ are connected to form a piperidinyl ring;
R$^7$ is 3-(1,1'-biphenyl)-yl;
R$^8$ is H;
R$^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected R$^{21}$ substituents;

R$^{10}$ is selected from the group consisting of: 3-methoxyphenyl and 3-F-phenyl (and in one example R$^{10}$ is 3-methoxy-phenyl, and in another example R$^{10}$ is 3-F-phenyl);

R$^9$ is 4-methyl-imidazolyl-1-yl; and all other substituents are as defined in formula I (including the provisos).

Another embodiment of this invention is directed to compounds of formula I (or pharmaceutically acceptable salts, solvates, esters or prodrugs thereof):

wherein:
U is C(R$^5$) or N;
R$^6$ is H;
R$^1$ and R$^2$ are connected to form a piperazinyl ring;
R$^7$ is 3-(1,1'-biphenyl)-yl;
R$^8$ is H;
R$^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected R$^{21}$ substituents;

R$^{10}$ is selected from the group consisting of: 3-methoxyphenyl and 3-F-phenyl (and in one example R$^{10}$ is 3-methoxy-phenyl, and in another example R$^{10}$ is 3-F-phenyl);

R$^9$ is 4-methyl-imidazolyl-1-yl; and all other substituents are as defined in formula I (including the provisos).

Another embodiment of this invention is directed to compounds of formula I (or pharmaceutically acceptable salts, solvates, esters or prodrugs thereof):

wherein:
U is C(R$^5$) or N;
R$^1$ is H;
R$^6$ and R$^2$ are connected to form a piperidinyl ring;
R$^7$ is 3-(1,1'-biphenyl)-yl;
R$^8$ is H;

R$^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected R$^{21}$ substituents;

R$^{10}$ is selected from the group consisting of: 3-methoxyphenyl and 3-F-phenyl (and in one example R$^{10}$ is 3-methoxy-phenyl, and in another example R$^{10}$ is 3-F-phenyl);

R$^9$ is 4-methyl-imidazolyl-1-yl; and all other substituents are as defined in formula I (including the provisos).

Another embodiment of this invention is directed to compounds of formula I (or pharmaceutically acceptable salts, solvates, esters or prodrugs thereof):

wherein:
U is C(R$^5$) or N;
R$^1$ is H;
R$^6$ and R$^2$ are connected to form a piperazinyl ring;
R$^7$ is 3-(1,1'-biphenyl)-yl;
R$^8$ is H;
R$^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected R$^{21}$ substituents;

R$^{10}$ is selected from the group consisting of: 3-methoxyphenyl and 3-F-phenyl (and in one example R$^{10}$ is 3-methoxy-phenyl, and in another example R$^{10}$ is 3-F-phenyl);

R$^9$ is 4-methyl-imidazolyl-1-yl; and all other substituents are as defined in formula I (including the provisos).

Another embodiment of this invention is directed to compounds of formula I selected from the group consisting of:

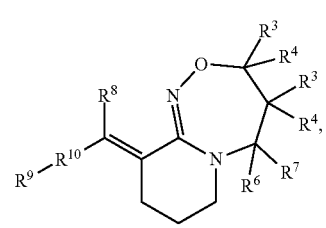

Z1

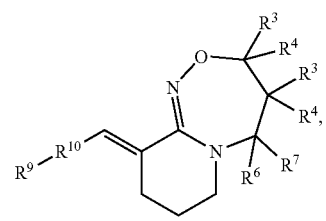

Z2

-continued
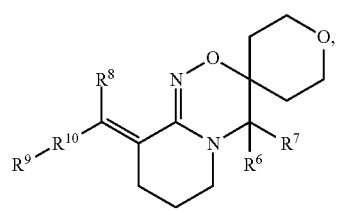 Z3
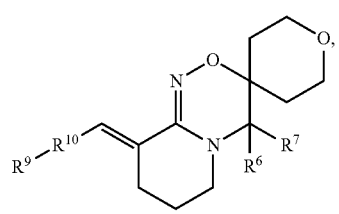 Z4
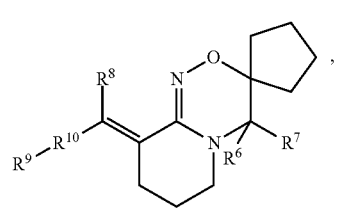 Z5
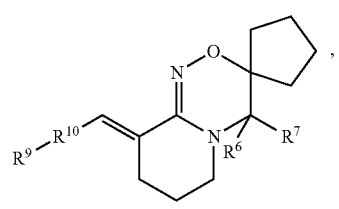 Z6
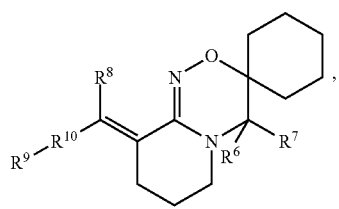 Z7
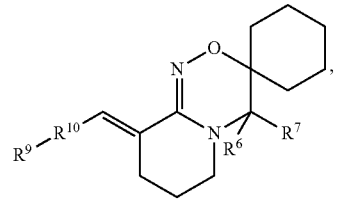 Z8
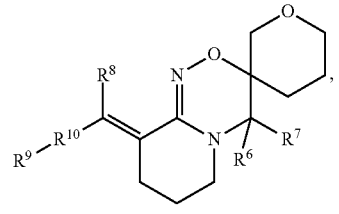 Z9
-continued
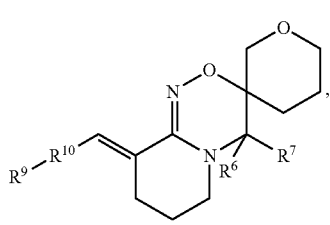 Z10
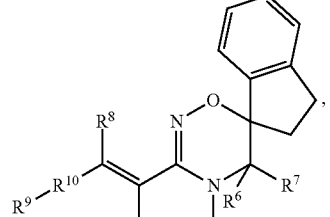 Z11
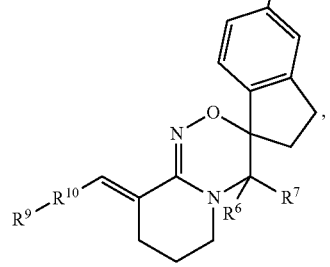 Z12
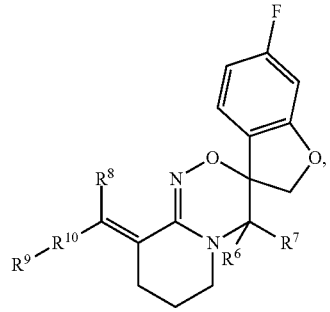 Z13
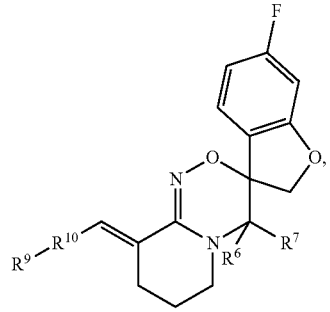 Z14

Z15 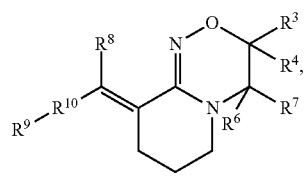
Z16 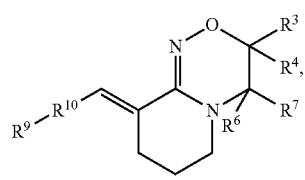
Z17 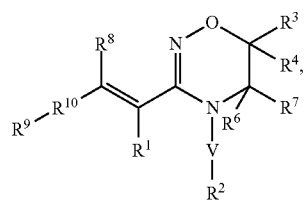
Z18 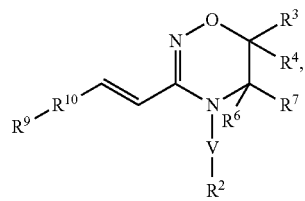
Z19 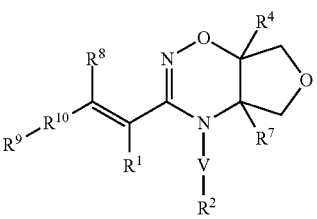
Z19 ( 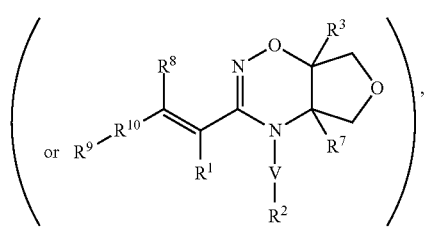 ),
Z20 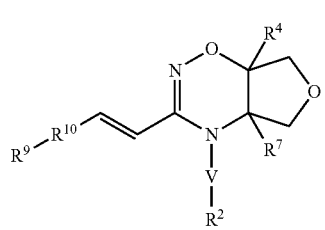
Z20 ( 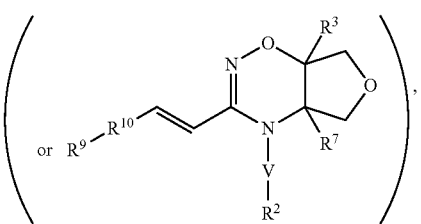 ),
Z21 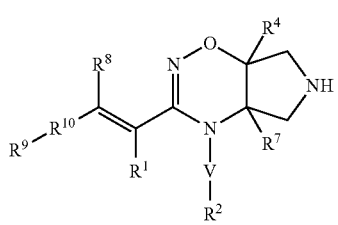
Z21 ( or 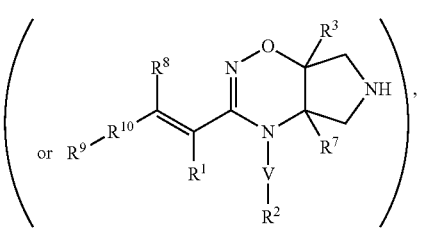 ),
Z22 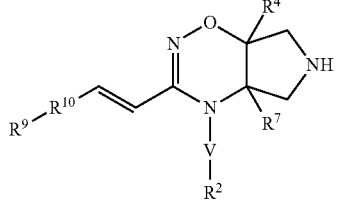
Z22 ( or 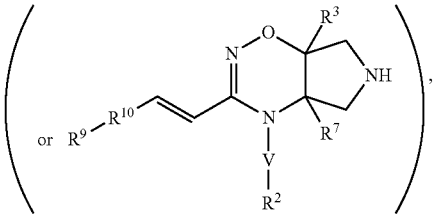 ),
Z23 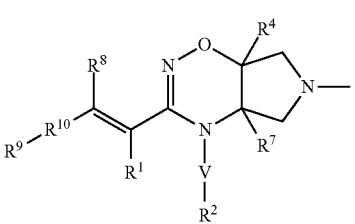
Z23 ( or 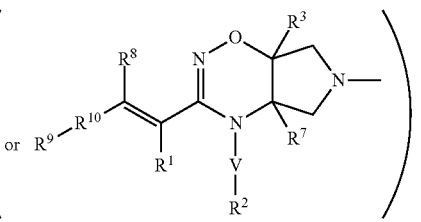 ) and

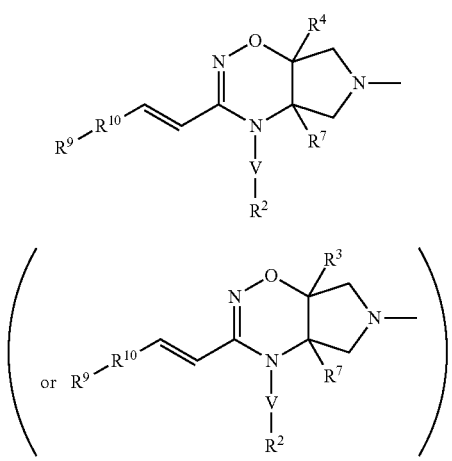

wherein all substituents are as defined for formula I.

Representative compounds of this invention include compounds 1 to 117 (identified in the methods below), the final compound of Method T and the final compound of Method U.

Another embodiment of this invention is directed to compound Z1

Another embodiment of this invention is directed to compound Z2.

Another embodiment of this invention is directed to compound Z3.

Another embodiment of this invention is directed to compound Z4.

Another embodiment of this invention is directed to compound Z5.

Another embodiment of this invention is directed to compound Z6.

Another embodiment of this invention is directed to compound Z7.

Another embodiment of this invention is directed to compound Z8.

Another embodiment of this invention is directed to compound Z9.

Another embodiment of this invention is directed to compound Z10.

Another embodiment of this invention is directed to compound Z11.

Another embodiment of this invention is directed to compound Z12.

Another embodiment of this invention is directed to compound Z13.

Another embodiment of this invention is directed to compound Z14.

Another embodiment of this invention is directed to compound Z15.

Another embodiment of this invention is directed to compound Z16.

Another embodiment of this invention is directed to compound Z17.

Another embodiment of this invention is directed to compound Z18.

Another embodiment of this invention is directed to compound Z19.

Another embodiment of this invention is directed to compound Z20.

Another embodiment of this invention is directed to compound Z21.

Another embodiment of this invention is directed to compound Z22.

Another embodiment of this invention is directed to compound Z23.

Another embodiment of this invention is directed to compound Z24.

Another embodiment of this invention is directed to compound 1.

Another embodiment of this invention is directed to compound 2.

Another embodiment of this invention is directed to compound 3.

Another embodiment of this invention is directed to compound 4.

Another embodiment of this invention is directed to compound 5.

Another embodiment of this invention is directed to compound 6.

Another embodiment of this invention is directed to compound 7.

Another embodiment of this invention is directed to compound 8.

Another embodiment of this invention is directed to compound 9.

Another embodiment of this invention is directed to compound 10.

Another embodiment of this invention is directed to compound 11.

Another embodiment of this invention is directed to compound 12.

Another embodiment of this invention is directed to compound 13.

Another embodiment of this invention is directed to compound 14.

Another embodiment of this invention is directed to compound 15.

Another embodiment of this invention is directed to compound 16.

Another embodiment of this invention is directed to compound 17.

Another embodiment of this invention is directed to compound 18.

Another embodiment of this invention is directed to compound 19.

Another embodiment of this invention is directed to compound 20.

Another embodiment of this invention is directed to compound 21.

Another embodiment of this invention is directed to compound 22.

Another embodiment of this invention is directed to compound 23.

Another embodiment of this invention is directed to compound 24.

Another embodiment of this invention is directed to compound 25.

Another embodiment of this invention is directed to compound 26.

Another embodiment of this invention is directed to compound 27.

Another embodiment of this invention is directed to compound 28.

Another embodiment of this invention is directed to compound 29.

Another embodiment of this invention is directed to compound 30.

Another embodiment of this invention is directed to compound 31.

Another embodiment of this invention is directed to compound 32.

Another embodiment of this invention is directed to compound 33.

Another embodiment of this invention is directed to compound 34.

Another embodiment of this invention is directed to compound 35.

Another embodiment of this invention is directed to compound 36.

Another embodiment of this invention is directed to compound 37.

Another embodiment of this invention is directed to compound 38.

Another embodiment of this invention is directed to compound 39.

Another embodiment of this invention is directed to compound 40.

Another embodiment of this invention is directed to compound 41.

Another embodiment of this invention is directed to compound 42.

Another embodiment of this invention is directed to compound 43.

Another embodiment of this invention is directed to compound 44.

Another embodiment of this invention is directed to compound 45.

Another embodiment of this invention is directed to compound 46.

Another embodiment of this invention is directed to compound 47.

Another embodiment of this invention is directed to compound 50.

Another embodiment of this invention is directed to compound 51.

Another embodiment of this invention is directed to compound 52.

Another embodiment of this invention is directed to compound 53.

Another embodiment of this invention is directed to compound 54.

Another embodiment of this invention is directed to compound 55.

Another embodiment of this invention is directed to compound 56.

Another embodiment of this invention is directed to compound 57.

Another embodiment of this invention is directed to compound 58.

Another embodiment of this invention is directed to compound 59.

Another embodiment of this invention is directed to compound 60.

Another embodiment of this invention is directed to compound 61.

Another embodiment of this invention is directed to compound 62.

Another embodiment of this invention is directed to compound 63.

Another embodiment of this invention is directed to compound 64.

Another embodiment of this invention is directed to compound 65.

Another embodiment of this invention is directed to compound 66.

Another embodiment of this invention is directed to compound 67.

Another embodiment of this invention is directed to compound 68.

Another embodiment of this invention is directed to compound 69.

Another embodiment of this invention is directed to compound 70.

Another embodiment of this invention is directed to compound 71.

Another embodiment of this invention is directed to compound 72.

Another embodiment of this invention is directed to compound 73.

Another embodiment of this invention is directed to compound 74.

Another embodiment of this invention is directed to compound 75.

Another embodiment of this invention is directed to compound 76.

Another embodiment of this invention is directed to compound 77.

Another embodiment of this invention is directed to compound 78.

Another embodiment of this invention is directed to compound 79.

Another embodiment of this invention is directed to compound 80.

Another embodiment of this invention is directed to compound 81.

Another embodiment of this invention is directed to compound 82.

Another embodiment of this invention is directed to compound 83.

Another embodiment of this invention is directed to compound 84.

Another embodiment of this invention is directed to compound 85.

Another embodiment of this invention is directed to compound 86.

Another embodiment of this invention is directed to compound 87.

Another embodiment of this invention is directed to compound 88.

Another embodiment of this invention is directed to compound 89.

Another embodiment of this invention is directed to compound 90.

Another embodiment of this invention is directed to compound 91.

Another embodiment of this invention is directed to compound 92.

Another embodiment of this invention is directed to compound 93.

Another embodiment of this invention is directed to compound 94.

Another embodiment of this invention is directed to compound 95.

Another embodiment of this invention is directed to compound 96.

Another embodiment of this invention is directed to compound 97.

Another embodiment of this invention is directed to compound 98.

Another embodiment of this invention is directed to compound 99.

Another embodiment of this invention is directed to compound 100.

Another embodiment of this invention is directed to compound 101.

Another embodiment of this invention is directed to compound 102.

Another embodiment of this invention is directed to compound 103.

Another embodiment of this invention is directed to compound 104.

Another embodiment of this invention is directed to compound 105.

Another embodiment of this invention is directed to compound 106.

Another embodiment of this invention is directed to compound 107.

Another embodiment of this invention is directed to compound 108.

Another embodiment of this invention is directed to compound 109.

Another embodiment of this invention is directed to compound 110.

Another embodiment of this invention is directed to compound 111.

Another embodiment of this invention is directed to compound 112.

Another embodiment of this invention is directed to compound 113.

Another embodiment of this invention is directed to compound 114.

Another embodiment of this invention is directed to compound 115.

Another embodiment of this invention is directed to compound 116.

Another embodiment of this invention is directed to compound 117.

Another embodiment of this invention is directed to the final compound of Method T.

Another embodiment of this invention is directed to the final compound of Method U.

Another embodiment of this invention is directed to a compound of formula I having the formula Z1 wherein $R^9$ is selected from the group consisting of 1 g to 52 g, $R^{10}$ is selected from the group consisting of 1A to 55A, and $R^3$, $R^4$, $R^6$, $R^7$ and $R^8$ are as defined for formula I.

Another embodiment of this invention is directed to a compound of formula I having the formula Z1 wherein $R^9$ is selected from the group consisting of 1 g to 13 g, $R^{10}$ is selected from the group consisting of 1A to 55A, and $R^3$, $R^4$, $R^6$, $R^7$ and $R^8$ are as defined for formula I.

Another embodiment of this invention is directed to a compound of formula I having the formula Z1 wherein the $R^9$—$R^{10}$— group is selected from the group consisting of 1b to 53b, and $R^3$, $R^4$, $R^6$, $R^7$ and $R^8$ are as defined for formula I.

Another embodiment of this invention is directed to a compound of formula I having the formula Z1 wherein the $R^9$—$R^{10}$— group is 50b, and $R^3$, $R^4$, $R^5$, $R^6$, $R^7$ and $R^8$ are as defined for formula I.

Another embodiment of this invention is directed to a compound of formula I having the formula Z1 wherein the $R^9$—$R^{10}$— group is selected from the group consisting of 1b to 53b, $R^3$, $R^4$ and $R^8$ are as defined for formula I, $R^6$ is H, and $R^7$ is a phenyl substituted with 1 to 3 halos.

Another embodiment of this invention is directed to a compound of formula I having the formula Z1 wherein the $R^9$—$R^{10}$— group is selected from the group consisting of 1b to 53b, $R^3$, $R^4$ and $R^8$ are as defined for formula I, $R^6$ is H, and $R^7$ is a phenyl substituted with 1 to 3 F.

Another embodiment of this invention is directed to a compound of formula I having the formula Z1 wherein the $R^9$—$R^{10}$— group is selected from the group consisting of 1b to 53b, $R^3$, $R^4$ and $R^8$ are as defined for formula I, $R^6$ is H, and $R^7$ is a phenyl substituted with 1 to 3 halos independently selected from the group consisting of Cl and F. In one example said phenyl is substituted with one Cl and one F.

Another embodiment of this invention is directed to a compound of formula I having the formula Z1 wherein the $R^9$—$R^{10}$— group is 50b, $R^3$, $R^4$ and $R^8$ are as defined for formula I, $R^6$ is H, and $R^7$ is a phenyl substituted with 1 to 3 halos.

Another embodiment of this invention is directed to a compound of formula I having the formula Z1 wherein the $R^9$—$R^{10}$— group is 50b, $R^3$, $R^4$ and $R^8$ are as defined for formula I, $R^6$ is H, and $R^7$ is a phenyl substituted with 1 to 3 F.

Another embodiment of this invention is directed to a compound of formula I having the formula Z1 wherein the $R^9$—$R^{10}$— group is 50b, $R^3$, $R^4$ and $R^8$ are as defined for formula I, $R^6$ is H, and $R^7$ is a phenyl substituted with 1 to 3 halos independently selected from the group consisting of Cl and F. In one example said phenyl is substituted with one Cl and one F.

Another embodiment of this invention is directed to a compound of formula I having the formula Z1 wherein the $R^9$—$R^{10}$— group is selected from the group consisting of 1b to 53b, $R^8$ is as defined for formula I, each $R^3$ and each $R^4$ is H, $R^6$ is H, and $R^7$ is a phenyl substituted with 1 to 3 halos.

Another embodiment of this invention is directed to a compound of formula I having the formula Z1 wherein the $R^9$—$R^{10}$— group is selected from the group consisting of 1b to 53b, $R^8$ is as defined for formula I, each $R^3$ and each $R^4$ is H, $R^6$ is H, and $R^7$ is a phenyl substituted with 1 to 3 F.

Another embodiment of this invention is directed to a compound of formula I having the formula Z1 wherein the $R^9$—$R^{10}$— group is selected from the group consisting of 1b to 53b, $R^8$ is as defined for formula I, each $R^3$ and each $R^4$ is H, $R^6$ is H, and $R^7$ is a phenyl substituted with 1 to 3 halos independently selected from the group consisting of Cl and F. In one example said phenyl is substituted with one Cl and one F.

Another embodiment of this invention is directed to a compound of formula I having the formula Z1 wherein the $R^9$—$R^{10}$— group is 50b, $R^8$ is as defined for formula I, each $R^3$ and each $R^4$ is H, $R^6$ is H, and $R^7$ is a phenyl substituted with 1 to 3 halos.

Another embodiment of this invention is directed to a compound of formula I having the formula Z1 wherein the $R^9$—$R^{10}$— group is 50b, $R^8$ is as defined for formula I, each $R^3$ and each $R^4$ is H, $R^6$ is H, and $R^7$ is a phenyl substituted with 1 to 3 F.

Another embodiment of this invention is directed to a compound of formula I having the formula Z1 wherein the $R^9$—$R^{10}$— group is 50b, $R^8$ is as defined for formula I, each $R^3$ and each $R^4$ is H, $R^6$ is H, and $R^7$ is a phenyl substituted with 1 to 3 halos independently selected from the group consisting of Cl and F. In one example said phenyl is substituted with one Cl and one F.

Another embodiment of this invention is directed to a compound of formula I having the formula Z2 wherein $R^9$ is selected from the group consisting of 1 g to 52 g, $R^{10}$ is selected from the group consisting of 1A to 55A, and $R^3$, $R^4$, and $R^7$ are as defined for formula I.

Another embodiment of this invention is directed to a compound of formula I having the formula Z2 wherein $R^9$ is selected from the group consisting of 1 g to 13 g, $R^{10}$ is selected from the group consisting of 1A to 55A, and $R^3$, $R^4$, and $R^7$ are as defined for formula I.

Another embodiment of this invention is directed to a compound of formula I having the formula Z2 wherein the $R^9$—$R^{10}$— group is selected from the group consisting of 1b to 53b, and $R^3$, $R^4$, $R^6$, and $R^7$ are as defined for formula I.

Another embodiment of this invention is directed to a compound of formula I having the formula Z2 wherein the $R^9$—$R^{10}$— group is 50b, and $R^3$, $R^4$, $R^6$, and $R^7$ are as defined for formula I.

Another embodiment of this invention is directed to a compound of formula I having the formula Z2 wherein the $R^9$—$R^{10}$— group is selected from the group consisting of 1b to 53b, $R^3$ and $R^4$ are as defined for formula I, $R^6$ is H, and $R^7$ is a phenyl substituted with 1 to 3 halos.

Another embodiment of this invention is directed to a compound of formula I having the formula Z2 wherein the $R^9$—$R^{10}$— group is selected from the group consisting of 1b to 53b, $R^3$ and $R^4$ are as defined for formula I, $R^6$ is H, and $R^7$ is a phenyl substituted with 1 to 3 F.

Another embodiment of this invention is directed to a compound of formula I having the formula Z2 wherein the $R^9$—$R^{10}$— group is selected from the group consisting of 1b to 53b, $R^3$ and $R^4$ are as defined for formula I, $R^6$ is H, and $R^7$ is a phenyl substituted with 1 to 3 halos independently selected from the group consisting of Cl and F. In one example said phenyl is substituted with one Cl and one F.

Another embodiment of this invention is directed to a compound of formula I having the formula Z2 wherein the $R^9$—$R^{10}$— group is 50b, $R^3$ and $R^4$ are as defined for formula I, $R^6$ is H, and $R^7$ is a phenyl substituted with 1 to 3 halos.

Another embodiment of this invention is directed to a compound of formula I having the formula Z2 wherein the $R^9$—$R^{10}$— group is 50b, $R^3$ and $R^4$ are as defined for formula I, $R^6$ is H, and $R^7$ is a phenyl) substituted with 1 to 3 F.

Another embodiment of this invention is directed to a compound of formula I having the formula Z2 wherein the $R^9$—$R^{10}$— group is 50b, $R^3$ and $R^4$ are as defined for formula I, $R^6$ is H, and $R^7$ is a phenyl substituted with 1 to 3 halos independently selected from the group consisting of Cl and F. In one example said phenyl is substituted with one Cl and one F.

Another embodiment of this invention is directed to a compound of formula I having the formula Z2 wherein the $R^9$—$R^{10}$— group is selected from the group consisting of 1b to 53b, each $R^3$ and each $R^4$ is H, $R^6$ is H, and $R^7$ is a phenyl substituted with 1 to 3 halos.

Another embodiment of this invention is directed to a compound of formula I having the formula Z2 wherein the $R^9$—$R^{10}$— group is selected from the group consisting of 1b to 53b, each $R^3$ and each $R^4$ is H, $R^6$ is H, and $R^7$ is a phenyl substituted with 1 to 3 F.

Another embodiment of this invention is directed to a compound of formula I having the formula Z2 wherein the $R^9$—$R^{10}$— group is selected from the group consisting of 1b to 53b, each $R^3$ and each $R^4$ is H, $R^6$ is H, and $R^7$ is a phenyl substituted with 1 to 3 halos independently selected from the group consisting of Cl and F. In one example said phenyl is substituted with one Cl and one F.

Another embodiment of this invention is directed to a compound of formula I having the formula Z2 wherein the $R^9$—$R^{10}$— group is 50b, each $R^3$ and each $R^4$ is H, $R^6$ is H, and $R^7$ is a phenyl substituted with 1 to 3 halos.

Another embodiment of this invention is directed to a compound of formula I having the formula Z2 wherein the $R^9$—$R^{10}$— group is 50b, each $R^3$ and each $R^4$ is H, $R^6$ is H, and $R^7$ is a phenyl substituted with 1 to 3 F.

Another embodiment of this invention is directed to a compound of formula I having the formula Z2 wherein the $R^9$—$R^{10}$— group is 50b, each $R^3$ and each $R^4$ is H, $R^6$ is H, and $R^7$ is a phenyl substituted with 1 to 3 halos independently selected from the group consisting of Cl and F. In one example said phenyl is substituted with one Cl and one F.

Other embodiments of this invention are directed to any one of the above embodiments directed to Z1 wherein $R^7$ is a phenyl substituted with an —$SF_5$ group, or an —$OSF_5$ group (e.g., p-$SF_5$-phenyl, or p-$OSF_5$-phenyl).

Another embodiment of this invention is directed to a compound of formula I having the formula Z3 wherein $R^9$ is selected from the group consisting of 1 g to 52 g, $R^{16}$ is selected from the group consisting of 1A to 55A, and $R^6$, $R^7$ and $R^8$ are as defined for formula I.

Another embodiment of this invention is directed to a compound of formula I having the formula Z3 wherein $R^9$ is selected from the group consisting of 1 g to 13 g, $R^{10}$ is selected from the group consisting of 1A to 55A, and $R^6$, $R^7$ and $R^8$ are as defined for formula I.

Another embodiment of this invention is directed to a compound of formula I having the formula Z3 wherein the $R^9$—$R^{10}$— group is selected from the group consisting of 1b to 53b, and $R^6$, $R^7$ and $R^8$ are as defined for formula I.

Another embodiment of this invention is directed to a compound of formula I having the formula Z3 wherein the $R^9$—$R^{10}$— group is 50b, and $R^6$, $R^7$ and $R^8$ are as defined for formula I.

Another embodiment of this invention is directed to a compound of formula I having the formula Z3 wherein the $R^9$—$R^{10}$— group is selected from the group consisting of 1b to 53b, $R^8$ is as defined for formula I, $R^6$ is H, and $R^7$ is a phenyl substituted with 1 to 3 substituents selected from the group consisting of halo (e.g., F), —$SF_5$, and —$OSF_5$.

Another embodiment of this invention is directed to a compound of formula I having the formula Z3 wherein the $R^9$—$R^{10}$— group is selected from the group consisting of 1b to 53b, $R^8$ is as defined for formula I, $R^6$ is H, and $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z3 wherein the $R^9$—$R^{10}$— group is 50b, $R^8$ is as defined for formula I, $R^6$ is H, $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z4 wherein $R^9$ is selected from the group consisting of 1 g to 52 g, $R^{10}$ is selected from the group consisting of 1A to 55A, and $R^6$ and $R^7$ are as defined for formula I.

Another embodiment of this invention is directed to a compound of formula I having the formula Z4 wherein $R^9$ is selected from the group consisting of 1 g to 13 g, $R^{10}$ is selected from the group consisting of 1A to 55A, and $R^6$ and $R^7$ are as defined for formula I.

Another embodiment of this invention is directed to a compound of formula I having the formula Z4 wherein the $R^9$—$R^{10}$— group is selected from the group consisting of 1b to 53b, and $R^6$ and $R^7$ are as defined for formula I.

Another embodiment of this invention is directed to a compound of formula I having the formula Z4 wherein the $R^9$—$R^{10}$— group is 50b, and $R^6$ and $R^7$ are as defined for formula I.

Another embodiment of this invention is directed to a compound of formula I having the formula Z4 wherein the $R^9$—$R^{10}$— group is selected from the group consisting of 1b to 53b, $R^6$ is H, and $R^7$ is a phenyl substituted with 1 to 3 substituents selected from the group consisting of halo (e.g., F), —$SF_5$, and —$OSF_5$.

Another embodiment of this invention is directed to a compound of formula I having the formula Z4 wherein the $R^9$—$R^{10}$— group is selected from the group consisting of 1b to 53b, $R^6$ is H, and $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z4 wherein the $R^9$—$R^{10}$— group is 50b, $R^6$ is H, $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z5 wherein $R^9$ is selected from the group consisting of 1 g to 52 g, $R^{10}$ is selected from the group consisting of 1A to 55A, and $R^6$, $R^7$ and $R^8$ are as defined for formula I.

Another embodiment of this invention is directed to a compound of formula I having the formula Z5 wherein $R^9$ is selected from the group consisting of 1 g to 13 g, $R^{16}$ is selected from the group consisting of 1A to 55A, and $R^6$, $R^7$ and $R^8$ are as defined for formula I.

Another embodiment of this invention is directed to a compound of formula I having the formula Z5 wherein the $R^9$—$R^{10}$— group is selected from the group consisting of 1b to 53b, and $R^6$, $R^7$ and $R^8$ are as defined for formula I.

Another embodiment of this invention is directed to a compound of formula I having the formula Z5 wherein the $R^9$—$R^{10}$— group is 50b, and $R^6$, $R^7$ and $R^8$ are as defined for formula I.

Another embodiment of this invention is directed to a compound of formula consisting of 1b to 53b, $R^8$ is as defined for formula I, $R^6$ is H, and $R^7$ is a phenyl substituted with 1 to 3 substituents selected from the group consisting of halo (e.g., F), —$SF_5$, and —$OSF_5$.

Another embodiment of this invention is directed to a compound of formula I having the formula Z5 wherein the $R^9$—$R^{10}$— group is selected from the group consisting of 1b to 53b, $R^8$ is as defined for formula I, $R^6$ is H, and $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z5 wherein the $R^9$—$R^{10}$— group is 50b, $R^8$ is as defined for formula I, $R^6$ is H, $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z6 wherein $R^9$ is selected from the group consisting of 1 g to 52 g, $R^{10}$ is selected from the group consisting of 1A to 55A, and $R^6$ and $R^7$ are as defined for formula I.

Another embodiment of this invention is directed to a compound of formula I having the formula Z6 wherein $R^9$ is selected from the group consisting of 1 g to 13 g, $R^{10}$ is selected from the group consisting of 1A to 55A, and $R^6$ and $R^7$ are as defined for formula I.

Another embodiment of this invention is directed to a compound of formula I having the formula Z6 wherein the $R^9$—$R^{10}$— group is selected from the group consisting of 1b to 53b, and $R^6$ and $R^7$ are as defined for formula I.

Another embodiment of this invention is directed to a compound of formula I having the formula Z6 wherein the $R^9$—$R^{10}$— group is 50b, and $R^6$ and $R^7$ are as defined for formula I.

Another embodiment of this invention is directed to a compound of formula I having the formula Z6 wherein the $R^9$—$R^{10}$— group is selected from the group consisting of 1b to 53b, $R^6$ is H, and $R^7$ is a phenyl substituted with 1 to 3 substituents selected from the group consisting of halo (e.g., F), —$SF_5$, and —$OSF_5$.

Another embodiment of this invention is directed to a compound of formula I having the formula Z6 wherein the $R^9$—$R^{10}$— group is selected from the group consisting of 1b to 53b, $R^6$ is H, and $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl), Another embodiment of this invention is directed to a compound of formula I having the formula Z6 wherein the $R^9$—$R^{10}$— group is 50b, $R^6$ is H, $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula having the formula Z7 wherein $R^9$ is selected from the group consisting of 1 g to 52 g, $R^{10}$ is selected from the group consisting of 1A to 55A, and $R^6$, $R^7$ and $R^8$ are as defined for formula I.

Another embodiment of this invention is directed to a compound of formula I having the formula Z7 wherein $R^9$ is selected from the group consisting of 1 g to 13 g, $R^{10}$ is selected from the group consisting of 1A to 55A, and $R^6$, $R^7$ and $R^8$ are as defined for formula I.

Another embodiment of this invention is directed to a compound of formula I having the formula Z7 wherein the $R^9$—$R^{10}$— group is selected from the group consisting of 1b to 53b, and $R^6$, $R^7$ and $R^8$ are as defined for formula I.

Another embodiment of this invention is directed to a compound of formula I having the formula Z7 wherein the $R^9$—$R^{10}$— group is 50b, and $R^6$, $R^7$ and $R^8$ are as defined for formula I.

Another embodiment of this invention is directed to a compound of formula I having the formula Z7 wherein the $R^9$—$R^{10}$— group is selected from the group consisting of 1b to 53b, $R^8$ is as defined for formula I, $R^6$ is H, and $R^7$ is a phenyl substituted with 1 to 3 substituents selected from the group consisting of halo (e.g., F), —$SF_5$, and —$OSF_5$.

Another embodiment of this invention is directed to a compound of formula I having the formula Z7 wherein the $R^9$—$R^{10}$— group is selected from the group consisting of 1b to 53b, $R^8$ is as defined for formula I, $R^6$ is H, and $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z7 wherein the $R^9$—$R^{10}$— group is 50b, $R^8$ is as defined for formula I, $R^6$ is H, R' is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z8 wherein $R^9$ is selected from the group consisting of 1 g to 52 g, $R^{10}$ is selected from the group consisting of 1A to 55A, and $R^6$ and $R^7$ are as defined for formula I.

Another embodiment of this invention is directed to a compound of formula I having the formula Z8 wherein $R^9$ is selected from the group consisting of 1 g to 13 g, $R^{10}$ is selected from the group consisting of 1A to 55A, and $R^6$ and $R^7$ are as defined for formula I.

Another embodiment of this invention is directed to a compound of formula I having the formula Z8 wherein the $R^9$—$R^{10}$— group is selected from the group consisting of 1b to 53b, and $R^6$ and $R^7$ are as defined for formula I.

Another embodiment of this invention is directed to a compound of formula I having the formula Z8 wherein the $R^9$—$R^{10}$— group is 50b, and $R^6$ and $R^7$ are as defined for formula I.

Another embodiment of this invention is directed to a compound of formula I having the formula Z8 wherein the $R^9$—$R^{10}$— group is selected from the group consisting of 1b to 53b, $R^6$ is H, and $R^7$ is a phenyl substituted with 1 to 3 substituents selected from the group consisting of halo (e.g., F), —$SF_5$, and —$OSF_5$.

Another embodiment of this invention is directed to a compound of formula I having the formula Z8 wherein the $R^9$—$R^{10}$— group is selected from the group consisting of 1b to 53b, $R^6$ is H, and $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z8 wherein the $R^9$—$R^{10}$— group is 50b, $R^6$ is H, $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z9 wherein $R^9$ is selected from the group consisting of 1 g to 52 g, $R^{16}$ is selected from the group consisting of 1A to 55A, and $R^6$, $R^7$ and $R^8$ are as defined for formula I.

Another embodiment of this invention is directed to a compound of formula I having the formula Z9 wherein $R^9$ is selected from the group consisting of 1 g to 13 g, $R^{16}$ is selected from the group consisting of 1A to 55A, and $R^6$, $R^7$ and $R^8$ are as defined for formula I.

Another embodiment of this invention is directed to a compound of formula I having the formula Z9 wherein the $R^9$—$R^{10}$— group is selected from the group consisting of 1b to 53b, and $R^6$, $R^7$ and $R^8$ are as defined for formula I.

Another embodiment of this invention is directed to a compound of formula I having the formula Z9 wherein the $R^9$—$R^{10}$— group is 50b, and $R^6$, $R^7$ and $R^8$ are as defined for formula I.

Another embodiment of this invention is directed to a compound of formula I having the formula Z9 wherein the $R^9$—$R^{10}$— group is selected from the group consisting of 1b to 53b, $R^8$ is as defined for formula I, $R^6$ is H, and $R^7$ is a phenyl substituted with 1 to 3 substituents selected from the group consisting of halo (e.g., F), —$SF_5$, and —$OSF_5$.

Another embodiment of this invention is directed to a compound of formula I having the formula Z9 wherein the $R^9$—$R^{10}$— group is selected from the group consisting of 1b to 53b, $R^6$ is as defined for formula I, $R^6$ is H, and $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z9 wherein the $R^9$—$R^{10}$— group is 50b, $R^8$ is as defined for formula I, $R^6$ is H, $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z10 wherein $R^9$ is selected from the group consisting of 1 g to 52 g, $R^{10}$ is selected from the group consisting of 1A to 55A, and $R^6$ and $R^7$ are as defined for formula I.

Another embodiment of this invention is directed to a compound of formula I having the formula Z10 wherein $R^9$ is selected from the group consisting of 1 g to 13 g, $R^{10}$ is selected from the group consisting of 1A to 55A, and $R^6$ and $R^7$ are as defined for formula I.

Another embodiment of this invention is directed to a compound of formula I having the formula Z10 wherein the $R^9$—$R^{10}$— group is selected from the group consisting of 1b to 53b, and $R^6$ and $R^7$ are as defined for formula I.

Another embodiment of this invention is directed to a compound of formula I having the formula Z10 wherein the $R^9$—$R^{10}$— group is 50b, and $R^6$ and $R^7$ are as defined for formula I.

Another embodiment of this invention is directed to a compound of formula I having the formula Z10 wherein the $R^9$—$R^{10}$— group is selected from the group consisting of 1b to 53b, $R^6$ is H, and $R^7$ is a phenyl substituted with 1 to 3 substituents selected from the group consisting of halo (e.g., F), —$SF_5$, and —$OSF_5$.

Another embodiment of this invention is directed to a compound of formula I having the formula Z10 wherein the $R^9$—$R^{10}$— group is selected from the group consisting of 1b to 53b, $R^6$ is H, and $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z10 wherein the $R^9$—$R^{10}$— group is 50b, $R^6$ is H, $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z11 wherein $R^9$ is selected from the group consisting of 1 g to 52 g, $R^{10}$ is selected from the group consisting of 1A to 55A, and $R^6$, $R^7$ and $R^8$ are as defined for formula I.

Another embodiment of this invention is directed to a compound of formula I having the formula Z11 wherein $R^9$ is selected from the group consisting of 1 g to 13 g, $R^{10}$ is selected from the group consisting of 1A to 55A, and $R^6$, $R^7$ and $R^8$ are as defined for formula I.

Another embodiment of this invention is directed to a compound of formula I having the formula Z11 wherein the $R^9$—$R^{10}$— group is selected from the group consisting of 1b to 53b, and $R^6$, $R^7$ and $R^8$ are as defined for formula I.

Another embodiment of this invention is directed to a compound of formula I having the formula Z11 wherein the $R^9$—$R^{10}$— group is 50b, and $R^6$, $R^7$ and $R^8$ are as defined for formula I.

Another embodiment of this invention is directed to a compound of formula I having the formula Z11 wherein the $R^9$—$R^{10}$— group is selected from the group consisting of 1b to 53b, $R^8$ is as defined for formula I, $R^6$ is H, and $R^7$ is a phenyl substituted with 1 to 3 substituents selected from the group consisting of halo (e.g., F), —$SF_5$, and —$OSF_5$.

Another embodiment of this invention is directed to a compound of formula I having the formula Z11 wherein the $R^9$—$R^{10}$— group is selected from the group consisting of 1b to 53b, $R^8$ is as defined for formula I, $R^6$ is H, and $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl).

In another example $R^7$ is phenyl substituted with one —$OSF_5$ group (e.g., $R^7$ is p-$OSF_5$-phenyl).

Another embodiment of this invention is directed to a compound of formula I having the formula Z11 wherein the $R^9$—$R^{10}$— group is 50b, $R^8$ is as defined for formula I, $R^6$ is H, $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z12 wherein $R^9$ is selected from the group consisting of 1 g to 52 g, $R^{10}$ is selected from the group consisting of 1A to 55A, and $R^6$ and $R^7$ are as defined for formula I.

Another embodiment of this invention is directed to a compound of formula I having the formula Z12 wherein $R^9$ is selected from the group consisting of 1 g to 13 g, $R^{10}$ is selected from the group consisting of 1A to 55A, and $R^6$ and $R^7$ are as defined for formula I.

Another embodiment of this invention is directed to a compound of formula I having the formula Z12 wherein the $R^9$—$R^{10}$— group is selected from the group consisting of 1b to 53b, and $R^6$ and $R^7$ are as defined for formula I.

Another embodiment of this invention is directed to a compound of formula I having the formula Z12 wherein the $R^9$—$R^{10}$— group is 50b, and $R^6$ and $R^7$ are as defined for formula I.

Another embodiment of this invention is directed to a compound of formula I having the formula Z12 wherein the $R^9$—$R^{10}$— group is selected from the group consisting of 1b to 53b, $R^6$ is H, and $R^7$ is a phenyl substituted with 1 to 3 substituents selected from the group consisting of halo (e.g., F), —$SF_5$, and —$OSF_5$.

Another embodiment of this invention is directed to a compound of formula I having the formula Z12 wherein the $R^9$—$R^{10}$— group is selected from the group consisting of 1b to 53b, $R^6$ is H, and $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z12 wherein the $R^9$—$R^{10}$— group is 50b, $R^6$ is H, $R^7$ is a phenyl substituted with 1 to 3 substituents selected from the group consisting of F, —$SF_5$, and —$OSF_5$. In one example $R^7$ is phenyl substituted with 1 to 3 F. In another example $R^7$ is phenyl substituted with one —$SF_5$ group (e.g., $R^7$ is p-$SF_5$-phenyl). In another example $R^7$ is phenyl substituted with one —$OSF_5$ group (e.g., $R^7$ is p-$OSF_5$-phenyl).

Another embodiment of this invention is directed to a compound of formula I having the formula Z13 wherein $R^9$ is selected from the group consisting of 1 g to 52 g, $R^{10}$ is selected from the group consisting of 1A to 55A, and $R^6$, $R^7$ and $R^8$ are as defined for formula I.

Another embodiment of this invention is directed to a compound of formula I having the formula Z13 wherein $R^9$ is selected from the group consisting of 1 g to 13 g, $R^{10}$ is selected from the group consisting of 1A to 55A, and $R^6$, $R^7$ and $R^8$ are as defined for formula I.

Another embodiment of this invention is directed to a compound of formula I having the formula Z13 wherein the $R^9$—$R^{10}$— group is selected from the group consisting of 1b to 53b, and $R^6$, $R^7$ and $R^8$ are as defined for formula I.

Another embodiment of this invention is directed to a compound of formula I having the formula Z13 wherein the $R^9$—$R^{10}$— group is 50b, and $R^6$, $R^7$ and $R^8$ are as defined for formula I.

Another embodiment of this invention is directed to a compound of formula I having the formula Z13 wherein the $R^9$—$R^{10}$— group is selected from the group consisting of 1b to 53b, $R^8$ is as defined for formula I, $R^6$ is H, and $R^7$ is a phenyl substituted with 1 to 3 substituents selected from the group consisting of halo (e.g., F), —SF$_5$, and —OSF$_5$.

Another embodiment of this invention is directed to a compound of formula I having the formula Z13 wherein the R$^9$—R$^{10}$— group is selected from the group consisting of 1b to 53b, R$^8$ is as defined for formula I, R$^6$ is H, and R$^7$ is a phenyl substituted with 1 to 3 substituents selected from the group consisting of F, —SF$_5$, and —OSF$_5$. In one example R$^7$ is phenyl substituted with 1 to 3 F. In another example R$^7$ is phenyl substituted with one —SF$_5$ group (e.g., R$^7$ is p-SF$_5$-phenyl). In another example R$^7$ is phenyl substituted with one —OSF$_5$ group (e.g., R$^7$ is p-OSF$_5$-phenyl).

Another embodiment of this invention is directed to a compound of formula I having the formula Z13 wherein the R$^9$—R$^{10}$— group is 50b, R$^8$ is as defined for formula I, R$^6$ is H, R$^7$ is a phenyl substituted with 1 to 3 substituents selected from the group consisting of F, —SF$_5$, and —OSF$_5$, In one example R$^7$ is phenyl substituted with 1 to 3 F. In another example R$^7$ is phenyl substituted with one —SF$_5$ group (e.g., R$^7$ is p-SF$_5$-phenyl). In another example R$^7$ is phenyl substituted with one —OSF$_5$ group (e.g., R$^7$ is p-OSF$_5$-phenyl).

Another embodiment of this invention is directed to a compound of formula I having the formula Z14 wherein R$^9$ is selected from the group consisting of 1 g to 52 g, R$^{10}$ is selected from the group consisting of 1A to 55A, and R$^6$ and R$^7$ are as defined for formula I.

Another embodiment of this invention is directed to a compound of formula I having the formula Z14 wherein R$^9$ is selected from the group consisting of 1 g to 13 g, R$^{10}$ is selected from the group consisting of 1A to 55A, and R$^6$ and R$^7$ are as defined for formula I.

Another embodiment of this invention is directed to a compound of formula I having the formula Z14 wherein the R$^9$—R$^{10}$— group is selected from the group consisting of 1b to 53b, and R$^6$ and R$^7$ are as defined for formula I.

Another embodiment of this invention is directed to a compound of formula I having the formula Z14 wherein the R$^9$—R$^{10}$— group is 50b, and R$^6$ and R$^7$ are as defined for formula I.

Another embodiment of this invention is directed to a compound of formula I having the formula Z14 wherein the R$^9$—R$^{10}$— group is selected from the group consisting of 1b to 53b, R$^6$ is H, and R$^7$ is a phenyl substituted with 1 to 3 substituents selected from the group consisting of halo (e.g., F), —SF$_5$, and —OSF$_5$.

Another embodiment of this invention is directed to a compound of formula I having the formula Z14 wherein the R$^9$—R$^{10}$— group is selected from the group consisting of 1b to 53b, R$^6$ is H, and R$^7$ is a phenyl substituted with 1 to 3 substituents selected from the group consisting of F, —SF$_5$, and —OSF$_5$. In one example R$^7$ is phenyl substituted with 1 to 3 F. In another example R$^7$ is phenyl substituted with one —SF$_5$ group (e.g., R$^7$ is p-SF$_5$-phenyl). In another example R$^7$ is phenyl substituted with one —OSF$_5$ group (e.g., R$^7$ is p-OSF$_5$-phenyl).

Another embodiment of this invention is directed to a compound of formula I having the formula Z14 wherein the R$^9$—R$^{10}$— group is 50b, R$^6$ is H, R$^7$ is a phenyl substituted with 1 to 3 substituents selected from the group consisting of F, —SF$_5$, and —OSF$_5$. In one example R$^7$ is phenyl substituted with 1 to 3 F. In another example R$^7$ is phenyl substituted with one —SF$_5$ group (e.g., R$^7$ is p-SF$_5$-phenyl).

In another example R$^7$ is phenyl substituted with one —OSF$_5$ group (e.g., R$^7$ is p-OSF$_5$-phenyl).

Another embodiment of this invention is directed to a compound of formula I having the formula Z15 wherein R$^9$ is selected from the group consisting of 1 g to 52 g, R$^{10}$ is selected from the group consisting of 1A to 55A, and R$^3$, R$^4$, R$^6$, R$^7$ and R$^8$ are as defined for formula I.

Another embodiment of this invention is directed to a compound of formula I having the formula Z15 wherein R$^9$ is selected from the group consisting of 1 g to 13 g, R$^{10}$ is selected from the group consisting of 1A to 55A, and R$^3$, R$^4$, R$^6$, R$^7$ and R$^8$ are as defined for formula I.

Another embodiment of this invention is directed to a compound of formula I having the formula Z15 wherein the R$^9$—R$^{10}$— group is selected from the group consisting of 1b to 53b, and R$^3$, R$^4$, R$^6$, R$^7$ and R$^8$ are as defined for formula I.

Another embodiment of this invention is directed to a compound of formula I having the formula Z15 wherein the R$^9$—R$^{10}$— group is 50b, and R$^3$, R$^4$, R$^6$, R$^7$ and R$^8$ are as defined for formula I.

Another embodiment of this invention is directed to a compound of formula I having the formula Z15 wherein the R$^9$—R$^{10}$— group is selected from the group consisting of 1b to 53b, one of R$^3$ and R$^4$ is H and the remaining R$^3$ or R$^4$ is selected from the group consisting of: H and phenyl substituted with 1 to 3 substituents selected from the group consisting of: halo (e.g., F), —SF$_5$ and —OSF$_5$, R$^8$ is as defined for formula I, R$^6$ is H, and R$^7$ is selected from the group consisting of; H, and phenyl substituted with 1 to 3 substituents selected from the group consisting of: halo (e.g., F), —SF$_5$ and —OSF$_5$, provided that if both R$^3$ and R$^4$ are H, then R$^7$ is not H (that is when R$^3$ and R$^4$ are both H, then R$^7$ is a phenyl substituted with 1 to 3 substituents selected from the group consisting of: halo (e.g., F), —SF$_5$ and —OSF$_5$) In one example, R$^7$ is H and one of R$^3$ or R$^4$ is phenyl substituted with —SF$_5$ or —OSF$_5$. In another example, R$^7$ is H and one of R$^3$ or R$^4$ is phenyl substituted with —SF$_5$ (e.g., the R$^3$ or R$^4$ substituent is -p-SF$_5$-phenyl. In another example R$^3$ and R$^4$ are H, and R$^7$ is phenyl substituted with 1 to 3 substituents selected from the group consisting of: halo (e.g., F), —SF$_5$ and —OSF$_5$ (and (i) in one example R$^7$ is phenyl substituted with an —SF$_5$ group (e.g., p-SF$_5$-phenyl), (ii) in another example R$^7$ is phenyl substituted with an —OSF$_5$ group (e.g., p—OSF$_5$-phenyl).

Another embodiment of this invention is directed to a compound of formula I having the formula Z15 wherein the R$^9$—R$^{10}$— group is 50b, one of R$^3$ and R$^4$ is H and the remaining R$^3$ or R$^4$ is selected from the group consisting of: H and phenyl substituted with 1 to 3 substituents selected from the group consisting of: halo (e.g., F), —SF$_5$ and —OSF$_5$, R$^8$ is as defined for formula I, R$^6$ is H, and R$^7$ is selected from the group consisting of; H, and phenyl substituted with 1 to 3 substituents selected from the group consisting of: halo (e.g., F), —SF$_5$ and —OSF$_5$, provided that if both R$^3$ and R$^4$ are H, then R$^7$ is not H (that is when R$^3$ and R$^4$ are both H, then R$^7$ is a phenyl substituted with 1 to 3 substituents selected from the group consisting of: halo (e.g., F), —SF$_5$ and —OSF$_5$). In one example, R$^7$ is H and one of R$^3$ or R$^4$ is phenyl substituted with —SF$_5$ or —OSF$_5$. In another example, R$^7$ is H and one of R$^3$ or R$^4$ is phenyl substituted with —SF$_5$ (e.g., the R$^3$ or R$^4$ substituent is -p-SF$_5$-phenyl. In another example R$^3$ and R$^4$ are H, and R$^7$ is phenyl substituted with 1 to 3 substituents selected from the group consisting of: halo (e.g., F), —SF$_5$ and —OSF$_5$ (and (i) in one example R$^7$ is phenyl substituted with an —SF$_5$ group (e.g., p-SF$_5$-phenyl), (ii) in another example R$^7$ is phenyl substituted with an —OSF$_5$ group (e.g., p—OSF$_5$-phenyl).

Another embodiment of this invention is directed to a compound of formula I having the formula Z16 wherein R$^9$ is selected from the group consisting of 1 g to 52 g, R$^{10}$ is selected from the group consisting of 1A to 55A, and R$^3$, R$^4$, R$^6$ and R$^7$ are as defined for formula I.

Another embodiment of this invention is directed to a compound of formula I having the formula Z16 wherein $R^9$ is selected from the group consisting of 1 g to 13 g, $R^{16}$ is selected from the group consisting of 1A to 55A, and $R^3$, $R^4$, $R^6$ and $R^7$ are as defined for formula I.

Another embodiment of this invention is directed to a compound of formula I having the formula Z16 wherein the $R^9$—$R^{10}$— group is selected from the group consisting of 1b to 53b, and $R^3$, $R^4$, $R^6$ and $R^7$ are as defined for formula I.

Another embodiment of this invention is directed to a compound of formula I having the formula Z16 wherein the $R^9$—$R^{10}$— group is 50b, and $R^3$, $R^4$, $R^6$ and $R^7$ are as defined for formula I.

Another embodiment of this invention is directed to a compound of formula having the formula Z16 wherein the $R^9$—$R^{10}$— group is selected from the group consisting of 1b to 53b, one of $R^3$ and $R^4$ is H and the remaining $R^3$ or $R^4$ is selected from the group consisting of: H and phenyl substituted with 1 to 3 substituents selected from the group consisting of: halo (e.g., F), —$SF_5$ and —$OSF_5$, $R^6$ is H, and $R^7$ is selected from the group consisting of; H, and phenyl substituted with 1 to 3 substituents selected from the group consisting of: halo (e.g., F), —$SF_5$ and —$OSF_5$, provided that if both $R^3$ and $R^4$ are H, then $R^7$ is not H (that is when $R^3$ and $R^4$ are both H, then $R^7$ is a phenyl substituted with 1 to 3 substituents selected from the group consisting of: halo (e.g., F), —$SF_5$ and —$OSF_5$). In one example, $R^7$ is H and one of $R^3$ or $R^4$ is phenyl substituted with —$SF_5$ or —$OSF_5$. In another example, $R^7$ is H and one of $R^3$ or $R^4$ is phenyl substituted with —$SF_5$ (e.g., the $R^3$ or $R^4$ substituent is -p-$SF_5$-phenyl. In another example $R^3$ and $R^4$ are H, and $R^7$ is phenyl substituted with 1 to 3 substituents selected from the group consisting of: halo (e.g., F), —$SF_5$ and —$OSF_5$ (and (i) in one example $R^7$ is phenyl substituted with an —$SF_5$ group (e.g., p-$SF_5$-phenyl), (ii) in another example $R^7$ is phenyl substituted with an —$OSF_5$ group (e.g., p—$OSF_5$-phenyl).

Another embodiment of this invention is directed to a compound of formula I having the formula Z16 wherein the $R^9$—$R^{10}$— group is 50b, one of $R^3$ and $R^4$ is H and the remaining $R^3$ or $R^4$ is selected from the group consisting of: H and phenyl substituted with 1 to 3 substituents selected from the group consisting of: halo (e.g., F), —$SF_5$ and —$OSF_5$, $R^6$ is H, and $R^7$ is selected from the group consisting of; H, and phenyl substituted with 1 to 3 substituents selected from the group consisting of: halo (e.g., F), —$SF_5$ and —$OSF_5$, provided that if both $R^3$ and $R^4$ are H, then $R^7$ is not H (that is when $R^3$ and $R^4$ are both H, then $R^7$ is a phenyl substituted with 1 to 3 substituents selected from the group consisting of: halo (e.g., F), —$SF_5$ and —$OSF_5$). In one example, $R^7$ is H and one of $R^3$ or $R^4$ is phenyl substituted with —$SF_5$ or —$OSF_5$. In another example, $R^7$ is H and one of $R^3$ or $R^4$ is phenyl substituted with —$SF_5$ (e.g., the $R^3$ or $R^4$ substituent is -p-$SF_5$-phenyl. In another example $R^3$ and $R^4$ are H, and $R^7$ is phenyl substituted with 1 to 3 substituents selected from the group consisting of: halo (e.g., F), —$SF_5$ and —$OSF_5$ (and (i) in one example $R^7$ is phenyl substituted with an —$SF_5$ group (e.g., p-$SF_5$-phenyl), (ii) in another example $R^7$ is phenyl substituted with an —$OSF_5$ group (e.g., p—$OSF_5$-phenyl).

Another embodiment of this invention is directed to a compound of formula I having the formula Z17 wherein $R^9$ is selected from the group consisting of 1 g to 52 g, $R^{10}$ is selected from the group consisting of 1A to 55A, and V, $R^1$, $R^2$, $R^3$, $R^4$, $R^6$, $R^7$ and $R^8$ are as defined for formula I.

Another embodiment of this invention is directed to a compound of formula I having the formula Z17 wherein $R^9$ is selected from the group consisting of 1 g to 13 g, $R^{10}$ is selected from the group consisting of 1A to 55A, and V, $R^1$, $R^2$, $R^3$, $R^4$, $R^6$, $R^7$ and $R^8$ are as defined for formula I.

Another embodiment of this invention is directed to a compound of formula I having the formula Z17 wherein the $R^9$—$R^{10}$— group is selected from the group consisting of 1b to 53b, and V, $R^1$, $R^2$, $R^3$, $R^4$, $R^6$, $R^7$ and $R^8$ are as defined for formula I.

Another embodiment of this invention is directed to a compound of formula I having the formula Z17 wherein the $R^9$—$R^{10}$— group is 50b, and V, $R^1$, $R^2$, $R^3$, $R^4$, $R^6$, $R^7$ and $R^8$ are as defined for formula I.

Another embodiment of this invention is directed to a compound of formula I having the formula Z17 wherein:

(1) the $R^9$—$R^{10}$— group is selected from the group consisting of 1b to 53b;

(2) $R^2$ is selected from the group consisting of (a) H, (b) alkyl, and (c) alkyl substituted with 1 to 5 $R^{21}$ groups;

(3) one of $R^3$ or $R^4$ is H, and the remaining $R^3$ or $R^4$ is selected from the group comprising:
   (a) aryl (e.g., phenyl),
   (b) aryl (e.g., phenyl) substituted with 1 to 3 independently selected $R^{21}$ groups (and (i) in one example said aryl is substituted with 1 to 3 halos, (ii) in another example said aryl is substituted with 1 to 3 F, (iii) in another example said aryl is substituted with 3 F, (iv) in another example said aryl is substituted with 2 F, and (v) in another example said aryl is substituted with 1 F),
   (c) heteroaryl (e.g., thienyl), (d) heteroaryl (e.g., thienyl) substituted with 1 to 3 independently selected $R^{21}$ groups (and (i) in one example said heteroaryl is substituted with 1 to 3 halos, (ii) in another example said heteroaryl is substituted with 1 to 3 F, and (iii) in another example said heteroaryl is substituted with 1 F),
   (d) cycloalkyl (e.g., cyclopropyl),
   (e) cycloalkyl (e.g., cyclopropyl) substituted with 1 to 3 independently $R^{21}$ substituents (and (i) in one example said cycloalkyl is substituted with 1 to 3 halos, and (ii) in another example said cycloalkyl is substituted with 1 to 3 F),
   (f) alkyl (e.g., methyl or ethyl),
   (g) alkyl substituted with 1 to 3 independently selected $R^{21}$ groups (and (i) in one example said alkyl is substituted with one —$OR^{15}$ group, (ii) in another example said alkyl is substituted with one —$OR^{15}$ group wherein $R^{15}$ is H, (iii) in another example said alkyl is substituted with one —$OR^{15}$ group wherein $R^{15}$ is $(R^{18})_r$-alkyl-, (iv) in another example said alkyl is substituted with one —$OR^{15}$ group wherein $R^{15}$ is $(R^{18})_r$-alkyl- and $R^{18}$ is —OH and r is 1, and (v) in another example said alkyl is substituted with one —$OR^{15}$ wherein $R^{15}$ is HO—$CH_2$—, or HO—$(CH_2)_2$—); and (4) $R^6$ is H;

(5) $R^7$ is selected from the group consisting of; H, and phenyl substituted with 1 to 3 substituents selected from the group consisting of: halo (e.g., F), —$SF_5$ and —$OSF_5$;

(6) $R^8$ is as defined for formula I;

(7) $R^1$ is as defined for formula I;

(8) V is a bond; and (9) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z17 wherein:

(1) the $R^9$—$R^{10}$— group is selected from the group consisting of 1b to 53b;

(2) $R^2$ is selected from the group consisting of (a) H, (b) alkyl, and (c) alkyl substituted with 1 to 5 $R^{21}$ groups;

(3) one of $R^3$ or $R^4$ is H, and the remaining $R^3$ or $R^4$ is selected from the group comprising:
- (a) phenyl,
- (b) phenyl substituted with 1 to 3 independently selected $R^{21}$ groups (and (i) in one example said phenyl is substituted with 1 to 3 halos, (ii) in another example said phenyl is substituted with 1 to 3 F, (iii) in another example said phenyl is substituted with 3 F, (iv) in another example said phenyl is substituted with 2 F, and (v) in another example said phenyl is substituted with 1 F),
- (c) thienyl,
- (d) thienyl substituted with 1 to 3 independently selected $R^{21}$ groups (and (i) in one example said thienyl is substituted with 1 to 3 halos, (ii) in another example said thienyl is substituted with 1 to 3 F, and (iii) in another example said thienyl is substituted with 1 F),
- (d) cyclopropyl,
- (e) cyclopropyl substituted with 1 to 3 independently $R^{21}$ substituents (and (i) in one example said cyclopropyl is substituted with 1 to 3 halos, and (ii) in another example said cyclopropyl is substituted with 1 to 3 F),
- (f) alkyl (e.g., methyl or ethyl, and (i) in one example methyl, and (ii) in another example ethyl),
- (g) -alkyl-OH (and in one example —$(CH_2)_3OH$),
- (h) -alkyl-O-alkyl-OH (and in one example —$CH_2$—O—$CH_2CH_2$—OH), (4) $R^6$ is H;

(5) $R^7$ is selected from the group consisting of: H, and phenyl substituted with 1 to 3 substituents selected from the group consisting of: halo (e.g., F), —$SF_5$ and —$OSF_5$;

(6) $R^8$ is as defined for formula I;

(7) $R^1$ is as defined for formula I;

(8) V is a bond; and (9) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z17 wherein:

(1) the $R^9$—$R^{10}$— group is selected from the group consisting of 1b to 53b;

(2) $R^2$ is selected from the group consisting of H, alkyl (e.g., methyl, ethyl and propyl, and in one example propyl), and alkyl (e.g., methyl, ethyl and propyl) substituted with 1 —OH group (and in one example the substituted alkyl is —$CH_2CH_2CH_2$—OH);

(3) one of $R^3$ or $R^4$ is H, and the remaining $R^3$ or $R^4$ is selected from the group comprising:
- (a) phenyl,
- (b) phenyl substituted with 1 to 3 independently selected $R^{21}$ groups (and (i) in one example said phenyl is substituted with 1 to 3 halos, (ii) in another example said phenyl is substituted with 1 to 3 F, (iii) in another example said phenyl is substituted with 3 F, (iv) in another example said phenyl is substituted with 2 F, and (v) in another example said phenyl is substituted with 1 F),
- (c) thienyl,
- (d) thienyl substituted with 1 to 3 independently selected $R^{21}$ groups (and (i) in one example said thienyl is substituted with 1 to 3 halos, (ii) in another example said thienyl is substituted with 1 to 3 F, and (iii) in another example said thienyl is substituted with 1 F),
- (d) cyclopropyl,
- (e) cyclopropyl substituted with 1 to 3 independently $R^{21}$ substituents (and (i) in one example said cyclopropyl is substituted with 1 to 3 halos, and (ii) in another example said cyclopropyl is substituted with 1 to 3 F),
- (f) alkyl (e.g., methyl or ethyl, and (i) in one example methyl, and (ii) in another example ethyl),
- (g) -alkyl-OH (and in one example —$(CH_2)_3OH$),
- (h) -alkyl-O-alkyl-OH (and in one example —$CH_2$—O—$CH_2CH_2$—OH), (4) $R^6$ is H;

(5) $R^7$ is selected from the group consisting of: H, and phenyl substituted with 1 to 3 substituents selected from the group consisting of: halo (e.g., F), —$SF_5$ and —$OSF_5$;

(6) $R^8$ is as defined for formula I;

(7) $R^1$ is as defined for formula I;

(8) V is a bond; and (9) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z17 wherein:

(1) the $R^9$—$R^{10}$— group is 50b;

(2) $R^2$ is selected from the group consisting of (a) H, (b) alkyl, and (c) alkyl substituted with 1 to 5 $R^{21}$ groups;

(3) one of $R^3$ or $R^4$ is H, and the remaining $R^3$ or $R^4$ is selected from the group comprising:
- (a) aryl (e.g., phenyl),
- (b) aryl (e.g., phenyl) substituted with 1 to 3 independently selected $R^{21}$ groups (and (i) in one example said aryl is substituted with 1 to 3 halos, (ii) in another example said aryl is substituted with 1 to 3 F, (iii) in another example said aryl is substituted with 3 F, (iv) in another example said aryl is substituted with 2 F, and (v) in another example said aryl is substituted with 1 F),
- (c) heteroaryl (e.g., thienyl), (d) heteroaryl (e.g., thienyl) substituted with 1 to 3 independently selected $R^{21}$ groups (and (i) in one example said heteroaryl is substituted with 1 to 3 halos, (ii) in another example said heteroaryl is substituted with 1 to 3 F, and (iii) in another example said heteroaryl is substituted with 1 F),
- (d) cycloalkyl (e.g., cyclopropyl),
- (e) cycloalkyl (e.g., cyclopropyl) substituted with 1 to 3 independently $R^{21}$ substituents (and (i) in one example said cycloalkyl is substituted with 1 to 3 halos, and (ii) in another example said cycloalkyl is substituted with 1 to 3 F),
- (f) alkyl (e.g., methyl or ethyl),
- (g) alkyl substituted with 1 to 3 independently selected $R^{21}$ groups (and (i) in one example said alkyl is substituted with one —$OR^{15}$ group, (ii) in another example said alkyl is substituted with one —$OR^{15}$ group wherein $R^{15}$ is H, (iii) in another example said alkyl is substituted with one —$OR^{15}$ group wherein $R^{15}$ is $(R^{18})_r$-alkyl-, (iv) in another example said alkyl is substituted with one —$OR^{15}$ group wherein $R^{15}$ is $(R^{18})_r$-alkyl- and $R^{18}$ is —OH and r is 1, and (v) in another example said alkyl is substituted with one —$OR^{15}$ wherein $R^{15}$ is HO—$CH_2$—, or HO—$(CH_2)_2$—); and (4) $R^6$ is H;

(5) $R^7$ is selected from the group consisting of; H, and phenyl substituted with 1 to 3 substituents selected from the group consisting of: halo (e.g., F), —$SF_5$ and —$OSF_5$;

(6) $R^8$ is as defined for formula I;

(7) $R^1$ is as defined for formula I;

(8) V is a bond; and (9) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z17 wherein:

(1) the $R^9$—$R^{10}$— group is 50b;

(2) $R^2$ is selected from the group consisting of (a) H, (b) alkyl, and (c) alkyl substituted with 1 to 5 $R^{21}$ groups;

(3) one of $R^3$ or $R^4$ is H, and the remaining $R^3$ or $R^4$ is selected from the group comprising:
 (a) phenyl,
 (b) phenyl substituted with 1 to 3 independently selected $R^{21}$ groups (and (i) in one example said phenyl is substituted with 1 to 3 halos, (ii) in another example said phenyl is substituted with 1 to 3 F, (iii) in another example said phenyl is substituted with 3 F, (iv) in another example said phenyl is substituted with 2 F, and (v) in another example said phenyl is substituted with 1 F),
 (c) thienyl,
 (d) thienyl substituted with 1 to 3 independently selected $R^{21}$ groups (and (i) in one example said thienyl is substituted with 1 to 3 halos, (ii) in another example said thienyl is substituted with 1 to 3 F, and (iii) in another example said thienyl is substituted with 1 F),
 (d) cyclopropyl,
 (e) cyclopropyl substituted with 1 to 3 independently $R^{21}$ substituents (and (i) in one example said cyclopropyl is substituted with 1 to 3 halos, and (ii) in another example said cyclopropyl is substituted with 1 to 3 F),
 (f) alkyl (e.g., methyl or ethyl, and (i) in one example methyl, and (ii) in another example ethyl),
 (g) -alkyl-OH (and in one example —$(CH_2)_3OH$),
 (h) -alkyl-O-alkyl-OH (and in one example —$CH_2$—O—$CH_2CH_2$—OH), (4) $R^6$ is H;

(5) $R^7$ is selected from the group consisting of; H, and phenyl substituted with 1 to 3 substituents selected from the group consisting of: halo (e.g., F), —$SF_5$ and —$OSF_5$;

(6) $R^8$ is as defined for formula I;

(7) $R^1$ is as defined for formula I;

(8) V is a bond; and (9) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z17 wherein:

(1) the $R^9$—$R^{10}$— group is 50b;

(2) $R^2$ is selected from the group consisting of H, alkyl (e.g., methyl, ethyl and propyl, and in one example propyl), and alkyl (e.g., methyl, ethyl and propyl) substituted with 1 —OH group (and in one example the substituted alkyl is —$CH_2CH_2CH_2$—OH);

(3) one of $R^3$ or $R^4$ is H, and the remaining $R^3$ or $R^4$ is selected from the group comprising:
 (a) phenyl,
 (b) phenyl substituted with 1 to 3 independently selected $R^{21}$ groups (and (i) in one example said phenyl is substituted with 1 to 3 halos, (ii) in another example said phenyl is substituted with 1 to 3 F, (iii) in another example said phenyl is substituted with 3 F, (iv) in another example said phenyl is substituted with 2 F, and (v) in another example said phenyl is substituted with 1 F),
 (c) thienyl,
 (d) thienyl substituted with 1 to 3 independently selected $R^{21}$ groups (and (i) in one example said thienyl is substituted with 1 to 3 halos, (ii) in another example said thienyl is substituted with 1 to 3 F, and (iii) in another example said thienyl is substituted with 1 F),
 (d) cyclopropyl,
 (e) cyclopropyl substituted with 1 to 3 independently $R^{21}$ substituents (and (i) in one example said cyclopropyl is substituted with 1 to 3 halos, and (ii) in another example said cyclopropyl is substituted with 1 to 3 F),
 (f) alkyl (e.g., methyl or ethyl, and (i) in one example methyl, and (ii) in another example ethyl),
 (g) -alkyl-OH (and in one example —$(CH_2)_3OH$),
 (h) -alkyl-O-alkyl-OH (and in one example —$CH_2$—O—$CH_2CH_2$—OH), (4) $R^6$ is H;

(5) $R^7$ is selected from the group consisting of; H, and phenyl substituted with 1 to 3 substituents selected from the group consisting of: halo (e.g., F), —$SF_5$ and —$OSF_5$;

(6) $R^8$ is as defined for formula I;

(7) $R^1$ is as defined for formula I;

(8) V is a bond; and (9) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z18 wherein $R^9$ is selected from the group consisting of 1 g to 52 g, $R^{10}$ is selected from the group consisting of 1A to 55A, and V, $R^2$, $R^3$, $R^4$, $R^6$ and $R^7$ are as defined for formula I.

Another embodiment of this invention is directed to a compound of formula I having the formula Z18 wherein $R^9$ is selected from the group consisting of 1 g to 13 g, $R^{10}$ is selected from the group consisting of 1A to 55A, and V, $R^2$, $R^3$, $R^4$, $R^6$ and $R^7$ are as defined for formula I.

Another embodiment of this invention is directed to a compound of formula I having the formula Z18 wherein the $R^9$—$R^{10}$— group is selected from the group consisting of 1b to 53b, and V, $R^2$, $R^3$, $R^4$, $R^6$ and $R^7$ are as defined for formula I.

Another embodiment of this invention is directed to a compound of formula I having the formula Z18 wherein the $R^9$—$R^{10}$— group is 50b, and V, $R^2$, $R^3$, $R^4$, $R^6$ and $R^7$ are as defined for formula I.

Another embodiment of this invention is directed to a compound of formula I having the formula Z18 wherein:
(1) the $R^9$—$R^{10}$— group is selected from the group consisting of 1b to 53b;
(2) $R^2$ is selected from the group consisting of (a) H, (b) alkyl, and (c) alkyl substituted with 1 to 5 $R^{21}$ groups;
(3) one of $R^3$ or $R^4$ is H, and the remaining $R^3$ or $R^4$ is selected from the group comprising:
  (a) aryl (e.g., phenyl),
  (b) aryl (e.g., phenyl) substituted with 1 to 3 independently selected $R^{21}$ groups (and (i) in one example said aryl is substituted with 1 to 3 halos, (ii) in another example said aryl is substituted with 1 to 3 F, (iii) in another example said aryl is substituted with 3 F, (iv) in another example said aryl is substituted with 2 F, and (v) in another example said aryl is substituted with 1 F),
  (c) heteroaryl (e.g., thienyl), (d) heteroaryl (e.g., thienyl) substituted with 1 to 3 independently selected $R^{21}$ groups (and (i) in one example said heteroaryl is substituted with 1 to 3 halos, (ii) in another example said heteroaryl is substituted with 1 to 3 F, and (iii) in another example said heteroaryl is substituted with 1 F),
  (d) cycloalkyl (e.g., cyclopropyl),
  (e) cycloalkyl (e.g., cyclopropyl) substituted with 1 to 3 independently $R^{21}$ substituents (and (i) in one example said cycloalkyl is substituted with 1 to 3 halos, and (ii) in another example said cycloalkyl is substituted with 1 to 3 F),
  (f) alkyl (e.g., methyl or ethyl),
  (g) alkyl substituted with 1 to 3 independently selected $R^{21}$ groups (and (i) in one example said alkyl is substituted with one —$OR^{15}$ group, (ii) in another example said alkyl is substituted with one —$OR^{15}$ group wherein $R^{15}$ is H, (iii) in another example said alkyl is substituted with one —$OR^{15}$ group wherein $R^{15}$ is $(R^{18})_r$-alkyl-, (iv) in another example said alkyl is substituted with one —$OR^{15}$ group wherein $R^{15}$ is $(R^{18})_r$-alkyl- and $R^{18}$ is —OH and r is 1, and (v) in another example said alkyl is substituted with one —$OR^{15}$ wherein $R^{15}$ is HO—$CH_2$—, or HO—$(CH_2)_2$—); and
(4) $R^6$ is H;
(5) $R^7$ is selected from the group consisting of; H, and phenyl substituted with 1 to 3 substituents selected from the group consisting of: halo (e.g., F), —$SF_5$ and —$OSF_5$; and
(6) V is a bond; and
(7) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z18 wherein:
(1) the $R^9$—$R^{10}$— group is selected from the group consisting of 1b to 53b;
(2) $R^2$ is selected from the group consisting of (a) H, (b) alkyl, and (c) alkyl substituted with 1 to 5 $R^{21}$ groups;
(3) one of $R^3$ or $R^4$ is H, and the remaining $R^3$ or $R^4$ is selected from the group comprising:
  (a) phenyl,
  (b) phenyl substituted with 1 to 3 independently selected $R^{21}$ groups (and (i) in one example said phenyl is substituted with 1 to 3 halos, (ii) in another example said phenyl is substituted with 1 to 3 F, (iii) in another example said phenyl is substituted with 3 F, (iv) in another example said phenyl is substituted with 2 F, and (v) in another example said phenyl is substituted with 1 F),
  (c) thienyl,
  (d) thienyl substituted with 1 to 3 independently selected $R^{21}$ groups (and (i) in one example said thienyl is substituted with 1 to 3 halos, (ii) in another example said thienyl is substituted with 1 to 3 F, and (iii) in another example said thienyl is substituted with 1 F),
  (d) cyclopropyl,
  (e) cyclopropyl substituted with 1 to 3 independently $R^{21}$ substituents (and (i) in one example said cyclopropyl is substituted with 1 to 3 halos, and (ii) in another example said cyclopropyl is substituted with 1 to 3 F),
  (f) alkyl (e.g., methyl or ethyl, and (i) in one example methyl, and (ii) in another example ethyl),
  (g) -alkyl-OH (and in one example —$(CH_2)_3OH$),
  (h) -alkyl-O-alkyl-OH (and in one example —$CH_2$—O—$CH_2CH_2$—OH),
(4) $R^6$ is H;
(5) $R^7$ is selected from the group consisting of; H, and phenyl substituted with 1 to 3 substituents selected from the group consisting of: halo (e.g., F), —$SF_5$ and —$OSF_5$; and
(6) V is a bond; and
(7) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z18 wherein:
(1) the $R^9$—$R^{10}$— group is selected from the group consisting of 1b to 53b;
(2) $R^2$ is selected from the group consisting of H, alkyl (e.g., methyl, ethyl and propyl, and in one example propyl), and alkyl (e.g., methyl, ethyl and propyl) substituted with 1 —OH group (and in one example the substituted alkyl is —$CH_2CH_2CH_2$—OH);
(3) one of $R^3$ or $R^4$ is H, and the remaining $R^3$ or $R^4$ is selected from the group comprising:
  (a) phenyl,
  (b) phenyl substituted with 1 to 3 independently selected $R^{21}$ groups (and (i) in one example said phenyl is substituted with 1 to 3 halos, (ii) in another example said phenyl is substituted with 1 to 3 F, (iii) in another example said phenyl is substituted with 3 F, (iv) in another example said phenyl is substituted with 2 F, and (v) in another example said phenyl is substituted with 1 F),
  (c) thienyl,
  (d) thienyl substituted with 1 to 3 independently selected $R^{21}$ groups (and (i) in one example said thienyl is substituted with 1 to 3 halos, (ii) in another example said thienyl is substituted with 1 to 3 F, and (iii) in another example said thienyl is substituted with 1 F),
  (d) cyclopropyl, (e) cyclopropyl substituted with 1 to 3 independently $R^{21}$ substituents (and (i) in one example said cyclopropyl is substituted with 1 to 3 halos, and (ii) in another example said cyclopropyl is substituted with 1 to 3 F), (f) alkyl (e.g., methyl or ethyl, and (i) in one example methyl, and (ii) in another example ethyl), (g) -alkyl-OH (and in one example —$(CH_2)_3OH$), (h) -alkyl-O-alkyl-OH (and in one example —$CH_2$—O—$CH_2CH_2$—OH), (4) $R^6$ is H;

(5) $R^7$ is selected from the group consisting of: H, and phenyl substituted with 1 to 3 substituents selected from the group consisting of: halo (e.g., F), —$SF_5$ and —$OSF_5$; and (6) V is a bond; and (7) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z18 wherein:

(1) the $R^9$—$R^{10}$— group is 50b;

(2) $R^2$ is selected from the group consisting of (a) H, (b) alkyl, and (c) alkyl substituted with 1 to 5 $R^{21}$ groups;

(3) one of $R^3$ or $R^4$ is H, and the remaining $R^3$ or $R^4$ is selected from the group comprising:

(a) aryl (e.g., phenyl), (b) aryl (e.g., phenyl) substituted with 1 to 3 independently selected $R^{21}$ groups (and (i) in one example said aryl is substituted with 1 to 3 halos, (ii) in another example said aryl is substituted with 1 to 3 F, (iii) in another example said aryl is substituted with 3 F, (iv) in another example said aryl is substituted with 2 F, and (v) in another example said aryl is substituted with 1 F), (c) heteroaryl (e.g., thienyl), (d) heteroaryl (e.g., thienyl) substituted with 1 to 3 independently selected $R^{21}$ groups (and (i) in one example said heteroaryl is substituted with 1 to 3 halos, (ii) in another example said heteroaryl is substituted with 1 to 3 F, and (iii) in another example said heteroaryl is substituted with 1 F), (d) cycloalkyl (e.g., cyclopropyl), (e) cycloalkyl (e.g., cyclopropyl) substituted with 1 to 3 independently $R^{21}$ substituents (and (i) in one example said cycloalkyl is substituted with 1 to 3 halos, and (ii) in another example said cycloalkyl is substituted with 1 to 3 F), (f) alkyl (e.g., methyl or ethyl), (g) alkyl substituted with 1 to 3 independently selected $R^{21}$ groups (and (i) in one example said alkyl is substituted with one —$OR^{15}$ group, (ii) in another example said alkyl is substituted with one —$OR^{15}$ group wherein $R^{15}$ is H, (iii) in another example said alkyl is substituted with one —$OR^{15}$ group wherein $R^{15}$ is $(R^{18})_r$-alkyl-, (iv) in another example said alkyl is substituted with one —$OR^{15}$ group wherein $R^{15}$ is $(R^{18})_r$-alkyl- and $R^{18}$ is —OH and r is 1, and (v) in another example said alkyl is substituted with one —$OR^{15}$ wherein $R^{15}$ is HO—$CH_2$—, or HO—$(CH_2)_2$—); and (4) $R^6$ is H;

(5) $R^7$ is selected from the group consisting of: H, and phenyl substituted with 1 to 3 substituents selected from the group consisting of: halo (e.g., F), —$SF_5$ and —$OSF_5$; and (6) V is a bond; and (7) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z18 wherein:

(1) the $R^9$—$R^{10}$— group is 50b;

(2) $R^2$ is selected from the group consisting of (a) H, (b) alkyl, and (c) alkyl substituted with 1 to 5 $R^{21}$ groups;

(3) one of $R^3$ or $R^4$ is H, and the remaining $R^3$ or $R^4$ is selected from the group comprising:

(a) phenyl, (b) phenyl substituted with 1 to 3 independently selected $R^{21}$ groups (and (i) in one example said phenyl is substituted with 1 to 3 halos, (ii) in another example said phenyl is substituted with 1 to 3 F, (iii) in another example said phenyl is substituted with 3 F, (iv) in another example said phenyl is substituted with 2 F, and (v) in another example said phenyl is substituted with 1 F), (c) thienyl, (d) thienyl substituted with 1 to 3 independently selected $R^{21}$ groups (and (i) in one example said thienyl is substituted with 1 to 3 halos, (ii) in another example said thienyl is substituted with 1 to 3 F, and (iii) in another example said thienyl is substituted with 1 F), (d) cyclopropyl, (e) cyclopropyl substituted with 1 to 3 independently $R^{21}$ substituents (and (i) in one example said cyclopropyl is substituted with 1 to 3 halos, and (ii) in another example said cyclopropyl is substituted with 1 to 3 F), (f) alkyl (e.g., methyl or ethyl, and (i) in one example methyl, and (ii) in another example ethyl), (g) -alkyl-OH (and in one example —$(CH_2)_3OH$), (h) -alkyl-O-alkyl-OH (and in one example —$CH_2$—O—$CH_2CH_2$—OH), (4) $R^6$ is H;

(5) $R^7$ is selected from the group consisting of: H, and phenyl substituted with 1 to 3 substituents selected from the group consisting of: halo (e.g., F), —$SF_5$ and —$OSF_5$; and (6) V is a bond; and (7) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z18 wherein:

(1) the $R^9$—$R^{10}$— group is 50b;

(2) $R^2$ is selected from the group consisting of H, alkyl (e.g., methyl, ethyl and propyl, and in one example propyl), and alkyl (e.g., methyl, ethyl and propyl) substituted with 1 —OH group (and in one example the substituted alkyl is —$CH_2CH_2CH_2$—OH);

(3) one of $R^3$ or $R^4$ is H, and the remaining $R^3$ or $R^4$ is selected from the group comprising:

(a) phenyl, (b) phenyl substituted with 1 to 3 independently selected $R^{21}$ groups (and (i) in one example said phenyl is substituted with 1 to 3 halos, (ii) in another example said phenyl is substituted with 1 to 3 F, (iii) in another example said phenyl is substituted with 3 F, (iv) in another example said phenyl is substituted with 2 F, and (v) in another example said phenyl is substituted with 1 F), (c) thienyl, (d) thienyl substituted with 1 to 3 independently selected $R^{21}$ groups (and (i) in one example said thienyl is substituted with 1 to 3 halos, (ii) in another example said thienyl is substituted with 1 to 3 F, and (iii) in another example said thienyl is substituted with 1 F), (d) cyclopropyl, (e) cyclopropyl substituted with 1 to 3 independently $R^{21}$ substituents (and (i) in one example said cyclopropyl is substituted with 1 to 3 halos, and (ii) in another example said cyclopropyl is substituted with 1 to 3 F), (f) alkyl (e.g., methyl or ethyl, and (i) in one example methyl, and (ii) in another example ethyl), (g) -alkyl-OH (and in one example —$(CH_2)_3$OH), (h) -alkyl-O-alkyl-OH (and in one example —$CH_2$—O—$CH_2CH_2$—OH), (4) $R^6$ is H;

(5) $R^7$ is selected from the group consisting of: H, and phenyl substituted with 1 to 3 substituents selected from the group consisting of: halo (e.g., F), —$SF_5$ and —$OSF_5$; and (6) V is a bond; and (7) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z19 wherein $R^9$ is selected from the group consisting of 1 g to 52 g, $R^{10}$ is selected from the group consisting of 1A to 55A, and V, $R^1$, $R^2$, $R^3$ or $R^4$, $R^7$ and $R^8$ are as defined for formula I.

Another embodiment of this invention is directed to a compound of formula I having the formula Z19 wherein $R^9$ is selected from the group consisting of 1 g to 13 g, $R^{10}$ is selected from the group consisting of 1A to 55A, and V, $R^1$, $R^2$, $R^3$ or $R^4$, $R^7$ and $R^8$ are as defined for formula I.

Another embodiment of this invention is directed to a compound of formula I having the formula Z19 wherein the $R^9$—$R^{10}$— group is selected from the group consisting of 1b to 53b, and V, $R^1$, $R^2$, $R^3$ or $R^4$, $R^7$ and $R^8$ are as defined for formula I.

Another embodiment of this invention is directed to a compound of formula I having the formula Z19 wherein the $R^9$—$R^{10}$— group is 50b, and V, $R^1$, $R^2$, $R^3$ or $R^4$, $R^7$ and $R^8$ are as defined for formula I.

Another embodiment of this invention is directed to a compound of formula I having the formula Z19 wherein:

(1) the $R^9$—$R^{10}$— group is selected from the group consisting of 1b to 53b;

(2) $R^2$ is selected from the group consisting of (a) H, (b) alkyl, and (c) alkyl substituted with 1 to 5 $R^{21}$ groups, and in one example $R^2$ is alkyl (e.g., methyl), and in another example $R^2$ is H;

(3) $R^3$ (or $R^4$) is H, (4) $R^7$ is phenyl substituted with 1 to 3 substituents selected from the group consisting of: halo (e.g., F), —$SF_5$ and —$OSF_5$;

(5) $R^8$ is as defined for formula I;

(6) $R^1$ is as defined for formula I;

(7) V is a bond; and (8) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z19 wherein:

(1) the $R^9$—$R^{10}$— group is 50b;

(2) $R^2$ is selected from the group consisting of (a) H, (b) alkyl, and (c) alkyl substituted with 1 to 5 $R^{21}$ groups, and in one example $R^2$ is alkyl (e.g., methyl), and in another example $R^2$ is H;

(3) $R^3$ (or $R^4$) is H, (4) $R^7$ is phenyl substituted with 1 to 3 substituents selected from the group consisting of: halo (e.g., F), —$SF_5$ and —$OSF_5$;

(5) $R^8$ is as defined for formula I;

(6) $R^1$ is as defined for formula I;

(7) V is a bond; and (8) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z20 wherein $R^9$ is selected from the group consisting of 1 g to 52 g, $R^{10}$ is selected from the group consisting of 1A to 55A, and V, $R^2$, $R^3$ or $R^4$, and $R^7$ are as defined for formula I.

Another embodiment of this invention is directed to a compound of formula I having the formula Z20 wherein $R^9$ is selected from the group consisting of 1 g to 13 g, $R^{10}$ is selected from the group consisting of 1A to 55A, and V, $R^2$, $R^3$ or $R^4$, and $R^7$ are as defined for formula I.

Another embodiment of this invention is directed to a compound of formula I having the formula Z20 wherein the $R^9$—$R^{10}$— group is selected from the group consisting of 1b to 53b, and V, $R^2$, $R^3$ or $R^4$, and $R^7$ are as defined for formula I.

Another embodiment of this invention is directed to a compound of formula I having the formula Z20 wherein the $R^9$—$R^{10}$— group is 50b, and V, $R^2$, $R^3$ or $R^4$, and $R^7$ are as defined for formula I.

Another embodiment of this invention is directed to a compound of formula I having the formula Z20 wherein:

(1) the $R^9$—$R^{10}$— group is selected from the group consisting of 1b to 53b;

(2) $R^2$ is selected from the group consisting of (a) H, (b) alkyl, and (c) alkyl substituted with 1 to 5 $R^{21}$ groups, and in one example $R^2$ is alkyl (e.g., methyl), and in another example $R^2$ is H;

(3) $R^3$ (or $R^4$) is H, (4) $R^7$ is phenyl substituted with 1 to 3 substituents selected from the group consisting of: halo (e.g., F), —$SF_5$ and —$OSF_5$;

(5) V is a bond; and (6) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z20 wherein:
(1) the $R^9$—$R^{10}$— group is 50b;
(2) $R^2$ is selected from the group consisting of (a) H, (b) alkyl, and (c) alkyl substituted with 1 to 5 $R^{21}$ groups, and in one example $R^2$ is alkyl (e.g., methyl), and in another example $R^2$ is H;
(3) $R^3$ (or $R^4$) is H,
(4) $R^7$ is phenyl substituted with 1 to 3 substituents selected from the group consisting of: halo (e.g., F), —$SF_5$ and —$OSF_5$;
(5) V is a bond; and
(6) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z21 wherein $R^9$ is selected from the group consisting of 1 g to 52 g, $R^{10}$ is selected from the group consisting of 1A to 55A, and V, $R^1$, $R^2$, $R^3$ or $R^4$, $R^7$ and $R^8$ are as defined for formula I.

Another embodiment of this invention is directed to a compound of formula I having the formula Z21 wherein $R^9$ is selected from the group consisting of 1 g to 13 g, $R^{10}$ is selected from the group consisting of 1A to 55A, and V, $R^1$, $R^2$, $R^3$ or $R^4$, $R^7$ and $R^8$ are as defined for formula I.

Another embodiment of this invention is directed to a compound of formula I having the formula Z21 wherein the $R^9$—$R^{10}$— group is selected from the group consisting of 1b to 53b, and V, $R^1$, $R^2$, $R^3$ or $R^4$, $R^7$ and $R^8$ are as defined for formula I.

Another embodiment of this invention is directed to a compound of formula I having the formula Z21 wherein the $R^9$—$R^{10}$— group is 50b, and V, $R^1$, $R^2$, $R^3$ or $R^4$, $R^7$ and $R^8$ are as defined for formula I.

Another embodiment of this invention is directed to a compound of formula I having the formula Z21 wherein:
(1) the $R^9$-$R^{10}$— group is selected from the group consisting of 1b to 53b;
(2) $R^2$ is selected from the group consisting of (a) H, (b) alkyl, and (c) alkyl substituted with 1 to 5 $R^{21}$ groups, and in one example $R^2$ is alkyl (e.g., methyl), and in another example $R^2$ is H;
(3) $R^3$ (or $R^4$) is H,
(4) $R^7$ is phenyl substituted with 1 to 3 substituents selected from the group consisting of: halo (e.g., F), —$SF_5$ and —$OSF_5$;
(5) $R^8$ is as defined for formula I;
(6) $R^1$ is as defined for formula I;
(7) V is a bond; and
(8) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z21 wherein:
(1) the $R^9$—$R^{10}$— group is 50b;
(2) $R^2$ is selected from the group consisting of (a) H, (b) alkyl, and (c) alkyl substituted with 1 to 5 $R^{21}$ groups, and in one example $R^2$ is alkyl (e.g., methyl), and in another example $R^2$ is H;
(3) $R^3$ (or $R^4$) is H,
(4) $R^7$ is phenyl substituted with 1 to 3 substituents selected from the group consisting of: halo (e.g., F), —$SF_5$ and —$OSF_5$;
(5) $R^8$ is as defined for formula I;
(6) $R^1$ is as defined for formula I;
(7) V is a bond; and
(8) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z22 wherein $R^9$ is selected from the group consisting of 1 g to 52 g, $R^{10}$ is selected from the group consisting of 1A to 55A, and V, $R^2$, $R^3$ or $R^4$, and $R^7$ are as defined for formula I.

Another embodiment of this invention is directed to a compound of formula I having the formula Z22 wherein $R^9$ is selected from the group consisting of 1 g to 13 g, $R^{10}$ is selected from the group consisting of 1A to 55A, and V, $R^2$, $R^3$ or $R^4$, and $R^7$ are as defined for formula I.

Another embodiment of this invention is directed to a compound of formula I having the formula Z22 wherein the $R^9$—$R^{10}$— group is selected from the group consisting of 1b to 53b, and V, $R^2$, $R^3$ or $R^4$, and $R^7$ are as defined for formula I.

Another embodiment of this invention is directed to a compound of formula I having the formula Z22 wherein the $R^9$—$R^{10}$— group is 50b, and V, $R^2$, $R^3$ or $R^4$, and $R^7$ are as defined for formula I.

Another embodiment of this invention is directed to a compound of formula I having the formula Z22 wherein:
(1) the $R^9$—$R^{10}$— group is selected from the group consisting of 1b to 53b;
(2) $R^2$ is selected from the group consisting of (a) H, (b) alkyl, and (c) alkyl substituted with 1 to 5 $R^{21}$ groups, and in one example $R^2$ is alkyl (e.g., methyl), and in another example $R^2$ is H;
(3) $R^3$ (or $R^4$) is H,
(4) $R^7$ is phenyl substituted with 1 to 3 substituents selected from the group consisting of: halo (e.g., F), —$SF_5$ and —$OSF_5$;
(5) V is a bond; and
(6) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

Another embodiment of this invention is directed to a compound of formula I having the formula Z22 wherein:

(1) the $R^9$—$R^{10}$— group is 50b;
(2) $R^2$ is selected from the group consisting of (a) H, (b) alkyl, and (c) alkyl substituted with 1 to 5 $R^{21}$ groups, and in one example $R^2$ is alkyl (e.g., methyl), and in another example $R^2$ is H;
(3) $R^3$ (or $R^4$) is H,
(4) $R^7$ is phenyl substituted with 1 to 3 substituents selected from the group consisting of: halo (e.g., F), —SF$_5$ and —OSF$_5$;
(5) V is a bond; and
(6) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —SF$_5$ group, and (vii) in another example $R^7$ is phenyl substituted with one —OSF$_5$ group.

Another embodiment of this invention is directed to a compound of formula I having the formula Z23 wherein $R^9$ is selected from the group consisting of 1 g to 52 g, $R^{10}$ is selected from the group consisting of 1A to 55A, and V, $R^1$, $R^2$, $R^3$ or $R^4$, $R^7$ and $R^8$ are as defined for formula I.

Another embodiment of this invention is directed to a compound of formula I having the formula Z23 wherein $R^9$ is selected from the group consisting of 1 g to 13 g, $R^{10}$ is selected from the group consisting of 1A to 55A, and V, $R^1$, $R^2$, $R^3$ or $R^4$, $R^7$ and $R^8$ are as defined for formula I.

Another embodiment of this invention is directed to a compound of formula I having the formula Z23 wherein the $R^9$—$R^{10}$— group is selected from the group consisting of 1b to 53b, and V, $R^1$, $R^2$, $R^3$ or $R^4$, $R^7$ and $R^8$ are as defined for formula I.

Another embodiment of this invention is directed to a compound of formula I having the formula Z23 wherein the $R^9$—$R^{10}$— group is 50b, and V, $R^1$, $R^2$, $R^3$ or $R^4$, $R^7$ and $R^8$ are as defined for formula I.

Another embodiment of this invention is directed to a compound of formula I having the formula Z23 wherein:
(1) the $R^9$—$R^{10}$— group is selected from the group consisting of 1b to 53b;
(2) $R^2$ is selected from the group consisting of (a) H, (b) alkyl, and (c) alkyl substituted with 1 to 5 $R^{21}$ groups, and in one example $R^2$ is alkyl (e.g., methyl), and in another example $R^2$ is H;
(3) $R^3$ (or $R^4$) is H,
(4) $R^7$ is phenyl substituted with 1 to 3 substituents selected from the group consisting of: halo (e.g., F), —SF$_5$ and —OSF$_5$;
(5) $R^8$ is as defined for formula I;
(6) $R^1$ is as defined for formula I;
(7) V is a bond; and
(8) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —SF$_5$ group, and (vii) in another example $R^7$ is phenyl substituted with one —OSF$_5$ group.

Another embodiment of this invention is directed to a compound of formula I having the formula Z23 wherein:
(1) the $R^9$—$R^{10}$— group is 50b;
(2) $R^2$ is selected from the group consisting of (a) H, (b) alkyl, and (c) alkyl substituted with 1 to 5 $R^{21}$ groups, and in one example $R^2$ is alkyl (e.g., methyl), and in another example $R^2$ is H;
(3) $R^3$ (or $R^4$) is H,
(4) $R^7$ is phenyl substituted with 1 to 3 substituents selected from the group consisting of: halo (e.g., F), —SF$_5$ and —OSF$_5$;
(5) $R^8$ is as defined for formula I;
(6) $R^1$ is as defined for formula I;
(7) V is a bond; and
(8) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —SF$_5$ group, and (vii) in another example $R^7$ is phenyl substituted with one —OSF$_5$ group.

Another embodiment of this invention is directed to a compound of formula I having the formula Z24 wherein $R^9$ is selected from the group consisting of 1 g to 52 g, $R^{10}$ is selected from the group consisting of 1A to 55A, and V, $R^2$, $R^3$ or $R^4$, and $R^7$ are as defined for formula I.

Another embodiment of this invention is directed to a compound of formula I having the formula Z24 wherein $R^9$ is selected from the group consisting of 1 g to 13 g, $R^{10}$ is selected from the group consisting of 1A to 55A, and V, $R^2$, $R^3$ or $R^4$, and $R^7$ are as defined for formula I.

Another embodiment of this invention is directed to a compound of formula I having the formula Z24 wherein the $R^9$—$R^{10}$— group is selected from the group consisting of 1b to 53b, and V, $R^2$, $R^3$ or $R^4$, and $R^7$ are as defined for formula I.

Another embodiment of this invention is directed to a compound of formula I having the formula Z24 wherein the $R^9$—$R^{10}$— group is 50b, and V, $R^2$, $R^3$ or $R^4$, and $R^7$ are as defined for formula I.

Another embodiment of this invention is directed to a compound of formula I having the formula Z24 wherein:
(1) the $R^9$—$R^{10}$— group is selected from the group consisting of 1b to 53b;
(2) $R^2$ is selected from the group consisting of (a) H, (b) alkyl, and (c) alkyl substituted with 1 to 5 $R^{21}$ groups, and in one example $R^2$ is alkyl (e.g., methyl), and in another example $R^2$ is H;
(3) $R^3$ (or $R^4$) is H,
(4) $R^7$ is phenyl substituted with 1 to 3 substituents selected from the group consisting of: halo (e.g., F), —SF$_5$ and —OSF$_5$;
(5) V is a bond; and
(6) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —SF$_5$ group, and (vii) in another example $R^7$ is phenyl substituted with one —OSF$_5$ group.

Another embodiment of this invention is directed to a compound of formula I having the formula Z24 wherein:
(1) the $R^9$—$R^{10}$— group is 50b;
(2) $R^2$ is selected from the group consisting of (a) H, (b) alkyl, and (c) alkyl substituted with 1 to 5 $R^{21}$ groups, and in one example $R^2$ is alkyl (e.g., methyl), and in another example $R^2$ is H;
(3) $R^3$ (or $R^4$) is H,
(4) $R^7$ is phenyl substituted with 1 to 3 substituents selected from the group consisting of: halo (e.g., F), —SF$_5$ and —OSF$_5$;

(5) V is a bond; and (6) (i) in one example $R^7$ is phenyl substituted with 1 to 3 halos, (ii) in another example $R^7$ is phenyl substituted with 1 to 3 F, (iii) in another example $R^7$ is phenyl substituted with 3 F, (iv) in another example $R^7$ is phenyl substituted with 2 F, (v) in another example $R^7$ is phenyl substituted with one F, (vi) in another example $R^7$ is phenyl substituted with one —$SF_5$ group, and (vii) in another example $R^7$ is phenyl substituted with one —$OSF_5$ group.

In the embodiments below Groups A, B, C and D are as defined as follows:

(1) Group A: compounds Z1 to Z24;
(2) Group B: compounds 1 to 117, the final compound of Method T and the final compound of Method U;
(3) Group C: compounds 1 to 68; and
(4) Group D: compounds 69 to 117.

Another embodiment of this invention is directed to compounds of formula I.

Another embodiment of this invention is directed to a compound of formula I selected from the group consisting of Group A.

Another embodiment of this invention is directed to a pharmaceutically acceptable salt of a compound of formula I. And in one example the salt is a salt of a compound selected from the group consisting of Group A. And in another example the salt is a salt of a compound selected from the group consisting of Group B. And in another example the salt is a salt of a compound selected from the group consisting of Group C. And in another example the salt is a salt of a compound selected from the group consisting of Group D.

Another embodiment of this invention is directed to a pharmaceutically acceptable ester of a compound of formula I. And in one example the ester is an ester of a compound selected from the group consisting of Group A. And in another example the ester is an ester of a compound selected from the group consisting of Group B. And in another example the ester is an ester of a compound selected from the group consisting of Group C. And in another example the ester is an ester of a compound selected from the group consisting of Group D.

Another embodiment of this invention is directed to a solvate of a compound of formula I. And in one example the solvate is a solvate of a compound selected from the group consisting of Group A. And in another example the solvate is a solvate of a compound selected from the group consisting of Group B. And in another example the solvate is a solvate of a compound selected from the group consisting of Group C. And in another example the solvate is a solvate of a compound selected from the group consisting of Group D.

Another embodiment of this invention is directed to a compound of formula I in pure and isolated form. And in one example the compound of formula I is selected from the group consisting of Group C. And in one example the compound of formula I is selected from the group consisting of Group D.

Another embodiment of this invention is directed to a compound of formula I in pure form. And in one example the compound of formula I is selected from the group consisting of Group C. And in one example the compound of formula I is selected from the group consisting of Group D.

Another embodiment of this invention is directed to a compound of formula I in isolated form. And in one example the compound of formula I is selected from the group consisting of Group C. And in one example the compound of formula I is selected from the group consisting of Group D.

Another embodiment of this invention is directed to a compound of formula I selected from the group consisting of Group B.

Another embodiment of this invention is directed to a compound of formula I selected from the group consisting of Group C.

Another embodiment of this invention is directed to a compound of formula I selected from the group consisting of Group D Another embodiment of this invention is directed to a pharmaceutical composition comprising a therapeutically effective amount of at least one compound of Formula I, or a pharmaceutically acceptable salt, solvate, or ester thereof, and at least one pharmaceutically acceptable carrier.

Another embodiment of this invention is directed to a pharmaceutical composition comprising an effective amount of one or more (e.g., one) compounds of formula I and a pharmaceutically acceptable carrier.

Another embodiment of this invention is directed to a pharmaceutical composition comprising an effective amount of a pharmaceutically acceptable salt of one or more (e.g., one) compounds of formula I and a pharmaceutically acceptable carrier.

Another embodiment of this invention is directed to a pharmaceutical composition comprising an effective amount of a pharmaceutically acceptable ester of one or more (e.g., one) compounds of formula I and a pharmaceutically acceptable carrier.

Another embodiment of this invention is directed to a pharmaceutical composition comprising an effective amount of a solvate of one or more (e.g., one) compounds of formula I and a pharmaceutically acceptable carrier.

Another embodiment of this invention is directed to a pharmaceutical composition comprising an effective amount of one or more (e.g., one) compounds of formula I, and an effective amount of one or more (e.g., one) other pharmaceutically active ingredients (e.g., drugs), and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising a therapeutically effective amount of at least one compound of Formula I, or a pharmaceutically acceptable salt, solvate, or ester thereof, and at least one pharmaceutically acceptable carrier, and a therapeutically effective amount of one or more compounds selected from the group consisting of cholinesterase inhibitors, Aβ antibody inhibitors, gamma secretase inhibitors and beta secretase inhibitors.

Another embodiment of this invention is directed to a pharmaceutical composition comprising an effective amount of one or more (e.g., one) compounds of formula I, and effective amount of one or more BACE inhibitors, and a pharmaceutically acceptable carrier.

Another embodiment of this invention is directed to a pharmaceutical composition comprising an effective amount of one or more (e.g., one) compounds of formula I, and effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds of formula I, and effective amount of one or more muscarinic antagonists (e.g., m₁ or m₂ antagonists), and a pharmaceutically acceptable carrier.

Another embodiment of this invention is directed to a pharmaceutical composition comprising an effective amount of one or more (e.g., one) compounds of formula I, and effective amount of Exelon (rivastigmine), and a pharmaceutically acceptable carrier.

Another embodiment of this invention is directed to a pharmaceutical composition comprising an effective amount of one or more (e.g., one) compounds of formula I, and effective amount of Cognex (tacrine), and a pharmaceutically acceptable carrier.

Another embodiment of this invention is directed to a pharmaceutical composition comprising an effective amount of one or more (e.g., one) compounds of formula I, and effective amount of a Tau kinase inhibitor, and a pharmaceutically acceptable carrier.

Another embodiment of this invention is directed to a pharmaceutical composition comprising an effective amount of one or more (e.g., one) compounds of formula I, and effective amount of one or more Tau kinase inhibitor (e.g., GSK3 beta inhibitor, cdk5 inhibitor, ERK inhibitor), and a pharmaceutically acceptable carrier.

Another embodiment of this invention is directed to a pharmaceutical composition comprising an effective amount of one or more (e.g., one) compounds of formula I, and effective amount of one anti-Abeta vaccine (active immunization), and a pharmaceutically acceptable carrier.

Another embodiment of this invention is directed to a pharmaceutical composition comprising an effective amount of one or more (e.g., one) compounds of formula I, and effective amount of one or more APP ligands, and a pharmaceutically acceptable carrier.

Another embodiment of this invention is directed to a pharmaceutical composition comprising an effective amount of one or more (e.g., one) compounds of formula I, and effective amount of one or more agents that upregulate insulin degrading enzyme and/or neprilysin, and a pharmaceutically acceptable carrier.

Another embodiment of this invention is directed to a pharmaceutical composition comprising an effective amount of one or more (e.g., one) compounds of formula I, and effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe), and a pharmaceutically acceptable carrier.

Another embodiment of this invention is directed to a pharmaceutical composition comprising an effective amount of one or more (e.g., one) compounds of formula I, and effective amount of one or more fibrates (for example, clofibrate, Clofibride, Etofibrate, Aluminium Clofibrate), and a pharmaceutically acceptable carrier Another embodiment of this invention is directed to a pharmaceutical composition comprising an effective amount of one or more (e.g., one) compounds of formula I, and effective amount of one or more LXR agonists, and a pharmaceutically acceptable carrier.

Another embodiment of this invention is directed to a pharmaceutical composition comprising an effective amount of one or more (e.g., one) compounds of formula I, and effective amount of one or more LRP mimics, and a pharmaceutically acceptable carrier.

Another embodiment of this invention is directed to a pharmaceutical composition comprising an effective amount of one or more (e.g., one) compounds of formula I, and effective amount of one or more 5-HT6 receptor antagonists, and a pharmaceutically acceptable carrier.

Another embodiment of this invention is directed to a pharmaceutical composition comprising an effective amount of one or more (e.g., one) compounds of formula I, and effective amount of one or more nicotinic receptor agonists, and a pharmaceutically acceptable carrier.

Another embodiment of this invention is directed to a pharmaceutical composition comprising an effective amount of one or more (e.g., one) compounds of formula I, and effective amount of one or more H3 receptor antagonists, and a pharmaceutically acceptable carrier.

Another embodiment of this invention is directed to a pharmaceutical composition comprising an effective amount of one or more (e.g., one) compounds of formula I, and effective amount of one or more histone deacetylase inhibitors, and a pharmaceutically acceptable carrier.

Another embodiment of this invention is directed to a pharmaceutical composition comprising an effective amount of one or more (e.g., one) compounds of formula I, and effective amount of one or more hsp90 inhibitors, and a pharmaceutically acceptable carrier.

Another embodiment of this invention is directed to a pharmaceutical composition comprising an effective amount of one or more (e.g., one) compounds of formula I, and effective amount of one or more m1 muscarinic receptor agonists, and a pharmaceutically acceptable carrier.

Another embodiment of this invention is directed to combinations, i.e., a pharmaceutical composition, comprising a pharmaceutically acceptable carrier, an effective (i.e., therapeutically effective) amount of one or more compounds of formula I, in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors.

Another embodiment of this invention is directed to a pharmaceutical composition comprising an effective amount of one or more (e.g., one) compounds of formula I, and effective amount of one or more 5-HT6 receptor antagonists mGluR1 or mGluR5 positive allosteric modulators or agonists, and a pharmaceutically acceptable carrier.

Another embodiment of this invention is directed to a pharmaceutical composition comprising an effective amount of one or more (e.g., one) compounds of formula I, and effective amount of one or more one mGluR2/3 antagonists, and a pharmaceutically acceptable carrier.

Another embodiment of this invention is directed to a pharmaceutical composition comprising an effective amount of one or more (e.g., one) compounds of formula I, and effective amount of one or more anti-inflammatory agents that can reduce neuroinflammation, and a pharmaceutically acceptable carrier.

Another embodiment of this invention is directed to a pharmaceutical composition comprising an effective amount of one or more (e.g., one) compounds of formula I, and effective amount of one or more Prostaglandin EP2 receptor antagonists, and a pharmaceutically acceptable carrier.

Another embodiment of this invention is directed to a pharmaceutical composition comprising an effective amount of one or more (e.g., one) compounds of formula I, and effective amount of one or more PAI-1 inhibitors, and a pharmaceutically acceptable carrier.

Another embodiment of this invention is directed to a pharmaceutical composition comprising an effective amount of one or more (e.g., one) compounds of formula I, and effective amount of one or more agents that can induce Abeta efflux such as gelsolin, and a pharmaceutically acceptable carrier.

Other embodiments of this invention are directed to any one of the above embodiments directed to pharmaceutical compositions wherein the compound of formula I is selected from the group consisting of Group A.

Other embodiments of this invention are directed to any one of the above embodiments directed to pharmaceutical compositions wherein the compound of formula I is selected from the group consisting of Group B.

Other embodiments of this invention are directed to any one of the above embodiments directed to pharmaceutical compositions wherein the compound of formula I is selected from the group consisting of Group C.

Other embodiments of this invention are directed to any one of the above embodiments directed to pharmaceutical compositions wherein the compound of formula I is selected from the group consisting of Group D.

The compounds of formula I can be useful as gamma secretase modulators and can be useful in the treatment and prevention of diseases such as, for example, central nervous system disorders (such as Alzheimers disease and Downs Syndrome), mild cognitive impairment, glaucoma, cerebral amyloid angiopathy, stroke, dementia, microgliosis, brain inflammation, and olfactory function loss.

Another embodiment of this invention is directed to a method of treating a central nervous system disorder comprising administering a therapeutically effective amount of at least one compound of Formula I to a patient in need of such treatment.

Another embodiment of this invention is directed to a method of treating a central nervous system disorder comprising administering a therapeutically effective amount of a pharmaceutical composition comprising a therapeutically effective amount of at least one compound of Formula I, or a pharmaceutically acceptable salt, solvate, or ester thereof, and at least one pharmaceutically acceptable carrier.

Another embodiment of this invention is directed to a method of treating a central nervous system disorder comprising administering a therapeutically effective amount of a pharmaceutical composition comprising a therapeutically effective amount of at least one compound of Formula I, or a pharmaceutically acceptable salt, solvate, or ester thereof, and at least one pharmaceutically acceptable carrier, and a therapeutically effective amount of one or more compounds selected from the group consisting of cholinesterase inhibitors, Aβ antibody inhibitors, gamma secretase inhibitors and beta secretase inhibitors.

Another embodiment of this invention is directed to a method for modulating (including inhibiting, antagonizing and the like) gamma-secretase comprising administering an effective amount of one or more (e.g., one) compounds of formula I to a patient in need of such treatment.

Another embodiment of this invention is directed to a method for modulating (including inhibiting, antagonizing and the like) gamma-secretase, comprising administering an effective amount of a compound of formula I to a patient in need of treatment.

Another embodiment of this invention is directed to a method of treating one or more neurodegenerative diseases, comprising administering an effective amount of one or more (e.g., one) compounds of formula I to a patient in need of treatment.

Another embodiment of this invention is directed to a method of treating one or more neurodegenerative diseases, comprising administering an effective amount of a compound of formula I to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of one or more (e.g., one) compounds of formula I to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of a compound of formula I to a patient in need of treatment.

Another embodiment of this invention is directed to a method of treating Alzheimer's disease, comprising administering an effective amount of one or more (e.g., one) compounds of formula I to a patient in need of treatment.

Another embodiment of this invention is directed to a method of treating Alzheimer's disease, comprising administering an effective amount of a compound of formula I to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of one or more (e.g., one) compounds of formula I to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of a compound of formula I to a patient in need of treatment.

Another embodiment of this invention is directed to a method of treating mild cognitive impairment, comprising administering an effective amount of one or more (e.g., one) compounds of formula I to a patient in need of treatment.

Another embodiment of this invention is directed to a method of treating glaucoma, comprising administering an effective amount of one or more (e.g., one) compounds of formula I to a patient in need of treatment.

Another embodiment of this invention is directed to a method of treating cerebral amyloid angiopathy, comprising administering an effective amount of one or more (e.g., one) compounds of formula I to a patient in need of treatment.

Another embodiment of this invention is directed to a method of treating stroke, comprising administering an effective amount of one or more (e.g., one) compounds of formula I to a patient in need of treatment.

Another embodiment of this invention is directed to a method of treating dementia, comprising administering an effective amount of one or more (e.g., one) compounds of formula I to a patient in need of treatment.

Another embodiment of this invention is directed to a method of treating microgliosis, comprising administering an effective amount of one or more (e.g., one) compounds of formula I to a patient in need of treatment.

Another embodiment of this invention is directed to a method of treating brain inflammation, comprising administering an effective amount of one or more (e.g., one) compounds of formula I to a patient in need of treatment.

Another embodiment of this invention is directed to a method of treating olfactory function loss, comprising administering an effective amount of one or more (e.g., one) compounds of formula I to a patient in need of treatment.

Another embodiment of this invention is directed to a method of treating Downs syndrome, comprising administering an effective amount of one or more (e.g., one) compounds of formula I to a patient in need of treatment.

Another embodiment of this invention is directed to a method of treating Downs syndrome, comprising administering an effective amount of a compound of formula I to a patient in need of treatment.

Other embodiments of this invention are directed to any one of the above embodiments directed to methods of treating wherein the compound of formula I is selected from the group consisting of Group A.

Other embodiments of this invention are directed to any one of the above embodiments directed to methods of treating wherein the compound of formula I is selected from the group consisting of Group B.

Other embodiments of this invention are directed to any one of the above embodiments directed to methods of treating wherein the compound of formula I is selected from the group consisting of Group C.

Other embodiments of this invention are directed to any one of the above embodiments directed to methods of treating wherein the compound of formula I is selected from the group consisting of Group D.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula I and the administration of an effective amount of one or more (e.g., one) other pharmaceutical active ingredients (e.g., drugs). The compounds of formula I and the other drugs can be administered separately (i.e., each is in its own separate dosage form), or the compounds of formula I can be combined with the other drugs in the same dosage form.

Thus, other embodiments of this invention are directed to any one of the methods of treatment, or methods of inhibiting, described herein, wherein an effective amount of the compound of formula I is used in combination with an effective amount of one or more other pharmaceutically active ingredients (e.g., drugs). The other pharmaceutically active ingredients (i.e., drugs) are selected from the group consisting of: BACE inhibitors (beta secretase inhibitors), muscarinic antagonists (e.g., m1 agonists or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Another embodiment of this invention is directed to a method of treating Alzheimer's disease, comprising administering an effective amount of one or more (e.g., one) compounds of formula I, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of a compound of formula I, in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of one or more (e.g., one) compounds of formula I, in combination with an effective amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective amount of one or more (e.g., one) compounds of formula I, in combination with an effective amount of one or more BACE inhibitors.

Another embodiment of this invention is directed to a method of treating Alzheimer's disease, comprising administering an effective amount of one or more compounds of formula I, in combination with an effective amount of Exelon (rivastigmine).

Another embodiment of this invention is directed to a method of treating Alzheimer's disease, comprising administering an effective amount of one or more compounds of formula I, in combination with an effective amount of Cognex (tacrine).

Another embodiment of this invention is directed to a method of treating Alzheimer's disease, comprising administering an effective amount of one or more compounds of formula I, in combination with an effective amount of a Tau kinase inhibitor.

Another embodiment of this invention is directed to a method of treating Alzheimer's disease, comprising administering an effective amount of one or more compounds of formula I, in combination with an effective amount of one or more Tau kinase inhibitor (e.g., GSK3beta inhibitor, cdk5 inhibitor, ERK inhibitor).

This invention also provides a method of treating Alzheimer's disease, comprising administering an effective amount of one or more compounds of formula I, in combination with an effective amount of one anti-Abeta vaccination (active immunization).

Another embodiment of this invention is directed to a method of treating Alzheimer's disease, comprising administering an effective amount of one or more compounds of formula I, in combination with an effective amount of one or more APP ligands.

Another embodiment of this invention is directed to a method of treating Alzheimer's disease, comprising administering an effective amount of one or more compounds of formula I, in combination with an effective amount of one or more agents that upregulate insulin degrading enzyme and/or neprilysin.

Another embodiment of this invention is directed to a method of treating Alzheimer's disease, comprising administering an effective amount of one or more compounds of formula I, in combination with an effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe).

This invention also provides a method of treating Alzheimer's disease, comprising administering an effective amount of one or more compounds of formula I, in combination with an effective amount of one or more fibrates (for example, clofibrate, Clofibride, Etofibrate, Aluminium Clofibrate).

Another embodiment of this invention is directed to a method of treating Alzheimer's disease, comprising administering an effective amount of one or more compounds of formula I, in combination with an effective amount of one or more LXR agonists.

Another embodiment of this invention is directed to a method of treating Alzheimer's disease, comprising administering an effective amount of one or more compounds of formula I, in combination with an effective amount of one or more LRP mimics.

Another embodiment of this invention is directed to a method of treating Alzheimer's disease, comprising administering an effective amount of one or more compounds of formula I, in combination with an effective amount of one or more 5-HT6 receptor antagonists.

Another embodiment of this invention is directed to a method of treating Alzheimer's disease, comprising administering an effective amount of one or more compounds of formula I, in combination with an effective amount of one or more nicotinic receptor agonists.

Another embodiment of this invention is directed to a method of treating Alzheimer's disease, comprising administering an effective amount of one or more compounds of formula I, in combination with an effective amount of one or more H3 receptor antagonists.

This invention also provides a method of treating Alzheimer's disease, comprising administering an effective amount of one or more compounds of formula I, in combination with an effective amount of one or more histone deacetylase inhibitors.

Another embodiment of this invention is directed to a method of treating Alzheimer's disease, comprising administering an effective amount of one or more compounds of formula I, in combination with an effective amount of one or more hsp90 inhibitors.

Another embodiment of this invention is directed to a method of treating Alzheimer's disease, comprising administering an effective amount of one or more compounds of formula I, in combination with an effective amount of one or more m1 muscarinic receptor agonists.

Another embodiment of this invention is directed to a method of treating Alzheimer's disease, comprising administering an effective amount of one or more compounds of formula I, in combination with an effective amount of one or more 5-HT6 receptor antagonists mGluR1 or mGluR5 positive allosteric modulators or agonists.

Another embodiment of this invention is directed to a method of treating Alzheimer's disease, comprising administering an effective amount of one or more compounds of formula I, in combination with an effective amount of one or more mGiuR2/3 antagonists.

Another embodiment of this invention is directed to a method of treating Alzheimer's disease, comprising administering an effective amount of one or more compounds of formula I, in combination with an effective amount of one or more anti-inflammatory agents that can reduce neuroinflammation.

Another embodiment of this invention is directed to a method of treating Alzheimer's disease, comprising administering an effective amount of one or more compounds of formula I, in combination with an effective amount of one or more Prostaglandin EP2 receptor antagonists.

Another embodiment of this invention is directed to a method of treating Alzheimer's disease, comprising administering an effective amount of one or more compounds of formula I, in combination with an effective amount of one or more PAM-1 inhibitors.

Another embodiment of this invention is directed to a method of treating Alzheimer's disease, comprising administering an effective amount of one or more compounds of formula I, in combination with an effective amount of one or more agents that can induce Abeta efflux such as gelsolin.

Another embodiment of this invention is directed to a method of treating Downs syndrome, comprising administering an effective amount of one or more (e.g., one) compounds of formula I, in combination with an effective amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective amount of a compound of formula I, in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Other embodiments of this invention are directed to any one of the above embodiments directed to combination therapies (i.e., the above methods of treating wherein compounds of formula I are used in combination with other pharmaceutically active ingredients, i.e., drugs) wherein the compound of formula I is selected from the group consisting of Group A.

Other embodiments of this invention are directed to any one of the above embodiments directed to combination therapies (i.e., the above methods of treating wherein compounds of formula I are used in combination with other pharmaceutically active ingredients, i.e., drugs) wherein the compound of formula I is selected from the group consisting of Group B.

Other embodiments of this invention are directed to any one of the above embodiments directed to combination therapies (i.e., the above methods of treating wherein compounds of formula I are used in combination with other pharmaceutically active ingredients, i.e., drugs) wherein the compound of formula I is selected from the group consisting of Group C.

Other embodiments of this invention are directed to any one of the above embodiments directed to combination therapies (i.e., the above methods of treating wherein compounds of formula I are used in combination with other pharmaceutically active ingredients, i.e., drugs) wherein the compound of formula I is selected from the group consisting of Group D.

This invention also provides a kit comprising, in separate containers, in a single package, pharmaceutical compositions for use in combination, wherein one container comprises an effective amount of a compound of formula I in a pharmaceutically acceptable carrier, and another container (i.e., a second container) comprises an effective amount of another pharmaceutically active ingredient (as described above), the combined quantities of the compound of formula I and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase, or (e) mild cognitive impairment, or (f) glaucoma, or (g) cerebral amyloid angiopathy, or (h) stroke, or (i) dementia, or (j) microgliosis, or (k) brain inflammation, or (l) olfactory function loss.

This invention also provides a kit comprising, in separate containers, in a single package, pharmaceutical compositions for use in combination, wherein one container comprises an effective amount of a compound of formula I in a pharmaceutically acceptable carrier, and another container (i.e., a second container) comprises an effective amount of another pharmaceutically active ingredient (as described above), the combined quantities of the compound of formula I and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Other embodiments of this invention are directed to any one of the above embodiments directed to kits wherein the compound of formula I is selected from the group consisting of Group A.

Other embodiments of this invention are directed to any one of the above embodiments directed to kits wherein the compound of formula I is selected from the group consisting of Group B.

Other embodiments of this invention are directed to any one of the above embodiments directed to kits wherein the compound of formula I is selected from the group consisting of Group C.

Other embodiments of this invention are directed to any one of the above embodiments directed to kits wherein the compound of formula I is selected from the group consisting of Group D.

As used above, and throughout this disclosure, the following terms, unless otherwise indicated, shall be understood to have the following meanings:

"ADDP" means 1,1'-(azodicarbonyl)dipiperidine.
"AIBN" means 2,2'-azobis(2-methylpropionitrile).
"CAN" means ammonium cerium (IV) nitrate.
"DCC" means N,N'-dicyclohexylcarbodiimide.
"DCM" means dichloromethane.
"(DHQ)₂PHAL" means

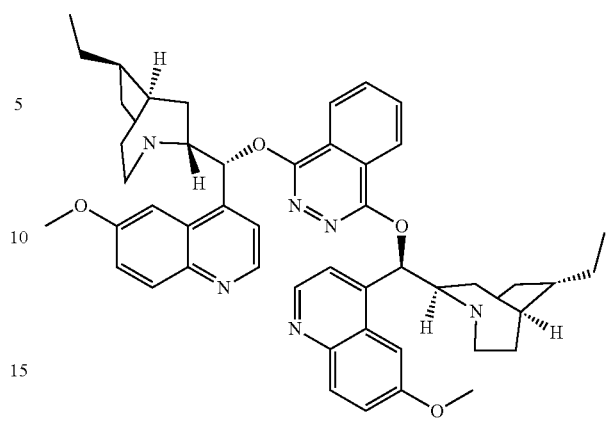

"DMF" means dimethylformamide.
"EDCI" means N-ethyl-N'-dimethylaminopropyl carbodiimide.
"HOBT" means 1-hydroxylbenzotriazole.
"LDA" means lithium diisopropylamide.
"TBAF" means tetra-N-butylammonium fluoride.
"TBSO" means tert-butyldimethylsilyloxy.
"TEA" means triethylamine.
"TEA" means trifluoroacetic acid.
"TfO" means trifluoromethylsulfonyloxy.
"At least one" means one or more than one, for example, 1, 2 or 3, or in another example, 1 or 2, or in another example 1.
"One or more" with reference to the use of the compounds of this invention means that one or more than one compound is used, for example, 1, 2 or 3, or in another example, 1 or 2, or in another example 1.
"Patient" includes both human and animals.
"Mammal" means humans and other mammalian animals.

It is noted that the carbons of formula I and other formulas herein may be replaced with 1 to 3 silicon atoms so long as all valency requirements are satisfied.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)₂, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine. "Halo" refers to fluoro, chloro, bromo or iodo.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

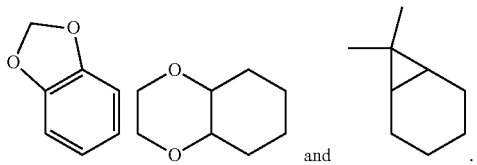 and

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a heterocyclyl ring wherein a single moiety (e.g =O) simultaneously replaces two available hydrogens on the same carbon atom on a ring system. An example of such moiety is pyrrolidone:

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4- tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

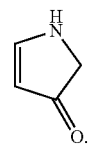

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

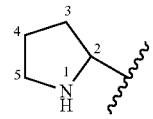

there is no —OH attached directly to carbons marked 2 and 5.

It should also be noted that tautomeric forms such as, for example, the moieties:

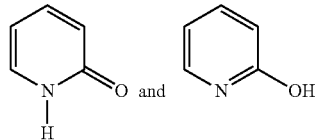 [SMILES: O=c1cccc[nH]1 ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a tower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1- naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as β-dimethylaminoethyl), carbamoyl-$(C_1$-$C_2)$alkyl, N,N-di $(C_1$-$C_2)$alkylcarbamoyl-$(C_1$-$C_2)$alkyl and piperidino-, pyrrolidino- or morpholino$(C_2$-$C_3)$ alkyl, and the like.

Similarly, if a compound of Formula (I) contains an alcohol functional group, a prodrug can be formed by the replacement of the hydrogen atom of the alcohol group with a group such as, for example, $(C_1$-$C_6)$alkanoyloxymethyl, 1-(($C_1$-$C_6)$alkanoyloxy)ethyl, 1-methyl-1-(($C_1$-$C_6)$alkanoyloxy)ethyl, $(C_1$-$C_6)$alkoxycarbonyloxymethyl, N—$(C_1$-$C_6)$alkoxycarbonylaminomethyl, succinoyl, $(C_1$-$C_6)$alkanoyl, α-amino $(C_1$-$C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1$-$C_{10})$alkyl, $(C_3$-$C_7)$ cycloalkyl, benzyl, or R-carbonyl is a natural α-aminoacyl or natural α-aminoacyl, —$C(OH)C(O)OY^1$ wherein $Y^1$ is H, $(C_1$-$C_6)$alkyl or benzyl, —$C(OY^2)Y^3$ wherein $Y^2$ is $(C_1$-$C_4)$ alkyl and $Y^3$ is $(C_1$-$C_6)$alkyl, carboxy $(C_1$-$C_6)$alkyl, amino $(C_1$-$C_4)$alkyl or mono-N— or di-N,N—$(C_1$-$C_6)$alkylaminoalkyl, —$C(Y^4)Y^5$ wherein $Y^4$ is H or methyl and $Y^5$ is mono-N— or di-N,N—$(C_1$-$C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, *Camille G.* (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates, esters and prodrugs thereof, may exist in their tautomeric form (for example, as an amide, enol, keto or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers, Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula I, and of the salts, solvates, esters and prodrugs of the compounds of Formula I, are intended to be included in the present invention.

The compounds according to the invention can have pharmacological properties; in particular, the compounds of Formula I can be modulators of gamma secretase (including inhibitors, antagonists and the like).

More specifically, the compounds of Formula I can be useful in the treatment of a variety of disorders of the central nervous system including, for example, including, but not limited to, Alzheimer's disease, AIDS-related dementia, Parkinson's disease, amyotrophic lateral sclerosis, retinitis pigmentosa, spinal muscular atrophy and cerebellar degeneration and the like.

Another aspect of this invention is a method of treating a mammal (e.g., human) having a disease or condition of the central nervous system by administering a therapeutically effective amount of at least one compound of Formula I, or a pharmaceutically acceptable salt, solvate, ester or prodrug of said compound to the mammal.

A preferred dosage is about 0.001 to 500 mg/kg of body weight/day of the compound of Formula I. An especially preferred dosage is about 0.01 to 25 mg/kg of body weight/day of a compound of Formula I, or a pharmaceutically acceptable salt or solvate of said compound.

The compounds of this invention may also be useful in combination (administered together or sequentially) with one or more additional agents listed above.

The compounds of this invention may also be useful in combination (administered together or sequentially) with one or more compounds selected from the group consisting of Aβ antibody inhibitors, gamma secretase inhibitors and beta secretase inhibitors.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of Formula I, or a pharmaceutically acceptable salt, solvate, ester or prodrug thereof, and an amount of one or more additional agents listed above wherein the amounts of the compounds/treatments result in desired therapeutic effect.

The pharmacological properties of the compounds of this invention may be confirmed by a number of pharmacological assays. Certain assays are exemplified later in this document.

This invention is also directed to pharmaceutical compositions which comprise at least one compound of Formula I, or a pharmaceutically acceptable salt, solvate, ester or prodrug of said compound and at least one pharmaceutically acceptable carrier.

Other embodiments of this invention are directed to pharmaceutically acceptable salts of any one of the compounds in Group A.

Other embodiments of this invention are directed to pharmaceutically acceptable salts of any one of the compounds in Group B.

Other embodiments of this invention are directed to pharmaceutically acceptable salts of any one of the compounds in Group C.

Other embodiments of this invention are directed to pharmaceutically acceptable salts of any one of the compounds in Group D.

Other embodiments of this invention are directed to pharmaceutically acceptable esters of any one of the compounds Group A.

Other embodiments of this invention are directed to pharmaceutically acceptable esters of any one of the compounds Group B.

Other embodiments of this invention are directed to pharmaceutically acceptable esters of any one of the compounds Group C.

Other embodiments of this invention are directed to pharmaceutically acceptable esters of any one of the compounds Group D.

Other embodiments of this invention are directed to solvates of any one of the compounds in Group A.

Other embodiments of this invention are directed to solvates of any one of the compounds in Group B.

Other embodiments of this invention are directed to solvates of any one of the compounds in Group C.

Other embodiments of this invention are directed to solvates of any one of the compounds in Group D.

One embodiment of this invention is directed to a compound of formula I.

Another embodiment of this invention is directed to a pharmaceutically acceptable salt of a compound of formula I.

Another embodiment of this invention is directed to a pharmaceutically acceptable ester of a compound of formula I.

Another embodiment of this invention is directed to a solvate of a compound of formula I.

Another embodiment of this invention is directed to a compound of formula I in isolated form.

Another embodiment of this invention is directed to a compound of formula I in pure form.

Another embodiment of this invention is directed to a compound of formula I in pure and isolated form.

Another embodiment of this invention is directed to a pharmaceutical composition comprising an effective amount of one or more (e.g., one) compounds of formula I and a pharmaceutically acceptable carrier.

Another embodiment of this invention is directed to a pharmaceutical composition comprising an effective amount of a pharmaceutically acceptable salt of one or more (e.g., one) compounds of formula I and a pharmaceutically acceptable carrier.

Another embodiment of this invention is directed to a pharmaceutical composition comprising an effective amount of a pharmaceutically acceptable ester of one or more (e.g., one) compounds of formula I and a pharmaceutically acceptable carrier.

Another embodiment of this invention is directed to a pharmaceutical composition comprising an effective amount of a solvate of one or more (e.g., one) compounds of formula I and a pharmaceutically acceptable carrier.

Another embodiment of this invention is directed to a pharmaceutical composition comprising an effective amount of one or more (e.g., one) compounds of formula I, and an effective amount of one or more (e.g., one) other pharmaceutically active ingredients (e.g.,) drugs, and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising an effective amount of one or more (e.g., one) compounds of formula I, and effective amount of one or more BACE inhibitors, and a pharmaceutically acceptable carrier.

Another embodiment of this invention is directed to a pharmaceutical composition comprising an effective amount of one or more (e.g., one) compounds of formula I, and effective amount of one or more cholinesterase inhibitors (e.g., acetyl- and/or butyrylchlolinesterase inhibitors), and a pharmaceutically acceptable carrier.

The compounds of formula I can be useful as gamma secretase modulators and can be useful in the treatment and prevention of diseases such as, for example, central nervous system disorders such as Alzheimers disease and Downs Syndrome.

Thus, another embodiment of this invention is directed to a method for modulating (including inhibiting, antagonizing and the like) gamma-secretase comprising administering an effective amount of one or more (e.g., one) compounds of formula I to a patient in need of such treatment.

Another embodiment of this invention is directed to a method for modulating (including inhibiting, antagonizing and the like) gamma-secretase, comprising administering an effective amount of a compound of formula I to a patient in need of treatment.

Another embodiment of this invention is directed to a method of treating one or more neurodegenerative diseases, comprising administering an effective amount of one or more (e.g., one) compounds of formula I to a patient in need of treatment.

Another embodiment of this invention is directed to a method of treating one or more neurodegenerative diseases, comprising administering an effective amount of a compound of formula I to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of one or more (e.g., one) compounds of formula I to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of a compound of formula I to a patient in need of treatment.

Another embodiment of this invention is directed to a method of treating Alzheimer's disease, comprising administering an effective amount of one or more (e.g., one) compounds of formula I to a patient in need of treatment.

Another embodiment of this invention is directed to a method of treating Alzheimer's disease, comprising administering an effective amount of a compound of formula I to a patient in need of treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula I and the administration of an effective amount of one or more (e.g., one) other pharmaceutical active ingredients (e.g., drugs). The compounds of formula I and the other drugs can be administered separately (i.e., each is in its own separate dosage form), or the compounds of formula I can be combined with the other drugs in the same dosage form.

Thus, other embodiments of this invention are directed to any one of the methods of treatment, or methods of inhibiting, described herein, wherein an effective amount of the compound of formula I is used in combination with an effective amount of one or more other pharmaceutically active ingredients selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Another embodiment of this invention is directed to a method of treating Alzheimer's disease, comprising administering an effective amount of one or more (e.g., one) compounds of formula I, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of a compound of formula I, in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of one or more (e.g., one) compounds of formula I, in combination with an effective amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective amount of one or more (e.g., one) compounds of formula I, in combination with an effective amount of one or more BACE inhibitors.

Another embodiment of this invention is directed to a method of treating Alzheimer's disease, comprising administering an effective amount of one or more compounds of formula I, in combination with an effective amount of Exelon (rivastigmine).

Another embodiment of this invention is directed to a method of treating Alzheimer's disease, comprising administering an effective amount of one or more compounds of formula I, in combination with an effective amount of Cognex (tacrine).

Another embodiment of this invention is directed to a method of treating Alzheimer's disease, comprising administering an effective amount of one or more compounds of formula I, in combination with an effective amount of a Tau kinase inhibitor.

Another embodiment of this invention is directed to a method of treating Alzheimer's disease, comprising administering an effective amount of one or more compounds of formula I, in combination with an effective amount of one or more Tau kinase inhibitor (e.g., GSK3beta inhibitor, cdk5 inhibitor, ERK inhibitor).

This invention also provides a method of treating Alzheimer's disease, comprising administering an effective amount of one or more compounds of formula I, in combination with an effective amount of one anti-Abeta vaccination (active immunization).

Another embodiment of this invention is directed to a method of treating Alzheimer's disease, comprising administering an effective amount of one or more compounds of formula I, in combination with an effective amount of one or more APP ligands.

Another embodiment of this invention is directed to a method of treating Alzheimer's disease, comprising administering an effective amount of one or more compounds of formula I, in combination with an effective amount of one or more agents that upregulate insulin degrading enzyme and/or neprilysin.

Another embodiment of this invention is directed to a method of treating Alzheimer's disease, comprising administering an effective amount of one or more compounds of formula I, in combination with an effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe).

This invention also provides a method of treating Alzheimer's disease, comprising administering an effective amount of one or more compounds of formula I, in combination with an effective amount of one or more fibrates (for example, clofibrate, Clofibride, Etofibrate, Aluminium Clofibrate).

Another embodiment of this invention is directed to a method of treating Alzheimer's disease, comprising administering an effective amount of one or more compounds of formula I, in combination with an effective amount of one or more LXR agonists.

Another embodiment of this invention is directed to a method of treating Alzheimer's disease, comprising administering an effective amount of one or more compounds of formula I, in combination with an effective amount of one or more LRP mimics.

Another embodiment of this invention is directed to a method of treating Alzheimer's disease, comprising administering an effective amount of one or more compounds of formula I, in combination with an effective amount of one or more 5-HT6 receptor antagonists.

Another embodiment of this invention is directed to a method of treating Alzheimer's disease, comprising administering an effective amount of one or more compounds of formula I, in combination with an effective amount of one or more nicotinic receptor agonists.

Another embodiment of this invention is directed to a method of treating Alzheimer's disease, comprising administering an effective amount of one or more compounds of formula I, in combination with an effective amount of one or more H3 receptor antagonists.

This invention also provides a method of treating Alzheimer's disease, comprising administering an effective amount of one or more compounds of formula I, in combination with an effective amount of one or more histone deacetylase inhibitors.

Another embodiment of this invention is directed to a method of treating Alzheimer's disease, comprising administering an effective amount of one or more compounds of formula I, in combination with an effective amount of one or more hsp90 inhibitors.

Another embodiment of this invention is directed to a method of treating Alzheimer's disease, comprising administering an effective amount of one or more compounds of formula I, in combination with an effective amount of one or more m1 muscarinic receptor agonists.

Another embodiment of this invention is directed to a method of treating Alzheimer's disease, comprising administering an effective amount of one or more compounds of formula I, in combination with an effective amount of one or more 5-HT6 receptor antagonists mGluR1 or mGluR5 positive allosteric modulators or agonists Another embodiment of this invention is directed to a method of treating Alzheimer's disease, comprising administering an effective amount of one or more compounds of formula I, in combination with an effective amount of one or more mGluR2/3 antagonists.

Another embodiment of this invention is directed to a method of treating Alzheimer's disease, comprising administering an effective amount of one or more compounds of formula I, in combination with an effective amount of one or more anti-inflammatory agents that can reduce neuroinflammation.

Another embodiment of this invention is directed to a method of treating Alzheimer's disease, comprising administering an effective amount of one or more compounds of formula I, in combination with an effective amount of one or more Prostaglandin EP2 receptor antagonists.

This invention also provides a method of treating Alzheimer's disease, comprising administering an effective amount of one or more compounds of formula I, in combination with an effective amount of one or more PAI-1 inhibitors.

This invention also provides a method of treating Alzheimer's disease, comprising administering an effective amount of one or more compounds of formula I, in combination with an effective amount of one or more agents that can induce Abeta efflux such as gelsolin.

This invention also provides a method of treating Downs syndrome, comprising administering an effective amount of one or more (e.g., one) compounds of formula I to a patient in need of treatment.

This invention also provides a method of treating Downs syndrome, comprising administering an effective amount of a compound of formula I to a patient in need of treatment.

This invention also provides a method of treating Downs syndrome, comprising administering an effective amount of one or more (e.g., one) compounds of formula I, in combination with an effective amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Downs syndrome, comprising administering an effective amount of a compound of formula I, in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating mild cognitive impairment, comprising administering an effective amount of one or more (e.g., one) compounds of formula I to a patient in need of treatment.

This invention also provides a method of treating glaucoma, comprising administering an effective amount of one or more (e.g., one) compounds of formula I to a patient in need of treatment.

This invention also provides a method of treating cerebral amyloid angiopathy, comprising administering an effective amount of one or more (e.g., one) compounds of formula I to a patient in need of treatment.

This invention also provides a method of treating stroke, comprising administering an effective amount of one or more (e.g., one) compounds of formula I to a patient in need of treatment.

This invention also provides a method of treating dementia, comprising administering an effective amount of one or more (e.g., one) compounds of formula I to a patient in need of treatment.

This invention also provides a method of treating microgliosis, comprising administering an effective amount of one or more (e.g., one) compounds of formula I to a patient in need of treatment.

This invention also provides a method of treating brain inflammation, comprising administering an effective amount of one or more (e.g., one) compounds of formula I to a patient in need of treatment.

This invention also provides a method of treating olfactory function loss, comprising administering an effective amount of one or more (e.g., one) compounds of formula I to a patient in need of treatment.

This invention also provides combinations (i.e., pharmaceutical compositions) comprising an effective amount of one or more (e.g., one) compounds of formula I, in combination with an effective amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

This invention also provides a kit comprising, in separate containers, in a single package, pharmaceutical compositions for use in combination, wherein one container comprises an effective amount of a compound of formula I in a pharmaceutically acceptable carrier, and another container (i.e., a second container) comprises an effective amount of another pharmaceutically active ingredient (as described above), the combined quantities of the compound of formula I and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Another embodiment of this invention is directed to a compound of Group A, Group B, Group C or Group D in isolated form.

Another embodiment of this invention is directed to a compound of Group A, Group B, Group C or Group D in pure form.

Another embodiment of this invention is directed to a compound of Group A, Group B, Group C or Group D in pure and isolated form.

Another embodiment is directed to a pharmaceutical composition comprising an effective amount of one or more (e.g., one) compounds of Group A, Group B, Group C or Group D and a pharmaceutically acceptable carrier.

Another embodiment is directed to a pharmaceutical composition comprising an effective amount of a pharmaceutically acceptable salt of one or more (e.g., one) compounds of Group A, Group B, Group C or Group D, and a pharmaceutically acceptable carrier.

Another embodiment is directed to a pharmaceutical composition comprising an effective amount of a pharmaceutically acceptable ester of one or more (e.g., one) compounds of Group A, Group B, Group C or Group D, and a pharmaceutically acceptable carrier.

Another embodiment is directed to a pharmaceutical composition comprising an effective amount of a solvate of one or more (e.g., one) compounds of Group A, Group B, Group C or Group D, and a pharmaceutically acceptable carrier.

Another embodiment of this invention is directed to a pharmaceutical composition comprising an effective amount of one or more (e.g., one) compounds of Group A, Group B, Group C or Group D, and an effective amount of one or more (e.g., one) other pharmaceutically active ingredients (e.g., drugs), and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising an effective amount of one or more (e.g., one) compounds of Group A, Group B, Group C or Group D, and effective amount of one or more BACE inhibitors, and a pharmaceutically acceptable carrier.

Another embodiment of this invention is directed to a pharmaceutical composition comprising an effective amount of one or more (e.g., one) compounds of Group A, Group B, Group C or Group D, and an effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more muscarinic antagonists (e.g., $m_1$ agonists or $m_2$ antagonists), and a pharmaceutically acceptable carrier.

Another embodiment of this invention is directed to a pharmaceutical composition comprising an effective amount of one or more (e.g., one) compounds of Group A, Group B, Group C or Group D, and effective amount of Exelon (rivastigmine), and a pharmaceutically acceptable carrier.

Another embodiment of this invention is directed to a pharmaceutical composition comprising an effective amount of one or more (e.g., one) compounds of Group A, Group B, Group C or Group D, and effective amount of Cognex (tacrine), and a pharmaceutically acceptable carrier.

Another embodiment of this invention is directed to a pharmaceutical composition comprising an effective amount of one or more (e.g., one) compounds of Group A, Group B, Group C or Group D, and effective amount of a Tau kinase inhibitor, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more Tau kinase inhibitor (e.g., GSK3beta inhibitor, cdk5 inhibitor, ERK inhibitor), and a pharmaceutically acceptable carrier.

Another embodiment of this invention is directed to a pharmaceutical composition comprising an effective amount of one or more (e.g., one) compounds of Group A, Group B, Group C or Group D, and effective amount of one anti-Abeta vaccine (active immunization), and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more APP ligands, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more agents that upregulate insulin degrading enzyme and/or neprilysin, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe), and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more fibrates (for example, clofibrate, Clofibride, Etofibrate, Aluminium Clofibrate), and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more LXR agonists, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more LRP mimics, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more 5-HT6 receptor antagonists, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more nicotinic receptor agonists, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more H3 receptor antagonists, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more histone deacetylase inhibitors, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more hsp90 inhibitors, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more m1 muscarinic receptor agonists, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more 5-HT6 receptor antagonists mGluR1 or mGluR5 positive allosteric modulators or agonists, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more one mGiuR2/3 antagonists, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more anti-inflammatory agents that can reduce neuroinflammation, and a pharmaceutically acceptable carrier.

Another embodiment of this invention is directed to a pharmaceutical composition comprising an effective amount of one or more (e.g., one) compounds of Group A, Group B, Group C or Group D and effective amount of one or more Prostaglandin EP2 receptor antagonists, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more PAM inhibitors, and a pharmaceutically acceptable carrier.

Another embodiment of this invention is directed to a pharmaceutical composition comprising an effective amount of one or more (e.g., one) compounds of Group A, Group B, Group C or Group D, and effective amount of one or more agents that can induce Abeta efflux such as gelsolin, and a pharmaceutically acceptable carrier.

The compounds of formula I selected from the group consisting of Group A, Group B, Group C or Group D can be useful as gamma secretase modulators and can be useful in the treatment and prevention of diseases such as, for example, central nervous system disorders (such as Alzheimers disease and Downs Syndrome), and treating mild cognitive impairment, glaucoma, cerebral amyloid angiopathy, stroke, dementia, microgliosis, brain inflammation, and olfactory function loss.

Thus, another embodiment of this invention is directed to a method for modulating (including inhibiting, antagonizing and the like) gamma-secretase comprising administering an effective (i.e., therapeutically effective) amount of one or more (e.g., one) compounds of Group A, Group B, Group C or Group D to a patient in need of such treatment.

Another embodiment of this invention is directed to a method for modulating (including inhibiting, antagonizing and the like) gamma-secretase, comprising administering an effective (i.e., therapeutically effective) amount of a compound of Group A, Group B, Group C or Group D to a patient in need of treatment.

Another embodiment of this invention is directed to a method of treating one or more neurodegenerative diseases, comprising administering an effective (i.e., therapeutically effective) amount of one or more (e.g., one) compounds of Group A, Group B, Group C or Group D to a patient in need of treatment.

Another embodiment of this invention is directed to a method of treating one or more neurodegenerative diseases, comprising administering an effective (i.e., therapeutically effective) amount of a compound of Group A, Group B, Group C or Group D to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of one or more (e.g., one) compounds of Group A, Group B, Group C or Group D to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of a compound of Group A, Group B, Group C or Group D to a patient in need of treatment.

Another embodiment of this invention is directed to a method of treating Alzheimer's disease, comprising administering an effective (i.e., therapeutically effective) amount of one or more (e.g., one) compounds of Group A, Group B, Group C or Group D to a patient in need of treatment.

Another embodiment of this invention is directed to a method of treating Alzheimer's disease, comprising administering an effective (i.e., therapeutically effective) amount of a compound of Group A, Group B, Group C or Group D to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of one or more (e.g., one) compounds of Group A, Group B, Group C or Group D to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of a compound of Group A, Group B, Group C or Group D to a patient in need of treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of Group A, Group B, Group C or Group D, and the administration of one or more (e.g., one) other pharmaceutical active ingredients (e.g., drugs). The compounds of Group A, Group B, Group C or Group D, and the other drugs can be administered separately (i.e., each is in its own separate dosage form), or the compounds of formula (I) can be combined with the other drugs in the same dosage form.

Thus, other embodiments of this invention are directed to any one of the methods of treatment, or methods of inhibiting, described herein, wherein the compounds of Group A, Group B, Group C or Group D are used in combination with an effective amount of one or more other pharmaceutically active ingredients selected from the group consisting of: BACE inhibitors (beta secretase inhibitors); muscarinic antagonists (e.g., $m_1$ agonists or $m_2$ antagonists); cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of Group A, Group B, Group C or Group D, and the administration of one or more (e.g., one) other pharmaceutical active ingredients (e.g., drugs). The compounds of Group A, Group B, Group C, Group D or Group E, and the other drugs can be administered separately (i.e., each is in its own separate dosage form), or the compounds of Group A, Group B, Group C or Group D can be combined with the other drugs in the same dosage form.

Thus, other embodiments of this invention are directed to any one of the methods of treatment, or methods of inhibiting, described herein, wherein the compounds of Group A, Group B, Group C or Group D are used in combination with an effective amount of one or more other pharmaceutically active ingredients selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Other embodiments of this invention are directed to any one of the methods of treatment, or methods of inhibiting, described herein, wherein the compounds of Group A, Group B, Group C or Group D are used in combination with an effective amount of one or more other pharmaceutically active ingredients selected from the group consisting of: BACE inhibitors (beta secretase inhibitors), muscarinic antagonists (e.g., m$_1$ agonists or m$_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; GABA$_A$ inverse agonists; inhibitors of amyloid aggregation; glycogen synthase kinase beta inhibitors; promoters of alpha secretase activity; PDE-10 inhibitors; and cholesterol absorption inhibitors (e.g., ezetimibe).

Other embodiments of this invention are directed to any one of the methods of treatment, or methods of inhibiting, described herein, wherein the compounds of Group A, Group B, Group C or Group D are used in combination with an effective amount of one or more other pharmaceutically active ingredients selected from the group consisting of: Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; 1-13 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Another embodiment of this invention is directed to a method of treating Alzheimer's disease, comprising administering an effective (i.e., therapeutically effective) amount of one or more (e.g., one) compounds of Group A, Group B, Group C or Group D, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of a compound of Group A, Group B, Group C or Group D, in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of one or more (e.g., one) compounds of formula (I) selected from the group consisting of: in combination with an effective (i.e., therapeutically effective) amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective (i.e., therapeutically effective) amount of one or more (e.g., one) compounds of Group A, Group B, Group C or Group D, in combination with an effective (i.e., therapeutically effective) amount of one or more BACE inhibitors.

Another embodiment of this invention is directed to a method of treating Alzheimer's disease, comprising administering an effective (i.e., therapeutically effective) amount of a compound of Group A, Group B, Group C or Group D, in combination with an effective (i.e., therapeutically effective) amount of one or more BACE inhibitors.

Another embodiment of this invention is directed to a method of treating Downs syndrome, comprising administering an effective (i.e., therapeutically effective) amount of one or more (e.g., one) compounds of Group A, Group B, Group C or Group D to a patient in need of treatment.

Another embodiment of this invention is directed to a method of treating Downs syndrome, comprising administering an effective (i.e., therapeutically effective) amount of a compound of Group A, Group B, Group C or Group D, to a patient in need of treatment.

Another embodiment of this invention is directed to a method of treating Downs syndrome, comprising administering an effective (i.e., therapeutically effective) amount of one or more (e.g., one) compounds of Group A, Group B, Group C or Group D, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective (i.e., therapeutically effective) amount of a compound of Group A, Group B, Group C or Group D, in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to combinations (i.e., pharmaceutical compositions) comprising an effective (i.e., therapeutically effective) amount of one or more (e.g., one) compounds of Group A, Group B, Group C or Group D in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

This invention also provides a kit comprising, in separate containers, in a single package, pharmaceutical compositions for use in combination, wherein one container comprises an effective amount of one or more (e.g., one) compounds of formula (I) (e.g., compounds selected from the compounds of Group A, Group B, Group C or Group D) in a pharmaceutically acceptable carrier, and another container (i.e., a second container) comprises an effective amount of another pharmaceutically active ingredient (as described above), the combined quantities of the compounds of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

This invention also provides a kit comprising, in separate containers, in a single package, pharmaceutical compositions for use in combination, wherein one container comprises an effective amount of a compound selected from the group consisting of the compounds of formulas (I) (e.g. the compounds selected from the group consisting of: the compounds of Group A, Group B, Group C or Group D) in a pharmaceutically acceptable carrier, and another container (i.e., a second container) comprises an effective amount of another pharmaceutically active ingredient (as described above), the combined quantities of the compound of formulas (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Examples of cholinesterase inhibitors are tacrine, donepezil, rivastigmine, galantamine, pyridostigmine and neostigmine, with tacrine, donepezil, rivastigmine and galantamine being preferred.

Examples of $m_1$ agonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Examples of BACE inhibitors include those described in: US2005/0119227 published Jun. 2, 2005 (see also WO2005/016876 published Feb. 2, 2005), US2005/0043290 published Feb. 2, 2005 (see also WO2005/014540 published Feb. 2, 2005), WO2005/058311 published Jun. 30, 2005 (see also US2007/0072852 published Mar. 29, 2007), US2006/0111370 published May 25, 2006 (see also WO2006/065277 published Jun. 22, 2006), U.S. application Ser. No. 11/710,582 filed Feb. 23, 2007, US2006/0040994 published Feb. 23, 2006 (see also WO2006/014762 published Feb. 9, 2006), WO2006/014944 published Feb. 9, 2006 (see also US2006/0040948 published Feb. 23, 2006), WO2006/138266 published Dec. 28, 2006 (see also US2007/0010667 published Jan. 11, 2007), WO2006/138265 published Dec. 28, 2006, WO2006/138230 published Dec. 28, 2006, WO2006/138195 published Dec. 28, 2006 (see also US2006/0281729 published Dec. 14, 2006), WO2006/138264 published Dec. 28, 2006 (see also US2007/0060575 published Mar. 15, 2007), WO2006/138192 published Dec. 28, 2006 (see also US2006/0281730 published Dec. 14, 2006), WO2006/138217 published Dec. 28, 2006 (see also US2006/0287294 published Dec. 21, 2006), US2007/0099898 published 05/03/200 (see also WO2007/050721 published May 3, 2007), WO2007/053506 published May 10, 2007 (see also US2007/099875 published May 3, 2007), U.S. application Ser. No. 11/759,336 filed Jun. 7, 2007, U.S. Application Ser. No. 60/874,362 filed Dec. 12, 2006, and U.S. Application Ser. No. 60/874,419 filed Dec. 12, 2006, the disclosures of each being incorporated herein by reference thereto.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula I, or a pharmaceutically acceptable salt, solvate, ester or prodrug of said compound and a pharmaceutically acceptable carrier, vehicle or diluent.

Yet another aspect of this invention is a kit comprising an amount of at least one compound of Formula I, or a pharmaceutically acceptable salt, solvate, ester or prodrug of said compound and an amount of at least one additional agent listed above, wherein the amounts of the two or more ingredients result in desired therapeutic effect.

The invention disclosed herein is exemplified by the following illustrative example which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min— stop. The observed parent ion is given.

Method Q

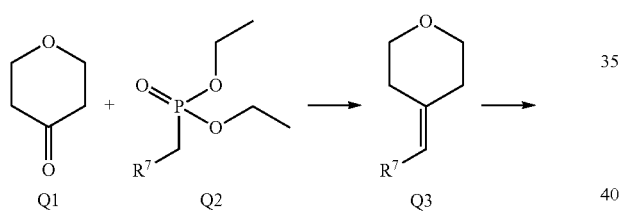

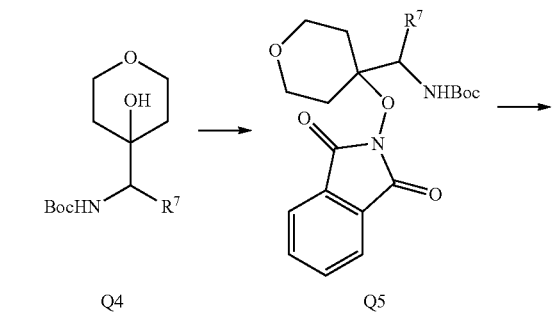

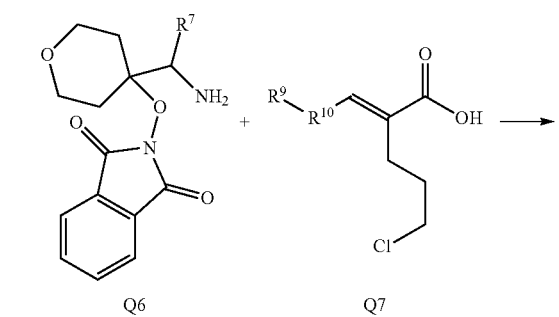

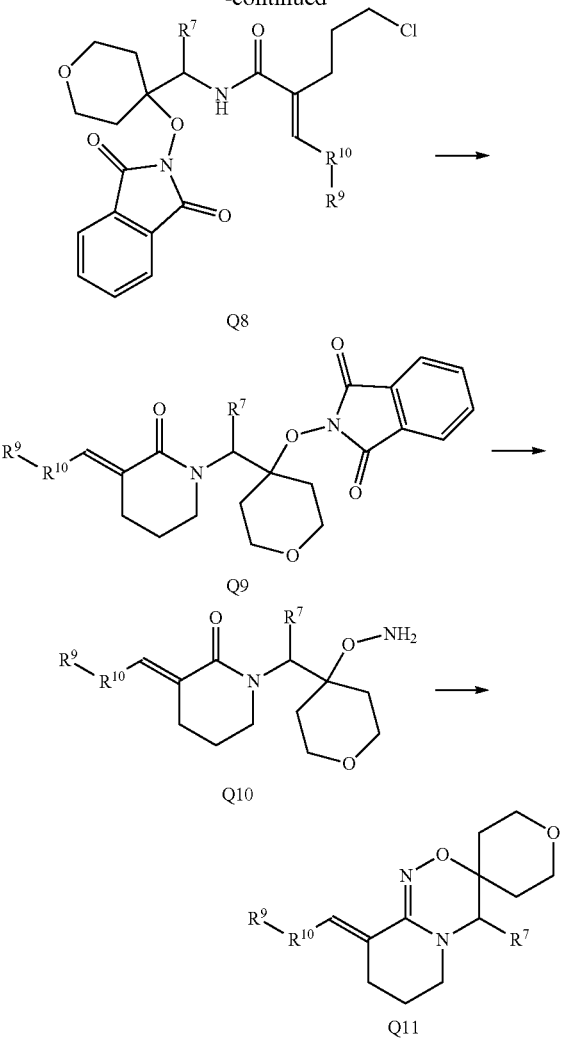

Method Q, Step 1

Q1 and Q2 (R$^7$=4-F-Phenyl) will react in THF in the presence of KOtBu to give compound Q3 (R$^7$=4-F-Phenyl) after work up and purification.

Method Q, Step 2

Q3 (R$^7$=4-F-Phenyl) will be converted to Q4 using a method similar to L. Barboni and C. Lambertucci; *J. Med. Chem.* 2001, 44, 1576;

To a stirred solution of tert-butyl carbamate (2.32 g, 15.3 mmol) in 2-propanol (20 mL), a solution of NaOH (604 mg) in water (37 mL), tert-butyl hypochlorite (1.73 mL) and (DHQ)$_2$PHAL (198 mg) in 2-propanol (17.3 mL) will be sequentially added. After stirring at room temperature for 10 min, 4.95 mmol of compound Q3 will be added, followed by K$_2$OsO$_2$(OH)$_4$ (73 mg). After stirring at room temperature for 7 h, the reaction will be worked up by cooling in a ice bath and addition of saturated Na$_2$SO$_3$ (49.5 mL). After further stirring for 15 min, the reaction mixture will be extracted with EtOAc, and the organic phase will be washed with brine, dried (Na$_2$SO$_4$) and evaporated. The residue will be chromatographed on silica gel (hexanes-EtOAc) to give Q4 (R$^7$=4-F-Phenyl).

Method Q, Step 3

To a THF solution of Q4 (R$^7$=4-F-Phenyl) will be added N-hydroxylphthalimide, ADDP and triphenylphosphine. The reaction will be stirred overnight to give compound Q5 (R⁷=4-F-Phenyl) after workup and purification.

Method Q, Step 4

Compound Q5 (R⁷=4-F-Phenyl) will be treated with TFA in DCM to give compound Q6 (R⁷=4-F-Phenyl).

Method Q, Step 5

Compound Q6 will be coupled with Q7 (R⁷=4-F-Phenyl, R¹⁰=3-MeO-Phenyl, R⁹=4-(4-Methyl-imidazol-1-yl)) using EDCI/TEA/DMF conditions to give Q8 (R⁷=4-F-Phenyl, R¹⁰=3-MeO-Phenyl, R⁹=4-(4-Methyl-imidazol-1-yl)) after workup and purification.

Method Q, Step 6

Compound Q8 (R⁷=4-F-Phenyl, R¹⁰=3-MeO-Phenyl, R⁹=4-(4-Methyl-imidazol-1-yl)) will be treated with NaH in DMF to give Q9 (R⁷=4-F-Phenyl, R¹⁰=3-MeO-Phenyl, R⁹=4-(4-Methyl-imidazol-1-yl)) after workup and purification.

Method Q, Step 7

Compound Q9 (R⁷=4-F-Phenyl, R¹⁰=3-MeO-Phenyl, R⁹=4-(4-Methyl-imidazol-1-yl)) will be treated with hydrazine in methanol to give compound Q10 (R⁷=4-F-Phenyl, R¹⁰=3-MeO-Phenyl, R⁹=4-(4-Methyl-imidazol-1-yl)) after workup and purification.

Method Q, Step 8

Compound Q10 (R⁷=4-F-Phenyl, R¹⁰=3-MeO-Phenyl, R⁹=4-(4-Methyl-imidazol-1-yl)) will be converted to Q11 through reflux with a mixture of P₂O₅ (30 mg) and EtOH (1 mL). The resulted mixture will be stirred at 80° C. overnight to give compound Q11 (R⁷=4-F-Phenyl, R¹⁰=3-MeO-Phenyl, R⁹=4-(4-Methyl-imidazol-1-yl))after workup and purification.

The following compounds will be synthesized using method similar to method Q.

-continued

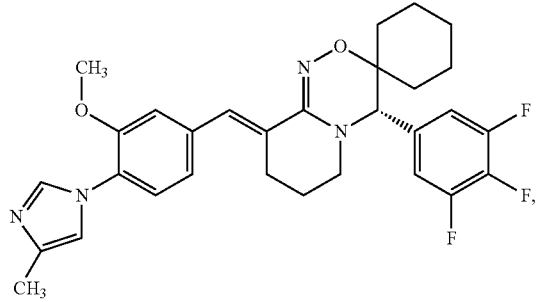

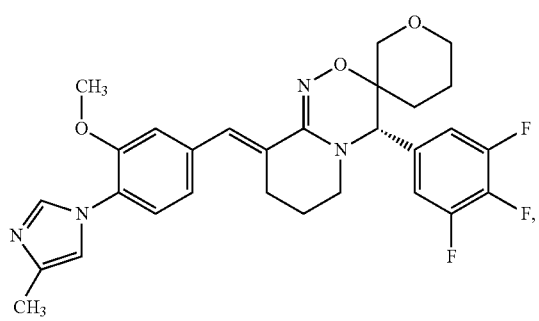

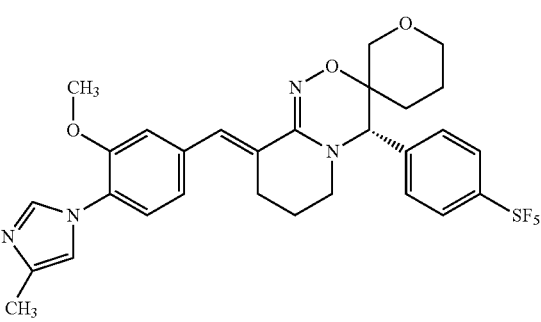

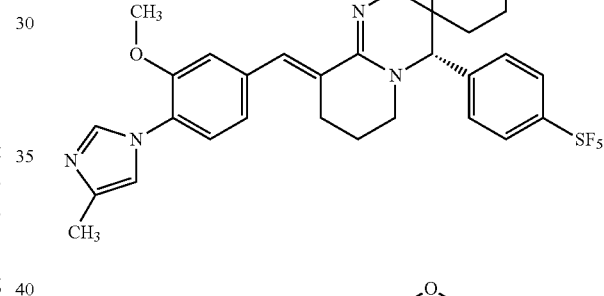

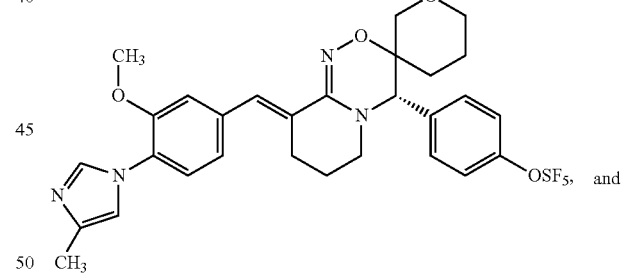

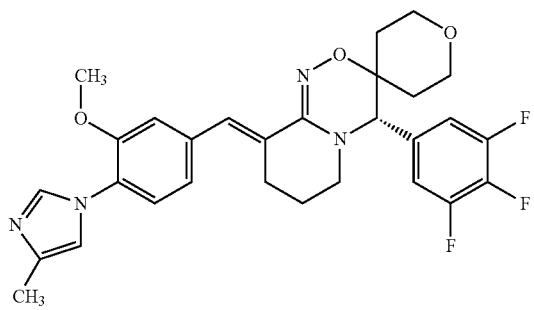

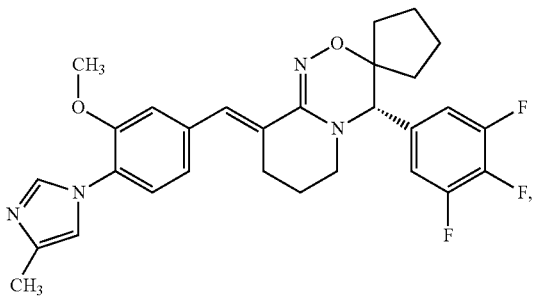

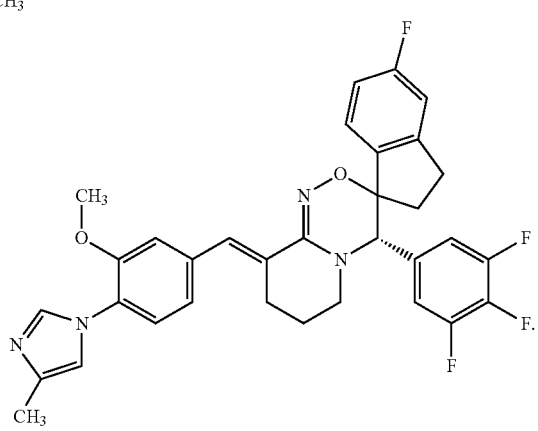

Method R

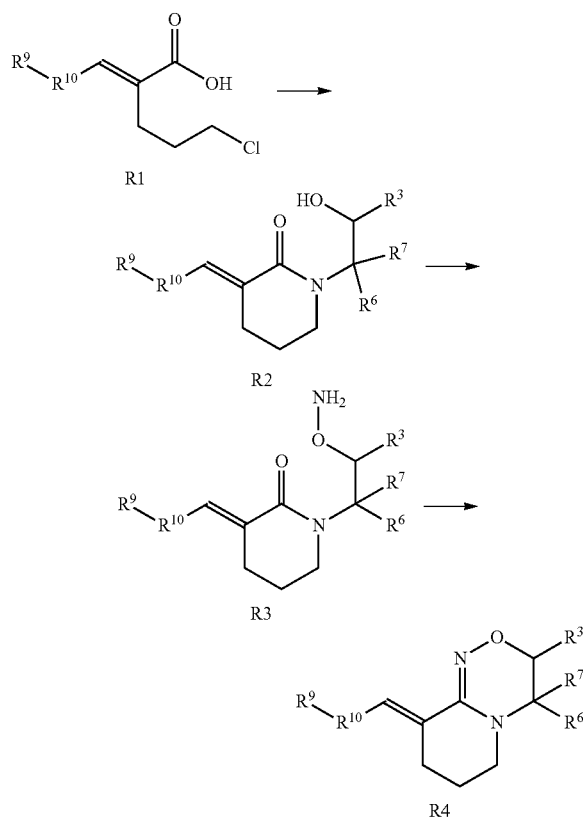

Method R, Step 1:

To a stirring mixture of 2-amino-1-(4-SF$_5$-phenyl)ethanol (1 mmol), acid R$^1$ (R$^{16}$=3-MeO-Phenyl, R$^9$=4-(4-Methyl-imidazol-1-yl), 1.0 mmol), HOBT (1.5 mmol) and DIEA (6 mmol) in anhydrous DMF (5 mL) will be added EDCI (1.5 mmol). The solution resulted will be stirred overnight at rt. Upon removal of DMF under high vacuum, the residue will be taken up into EtOAc (100 mL) and saturated NaHCO$_3$ (30 mL). The EtOAc layer will be collected and dried over Na$_2$SO$_4$. After removal of EtOAc, the residue will be dissolved in THF (10 mL). To this THF solution will be added NaOMe (2 mmol, 4.2 M in MeOH). The mixture will be stirred over night at rt. After which, the THF will be removed and residue partitioned between EtOAc and H$_2$O. The EtOAc layer will be collected and dried over Na$_2$SO$_4$. After removal of EtOAc, the residue will be purified through flash chromatography to afford the desired lactam R$^2$ (R$^6$=R$^7$=H, R$^3$=4-SF$_5$-Phenyl, R$^{10}$=3-MeO-Phenyl, R$^9$=4-(4-Methyl-imidazol-1-yl)).

Method R, Step 2

The lactam R$^2$ (R$^6$=R$^7$=H, R$^3$=4-SF$_5$-Phenyl, R$^{10}$=3-MeO-Phenyl, R$^9$=4-(4-Methyl-imidazol-1-yl)), 0.5 mmol) will be mixed with PPh$_3$ (1 mmol) and N-hydroxylphthalim-ide (1 mmol) in anhydrous THF (5 mL) under N$_2$. The mixture will be cooled to −10° C. and DIAD (1 mmol) will be added dropwisely. The mixture will be allowed to warm up to rt and stirred for overnight before removal of THF. The reaction will be worked up and the purified product will be treated with hydrazine in a mixture of DCM and methanol at rt for 1 hr. The reaction mixture will be diluted with EtOAc, washed with brine twice and dried over MgSO$_4$, filtered, and evaporated to provide compound hydroxyamine R3 (R$^6$=R$^7$=H, R$^3$=4-SF$_5$-Phenyl, R$^{10}$=3-MeO-Phenyl, R$^9$=4-(4-Methyl-imidazol-1-yl)).

Method R, Step 3

The hydroxylamine R$^3$ (R$^6$=R$^7$=H, R$^3$=4-SF$_5$-Phenyl, R$^{16}$=3-MeO-Phenyl, R$^9$=4-(4-Methyl-imidazol-1-yl)), 10 mg) will be dissolved in EtOH (1 mL). This solution will be added to a premixed mixture of P$_2$O$_5$ (30 mg) and EtOH (1 mL). The resulted mixture will be stirred at 80° C. overnight. After the reaction mixture is cooled down, diluted with CH$_2$Cl$_2$ (50 mL) and water, excess K$_2$CO$_3$ will be added to adjust the pH to −9-10. The organic layer will be collected and dried over Na$_2$SO$_4$. After removal of the CH$_2$Cl$_2$, the residue will be purified with flash chromatography to afford the desired final product R$^4$ (R$^6$=R$^7$=H, R$^3$=4-SF$_5$-phenyl R$^{10}$=3-MeO-Phenyl, R$^9$=4-(4-Methyl-imidazol-1-yl)).

Method S

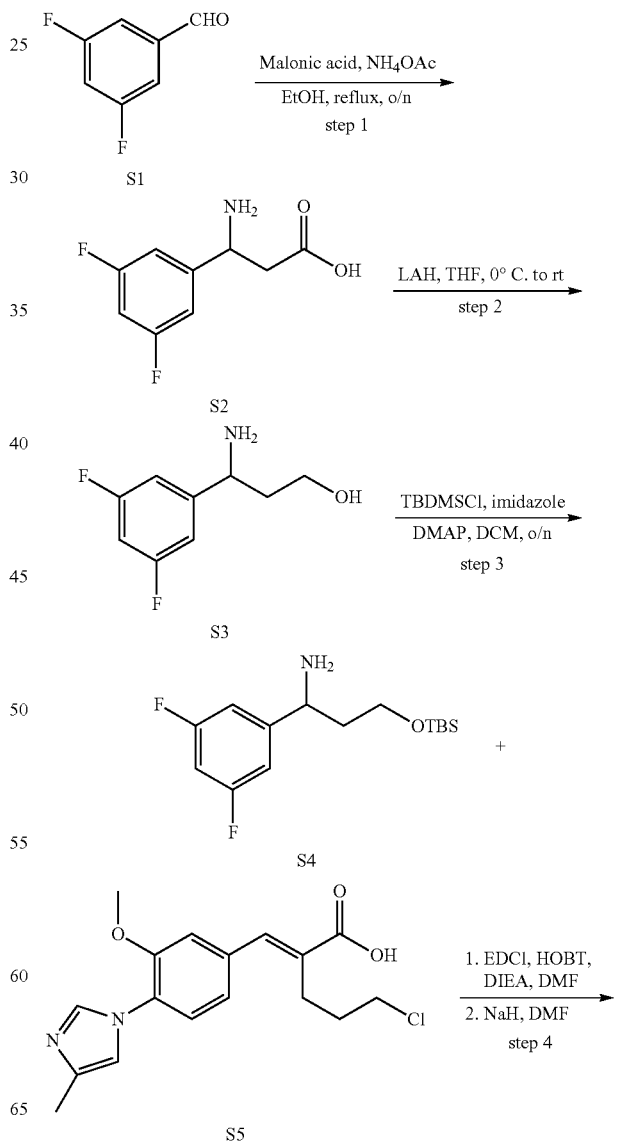

-continued

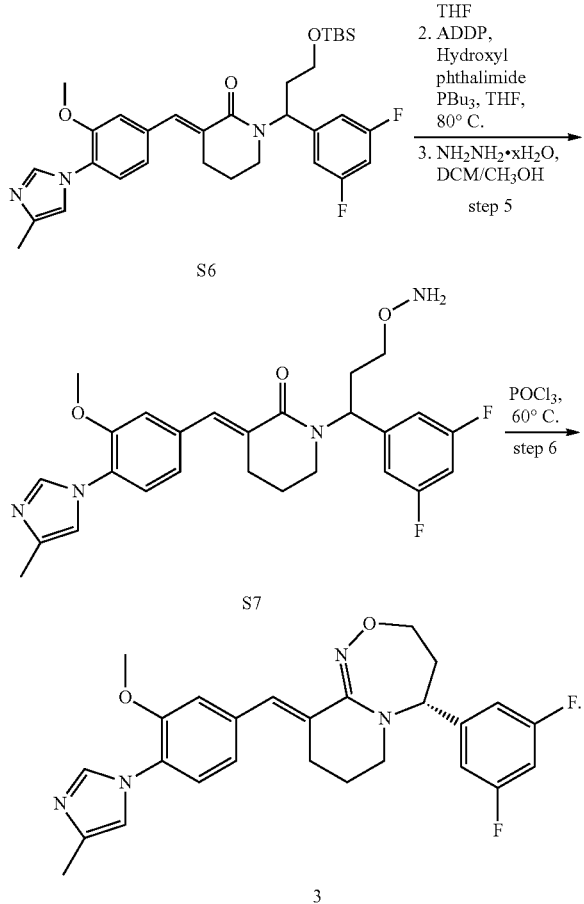

Step 1:

The mixture of 3,5-difluorobenzylaldehyde (S1) (27.09 g, 0.19 mol, 1.0 equiv.), malonic acid (19.84 g, 0.19 mol, 1.0 equiv.), and ammonium acetate (29.39 g, 0.38 mol, 2.0 equiv.) in ethanol (300 mL) was stirred under reflux overnight. The white precipitate was filtered, rinsed with cold ethanol, dried under vacuum, and compound S2 was obtained (21.28 g, 0.11 mol, 56% yield). $^1$H NMR (CD$_3$OD): δ: 7.18-7.05 (m, 2 H); 7.00-6.95 (m, 1H), 4.53 (t, J=7.0 Hz, 1H), 2.66 (d, J=7.2 Hz, 2H). Electrospray MS: Obs. [M+H]: 202.1.

Step 2:

At 0° C., to a suspension of LAH (7.58 g, 0.20 mol, 5.0 equiv.) in THF (100 mL) was added compound S1 (8.03 g, 0.04 mol, 1.0 equiv.) in THF (500 mL) slowly, it was warmed to rt slowly and stirred overnight. After the completion of the reaction, it was cooled to 0° C., quenched with brine slowly till the grey reaction mixture turned white slurry. The reaction mixture was filtered through Celite, rinsed with DCM, dried over MgSO$_4$, filter, and evaporated to provided amino alcohol S3 (5.93 g, 0.03 mol, yield 79%). $^1$H NMR (CDCl$_3$) δ: 6.86-6.80 (m, 2 H); 6.72-6.64 (m, 1H), 4.13 (dd, J=7.4, 5.4 Hz, 1 H); 3.78 (t, J=5.6 Hz, 2H), 1.92-1.80 (m, 2H). Electrospray MS: Obs. [M+H]: 188.2.

Step 3:

To amino alcohol S3 (5.93 g, 31.70 mmol, 1.0 equiv.) in DCM (200 mL) was added TBDMSCl (9.56 g, 63.41 mmol, 2.0 equiv.), imidazole (5.39 g, 79.26 mmol, 2.5 equiv.) and DMAP (0.295 g, 5% w/w cat.) respectively, and the reaction mixture was stirred overnight. It was quenched with saturated NH$_4$Cl, extracted with DCM, combined DCM layers were washed with brine, dried over MgSO$_4$, filtered, and evaporated. The crude reaction mixture was purified by column chromatography (enluent: CH$_3$OH/CH$_3$OH=0% to 10%), and provided compound S4 (6.76 g, 22.43 mmol, yield 71%). $^1$H NMR (CDCl$_3$) δ: 6.86-6.80 (m, 2 H); 6.70-6.60 (m, 1H), 4.12 (t, J=6.6 Hz, 1 H); 3.72-3.64 (m, 1H), 3.62-3.55 (m, 1H), 1.84-1.76 (m, 2H), 0.90 (s, 9H), 0.04 (s, 6H). Electrospray MS: Obs. [M+H]: 302.4.

Step 4:

Compound S6 was made following procedures similar to that of Method R Step 1.

Step 5:

Compound S7 was made following procedures similar to that of Method R Step 2.

Step 6:

The reaction mixture of compound S7 (0.187 g, 0.38 mmol) in POCl$_3$ (10 mL) was heated at 60° C. overnight. POCl$_3$ was removed, the residue was diluted with DCM (200 mL), washed with saturated NaHCO$_3$ (2×50 mL), dried over MgSO$_4$, filtered, and evaporated. The crude reaction mixture was purified by reverse phase, and followed by chiral separation to provide compound 3 (0.0284 g, yield 16%). $^1$H NMR (CDCl$_3$) δ: 7.72 (s, 1H), 7.56 (s, 1H), 7.24 (d, J=8.4 Hz, 1H), 7.12-7.00 (m, 4H), 6.93 (s, 1H), 6.68-6.80 (m, 1H), 4.38 (s, 1H), 4.10-4.02 (m, 1H), 3.85 (s, 3H), 3.75-3.62 (m, 1H), 3.24-3.14 (m, 1H), 3.04-2.86 (m, 2H), 2.80-2.64 (m, 1H), 2.63-2.56 (m, 1H), 2.29 (s, 3H), 2.24-2.16 (m, 1H), 2.00-1.86 (m, 1H), 1.86-1.76 (m, 1H). LCMS: Obs. [M+H]: 465.3.

Table 1 below lists compounds prepared by using the procedures in Method S.

TABLE 1

| Compound | Structure | Rt (min) | Obs. Mass |
|---|---|---|---|
| 1 | racemate | 2.3 | 477.24 |

TABLE 1-continued

| Compound | Structure | Rt (min) | Obs. Mass |
|---|---|---|---|
| 2 | racemate | 2.5 | 465.26 |
| 3 | Enantiomer 1 | 2.4 | 465.26 |
| 4 | Enantiomer 2 | 2.5 | 465.26 |
| 5 | racemate | 2.5 | 483.27 |
| 6 | Enantiomer 1 | 2.6 | 483.27 |

TABLE 1-continued

| Compound | Structure | Rt (min) | Obs. Mass |
|---|---|---|---|
| 7 | Enantiomer 2 | 2.6 | 483.27 |
| 8 | Enantiomer 1 | 2.3 | 447.24 |
| 9 | racemate | 2.5 | 465.26 |
| 10 | racemate | 2.4 | 447.2 |
| 11 | racemate | 2.4 | 465.26 |

TABLE 1-continued
| Compound | Structure | Rt (min) | Obs. Mass |
|---|---|---|---|
| 12 | 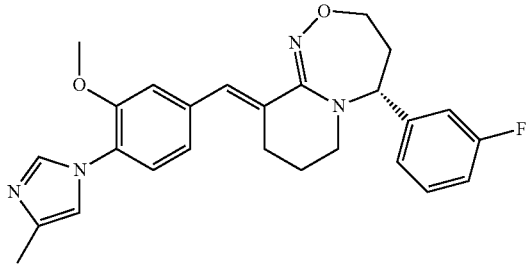 Enantiomer 1 | 2.3 | 447.25 |
| 13 | 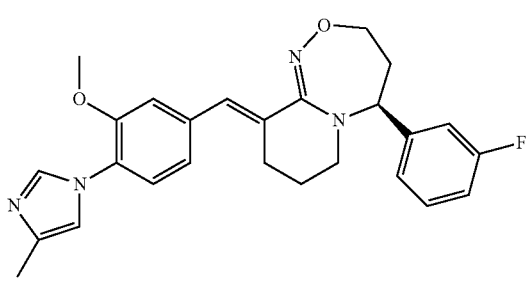 Enantiomer 2 | 0.9 | 447.25 |
| 14 | 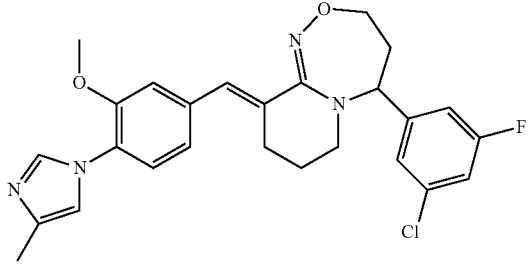 racemate | 2.6 | 481.26 |
| 15 | 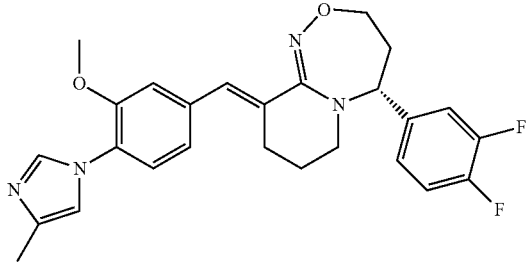 Enantiomer 1 | 2.5 | 465.26 |
| 16 | 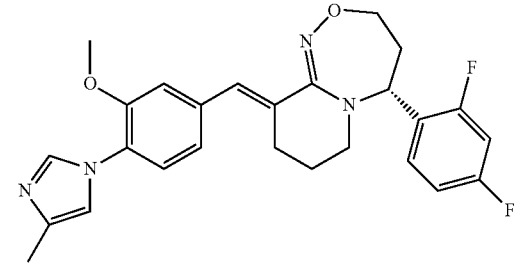 Enantiomer 1 | 2.5 | 465.26 |

TABLE 1-continued

| Compound | Structure | Rt (min) | Obs. Mass |
|---|---|---|---|
| 17 | Enantiomer 2 | 2.6 | 481.26 |
| 18 | Enantiomer 1 | 2.6 | 481.26 |
| 19 | Enantiomer 2 | 2.5 | 465.26 |
| 20 | Enantiomer 2 | 2.5 | 465.26 |
| 21 | Enantiomer 2 | 2.5 | 481.26 |

TABLE 1-continued

| Compound | Structure | Rt (min) | Obs. Mass |
|---|---|---|---|
| 22 | Enantiomer 1 | 3.5 | 481.26 |
| 23 | racemate | 2.7 | 497.27 |
| 24 | Enantiomer 1 | 3.5 | 481.26 |
| 25 | Enantiomer 2 | 3.5 | 481.26 |

TABLE 1-continued
| Compound | Structure | Rt (min) | Obs. Mass |
|---|---|---|---|
| 26 | Enantiomer 1 | 1.9 | 523.2 |
| 27 | Enantiomer 1 | 3.1 | 481.26 |
Method T
Compound T1 (R²=Me, R³=R⁶=H, R⁷=p-F-phenyl, R¹⁰=3-MeO-Phenyl, R⁹=4-(4-Methyl-imidazol-1-yl)), synthesized using a method similar to method R, will be converted to T2 (R²=Me, R³=R⁶=H, R⁷=p-F-phenyl, R¹⁰=3-MeO-Phenyl, R⁹=4-(4-Methyl-imidazol-1-yl)), using a method similar to method R.
Method U
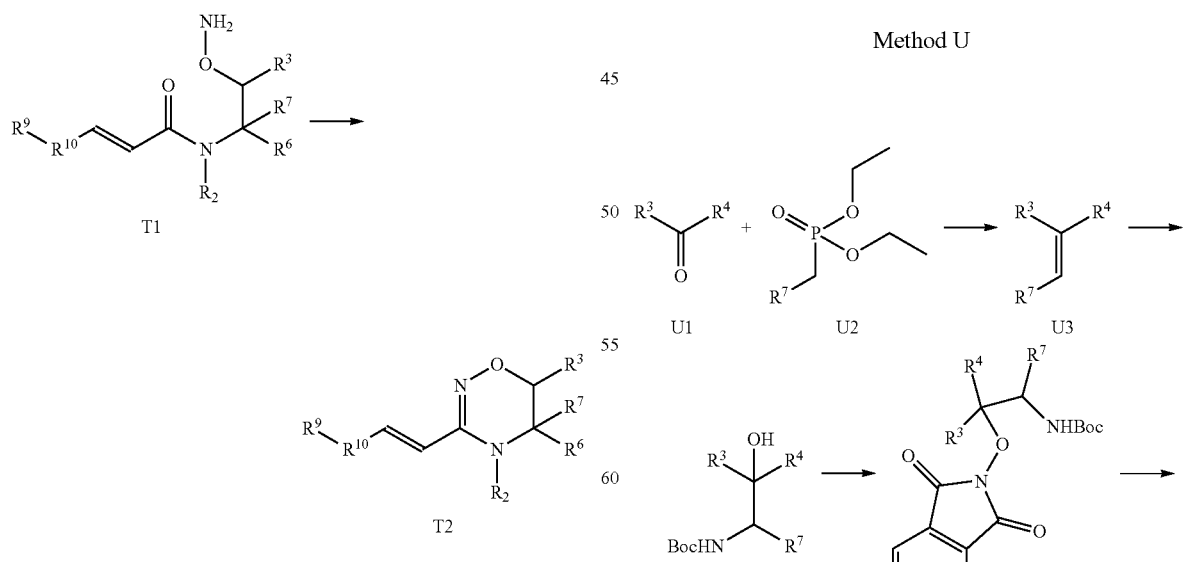

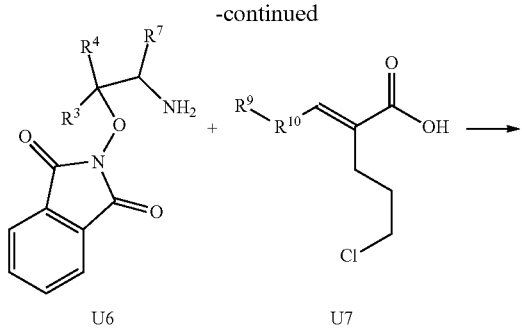

U6    U7

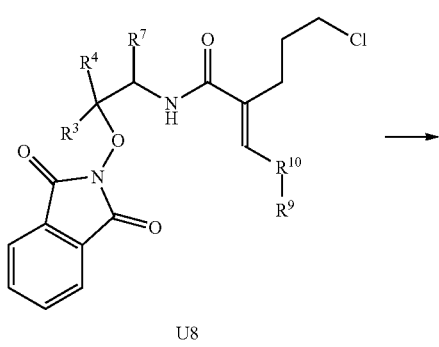

U8

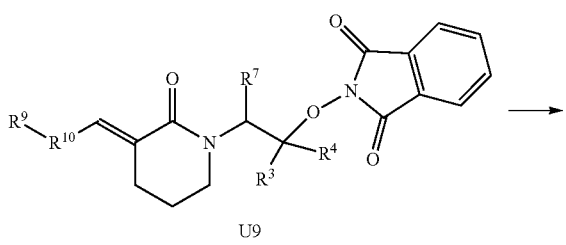

U9

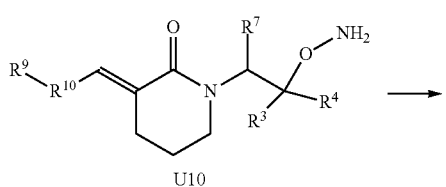

U10

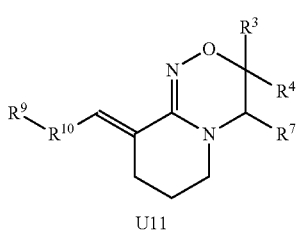

U11

Method U, Step 1

U1 ($R^3$=$R^4$=Me) and U2 ($R^7$=4-F-Phenyl) will react in THF in the presence of KOtBu to give compound U3 ($R^7$=4-F-Phenyl, $R^3$=$R^4$=Me) after work up and purification.

Method U, Step 2

U3 ($R^7$=4-F-Phenyl, $R^3$=$R^4$=Me) will be converted to U4 ($R^7$=4-F-Phenyl, $R^3$=$R^4$=Me) using a method similar to L. Barboni and C. Lambertucci; *J. Med. Chem.* 2001, 44, 1576;

To a stirred solution of tert-butyl carbamate (2.32 g, 15.3 mmol) in 2-propanol (20 mL), a solution of NaOH (604 mg) in water (37 mL), tert-butyl hypochlorite (1.73 mL) and (DHQ)$_2$PHAL (198 mg) in 2-propanol (17.3 mL) will be sequentially added. After stirring at room temperature for 10 min, 4.95 mmol of compound Q3 will be added, followed by $K_2OsO_2(OH)_4$ (73 mg). After stirring at room temperature for 7 h, the reaction will be worked up by cooling in a ice bath and addition of saturated $Na_2SO_3$ (49.5 mL). After further stirring for 15 min, the reaction mixture will be extracted with EtOAc, and the organic phase will be washed with brine, dried ($Na_2SO_4$) and evaporated. The residue will be chromatographed on silica gel (hexanes-EtOAc) to give U4 ($R^7$=4-F-Phenyl, $R^3$=$R^4$=Me).

Method U, Step 3

To a THF solution of U4 ($R^7$=4-F-Phenyl, $R^3$=$R^4$=Me) will be added N-hydroxylphthalimide, ADDP and triphenylphosphine. The reaction will be stirred overnight to give compound U5 ($R^7$=4-F-Phenyl, $R^3$=$R^4$=Me) after workup and purification.

Method U, Step 4

Compound U5 ($R^7$=4-F-Phenyl, $R^3$=$R^4$=Me) will be treated with TFA in DCM to give compound U6 ($R^7$=4-F-Phenyl, $R^3$=$R^4$=Me).

Method U, Step 5

Compound Q6 will be coupled with U7 ($R^7$=4-F-Phenyl, $R^{10}$=3-MeO-Phenyl, $R^9$=4-(4-Methyl-imidazol-1-yl), $R^3$=$R^4$=Me) using EDCI/TEA/DMF conditions to give U8 ($R^7$=4-F-Phenyl, $R^{10}$=3-MeO-Phenyl, $R^9$=4-(4-Methyl-imidazol-1-yl), $R^3$=$R^4$=Me) after workup and purification.

Method U, Step 6

Compound U8 ($R^7$=4-F-Phenyl, $R^{10}$=3-MeO-Phenyl, $R^9$=4-(4-Methyl-imidazol-1-yl), $R^3$=$R^4$=Me) will be treated with NaH in DMF to give U9 ($R^7$=4-F-Phenyl, $R^{10}$=3-MeO-Phenyl, $R^9$=4-(4-Methyl-imidazol-1-yl), $R^3$=$R^4$=Me) after workup and purification.

Method U, Step 7

Compound U9 ($R^7$=4-F-Phenyl, $R^{10}$=3-MeO-Phenyl, $R^9$=4-(4-Methyl-imidazol-1-yl), $R^3$=$R^4$=Me) will be treated with hydrazine in methanol to give compound U10 ($R^7$=4-F-Phenyl, $R^{13}$=3-MeO-Phenyl, $R^9$=4-(4-Methyl-imidazol-1-yl), $R^3$=$R^4$=Me) after workup and purification.

Method U, Step 8

Compound U10 ($R^7$=4-F-Phenyl, $R^{10}$=3-MeO-Phenyl, $R^9$=4-(4-Methyl-imidazol-1-yl), $R^3$=$R^4$=Me) will be converted to U11 ($R^7$=4-F-Phenyl, $R^{10}$=3-MeO-Phenyl, $R^9$=4-(4-Methyl-imidazol-1-yl), $R^3$=$R^4$=Me) through refluxing with $P_2O_5$ in ethanol.

The compounds in Table 2 will be synthesized using a method similar to that listed in the "synthetic Method" column:

TABLE 2
| Structure | Synthetic Method |
|---|---|
| 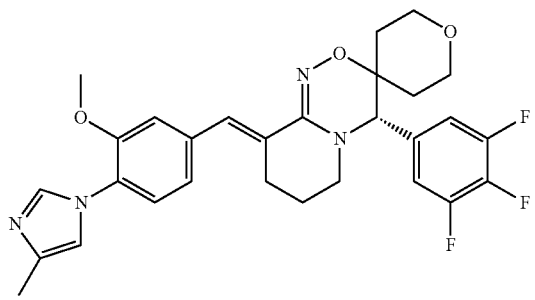 28 | Q |
| 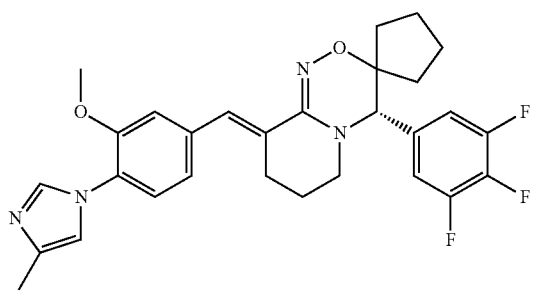 29 | Q |
| 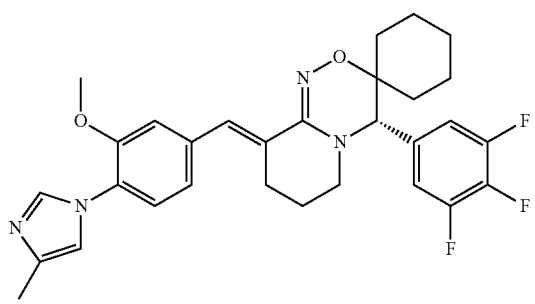 30 | Q |
| 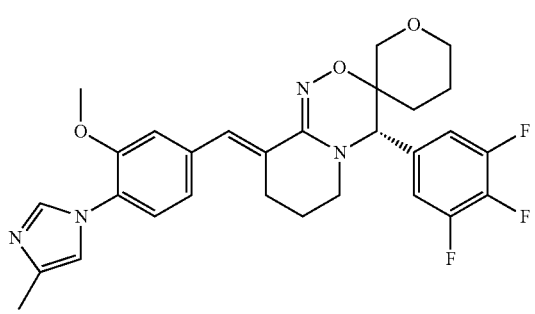 31 | Q |

TABLE 2-continued
| Structure | Synthetic Method |
|---|---|
| 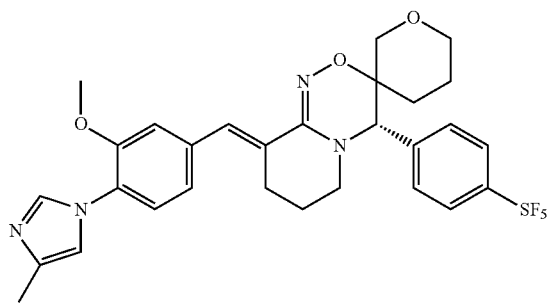<br>32 | Q |
| 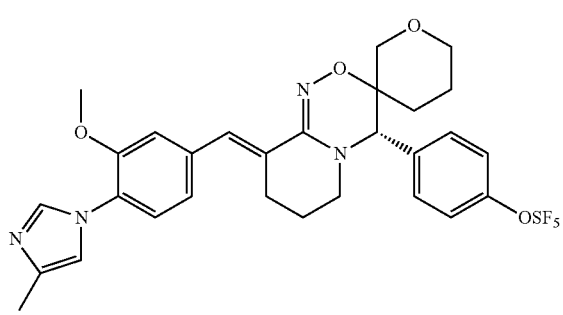<br>33 | Q |
| 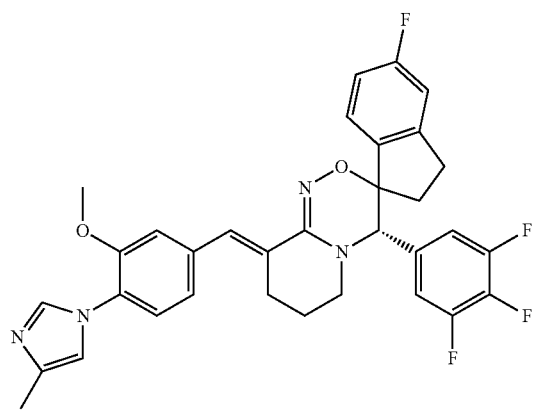<br>34 | Q |
| 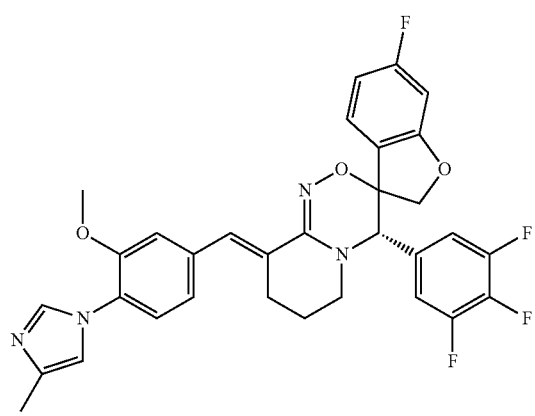<br>35 | Q |

TABLE 2-continued
| Structure | Synthetic Method |
|---|---|
| 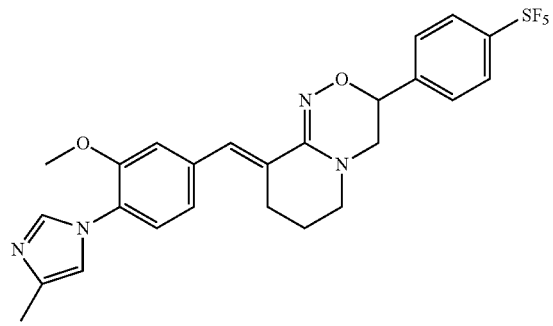 36 | R |
| 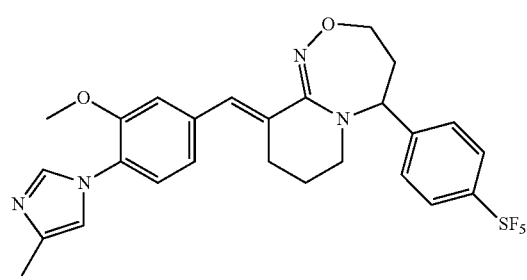 37 | S |
| 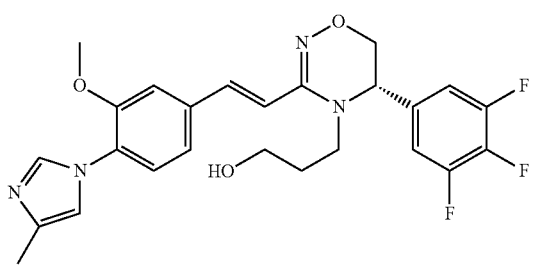 38 | T |
| 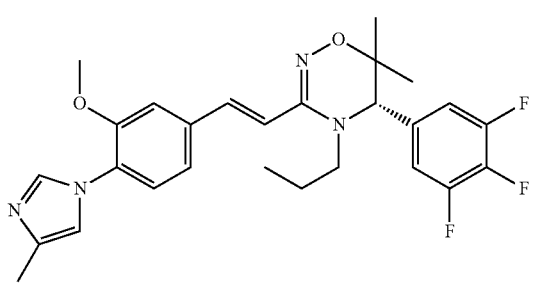 39 | T |

TABLE 2-continued
| Structure | Synthetic Method |
|---|---|
| 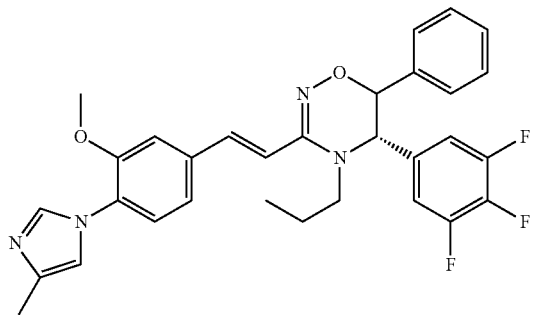<br>40 | T |
| 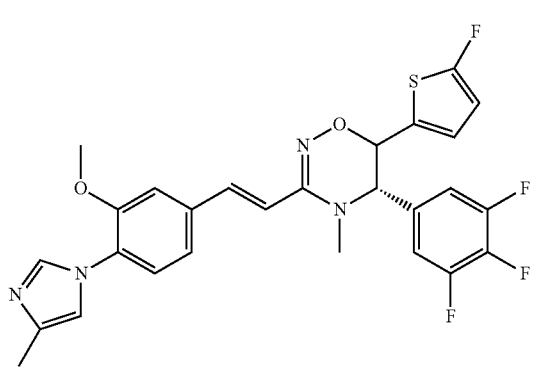<br>41 | T |
| 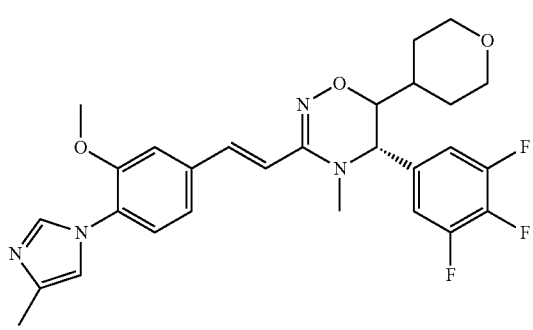<br>42 | T |
| 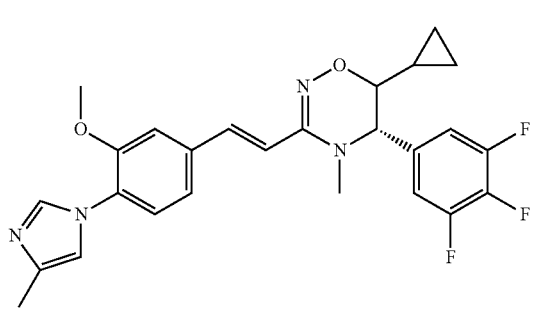<br>43 | T |

TABLE 2-continued

| Structure | Synthetic Method |
|---|---|
| (structure 44) | T |
| (structure 45) | T |
| (structure 46) | T |
| (structure 47) | T |
| (structure 48) | T |

TABLE 2-continued

| Structure | Synthetic Method |
|---|---|
| 49 | U |
| 50 | U |
| 51 | U |

Method V

-continued

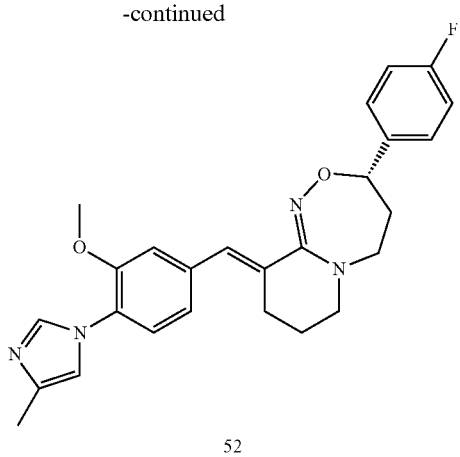

52

Synthesis of 3-tert-butyldimethylsilyloxy-3-(4-F-phenyl)propan-1-amine (V13)

At –78° C. to n-BuLi (2.5 M in Hexane, 27 mL, 67.8 mmol, 1.0 equiv.) in THF (200 mL) was added CH₃CN (3.9 mL, 3.06 g, 74.6 mmol, 1.1 Equiv.) slowly, after stirring for 1 hr., 4-F-benzoate ethyl ester (V9, 11.4 g, 67.8 mmol) in THF (10 mL) was added, and the reaction mixture was stirred at this temperature for another hr. The reaction was warmed to –60° C., stirred for 2 hrs, and diluted with EtOAc, washed with brine, dried over MgSO₄, filtered, and evaporated. The crude reaction mixture was recrystallized from EtOAc to afford compound 10 (5.20 g, 31.9 mmol, yield 47%). ¹H NMR (CDCl₃) δ: 8.00-7.92 (m, 2H), 7.23-7.18 (m, 2H), 4.06 (s, 3H).

At 0° C. to compound V10 (5.20 g, 31.9 mmol, 1.0 Equiv.) in EtOH (500 mL) was added NaBH₄ (12.18 g, 318.7 mmol, 10 Equiv.) and HOAc (3.83 g, 3.6 mL, 63.74 mmol, 2.0 Equiv.) respectively, it's warmed to rt and stirred at rt overnight. Solvent was removed, the crude reaction mixture was diluted with water and EtOAc, aqueous phase was separated and extracted with EtOAc (3×150 mL), the combined organic phase was washed with brine, dried over MgSO₄, filtered, and evaporated to provide V11. The crude mixture was used directly. ¹H NMR (CDCl₃) δ: 7.42-7.36 (m, 2H), 7.12-7.04 (m, 2H), 5.04 (broad s, 1H), 2.75 (d, J=6.4 Hz, 2H), 2.54-2.38 (broad s, 1H, OH).

Compound V12 was prepared by following a similar procedure to that of Method S, Step 3. ¹H NMR (CDCl₃) δ: 7.38-7.30 (m, 2H), 7.08-7.02 (m, 2H), 4.98-4.92 (m, 1H), 2.66-2.62 (m, 2H), 0.88 (s, 9H), 0.09 (s, 3H), –0.09 (s, 3H).

To BH₃.SMe₂ in THF (2.0 M in THF, 31.85 mL, 63.70 mmol, 2.0 Equiv.) was added compound V12 (8.90 g, 31.85 mmol, 1.0 Equiv.) in THF (100 mL) dropwise under reflux. After addition, it was stirred for 2 hrs at the same temperature till completion of the reaction. It was cooled to rt, quenched with MeOH (50 mL) slowly, and solvent was removed. The crude mixture was purified by the column chromatography (Eluent: 0.7 N NH₃ in CH₃OH/EtOAc=0% to 50%), and amine V13 (4.32 g, 15.2 mmol, yield 48%) was obtained.

Compound 52 was obtained from amine V13 following procedures similar to those of Steps 4-6 in Method S.

Following procedures similar to those of Methods S and V similar to the procedures described in Method V, the compounds in Table 3 were prepared.

TABLE 3

| Compound | Structure | Rt (min) | Obs. Mass |
|---|---|---|---|
| 52 | Enantiomer 1 | 2.7 | 447.25 |
| 53 | racemate | 3.4 | 429.24 |

TABLE 3-continued

| Compound | Structure | Rt (min) | Obs. Mass |
|---|---|---|---|
| 54 | Enantiomer 1 | 2.8 | 429.24 |
| 55 | Enantiomer 2 | 2.7 | 429.24 |
| 56 | Enantiomer 2 | 2.6 | 447.25 |
| 57 | racemate | 2.8 | 465.26 |

TABLE 3-continued

| Compound | Structure | Rt (min) | Obs. Mass |
|---|---|---|---|
| 58 | Enantiomer 2 | 2.8 | 465.26 |
| 59 | Enantiomer 2 | 2.8 | 465.26 |
| 60 | Enantiomer 1 | 2.8 | 483.27 |
| 61 | Enantiomer 2 | 2.8 | 483.27 |

TABLE 3-continued

| Compound | Structure | Rt (min) | Obs. Mass |
|---|---|---|---|
| 62 | Enantiomer 1 | 1.9 | 481.26 |
| 63 | Enantiomer 2 | 1.7 | 481.26 |

Method W

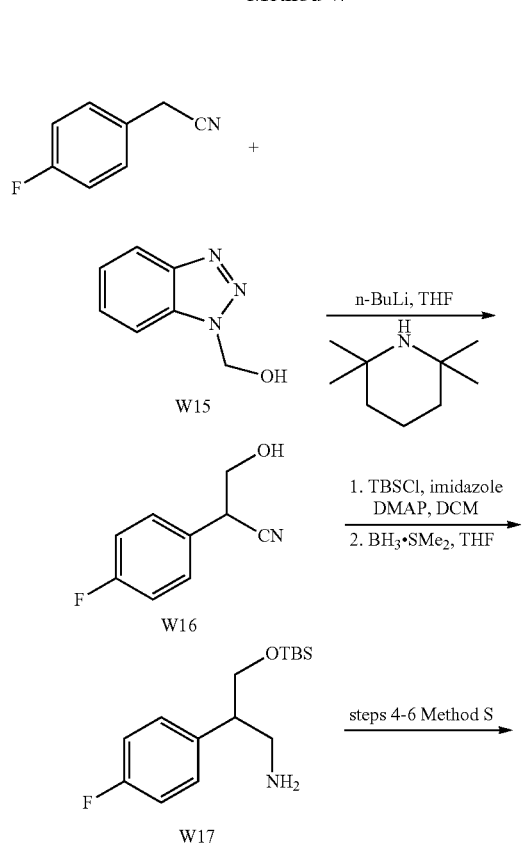

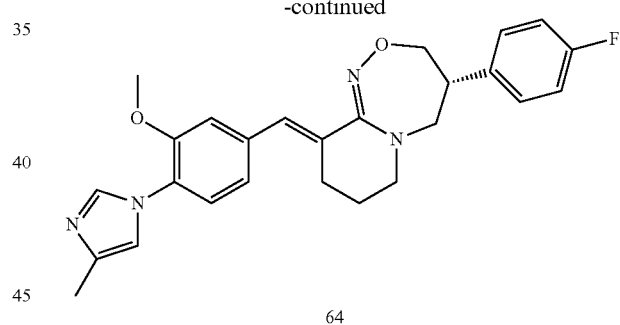

64

Synthesis of 3-tert-butyldimethylsilyloxy-2-(4-F-phenyl)propan-1-amine (W17)

To n-BuLi (2.5 M in Hexane, 50 mL, 0.12 mmol, 3.0 Equiv.) in THF (100 mL) was added 2,2,6,6-tetramethylpiperidine (17.654 g, 21 mL, 0.12 mmol, 3.0 Equiv.) slowly at −10° C., it was then stirred at 0° C. for 30 mins before cooling to −78° C. At this temperature, 2-(4-F-phenyl)acetonitrile (5 mL, 5.63 g, 41.7 mmol) was added to the above reaction mixture, and stirred for an additional 1 hr, and compound 15 (12.427 g, 83.3 mmol, 2.0 Equiv.) in THF (200 mL) was added via addition funnel over 30 mins. The reaction was stirred at −78° C. for another 2 hrs, quenched with water slowly, and warmed to rt. It was extracted with Et$_2$O, and washed with 4N NaOH (75 mL) and brine successively. The organic phase was dried over MgSO$_4$, filtered, and evaporated. The crude mixture was purified by column chromatography (Eluent: EtOAc/Hex=5% to 100%), and compound W16 (2.02 g, 12.2 mmol, 30%) was obtained. $^1$H NMR (CDCl$_3$) δ: 7.40-7.28 (m, 2H), 7.16-7.04 (m, 2H), 4.00-3.80 (m, 3H).

Compound W17 was prepared according to a procedure similar to Step 3 in Method S followed by a procedure similar to the preparation of V13 from V12 in Method V.

Compound 64 was prepared following procedures similar to those of Steps 4-6 in Method S.

Following procedures similar to those of Methods S and W, the compounds in Table 4 were prepared.

TABLE 4

| Compound | Structure | Rt (min) | Obs. Mass |
|---|---|---|---|
| 65 | Enantiomer 1 | 3.4 | 429.24 |
| 66 | Enantiomer 2 | 2.9 | 429.24 |
| 67 | Enantiomer 1 | 2.5 | 447.25 |
| 68 | Enantiomer 2 | 2.5 | 447.25 |

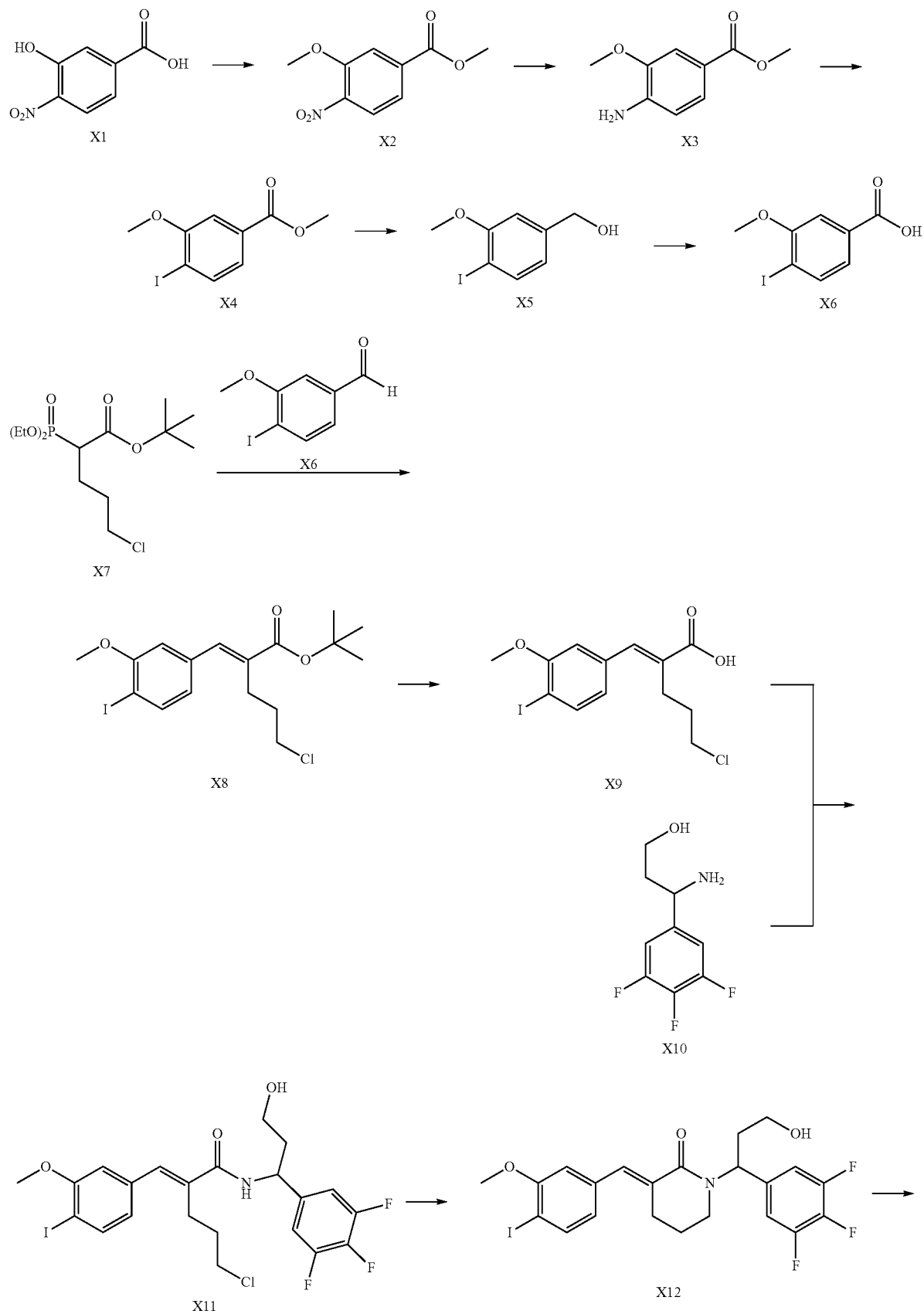

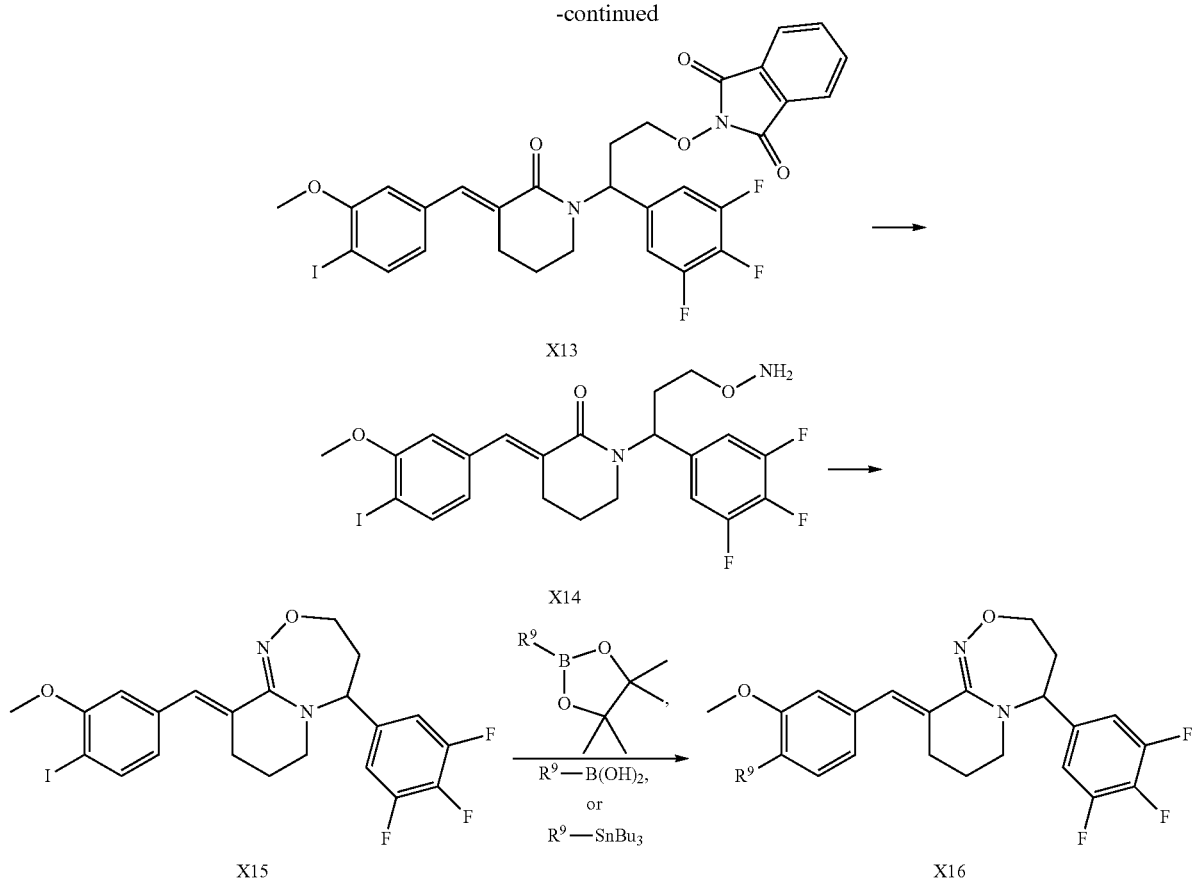

Compound X2:

To a 12 L 3-necked round bottomed flask equipped with an addition funnel, under nitrogen and containing a solution of X1 (302.7 g, 1.65 mol) in DMF (2.5 L) was added $K_2CO_3$ (905.3 g, 6.55 mol) portionwise over 5 min. Methyl iodide was then added dropwise via addition funnel over 70 min. and then the mixture was stirred overnight. The reaction mixture was slowly poured into an XL extractor containing a stirring mixture of water (7 L) and ice (3 L). The resulting mixture was extracted with ethyl acetate (1×6 L, 1×4 L), washed with water (1×4 L), and brine (1×2 L). The combined organic layers were dried over $MgSO_4$, filtered, and concentrated in vacuo to afford X2 (344g, 97%) as yellow needles. $^1$HNMR ($CDCl_3$, 400 MHz) δ 7.80 (d, 1H), 7.73 (d, 1H), 7.66 (dd, 1H), 3.99 (s, 3H), 3.94 (s, 3H).

Compound X3:

To a 2 L Parr bottle containing a mixture of X2 (95 g, 0.45 mol) in MeOH (anhydrous, 1.3 L) under nitrogen was added (Raney nickel slurry in water (15 ml) exchanged with methanol 3 times). The reaction mixture was hydrogenated in a Parr shaker at 45 psi overnight. The reaction sat for 30 min. The top layer of the reaction mixture was decanted and filtered. The residue was diluted with DCM (1 L), swirled for 5 min., and filtered resulting in X3 (>quantitative) as an off-white solid. $^1$HNMR ($CDCl_3$, 400 MHz) δ 7.52 (dd, 1H), 7.43 (d, 1H), 6.63 (d, 1H), 4.21 (s, 2H), 3.88 (s, 3H), 3.84 (s, 3H).

Compound X4:

To a 12 L 3-necked round bottomed flask equipped with a mechanical stirrer, thermometer, addition funnel, nitrogen inlet, and containing a suspension of X3 (252 g, 1.39 mol) in water (3.5 L) at 0° C. was added $H_2SO_4$ (20% vol., 700 mL). A solution of $NaNO_2$ (105.6 g, 1.53 mol) in water (550 mL) was added slowly over 1 h at 0° C. to 3° C. and the reaction mixture was stirred further for 1 h. Next, urea (25 g, 0.417 mol) was added to the reaction mixture portionwise and stirred for 15 min. Then a solution of KI (242.3 g, 1.46 mol) in water (600 mL) was added to the 0° C. reaction mixture over 30 min. The reaction mixture was then heated at 55° C. for 1.5 h. Next, ethyl acetate (4 L) was used to dissolve the reaction mixture and the resulting solution was poured slowly into a solution of $Na_2S_2O_5$ (650g) in ice water (4 L) and the flask was rinsed with ethyl acetate (2 L) and stirred for 15 min. The resulting layers were separated and the aqueous phase (pH~3) was extracted with ethyl acetate (2 L). The combined organic layers were washed with water (2 L×2), brine (1 L), dried over $Mg_2SO_4$, filtered, and concentrated in vacuo. The crude material was purified via silica gel plug (ethyl acetate/hexanes) to afford X4 (370g, 91%) as a white solid. $^1$HNMR ($CDCl_3$, 400 MHz) δ 7.83 (d, 1H), 7.43 (d, 1H), 7.35 (dd, 1H), 3.93 (s, 3H), 3.90 (s, 3H).

Compound X5:

To a 12 L 3-necked round bottomed flask equipped with a mechanical stirrer, thermometer, nitrogen inlet, and containing a solution of X4 (270 g, 0.925 mol) in THF (4 L) was added $LiBH_4$ (60.4 g, 2.77 mol) portionwise at room temperature. The reaction mixture was placed in an ice bath and methanol (135 mL) was added dropwise. After the addition was complete the ice bath was removed and the reaction was heated to 65° C. for 1 h. The reaction was then cooled in an ice bath and poured into an ice cold solution of saturated aq. $NH_4Cl$ (2 L) and ethyl acetate (4 L) followed by rinsing of the flask with ethyl acetate (2 L). The solution was stirred for 15 min., the layers were separated and the aqueous layer was extracted with ethyl acetate (4 L). The combined organic layers were washed with water (2 L×2), brine (1 L), dried over $MgSO_4$, filtered and concentrated in vacuo to afford X5 (>quantitative) as a light-yellow oil. $^1$HNMR (CDCl$_3$, 400 MHz) δ 7.70 (d, 1H), 6.86 (d, 1H), 6.67 (dd, 1H), 4.64 (d, 2H), 3.88 (s, 3H).

Compound X6:

To a 12 L 3-necked round bottomed flask equipped with a mechanical stirrer, thermometer, addition funnel, nitrogen inlet, and containing a solution of (COCl)$_2$ (123.7 g, 0.975 mol) in DCM (3.5 L) at −70° C. was added a solution of DMSO (173 g, 2.215 mol) in DCM (250 mL) over 30 min. and was stirred an additional 30 min. at −72° C. Next, a solution of X5 (234 g, 0.886 mol) in DCM (1 L) was added over 1.5 h to the reaction solution keeping the reaction temperature between −65° C. and −70° C. and then the reaction solution was stirred for an additional 30 min. at −70° C. Next, triethylamine (363 g, 3.587 mol) was added over 15 min. and then the reaction mixture was stirred for an additional 1 h at −65° C. The cooling bath was removed and the reaction mixture was poured into an extractor filled with ice water (3 L) and stirred for 15 min. The layers were separated and the aqueous layer was extracted with DCM (2 L). The combined organic layers were washed with HCl (1N, 1.5 L), water (2 L×3), brine (1 L), dried over MgSO$_4$, filtered, and dried in vacuo. The crude material was triturated with hexanes (300 mL), filtered, washed with hexanes (100 mL×2), and dried under vacuum to afford X6 (212.7 g, 92%) as an off-white solid. $^1$HNMR (CDCl$_3$, 400 MHz) δ 9.93 (s, 1H), 7.96 (d, 1H), 7.27 (d, 1H), 7.17 (dd, 1H), 3.94 (s, 3H).

Compound X8:

To a room temperature solution of X7 (50.0 g, 0.152 mol) and X6 (37.7 g, 0.144 mol) in THF/EtOH (350 mL/105 mL) and under nitrogen was added LiOH*H$_2$O (14.6 g, 0.349 mol). After 24 h, the reaction was diluted with ethyl acetate and water and the aqueous layer was extracted with ethyl acetate. The combined organic layers were dried over MgSO$_4$, and concentrated in vacuo. The crude material was purified by silica gel chromatography with ethyl acetate/hexanes to afford a yellow oil. The yellow oil was then dissolved in hot hexanes and gradually cooled to room temperature and then placed in an ice-bath. The resulting solid was filtered and washed with cold hexanes to afford X8 (23.97 g, 38%) as a white solid. $^1$HNMR (CDCl$_3$, 400 MHz) δ 7.76 (d, 1H), 7.52 (s, 1H), 6.75 (d, 1H), 6.68 (dd, 1H), 3.88 (s, 3H), 3.55 (t, 2H), 2.61 (m, 2H), 2.00 (m, 2H), 1.53 (s, 9H).

Compound X9:

To a round bottomed flask equipped with an addition funnel and nitrogen inlet and containing a 10° C. solution of X8 (23.97 g, 0.054 mol) in DCM (96 mL) was added trifluoroacetic acid (48 mL) dropwise over 45 minutes. After addition was complete, the cold bath was removed. After 3 h, the reaction was concentrated in vacuo and dried under vacuum to afford X9 (20.94 g, >100%) as an off-white solid. $^1$HNMR (CDCl$_3$, 400 MHz) δ 7.79 (t, 2H), 6.81 (d, 1H), 6.76 (dd, 1H), 3.90 (s, 3H), 3.59 (t, 2H), 2.70 (m, 2H), 2.05 (m, 2H); MS (LCMS, M+1) 381.0.

Compound X10:

Compound X10 was prepared following procedures similar to those of Steps 1 and 2 of Method S.

Compound X11:

If one were to couple Compounds X9 and X10 using a method similar to that of Method Q Step 5, then one would obtain compound X11.

Compound X12:

If one were to follow a method similar to Method Q Step 6 then one would convert Compound X11 to compound X12.

Compound X13:

If one were to use a method similar to Method Q Step 3 then one would convert Compound X12 will into compound X13.

Compound X14:

If one were to use a method similar to Method Q Step 7 then one would convert Compound X13 into compound X14.

Compound X15:

If one were to use a method similar to Method S Step 6 then one would convert Compound 14 into compound X15.

Compound 69:

If one were to heat compound X15 in a microwave reactor with Pd(PPh$_3$)$_4$, 1-methyl-1H-pyrazole-4-boronic acid pinacol ester, aqueous Na$_2$CO$_3$, and acetonitrile then one would obtain compound 69:

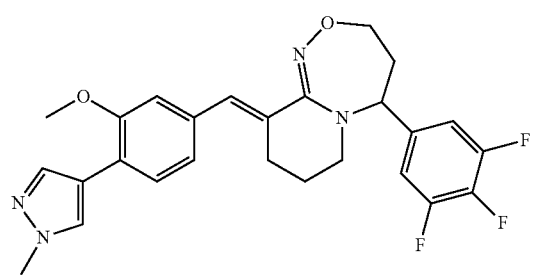

after work-up and purification.

Compound 70:

If one were to heat compound X15 in a microwave reactor with Pd(PPh$_3$)$_4$, 4-(tributylstannyl)-pyridazine, and dioxane then one would obtain compound 70:

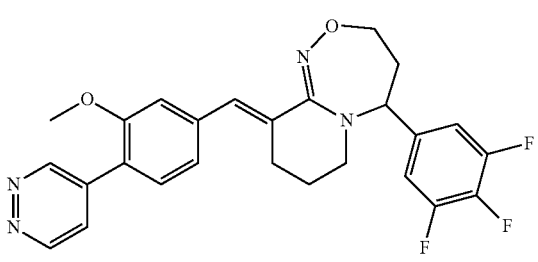

work-up and purification.

Compounds 71 to 107:

If one were to use the appropriate reagents to provide $R^9$ groups 14g to 50g identified in procedures similar to those in Method X and in the preparation of compounds 69 and 70, then one would obtain compounds of formula X16:

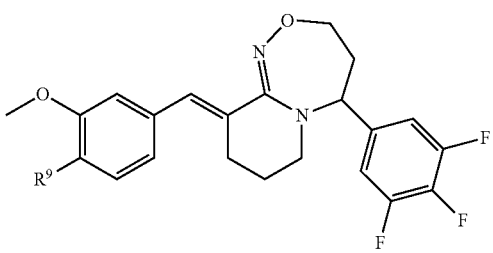

wherein R⁹ and the compound of formula X16 are identified in Table 5.
TABLE 5
| Compound | R⁹ |
|---|---|
| 71 | 14 g |
| 72 | 15 g |
| 73 | 16 g |
| 74 | 17 g |
| 75 | 18 g |
| 76 | 19 g |
| 77 | 20 g |
| 78 | 21 g |
| 79 | 22 g |
| 80 | 23 g |
| 81 | 24 g |
| 82 | 25 g |
| 83 | 26 g |
| 84 | 27 g |
| 85 | 28 g |
| 86 | 29 g |
| 87 | 30 g |
| 88 | 31 g |
| 89 | 32 g |
| 90 | 33 g |
| 91 | 34 g |
| 92 | 35 g |
| 93 | 36 g |
| 94 | 37 g |
| 95 | 38 g |
| 96 | 39 g |
| 97 | 40 g |
| 98 | 41 g |
| 99 | 42 g |
| 100 | 43 g |
| 101 | 44 g |
| 102 | 45 g |
| 103 | 46 g |
| 104 | 47 g |
| 105 | 48 g |
| 106 | 49 g |
| 107 | 50 g |
Method Y
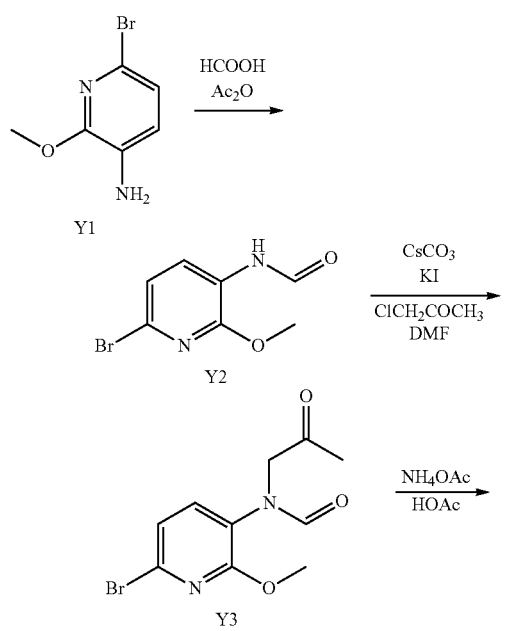
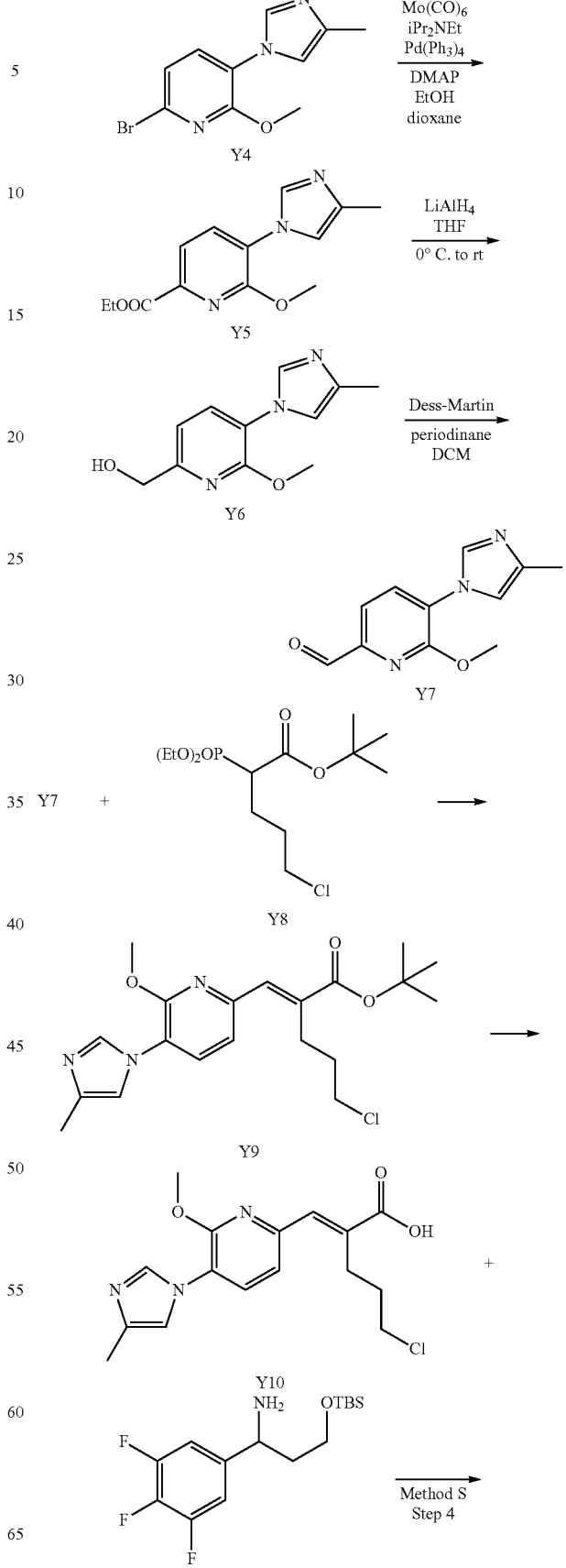

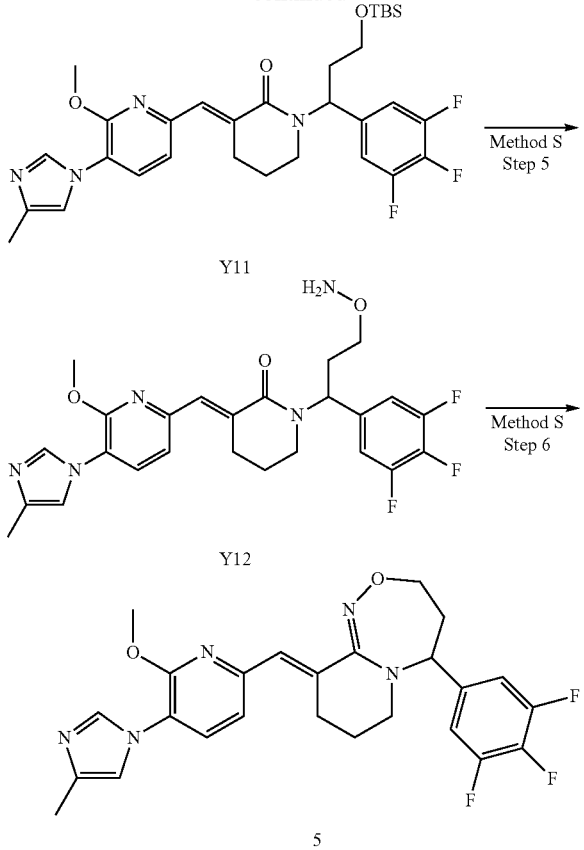

Preparation of Y2

Acetic anhydride (11.3 mL, 120 mmol) was added dropwise to formic acid (17.0 mL, 450 mmol) then stirred at room temperature for 24 minutes. The formic acid and acetic anhydride mixture was added to 6-bromo-2-methoxypyridin-3-amine (Y1) in 50 mL of THF via cannula. The reaction was stirred at room temperature for 30 minutes. An additional 10 mL of THF was used to aid the transfer. The reaction was stirred at room temperature for 2 h. The reaction was quenched with 140 mL of ice cold water. This solution was then filtered leaving a white solid. The solid was rinsed with additional water, dried on the filter, then left under vacuum overnight to yield 5.04 g (70%) of the formamide (Y2).

$^1$H NMR (CDCl$_3$ 400 MHz) δ 8.45-8.43 (m, 2H), 7.61 (br s, 1H), 7.08 (d, J=8.0 Hz, 1H), 4.03 (s, 3H).
MS: M+1=231.0.

Preparation of Y3

The formamide Y2 (5.04 g, 21.8 mmol) was dissolved in 40 mL of DMF. Potassium iodide (0.47 g, 2.83 mmol) was added followed by cesium carbonate (8.2 g, 42.5 mmol). Then chloroacetone (3.5 mL, 43.7 mmol) was added at room temperature and the solution was stirred for 3 h. The reaction was allowed to sit overnight in the freezer. The reaction was quenched with 200 mL of water and washed with 275 mL of Hex/EtOAc (1:3) solution. The organics were dried over sodium sulfate, filtered and concentrated. The reaction mixture was purified by column (330g, Hex./EtOAC, 100/0 to 50/50 over 54 min then 10 min of 50/50 then started up to 78% EtOAc in 72 min) to provide 7.16 g of Y3.

$^1$H NMR (CDCl$_3$ 400 MHz) δ 8.22 (s, 1H), 7.48 (d, J=7.8 Hz, 1H), 7.13 (d, J=7.8 Hz, 1H), 4.47 (s, 2H), 3.98 (s, 3H), 2.16 (s, 3H).
LCMS: M+1=278.1.

Preparation of Y4

The formamide Y3 (7.16 g, 25.0 mmol) was dissolved in acetic acid (90.0 mL, 1.58 mol) followed by addition of ammonium acetate (10.22 g, 132 mmol). The reaction was stirred at 130° C. for 2 h. During the reaction the solution became dark. The temperature of the reaction was increased to 140° C. for 1.3 h. The reaction was slowly cooled to room temperature. The reaction was quenched with 700 mL of 2N NH$_4$OH (giving the solution a pH of 6). The aqueous layer was washed with 500 mL of ethyl acetate. An additional 85 mL of ammonium hydroxide (conc.) was added to the aqueous layer (brought to pH 8) and the aqueous layer was washed with 200 mL of Ethyl acetate. The organic layer was dried over sodium sulfate then concentrated. The product was purified by column (330g silica, Hex./EtOAc from 100/0 to 0/100 in 55 min, then EtOAc for 1 h). This yielded 4.02 g (60%) of the imidazole Y4.

$^1$H NMR (CDCl$_3$ 400 MHz) δ 7.72 (d, J=1.6 Hz, 1H), 7.40 (d, J=7.8 Hz, 1H), 7.16 (d, J=7.8 Hz, 1H), 6.92 (d, J=1.6 Hz, 1H), 4.02 (s, 3H), 2.28 (s, 3H).
MS: M+1=268.2.

Preparation of Y5

6-bromo-2-methoxy-3-(4-methyl-1H-imidazol-1-yl)pyridine Y4 (1.01 g, 3.77 mmol) was divided into 4 vials (252, 257, 250, and 250 mg respectively). To each vial 1.5 mL of dioxane, Mo(CO)$_6$ (273, 275, 278, and 280 mg respectively, 1.11 g, 4.02 mmol total), diisopropylethylamine (330 uL each, 7.56 mmol total), palladium tetrakis (51.5, 51.6, 52.0, 56.9 mg respectively, 211.9 mg total, 5 mol %), 1.5 mL of EtOH each were added respectively. Dimethylaminopyridine (76, 66, 67, and 68 mg respectively, 277 mg, 2.27 mmol total) was added then immediately rinsed down the flask with 0.5 mL of EtOH and capped. The reaction was wheated at 150° C. for 15 minutes in the microwave on fixed time hold setting and high absorption setting. After reaction the solution had changed to a black color. The compound was filtered through celite and washed with EtOH then concentrated. The compound was purified by column (120 g, Hex./EtOAC, 100/0 to 50/50 over 45 min then to 100/0 over 20 min then 10 min of 0/100). This yielded 724 mg (74%) of ethyl 6-methoxy-5-(4-methyl-1H-imidazol-1-yl)picolinate (Y5).

$^1$H NMR (CDCl$_3$ 400 MHz) δ 7.79 (s, 1H), 7.67 (d, J=7.8 Hz, 1H), 7.54 (d, J=7.8 Hz, 1H), 6.93 (s, 1H), 4.30 (q, J=7.0 Hz, 2H), 3.99 (s, 3H), 2.16 (s, 3H), 4.30 (t, J=7.0 Hz, 3H).
MS: M+1=262.1.

Preparation of Y6

Compound Y5 (560 mg, 2.15 mmol) was dissolved in 85 mL of THF. The reaction was cooled to 0° C. A LAH pellet (390 mg, 10.3 mmol) was crushed up and added slowly. The reaction was stirred to 0° C. for 5 min then the ice bath was removed and the reaction was allowed to warm to room temperature. The solution was cooled to 0° C. and quenched with 80 mL cool water, slowly added at first with lots of initial bubbling. EtOAc was added and the aqueous layer was extracted with EtOAc three times. The organic layer was dried over sodium sulfate, and concentrated. The compound was purified by column (40 g, Hex./EtOAc, 0/100 to 0/100 over 50 min then, 10 min at 100% EtOAc to 20% MeOH in EtOAc in 25 min). This yielded 272.3 mg (58%) of (6-methoxy-5-(4-methyl-1H-imidazol-1-yl)pyridin-2-yl)methanol Y6.

¹H NMR (CDCl₃ 400 MHz) δ 7.72 (s, 1H), 7.53 (d, J=7.8 Hz, 1H), 7.00 (d, J=7.8 Hz, 1H), 6.93 (s, 1H), 4.73 (s, 2H), 4.01 (s, 3H), 3.77 (br s, 1H), 2.28 (s, 3H).

MS, M+1=220.0.

Preparation of Y7

The alcohol Y6 (272 mg, 1.24 mmol) was dissolved in 60 mL of DCM then Dess-Martin periodinane (1.043 g, 2.46 mmol) was added. The reaction was stirred at room temperature. Additional portions of Dess-Martin periodinane were added to the reaction over the next 1.7 h (100.6 mg, 0.24 mmol and 94 mg, 2.2 mmol respectively). The reaction was quenched with 65 mL of sodium thiosulfate solution. 70 mL of DCM was added then the layers were mixed and separated. The organic layer was then washed with sodium thiosulfate (30 mL) then Sat. sodium bicarbonate solution (2×70 mL). The organic layer was dried over sodium sulfate, filtered and concentrated. A white solid was obtained. The compound was purified by column (100% DCM to 3% MeOH in DCM over 40 min then 3% for 15 min). This yielded 251 mg (93%) of the desired aldehyde Y7.

¹H NMR (CDCl₃ 400 MHz) δ 9.98 (s, 1H), 7.94 (s, 1H), 7.70 (d, J=1.5 Hz, 1H), 7.05 (s, 1H), 4.14 (s, 3H), 2.31 (s, 3H) 1.69 (br s, 1H).

MS: M+1=218.1.

Preparation of Y9

If one were to follow a procedure similar to Method Q Step 1 then one would obtain Y9.

Preparation of Y10

If one were to treat Y9 with TFA in DCM at rt and one were to remove the solvent at the completion of the reaction then one would obtain Y10. The crude reaction of Y10 will be directly used in the preparation of Y11.

Preparation of Y11

Compound Y11 would be prepared if one were to follow a procedure similar to that of Method S Step 4.

Preparation of Y11

Compound Y12 would be prepared if one were to follow a procedure similar to that of Method S Step 5.

Preparation of Compound 5

Compound 5 would be prepared if one were to follow a procedure similar to that of Method S Step 6.

Method Z

Following procedures similar to those of Method R Steps 1 to 3, compounds 108 and 109 in Table 6 were prepared:

TABLE 6

| Compound | Observed Mass | Rt (min) |
|---|---|---|
| 108 | 393.22 | 2.4 |
| 109 | 393.22 | 2.4 |

Method AA

285

-continued

AA4

110

111

Step 1:
AA3 was made from AA1 and AA2 following a similar procedure to that of Method R, Step 1 using HATU as coupling reagent.

Steps 2-4:
AA4 was made from AB3 following similar procedures to that of Method R, Steps 2 to 3.

Step 5:
110 was prepared by using a similar procedure to that of Method S Step 6. LCMS: observed 380 (M+1), Step 6:
110 (6.5 mg, 0.017 mmole)) was treated with RCOCl (R=phenyl, 2.4 µL, 0.021 mmole) in 0.5 mL DCM and 8.8 µL (0.051 mmole) DIEA at rt for 3 h to give 111 (R=phenyl) after purification on a C18 column. LCMS: observed 484 (M+1).

286

Method AB

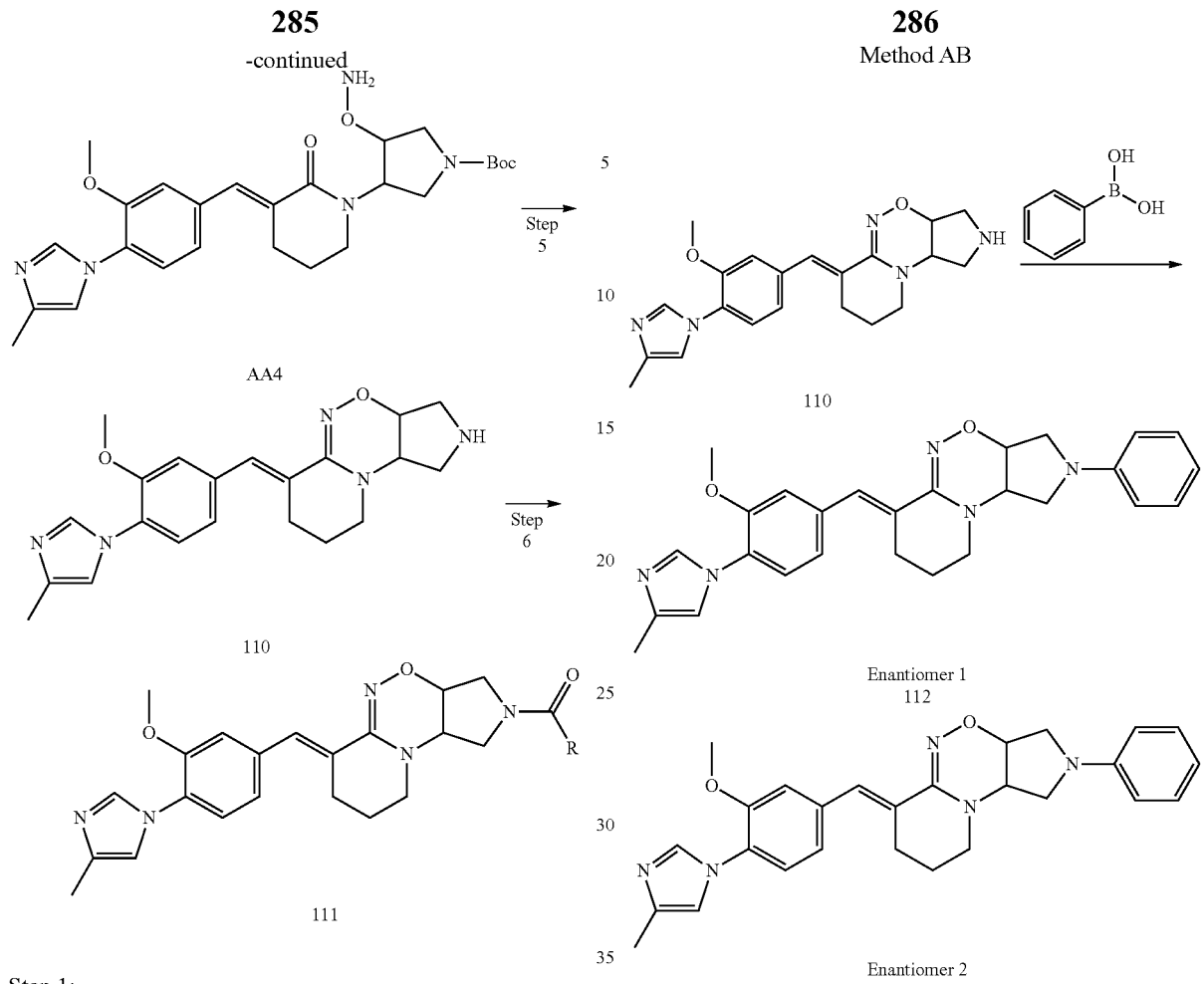

Enantiomer 1
112

Enantiomer 2
113

TEA (13.4 µL, 0.096 mmole) in 0.45 mL DCM was injected to a N₂ flushed sealed tube containing 110 (18.3 mg, 0.048 mmole), ArB(OH)₂ (Ar=phenyl, 5.9 mg, 0.048 mmole), and Cu(OAc)₂ (8.8 mg, 0.048 mmole). The reaction mixture was stirred at rt for 4 h, diluted with DCM and water. The aqueous phase was extracted with DCM. The crude was purified on a C18 column to give a racemate, which was resolved on a Lux Cellulose-1 column with isopropanol/hexane to give two enantiomers 112 and 113. LCMS: observed 456.2 (M+1).

Table 7 provides data for compounds 110-114. Compound 114 was prepared following a similar procedure to that of Method AA.

TABLE 7

| Compound | Structure | Rt (min) | Obs. Mass |
|---|---|---|---|
| 110 | 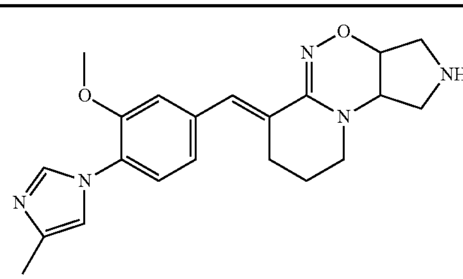 | 1.8 | 380.21 |

TABLE 7-continued

| Compound | Structure | Rt (min) | Obs. Mass |
|---|---|---|---|
| 111 | 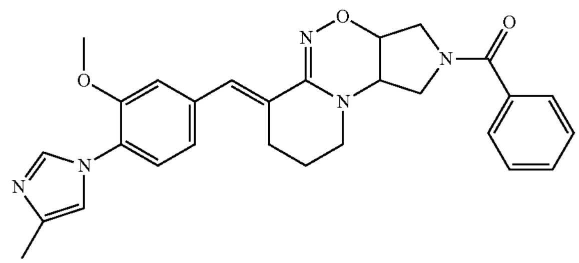 [SMILES: COc1cc(/C=C2\CCCN3C2=NOC2CN(C(=O)c4ccccc4)CC23)ccc1-n1cnc(C)c1] | 3 | 484.27 |
| 112 | Enatiomer 1 | 2.3 | 456.25 |
| 113 | Enatiomer 2 | 2.3 | 456.25 |
| 114 | 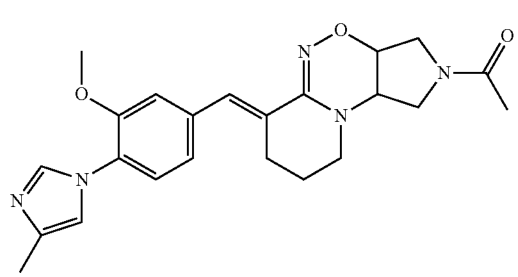 [SMILES: COc1cc(/C=C2\CCCN3C2=NOC2CN(C(C)=O)CC23)ccc1-n1cnc(C)c1] | 2.3 | 422.23 |

Method AC

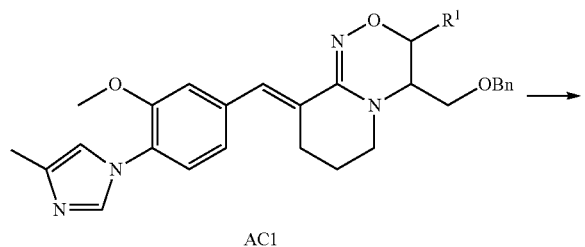

ACl

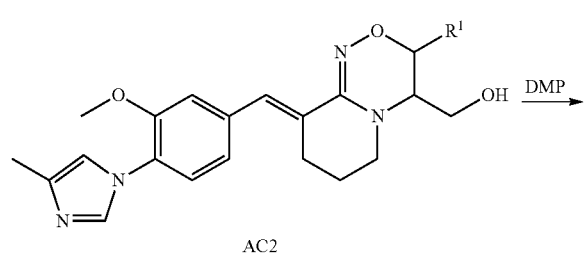

AC2

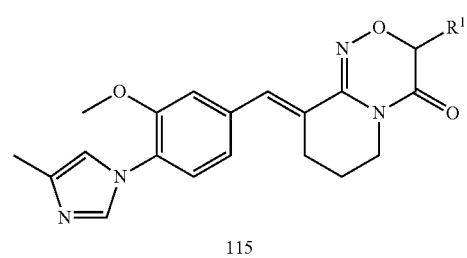

115

AC1 was prepared following a procedure similar to that of Method R.

A solution of AC1 (20 mg, $R^1$=H) in $CH_2Cl_2$ was cooled to −10° C. To this solution was then added $BCl_3$ (0.15 mL, 1M in hexanes). The resulted mixture was then allowed to warm up to room temperature. Stirring continued at room temperature for 2 hours before the reaction was quenched by addition of water. The organic layer was then separated and discarded. The water layer was basified and extracted with $CH_2Cl_2$ (3×20 mL). The combined organic layer was dried over $Na_2SO_4$. After removal of the volatile, the residue was purified by flash chromatography to afford the desired target AC2 ($R^1$=H). LCMS: observed 369.2 ($M^+$+1). $^1$H NMR (CDCl$_3$, 400 MHz, δ): 7.82 (1H, s), 7.54 (1H, s), 7.33 (1H, d, J=7.4 Hz), 7.04-7.08 (3H, m), 4.44 (1H, d, J=11.5 Hz), 3.95-4.08 (2H, m), 3.93 (3H, s), 3.84 (1H, d, J=12 Hz), 3.55 (1H, m), 3.44 (1H, m), 3.28 (1H, m), 2.79-2.94 (2H, m), 2.42 (3H, s), 2.02 (2H, m).

To a solution of AC2 ($R^1$=H, 180 mg) in $CH_2Cl_2$ was added Dess-Martin Periodate (700 mg). The resulted mixture was stirred at room temperature overnight. After which, the solution was washed with NaHCO3 and the crude mixture obtained was then purified through flash chromatography to yield the desired 115 ($R^1$=H). LCMS: observed 353.2 (M+1).

Method AD

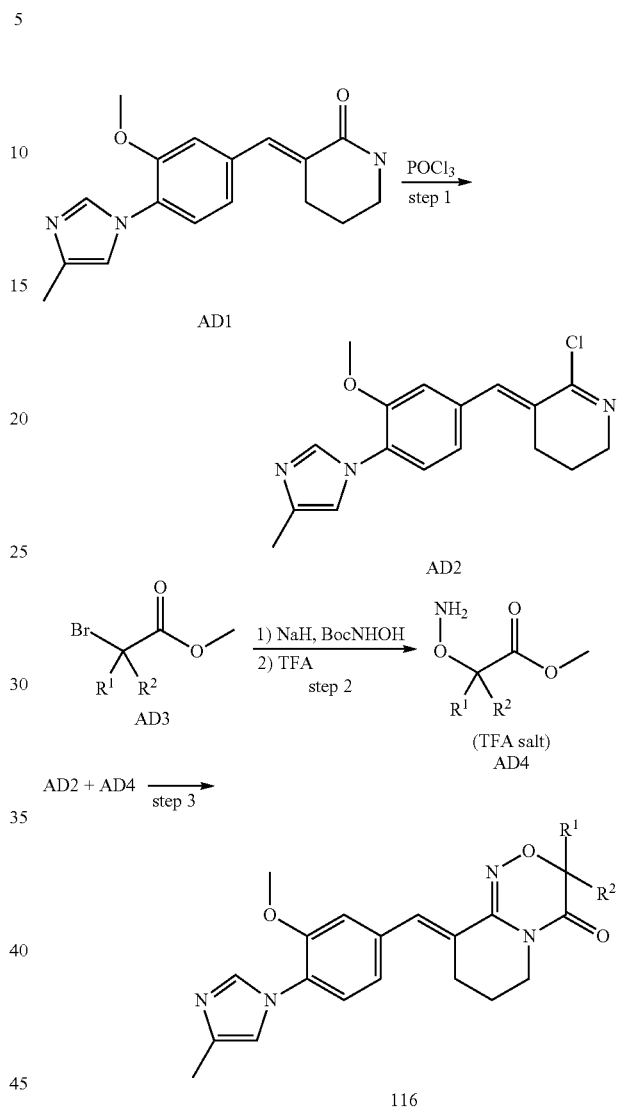

Step 1:
AD1, synthesized by a procedure similar to that described in Method R, was treated with $POCl_3$ at 100° C. to afford AD2.

Step 2:
AD3 ($R^1$ and $R^2$ together formed a cyclohexyl ring) was mixed with BocNHOH in DMSO and treated with NaH (1 equiv.) at 50° C. overnight. After aqueous work up, the crude mixture was then treated with TFA to afford AD4 ($R^1$ and $R^2$ together formed a cyclohexyl ring) as the TFA salt.

Step 3:
AD2 and AD4 ($R^1$ and $R^2$ together formed a cyclohexyl ring) was mixed in MeOH and heated at 120° C. for 1-3 hours. After reverse phase HPLC, 116 ($R^1$ and $R^2$ together formed a cyclohexyl ring) was obtained. LCMS: observed 421.2 (M+1).

Table 8 provides data for compounds 115-117. Compound 117 was prepared following a similar procedure to that of Method AD.

TABLE 8

| Compound | Structure | Rt (min) | Obs. Mass |
|---|---|---|---|
| 115 | 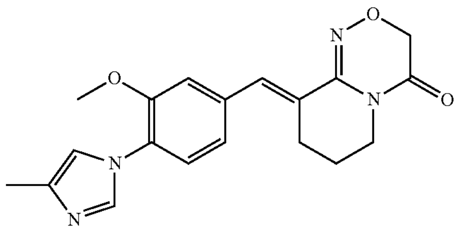 [SMILES: COc1cc(/C=C2\CCCN3C(=O)CON=C23)ccc1-n1cnc(C)c1] | 2.8 | 353.19 |
| 116 | 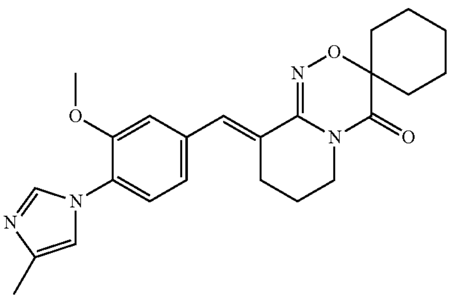 [SMILES: COc1cc(/C=C2\CCCN3C(=O)C4(CCCCC4)ON=C23)ccc1-n1cnc(C)c1] | 2.3 | 421.23 |
| 117 | 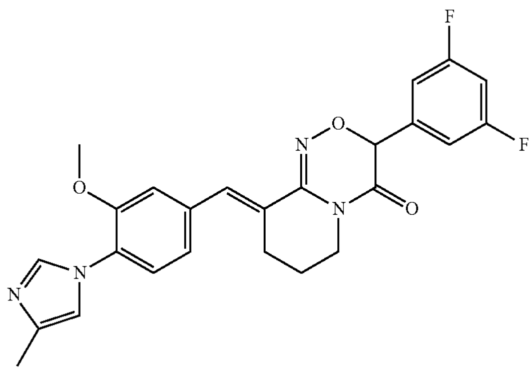 [SMILES: COc1cc(/C=C2\CCCN3C(=O)C(c4cc(F)cc(F)c4)ON=C23)ccc1-n1cnc(C)c1] | — | — |

Assay:

Secretase Reaction and Aβ Analysis in Whole Cells: HEK293 cells overexpressing APP with Swedish and London mutations were treated with the specified compounds for 5 hour at 37° C. in 100 ml of DMEM medium containing 10% fetal bovine serum. At the end of the incubation, total Aβ, Aβ40 and Aβ42 were measured using electrochemiluminescence (ECL) based sandwich immunoassays. Total Aβ was determined using a pair of antibodies TAG-WO2 and biotin-4G8, Aβ40 was identified with antibody pairs TAG-G2-10 and biotin-4G8, while Aβ42 was identified with TAG-G2-11 and biotin-4G8. The ECL signal was measured using Sector Imager 2400 (Meso Scale Discovery).

MS Analysis of Aβ Profile: Aβ profile in conditioned media was determined using surface enhanced laser desorption/ionization (SELDI) mass spectrometry. Conditioned media was incubated with antibody WO2 coated PS20 ProteinChip array. Mass spectra of Aβ captured on the array were read on SELDI ProteinChip Reader (Bio-Rad) according to manufacture's instructions.

CSF Aβ Analysis: Aβ in rat CSF was determined using MSD technology as described above. Aβ40 was measured using antibody pair Tag-G2-10 and biotin-4G8, while Aβ42 was measured using Tag-anti Aβ42 (Meso Scale Discovery) and biotin-4G8. The ECL signal was measured using Sector Imager 2400 (Meso Scale Discovery).

Matrix-assisted laser desorption/ionization mass spectrometric (MALDI MS) analysis of Aβ is performed on a Voyager-DE STR mass spectrometer (ABI, Framingham, Mass.). The instrument is equipped with a pulsed nitrogen laser (337 nm). Mass spectra are acquired in the linear mode with an acceleration voltage of 20 kV. Each spectrum presented in this work represents an average of 256 laser shots. To prepare the sample-matrix solution, 1 µL of immunoprecipitated Aβ sample is mixed with 3 µL of saturated α-cyano-4-hydroxycinnamic acid solution in 0.1% TFA/acetonitrile. The sample-matrix solution is then applied to the sample plate and dried at ambient temperature prior to mass spectrometric analysis. All the spectra are externally calibrated with a mixture of bovine insulin and ACTH (18-39 clip).

Compounds 1 to 27, 52 to 63, 65 to 68 and 109 to 115 had an Aβ42 $IC_{50}$ within the range of about 16 nM to about 14876 nM. Certain compounds of the invention had an Aβ42 $IC_{50}$ within the range of about 16 nM to about 115 nM.

Compounds 1 to 27, 52 to 63, 65 to 68 and 109 to 115 had Aβtotal/Aβ42 ratio within the range of about 1.3 to 650. Certain compounds of the invention had Aβtotal/A⊕42 ratio within the range of about 409 to 650.

While the present invention has been described in conjunction with the specific embodiments set forth above, many alternatives, modifications and other variations thereof will

What is claimed is:
1. A compound of the formula:

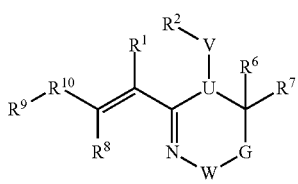

Formula I or a pharmaceutically acceptable salt thereof, wherein:
$R^1$ and $R^2$ are joined together to form a piperidine, wherein said piperidine is optionally substituted with 1-5 independently selected $R^{21}$ substituents;
U is N;
W is —O—;
G is —(C($R^3$)($R^4$))$_2$— (wherein each $R^3$ and each $R^4$ are independently selected);
V is a bond;
each $R^6$ and $R^7$ is independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
each $R^3$ is independently selected from the group consisting of H, halo, —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})R^{17})$, —$N(R^{15})C(O)OR^{16}$, —$C(O)R^{15}$, —$C(O)OR^{15}$, —$C(=NOR^{15})R^{16}$, —$C(O)N(R^{15})(R^{16})$, —$S(O)N(R^{15})(R^{16})$, $S(O)_2N(R^{15})(R^{16})$, —$S(O)R^{15}$, —$S(O)_2R^{24}$, —$P(O)(OR^{15})(OR^{16})$, =$NOR^{15}$, —$N_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;
each $R^4$ is independently selected from the group consisting of H, halo, —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16}R^{17})$, —$N(R^{15})S(O)N(R^{16})(R^{17})$, —$N(R^{15})C(O)N(R^{16})(R^{17})$, —$N(R^{15})C(O)OR^{16}$, —$C(O)R^{15}$, —$C(O)OR^{15}$, —$C(=NOR^{15})R^{16}$, —$C(O)N(R^{15})(R^{16})$, —$S(O)N(R^{15})(R^{16})$, —$S(O)_2N(R^{15})(R^{16})$, —$S(O)R^{15}$, —$S(O)_2R^{24}$, —$P(O)(OR^{15})(OR^{16})$, =$NOR^{15}$, —$N_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents, and provided that when one of $R^3$ or $R^4$ is selected from the group consisting of: —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{24}$, —$P(O)(OR^{15})(OR^{16})$, =$NOR^{15}$, and —$N_3$, then the other is not selected from the group consisting of: —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{24}$, —$P(O)(OR^{15})(OR^{16})$, =$NOR^{15}$, and —$N_3$;

$R^8$ is selected from the group consisting of H, halo, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl- being optionally substituted with 1-3 independently selected $R^{21}$ substituents;

$R^9$ is selected from the group consisting of

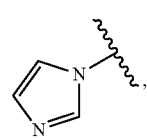
1g

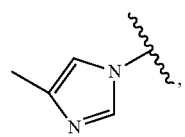
2g

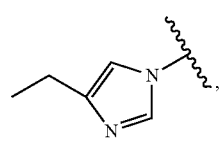
3g

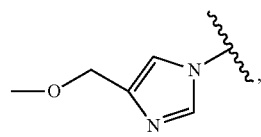
4g

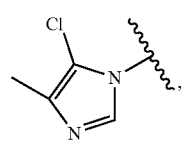
5g

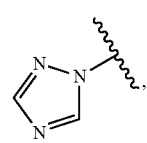
6g

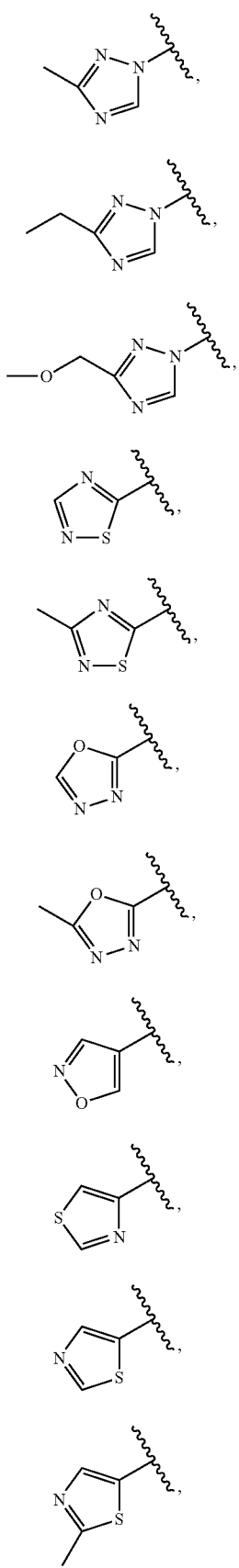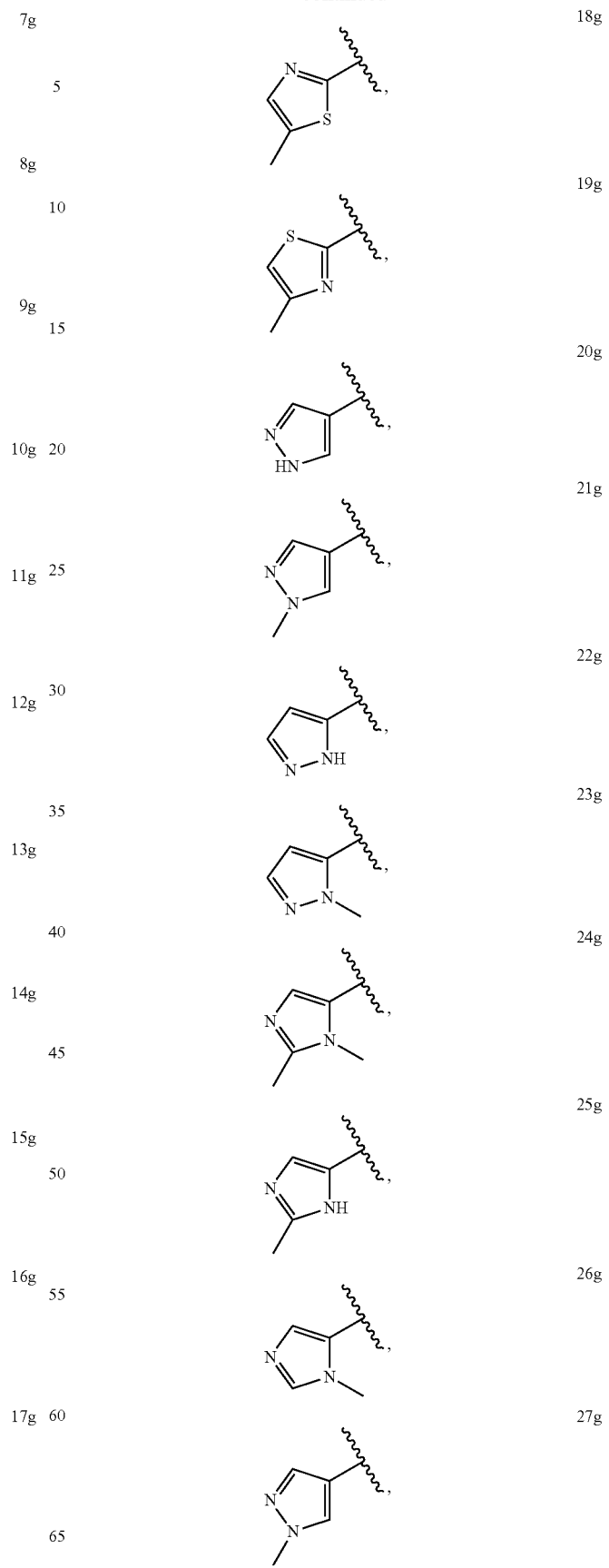

28g 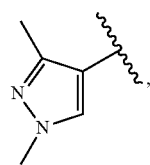
29g 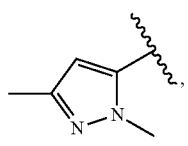
30g 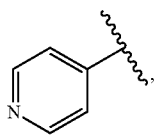
31g 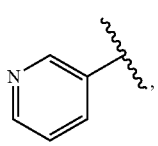
32g 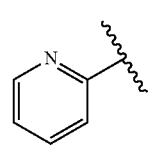
33g 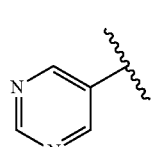
34g 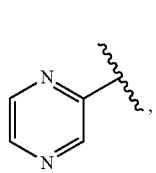
35g 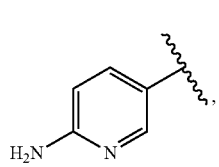
36g 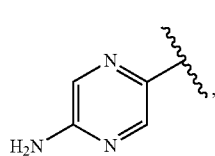
37g 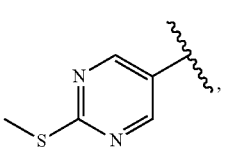
38g 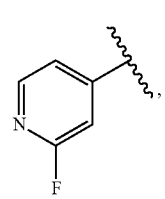
39g 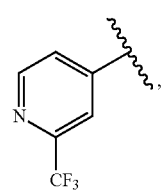
40g 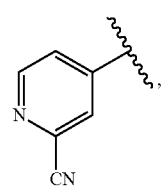
41g 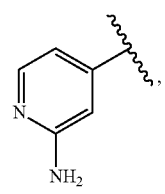
42g 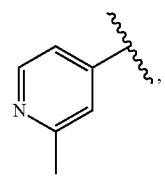
43g 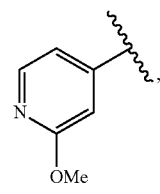
44g 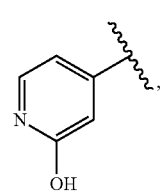
45g -continued 46g 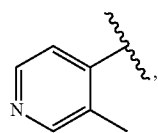, 47g 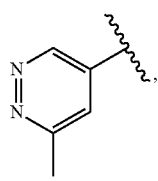, 48g 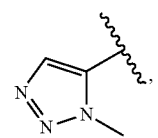, 49g 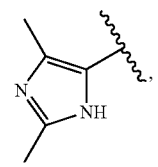, 50g 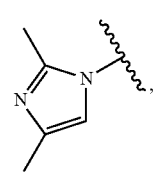, 51g 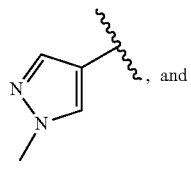, and 52g 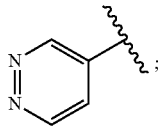;

$R^{10}$ is selected from the group consisting of

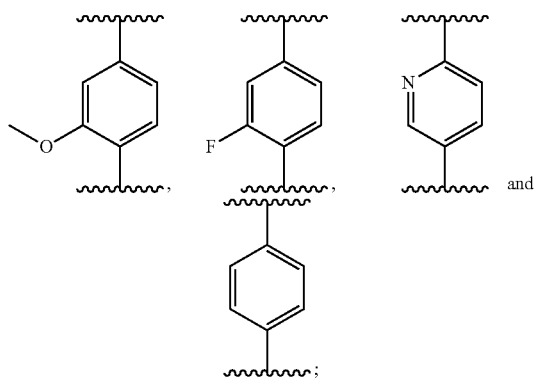

$R^{15}$, $R^{16}$ and $R^{17}$ are independently selected from the group consisting of H, alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl-, arylheterocyclyl-, $(R^{18})_r$-alkyl-, $(R^{18})_r$-cycloalkyl, $(R^{18})_r$-cycloalkylalkyl-, $(R^{18})_r$-heterocyclyl, $(R^{18})_r$-heterocyclylalkyl-, $(R^{18})_r$-aryl, $(R^{18})_r$-arylalkyl-, $(R^{18})_r$-heteroaryl and $(R^{18})_r$-heteroarylalkyl-; wherein r is 1-5;

each $R^{18}$ is independently selected from the group consisting of alkyl, alkenyl, alkynyl, aryl, arylalkyl-, arylalkenyl-, arylalkynyl-, —NO$_2$, halo, heteroaryl, HO-alkyoxyalkyl-, —CF$_3$, —CN, alkyl-CN, —C(O)R$^{19}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocyclyl), —S(O)$_2$N(alkyl)$_2$, —S(O)$_2$N(alkyl)(aryl), —OCF$_3$, —OH, —OR$^{20}$, —O-heterocyclyl, —O-cycloalkylalkyl, —O-heterocyclylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternately, two $R^{18}$ moieties on adjacent carbons can be linked together to form:

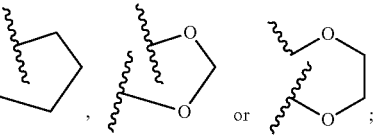

$R^{19}$ is selected from the group consisting of: alkyl, cycloalkyl, aryl, arylalkyl- and heteroarylalkyl-;

$R^{20}$ is selected from the group consisting of: alkyl, cycloalkyl, aryl, halo substituted aryl, arylalkyl-, heteroaryl and heteroarylalkyl-;

each $R^{21}$ group is independently selected from the group consisting of alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —OR$^{15}$, —C(O)R$^{15}$, —C(O)OR$^{15}$, —C(O)N(R$^{15}$)(R$^{16}$), —SF$_5$, —OSF$_5$, —Si(R$^{24}$)$_3$ wherein each R$^{24}$ is independently selected, —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$, —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)$_2$R$^{15}$, =NOR$^{15}$, —N$_3$, —NO$_2$ and —S(O)$_2$R$^{24}$; and wherein each of the R$^{21}$ alkyl, cycloalkenyl, cycloalkyl, cycloalkylalkyl-, heterocyclyl, heterocyclylalkyl-, aryl, arylalkyl-, heteroaryl, heteroarylalkyl-, alkenyl and alkynyl groups is optionally substituted with 1 to 5 independently selected R$^{22}$ groups;

each $R^{22}$ is independently selected from the group consisting of: alkyl, cycloalkyl, cycloalkenyl, heterocyclyl, aryl, heteroaryl, halo, —CN, —OR$^{15}$, —C(O)R$^{15}$, —C(O)OR$^{15}$, -alkyl-C(O)OR$^{15}$, C(O)N(R$^{15}$)(R$^{16}$), —SF$_5$, —OSF$_5$, —Si(R$^{24}$)$_3$ wherein each R$^{24}$ is independently selected, —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)$_2$R$^{16}$, —N(R15)S(O)$_2$R16, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —N$_3$, =NOR$^{15}$, -NO$_2$, -S(O)R$^{15}$ and —S(O)$_2$R$^{24}$; and each R$^{24}$ is independently selected from the group consisting of alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl-, arylheterocyclyl-, (R$^{18}$)$_r$-alkyl-, (R$^{18}$)$_r$-cycloalkyl-, (R$^{18}$)$_r$-cycloalkylalkyl-, (R$^{18}$)$_r$-heterocyclyl-, (R$^{18}$)$_r$-heterocyclylalkyl-, (R$^{18}$)$_r$-aryl-, (R$^{18}$)$_r$-arylalkyl-, (R$^{18}$)$_r$-heteroaryl- and (R$^{18}$)$_r$-heteroarylalkyl- (wherein R$^{18}$ and r are as defined above).

2. The compound of claim 1 or a pharmaceutically acceptable salt thereof, wherein at least one R$^{21}$ group selected from the group consisting of: —SF$_5$, —OSF$_5$, and —Si(R$^{24}$)$_3$ is present, and wherein each R$^{24}$ is independently selected, and wherein when there is more than one group, each group is independently selected.

3. The compound of claim 1 or a pharmaceutically acceptable salt thereof, wherein said compound is selected from the group consisting of:

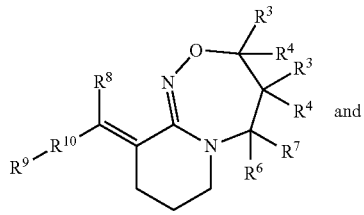

Z1

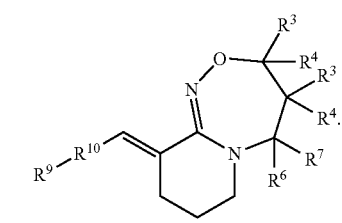

Z2 and

4. A compound which is selected from the group consisting of:

| Compound | Structure |
|---|---|
| 1 | ![racemate structure] racemate |
| 2 | ![racemate structure] racemate |
| 3 | ![Enantiomer 1 structure] Enantiomer 1 |
| 4 | ![Enantiomer 2 structure] Enantiomer 2 |
| 5 | ![racemate structure] racemate |
| 6 | ![Enantiomer 1 structure] Enantiomer 1 |

303
-continued
| Compound | Structure |
|---|---|
| 7 | 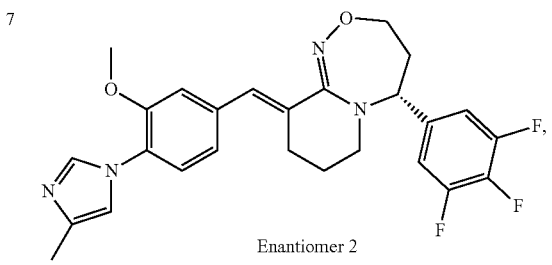<br>Enantiomer 2 |
| 8 | 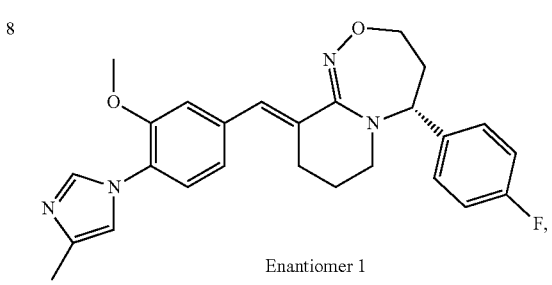<br>Enantiomer 1 |
| 9 | 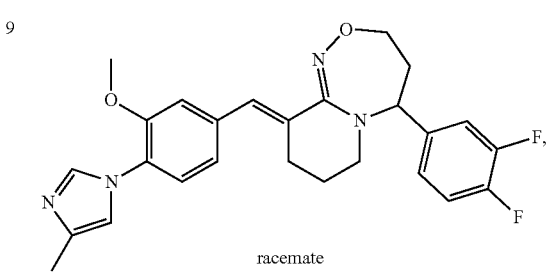<br>racemate |
| 10 | 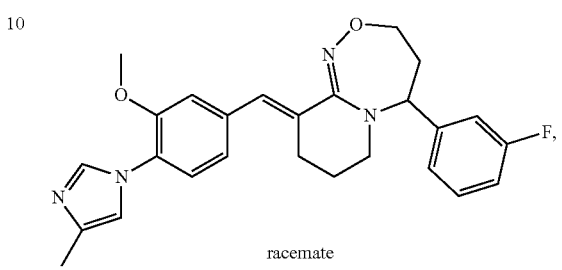<br>racemate |
| 11 | 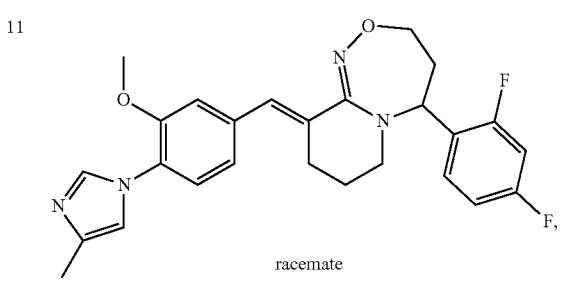<br>racemate |
304
-continued
| Compound | Structure |
|---|---|
| 12 | 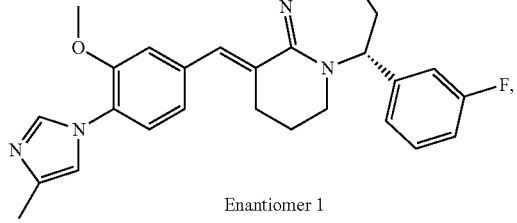<br>Enantiomer 1 |
| 13 | 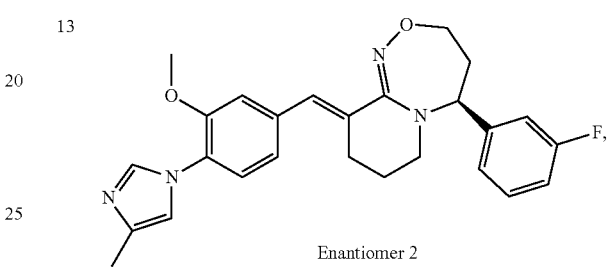<br>Enantiomer 2 |
| 14 | 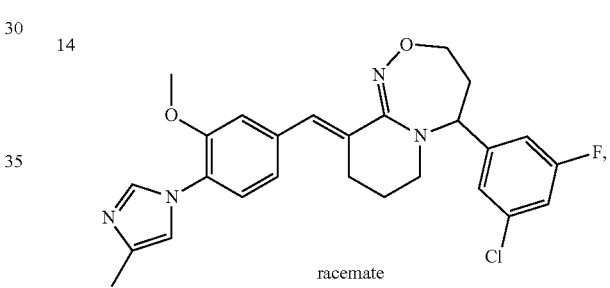<br>racemate |
| 15 | 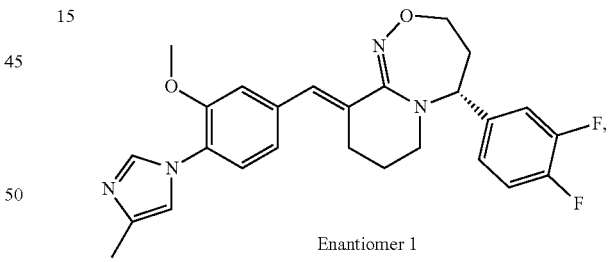<br>Enantiomer 1 |
| 16 | 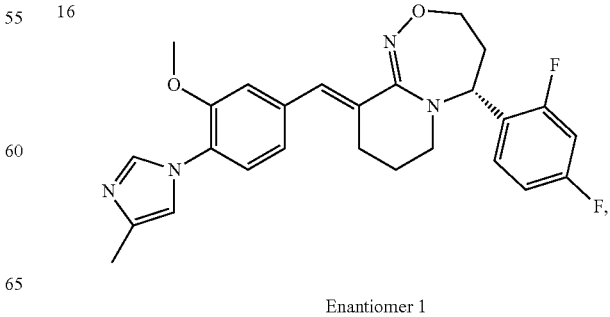<br>Enantiomer 1 |

| Compound | Structure |
|---|---|
| 17 | 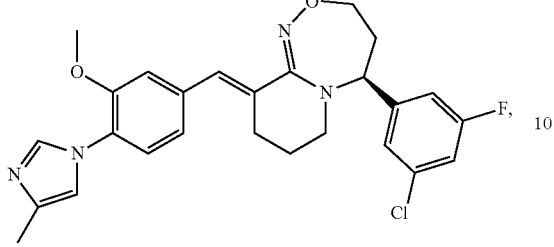<br>Enantiomer 2 |
| 18 | 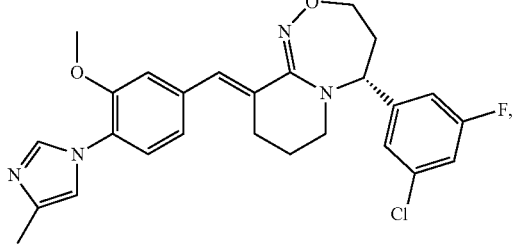<br>Enantiomer 1 |
| 19 | 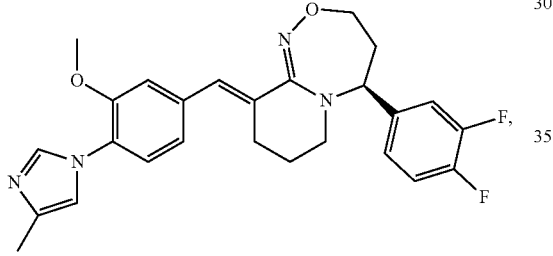<br>Enantiomer 2 |
| 20 | 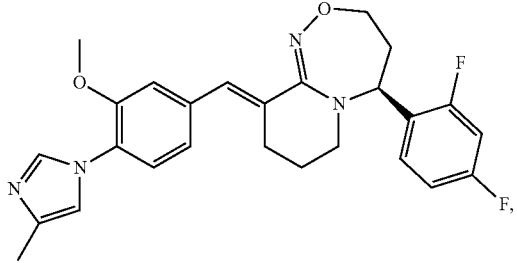<br>Enantiomer 2 |
| 21 | 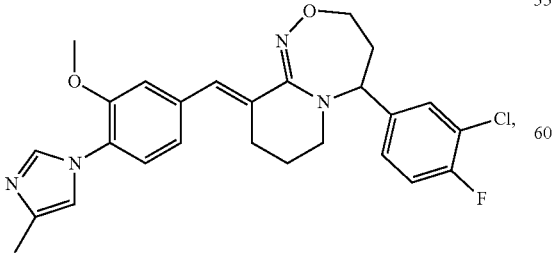<br>Enantiomer 2 |
| Compound | Structure |
|---|---|
| 22 | 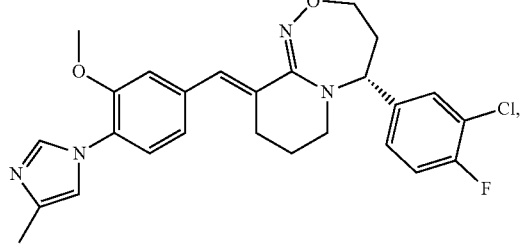<br>Enantiomer 1 |
| 23 | 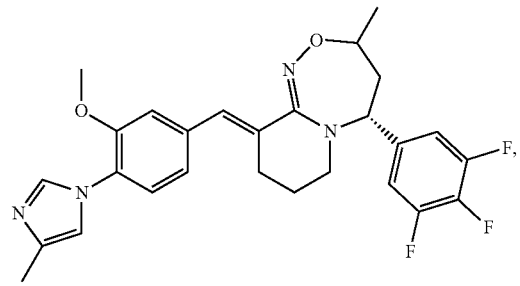<br>racemate |
| 24 | 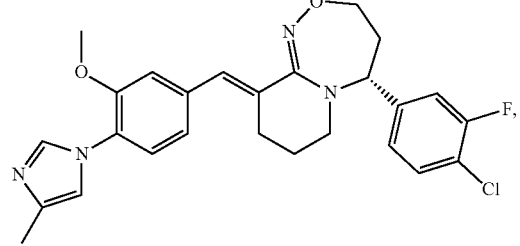<br>Enantiomer 1 |
| 25 | 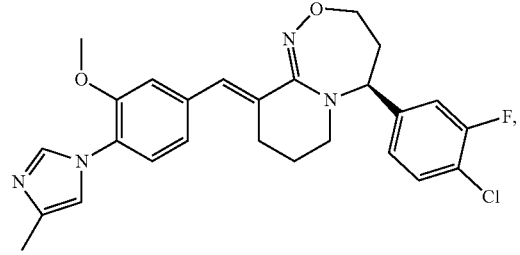<br>Enantiomer 2 |

| Compound | Structure |
|---|---|
| 26 | 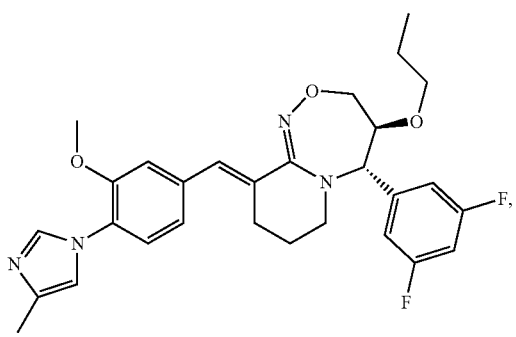<br>Enantiomer 1 |
| 27 | 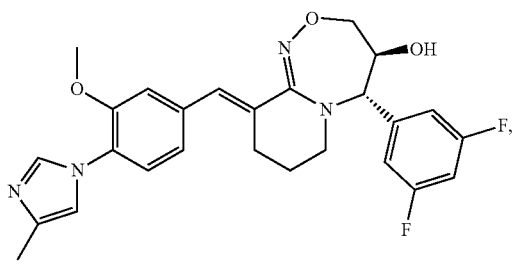<br>Enantiomer 1 |
| Compound | Structure |
|---|---|
| 52 | 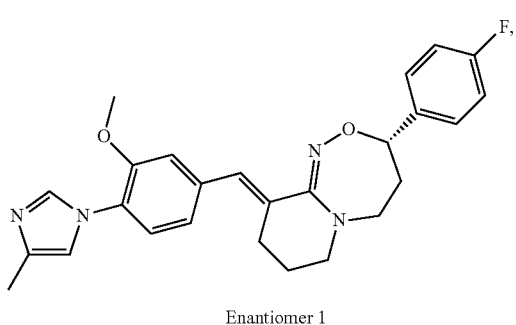 [SMILES: COc1cc(/C=C2\CCCN3CC[C@@H](c4ccc(F)cc4)ON=C23)ccc1-n1cnc(C)c1]<br>Enantiomer 1 |
| 53 | 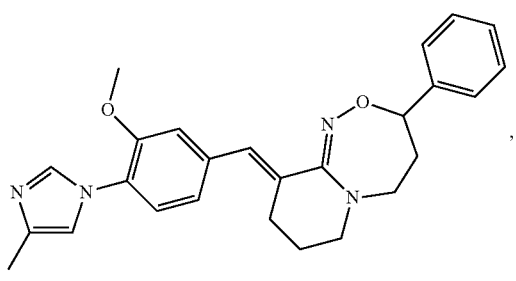<br>racemate |
| 54 | 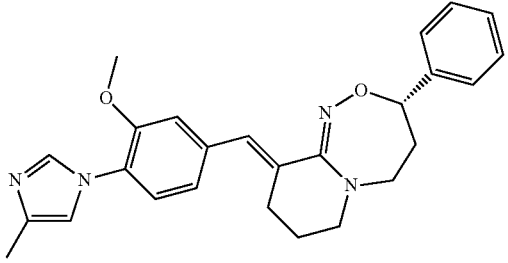<br>Enantiomer 1 |
| 55 | 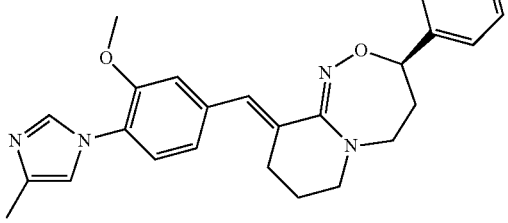<br>Enantiomer 2 |
| 56 | 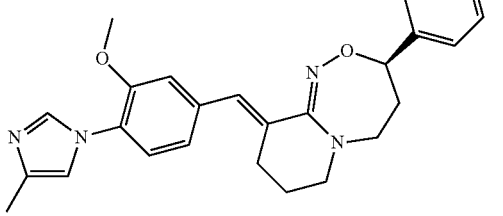<br>Enantiomer 2 |
| 57 | 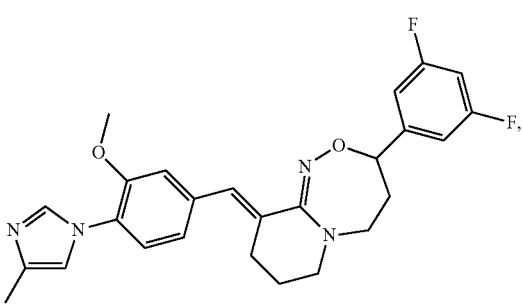<br>racemate |
| 58 | 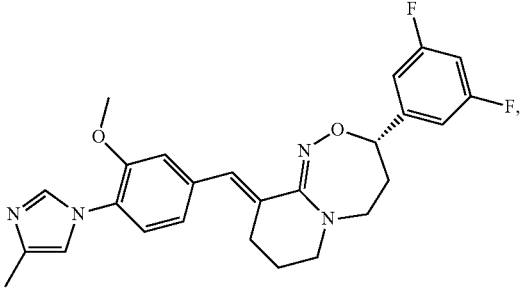<br>Enantiomer 2 |

| Compound | Structure |
|---|---|
| 59 | 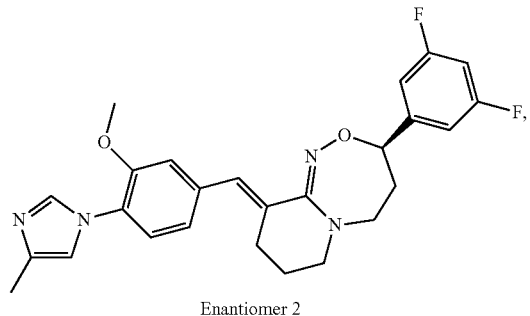 [SMILES: COc1cc(/C=C2\CCCN3CC[C@H](c4cc(F)cc(F)c4)ON=C23)ccc1-n1cnc(C)c1]
Enantiomer 2 |
| 60 | 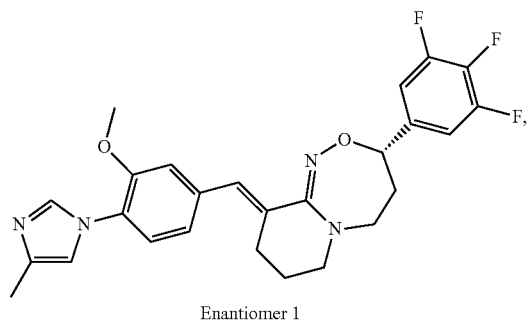 [SMILES: COc1cc(/C=C2\CCCN3CC[C@@H](c4cc(F)c(F)c(F)c4)ON=C23)ccc1-n1cnc(C)c1]
Enantiomer 1 |
| 61 | 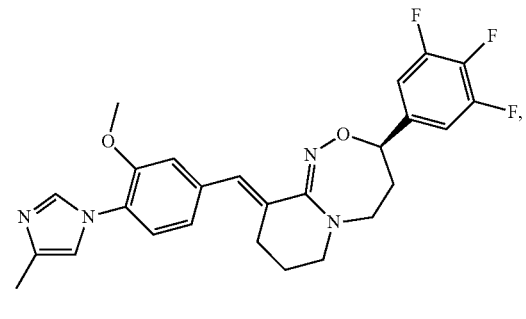
Enantiomer 2 |
| 62 | 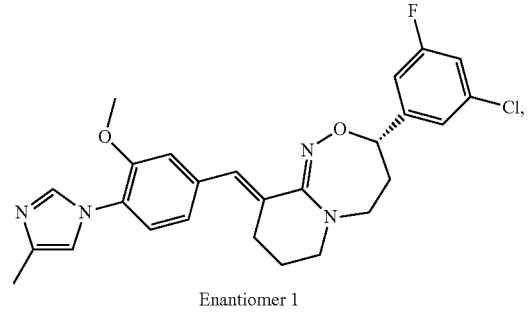 [SMILES: COc1cc(/C=C2\CCCN3CC[C@@H](c4cc(F)cc(Cl)c4)ON=C23)ccc1-n1cnc(C)c1]
Enantiomer 1 |
| Compound | Structure |
|---|---|
| 63 | 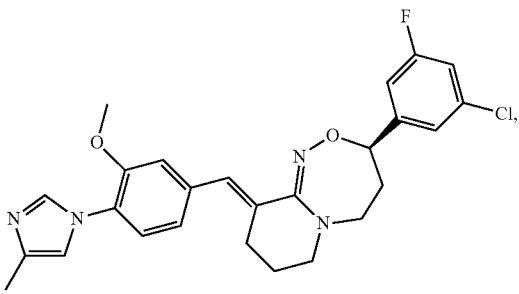
Enantiomer 2 |
| 64 | 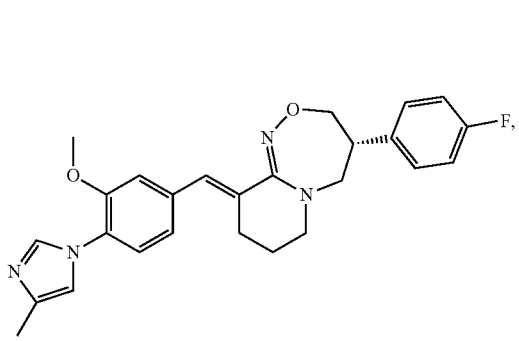 [SMILES: COc1cc(/C=C2\CCCN3C[C@@H](c4ccc(F)cc4)CON=C23)ccc1-n1cnc(C)c1]
| Compound | Structure |
|---|---|
| 65 | 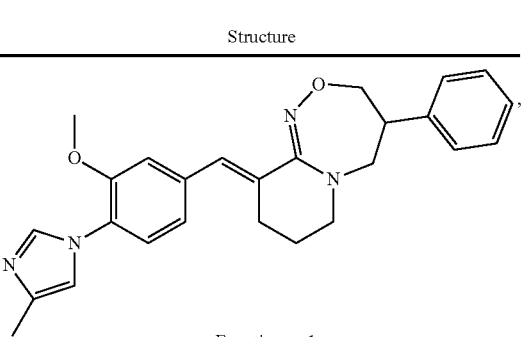
Enantiomer 1 |
| 66 | 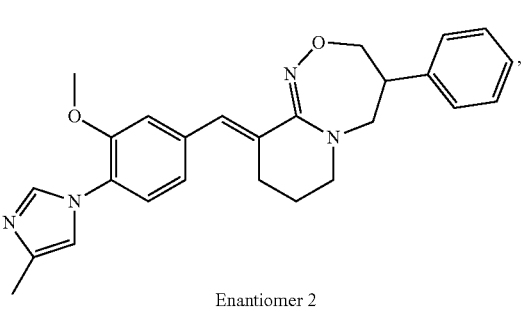 [SMILES: COc1cc(/C=C2\CCCN3CC(c4ccccc4)CON=C23)ccc1-n1cnc(C)c1]
Enantiomer 2 |

| Compound | Structure |
|---|---|
| 67 | *(Enantiomer 1)* |
| 68 | *(Enantiomer 2)* |
| 69 | 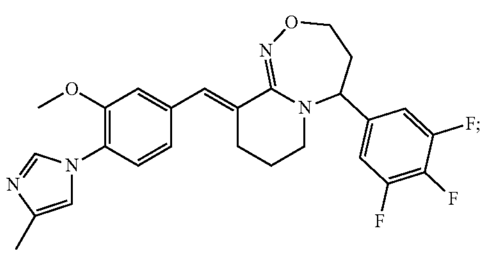 |

| Compound | Structure |
|---|---|
| 70 | | or a pharmaceutically acceptable salt thereof.

5. A pharmaceutical composition comprising a compound of claim 1 or a pharmaceutically acceptable salt thereof, and a pharmaceutically acceptable carrier.

6. A method of treating Alzheimer's disease, comprising administering an effective amount of one or more compounds of claim 1 or a pharmaceutically acceptable salt thereof to a patient in need of treatment.

7. The compound of claim 1 or a pharmaceutically acceptable salt thereof, wherein the $R^9$-$R^{10}$ moiety is

* * * * *